United States Patent
Ameriks et al.

(10) Patent No.: US 10,611,730 B2
(45) Date of Patent: Apr. 7, 2020

(54) BENZIMIDAZOLONE AND BENZOTHIAZOLONE COMPOUNDS AND THEIR USE AS AMPA RECEPTOR MODULATORS

(71) Applicant: Janssen Pharmaceutica NV, Beerse (BE)

(72) Inventors: Michael K. Ameriks, San Diego, CA (US); Suchitra Ravula, San Diego, CA (US); Devin M. Swanson, Carlsbad, CA (US); Bradley M. Savall, San Diego, CA (US)

(73) Assignee: Janssen Pharmaceutica NV, Beere (BE)

( * ) Notice: Subject to any disclaimer, the term of this patent is extended or adjusted under 35 U.S.C. 154(b) by 33 days.

(21) Appl. No.: 15/569,263

(22) PCT Filed: Apr. 28, 2016

(86) PCT No.: PCT/US2016/029780
§ 371 (c)(1),
(2) Date: Oct. 25, 2017

(87) PCT Pub. No.: WO2016/176449
PCT Pub. Date: Nov. 3, 2016

(65) Prior Publication Data
US 2019/0092735 A1  Mar. 28, 2019

Related U.S. Application Data

(60) Provisional application No. 62/154,291, filed on Apr. 29, 2015.

(51) Int. Cl.
| | |
|---|---|
| C07D 235/26 | (2006.01) |
| C07D 277/68 | (2006.01) |
| C07D 413/10 | (2006.01) |
| C07D 403/10 | (2006.01) |
| C07D 417/10 | (2006.01) |
| C07D 401/10 | (2006.01) |
| C07D 498/08 | (2006.01) |
| C07D 403/12 | (2006.01) |
| C07D 417/12 | (2006.01) |
| C07D 401/04 | (2006.01) |
| C07D 417/04 | (2006.01) |
| C07D 405/12 | (2006.01) |
| C07D 413/14 | (2006.01) |

(52) U.S. Cl.
CPC ......... C07D 235/26 (2013.01); C07D 277/68 (2013.01); C07D 401/04 (2013.01); C07D 401/10 (2013.01); C07D 403/10 (2013.01); C07D 403/12 (2013.01); C07D 405/12 (2013.01); C07D 413/10 (2013.01); C07D 413/14 (2013.01); C07D 417/04 (2013.01); C07D 417/10 (2013.01); C07D 417/12 (2013.01); C07D 498/08 (2013.01)

(58) Field of Classification Search
CPC .. C07D 235/26; C07D 277/68; C07D 413/10; C07D 403/10; C07D 417/10; C07D 401/10

See application file for complete search history.

(56) References Cited

U.S. PATENT DOCUMENTS

| | | | |
|---|---|---|---|
| 4,370,340 A | * | 1/1983 | Ueda ..................... C07C 205/12 514/367 |
| 5,688,809 A | | 11/1997 | Macor |
| 5,886,008 A | | 3/1999 | Macor |
| 7,842,698 B2 | | 11/2010 | Rueckle |

FOREIGN PATENT DOCUMENTS

| | | |
|---|---|---|
| EP | 869958 | 10/1998 |
| WO | WO 95/21836 | 8/1995 |
| WO | WO 2000/01376 | 1/2000 |
| WO | WO 02/10170 | 2/2002 |
| WO | WO 2002/14294 | 2/2002 |
| WO | WO 2007/135529 | 11/2007 |

(Continued)

OTHER PUBLICATIONS

Rowe, Raymond C, Paul J. Sheskey, and Marian E Quinn. Handbook of Pharmaceutical Excipients. London: Pharmaceutical Press, 6th Edition, 2009, p. 17 (Year: 2009).*

(Continued)

*Primary Examiner* — Laura L Stockton
(74) *Attorney, Agent, or Firm* — Thomas J. Dodd

(57) ABSTRACT

Provided herein are compounds of Formula (I), and pharmaceutically acceptable salts, N-oxides, or solvates thereof,

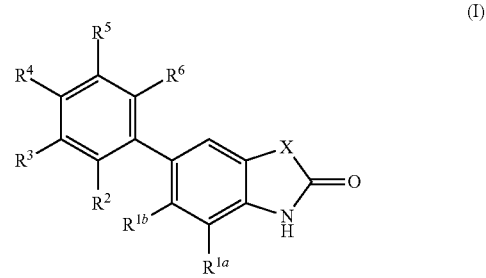

Also provided herein are pharmaceutical compositions comprising compounds of Formula (I) and methods of using compounds of Formula (I).

19 Claims, No Drawings

(56) References Cited

FOREIGN PATENT DOCUMENTS

| WO | WO 2008/053031 | 5/2008 |
|----|----------------|--------|
| WO | WO 2008/113795 | 9/2008 |
| WO | WO 2008/148832 | 12/2008 |
| WO | WO 2010/005528 | 1/2010 |
| WO | WO 2010/066658 | 6/2010 |
| WO | WO 2011/056985 | 5/2011 |
| WO | WO 2011/156245 | 12/2011 |
| WO | WO 2013/064984 | 5/2013 |
| WO | WO 2014/085153 | 6/2014 |
| WO | WO 2014/128585 | 8/2014 |

OTHER PUBLICATIONS

International Search Report for PCT/US2016/029780 dated Jun. 14, 2016.
International Search Report for PCT/US2016/029791 dated Jun. 9, 2016.
International Search Report for PCT/US2016/029801 dated Oct. 17, 2016.
International Search Report for PCT/US2016/029805 dated Jun. 8, 2016.
Bagshawe, Drug Dev Res. 1995, 34, 220-230.
Berge, et al., "Pharmaceutical Salts", J Pharm Sci., 1977, 66:1-19.
Bertolini, et al., J Med Chem. 1997, 40, 2011-2016.
Bodor, Adv Drug Res. 1984, 13, 224-331.
Brewer, G. J. (1997). "Isolation and culture of adult rat hippocampal neurons." Journal of Neuroscience Methods 71(2): 143-155.
Chen et al., Bipolar Disord., 13:1-15, 2011.
Cho et al. (2007). "Two families of TARP isoforms that have distinct effects on the kinetic properties of AMPA receptors and synaptic currents." Neuron 55(6): 890-904.
Du et al., J Neurosci 24: 6578-6589, 2004.
Du et al., J Neurosci 28: 68-79, 2008.
Engin and Treit, Behav Pharmacol 18:365-374, 2007.
Fleisher et al., Adv Drug Delivery Rev., 1996, 19, 115-130.
G.D. Considine, ed., Van Nostrand's Encyclopedia of Chemistry, p. 261, 5$^{th}$ ed. (2005).
Gill and Bredt, Neoropsychopharmacology, 36(1): 362-363 (2011).
Harrison, Brain 125:1428-1449, 2002.
Heckers and Konradi, Curr Top Behav Neurosci. 4:529-553, 2010.
Kambe, Tohru; Correia, Bruno E.; Niphakis, Micah J.; Cravatt, Benjamin F., Journal of the American Chemical Society (2014), 136(30), 10777-10782.
Lazzaro et al. (2002). "Functional characterization of CP-465,022, a selective, noncompetitive AMPA receptor antagonist." Neuropharmacology 42(2): 143-153.
Macor et al., "The discovery of a novel and potent benzodiazepine receptor pharmacophore", Bioorganic & Medicinal Chemistry Letters, Pergamon, Amsterdam, NL, vol . 5, No. 20, Oct. 19, 1995 (Oct. 19, 1995), pp. 2397-2402.
McNaughton et al., Behav Pharmacol 18: 329-346, 2007.
Nolen and Bloemkolk, Neuropsychobiology, 42 Suppl 1:11-7, 2000.
Robinson et al., J. Med Chem., 1996, 39(1), 10-18.
Paulekuhn, et al., "Trends in Active Pharmaceutical Ingredient Salt Selection based on Analysis of the Orange Book Database", J. Med. Chem., 2007, 50:6665-72.
Pirotte et al., "AMPA receptor positive allosteric modulators: a patent review", Expert Opinion Therapeutic Patents, vol. 23. No. 5, 2013, pp. 615-628.
Rogawski et al., Epilepsy Currents, 2011, vol. 11(2), pp. 56-63.
Schobel et al., Arch Gen Psych, 66:938-946, 2009.
Shan, et al., J Pharm Sci. 1997, 86 (7), 765-767.
Shi et al (2009) "The stoichiometry of AMPA receptors and TARPS varies by neuronal cell type." Neuron 62(5): 633-640.
Small et al, Nat. Rev. Neurosci. 12:585-601, 2011.
Strange et al. (2006). "Functional characterisation of homomeric ionotropic glutamate receptors GluR1-GluR6 in a fluorescence-based high throughput screening assay." Comb Chem High Throughput Screen 9(2): 147-158.
Tikhonova et al.,"Virtual screening of organic molecule databases . Design of focused libraries of potential I igands of NMDA and AMPA receptors", Russian Chemical Bulletin , Kluwer Academic Publishers-Plenum Publishers, NE, vol. 53, No. 6, Jun. 1, 2004, pp. 1335-1344.
Tomita et al. (2003). "Functional studies and distribution define a family of transmembrane AMPA receptor regulatory proteins." J Cell Biol 161(4): 805-816.2003.
Tregellas et al., Am J Psychiatry 171: 549-556, 2014.
Yeung et al., Hippocampus 23:278-286, 2013.
Yeung et al., Neuropharmacology 62: 155-160, 2012.

* cited by examiner

BENZIMIDAZOLONE AND BENZOTHIAZOLONE COMPOUNDS AND THEIR USE AS AMPA RECEPTOR MODULATORS

FIELD OF THE INVENTION

The present invention is related to compounds having AMPA receptor modulating properties, pharmaceutical compositions comprising these compounds, chemical processes for preparing these compounds and their use in the treatment of diseases associated with AMPA receptor activity in animals, in particular humans.

BACKGROUND OF THE INVENTION

Glutamate is the primary excitatory neurotransmitter in mammalian brain. Glutamatergic signaling participates in a wide range of neural functions including learning and memory, long-term potentiation and synaptic plasticity.

Glutamate receptors can be divided into two families. The ionotropic glutamate receptors form ion channels that activate upon binding agonist, opening a pore through the plasma membrane through which cations can flow. The metabotropic glutamate receptors are G-protein-coupled receptors, activating intracellular signal transduction cascades. The ionotropic glutamate receptors can be further subdivided into four sub-families, based upon sequence homology and selectivity to exogenous agonists. These sub-families are the AMPA (α-amino-3-hydroxyl-5-methyl-4-isoxazole-propionic acid), NMDA (N-methyl-D-aspartate), kainate, and delta receptors.

The AMPA subtype of glutamate receptors are glutamate-gated ion channels expressed primarily on postsynaptic membranes of excitatory synapses in the central nervous system. AMPA receptors assemble as tetramers of subunits. Mammals express four AMPA-receptor subunits, called GluA1-GluA4. Each GluA subunit can be expressed in multiple splice variants; the two most prominent splice variants are called flop and flip. GluA subunits freely form functional homo- and hetero-tetramers. The majority of RNA encoding GluA2 subunits is edited post-transcriptionally, altering a genetically-encoded glutamine to arginine. This RNA editing causes AMPA receptors to preferentially form with two GluA2 units, and also prevents calcium entry through the activated receptor.

In their native environment, the pore-forming GluA tetramers directly or indirectly associate with numerous auxiliary proteins which modify the trafficking, localization, gating characteristics, and pharmacology of the AMPA receptor (AMPAR). These auxiliary subunits include cytoskeletal and anchoring proteins, other signaling proteins, and several intracellular and transmembrane proteins with unknown function. The wide variety of proteins which can participate in AMPA receptor complexes vastly increases the ability of a neuron to tune the response characteristics of its synapses.

Transmembrane AMPA Receptor Regulatory Proteins (TARPs) are a fairly recently discovered family of proteins that have been found to associate with and modulate the activity of AMPA receptors. (Gill and Bredt, Neuropsychopharmacology 36(1): 362-363 (2011). Several TARPs exhibit regiospecific expression in the brain, leading to physiological differentiation of the AMPA receptor activity. For example, TARP γ2-dependent AMPA receptors are primarily localized in the cerebellum and cerebral cortex while TARP γ8-dependent AMPA receptors are localized primarily in the hippocampus.

AMPA receptors mediate the majority of fast neurotransmission across synaptic gaps. Thus, inhibition or negative modulation of AMPA receptors is an attractive strategy for therapeutic intervention in CNS disorders characterized by excessive neuronal activity. However, since AMPA receptor activity is so ubiquitous within CNS, general antagonism affects most areas of the CNS resulting in undesired effects, such as ataxia, sedation, and/or dizziness, which are shared by all known general AMPA receptor antagonists.

Epilepsy affects over 50 million people world-wide, with 30-40% of treated patients being resistant to current pharmacotherapies and only about 8% of treated patients being maintained seizure free. Epilepsy is often defined as when a person has two or more unprovoked epileptic seizures. The International League Against Epilepsy (ILAE) defines an epileptic seizure as "a transient occurrence of signs and/or symptoms due to abnormal excessive or synchronous neuronal activity in the brain." Seizures are thought to have a number of underlying causalities which adds to the difficulty in treating epilepsy. Seizures have been divided according to their clinical presentation including generalized seizures (absence, atonic, tonic-clonic (grand mal), and myoclonic), simple and complex partial onset seizures, gelastic seizures, dacrystic seizures, and status epilepticus. Current therapies target a variety of mechanisms including GABA γ-aminobutyric acid) receptor agonism, T-type calcium channel blockers, sodium channel modulators, synaptic vesicle protein SV2A modulation, and inhibition of GABA transaminase. More recently, AMPA receptor antagonists have been investigated for treatment of seizures as well.

AMPA receptor antagonists are known anticonvulsant agents. Typically, AMPA receptor antagonists have very narrow therapeutic dosing windows; the doses needed to obtain anti-convulsant activity are close to or overlap with doses at which undesired effects are observed. (Michael A. Rogawski. "Revisiting AMPA Receptors as an AntiEpileptic Drug Target" Epilepsy Currents 11.2 (2011).) However, certain anticonvulsant agents such as Talampanel ((8R)-7-Acetyl-5-(4-aminophenyl)-8,9-dihydro-8-methyl-7H-1,3-dioxolo[4,5-h][2,3]benzodiazepine), selurampanel (BGG492) (N-[7-isopropyl-6-(2-methyl-2H-pyrazol-3-yl)-2,4-dioxo-1,4-dihydro-2H-qui-nazolin-3-yl]methanesulfonamide), and perampanel (5'-(2-cyanophenyl)-1'-phenyl-2,3'-bipyridinyl-6'(1$^1$H)-one) are general (non-TARP dependent/non-selective) AMPA receptor antagonists. However, such general antagonism affects most areas of the CNS resulting in undesired effects, Glutamate as an excitatory neurotransmitter has been known to induce neurotoxicity by, for example, abnormal excitation of central nerves. Neurotoxicity is an adverse structural or functional change in the nervous system, and can take the form of subtle or gross biochemical changes, axonal degeneration, dendritic pruning or sprouting, loss or rearrangement of synapses, or cell death. Numerous nervous diseases involve a neurotoxic component, including and not limited to cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain and diabetic neuropathy.

Substances showing an antagonistic action to excitatory neurotransmitter receptors are potentially useful for the treatment of the above-mentioned conditions. For example, WO2000001376 suggests that inhibitors of the interaction of glutamate with the AMPA and/or kainate receptor complex could be useful in treating demyelinating disorders such as encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder; for example, CNS lupus erythematodes, polyarteritis nodosa, Sjogren syndrome, sarcoidosis, isolated cerebral vasculitis, etc.

Hippocampus links the limbic system to frontal cortex, thereby linking emotion to cognition (Small et al, Nat. Rev. Neurosci. 12:585-601, 2011). A meta-analysis of post-mortem neuro-pathology studies suggests that hippocampal volume is reduced in volume in patients with mood disorders (Harrison, Brain 125:1428-1449, 2002). Hippocampal neurons are particularly susceptible to stress-related atrophy. Pathological states characterized by excessive activity within hippocampus may be improved by a therapeutic intervention that selectively reduces hippocampal excitability. Modulation of neuronal excitability within hippocampus may provide a therapeutic benefit in mood disorders.

Excess activity in hippocampus has been observed in response to emotionally-charged stimuli in bipolar patients compared to controls (reviewed by Chen et al., Bipolar Disord., 13:1-15, 2011). Chronic treatment with mood stabilizers such as lithium or valproate reduced AMPA receptor surface expression in hippocampus (Du et al., J Neurosci 28: 68-79, 2008). Tricyclic antidepressants can trigger mania in bipolar patients (Nolen and Bloemkolk, Neuropsychobiology, 42 Suppl 1:11-7, 2000); these treatments can increase AMPA receptor surface expression in hippocampus (Du et al., J Neurosci 24: 6578-6589, 2004.)

In Gray's Neuropsychological Theory of Anxiety (2003), septum and hippocampus form a 'behavioral inhibition system' activated during anxiety-provoking conflict situations. A corollary of this theory is that anxiolytic drugs act by suppressing this 'behavioral inhibition system'. Indeed, intrahippocampal micro-infusion of GABAA agonists is sufficient to replicate their anxiolytic effects (Engin and Treit, Behav Pharmacol 18:365-374, 2007). Traditional anxiolytics with a variety of mechanisms-of-action, including GABAA-receptor antagonists, 5-HT$_{1A}$ receptor antagonists, and SSRIs, suppress brainstem-stimulated theta rhythm within hippocampus (McNaughton et al., Behav Pharmacol 18: 329-346, 2007). Direct injection of inhibitors of neuronal excitability into rodent hippocampus was shown to reduce the hippocampal theta rhythm, and to produce an anxiolytic phenotype. Intrahippocampal administration of ZD7288, an HCN channel inhibitor, slowed brainstem-stimulated theta rhythm in anesthetized rat and also increased the amount of time that rats spent in the open arms of an elevated plus maze (Yeung et al., Hippocampus 23:278-286, 2013). Intrahippocampal administration of phenytoin, a voltage-gated sodium channel inhibitor and anticonvulsant, showed similar effects on brainstem-stimulated theta rhythm frequency in anesthetized rat and was anxiolytic in conscious rat (Yeung et al., Neuropharmacology 62: 155-160, 2012).

Hippocampal overactivity has been observed in patients suffering from schizophrenia (Heckers and Konradi, Curr Top Behav Neurosci. 4:529-553, 2010). The degree of hyperactivity was be positively correlated to the severity of the symptoms (Tregellas et al., Am J Psychiatry 171: 549-556, 2014). Hypermetabolism in hippocampus (esp. CA1 region) correlates with disease progression in at-risk individuals, and with disease severity in patients diagnosed with schizophrenia (Schobel et al., Arch Gen Psych, 66:938-946, 2009). This over-activity, combined with the sensitivity of hippocampal neurons to excitotoxic damage, may lead to the observed decrease in hippocampal volume in schizophrenic patients. Neuroprotection in prodromal and early stages may prevent progressive damage (Kaur and Cadenhead, Curr Top Behav Neurosci, 2010).

In view of the clinical importance of AMPA receptors, the identification of compounds that modulate AMPA receptor function represents an attractive avenue into the development of new therapeutic agents. Such compounds are provided herein.

SUMMARY OF THE INVENTION

Provided herein are compounds which are AMPA receptor modulators. In another aspect, provided herein are compounds which modulate certain TARP dependent AMPA receptors. The compounds described herein are suitable for treatment of conditions involving AMPA receptor activity, and for treatment of conditions involving selective modulation of TARP dependent AMPA receptor activity, thereby allowing for treatment of conditions such as, inter alia, abnormal neurotransmission across synaptic gaps, excessive neuronal activity, abnormal excessive or synchronous neuronal activity in the brain, neurotoxicity (e.g., adverse structural or functional changes in the nervous system, subtle or gross biochemical changes, axonal degeneration, dendritic pruning or sprouting, loss or rearrangement of synapses, or cell death), neuronal excitability within hippocampus, neuronal excitotoxicity, hippocampal overactivity, and the like.

The invention is directed to the general and preferred embodiments defined, respectively, by the independent and dependent claims appended hereto, which are incorporated by reference herein. One aspect of this invention concerns compounds of Formula (I):

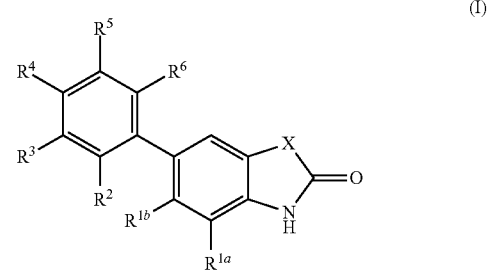

wherein
X is NH or S;
$R^{1a}$ and $R^{1b}$ are independently selected from the group consisting of H, $^3$H, halo, —CH$_3$, —CH$_2$CH$_3$, —CF$_3$, —OCH$_3$, —OCF$_3$, and —CN;
$R^2$ is selected from the group consisting of: halo; C$_{1-5}$alkyl; C$_{1-5}$alkenyl; C$_{1-5}$haloalkyl; C$_{1-5}$alkoxy; C$_{1-5}$haloalkoxy; —(C=O)H; —CH$_2$C(=O)NH(CH$_3$); —CO$_2$C$_{1-5}$alkyl; —CN; —CH$_2$CN; —CH(CH$_3$)CN; —C(CH$_3$)$_2$CN; —OCH$_2$CN; phenyl; phenyl substituted with halo, C$_{1-5}$alkoxy, or —CN; —O-phenyl; benzyl; benzyl substituted with halo; —O-benzyl; C$_{3-6}$cycloalkyl; —OC$_{3-6}$cycloalkyl; —O-thiazolyl; pyrimidinyl; pyridyl; pyridyl substituted with halo, $C_{1-5}$alkoxy, or $C_{1-5}$haloalkyl; —NH—$CH_2$-furyl; —$C_{3-6}$cycloalkyl substituted with CN; —$CH_2$morpholine; $CH_2$—N-methylpiperazine; pyrazolyl; pyrazole substituted with —$CH_2CH_2OCH_3$, or $C_{1-5}$alkyl; isoxazole substituted with two $C_{1-5}$alkyl; —O—$CH_2$—$C_{3-6}$cycloalkyl optionally substituted with halo; piperazine substituted with —$CO_2tBu$; —O-azetidine substituted with —$CO_2tBu$; and 8-quinolyl;

$R^3$ is selected from the group consisting of: H; halo; $C_{1-5}$alkyl; $C_{1-5}$haloalkyl; $C_{1-5}$alkoxy; $C_{1-5}$haloalkoxy; —CN; —$CH_2CN$; $CO_2C_{1-5}$alkyl; —$N(CH_3)_2$; —(C=O)$N(C_{1-5}$alkyl$)_2$; —(C=O)NH-cyclopropyl; —(C=O)NH-phenyl; —(C=O)morpholine; —O-cyclopropyl; —O—$CH_2$-cyclopropyl substituted with halo; —O-azetidinyl substituted with —$CO_2tBu$; $CH_2$-pyrrolidine; piperidine; piperidine substituted with —$OCH_3$; —$CH_2$-piperidine; —$CH_2$-piperidine substituted with —OH and halo; —$CH_2$-morpholine; $CH_2$-morpholine substituted with one or two $C_{1-5}$alkyl or $C_{1-5}$haloalkyl; $CH_2$-thiomorpholine; $CH_2$-piperazine substituted with —$CO_2tBu$; $CH_2$-azetidine substituted with halo; —$CH_{2-6}$-oxa-3-azabicyclo[3.1.1]heptan-3-yl; pyrazole substituted with $C_{1-5}$alkyl; pyridyl; 3,6-dihydro-2H-pyridine substituted with —$CO_2tBu$; imidazole; oxadiazolyl; and oxadiazole substituted with $C_{1-5}$alkyl, cyclopropyl, pyridyl, or $C_{1-5}$haloalkyl;

$R^4$ is selected from the group consisting of: H, halo, and $C_{1-5}$haloalkoxy;

$R^5$ is selected from the group consisting of: H, halo, $C_{1-5}$alkyl, $C_{1-5}$haloalkyl, —CN, $CO_2C_{1-5}$alkyl, —(C=O)NH-phenyl, —(C=O)pyrrolidine, and —(C=O)piperidine; and $R^6$ is selected from the group consisting of: H, halo, $C_{1-5}$alkyl, —$CH_2CN$, $C_{1-5}$alkoxy, $C_{1-5}$haloalkyl, and $C_{1-5}$haloalkoxy; and wherein when $R^6$ is H and $R^2$ is $C_{1-5}$alkoxy, $R^3$ is not $C_{1-5}$alkoxy; and pharmaceutically acceptable salts, N-oxides, or solvates of compounds of Formula (I).

Further embodiments are provided by pharmaceutically acceptable prodrugs of compounds of Formula (I), and pharmaceutically active metabolites of compounds of Formula (I).

In certain embodiments, the compounds of Formula (I) are compounds selected from those species described or exemplified in the detailed description below.

In a further aspect, the invention relates to enantiomers and diastereomers of the compounds of Formula (I), as well as their pharmaceutically acceptable salts.

In a further aspect, the invention relates to pharmaceutical compositions, comprising an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the chemical embodiments of the present invention are useful as AMPA receptor modulators. Thus, the invention is directed to a method for modulating AMPA receptor activity, including when such receptor is in a subject, comprising exposing AMPA receptor to an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of compounds of Formula (I).

In another aspect, the invention is directed to a method of treating a subject suffering from, or diagnosed with a disease, disorder, or medical condition mediated by AMPA receptor activity, comprising administering to the subject in need of such treatment an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of compounds of Formula (I). Additional embodiments of methods of treatment are set forth in the detailed description.

In another aspect, the method of studying isotopically labeled compounds of Formula (I) in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. For example, an $^{18}F$ or $^{11}C$ labeled compound may be particularly preferred for PET or SPECT studies.

Additional embodiments of this invention include methods of making compounds of Formula (I), pharmaceutically acceptable salts, N-oxides or solvates of compounds of Formula (I), pharmaceutically acceptable prodrugs of compounds of Formula (I), and pharmaceutically active metabolites of Formula (I).

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

In another aspect provided herein are compounds of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA). In another aspect provided herein are compounds of Formula (IB), as well as pharmaceutically acceptable salts, N-oxides or solvates of compounds of Formula (IB), pharmaceutically acceptable prodrugs of compounds of Formula (IB), and pharmaceutically active metabolites of Formula (IB). In a further aspect, provided herein are pharmaceutical compositions, comprising an effective amount of a compound of Formula (IA) or Formula (IB), as well as pharmaceutically acceptable salts, N-oxides or solvates of compounds of Formula (IA) or Formula (IB), pharmaceutically acceptable prodrugs of compounds of Formula (IA) or Formula (IB), and pharmaceutically active metabolites of Formula (IA) or Formula (IB). In a further aspect, provided herein are compounds of Formula (IA) or Formula (IB), as well as pharmaceutically acceptable salts, N-oxides or solvates of compounds of Formula (IA) or Formula (IB), pharmaceutically acceptable prodrugs of compounds of Formula (IA) or Formula (IB), and pharmaceutically active metabolites of Formula (IA) or Formula (IB), for the treatment of any condition described herein.

DETAILED DESCRIPTION

In one aspect, provided herein are compounds of Formula (I), and pharmaceutically acceptable salts, N-oxides, or solvates thereof,

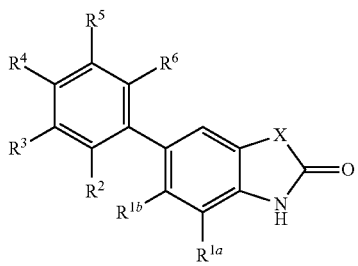

wherein
X is NH or S;
R$^{1a}$ and R$^{1b}$ are independently selected from the group consisting of H, $^3$H, halo, —CH$_3$, —CH$_2$CH$_3$, —CF$_3$, —OCH$_3$, —OCF$_3$, and —CN;
R$^2$ is selected from the group consisting of: halo; C$_{1-5}$alkyl; C$_{1-5}$alkenyl; C$_{1-5}$haloalkyl; C$_{1-5}$alkoxy; C$_{1-5}$haloalkoxy; —(C=O)H; —CH$_2$C(=O)NH(CH$_3$); —CO$_2$C$_{1-5}$alkyl; —CN; —CH$_2$CN; —CH(CH$_3$)CN; —C(CH$_3$)$_2$CN; —OCH$_2$CN; phenyl; phenyl substituted with halo, C$_{1-5}$alkoxy, or —CN; —O-phenyl; benzyl; benzyl substituted with halo; —O-benzyl; C$_{3-6}$cycloalkyl; —OC$_{3-6}$cycloalkyl; —O-thiazolyl; pyrimidinyl; pyridyl; pyridyl substituted with halo, C$_{1-5}$alkoxy, or C$_{1-5}$haloalkyl; —NH—CH$_2$-furyl; —C$_{3-6}$cycloalkyl substituted with CN; —CH$_2$morpholine; CH$_2$—N-methylpiperazine; pyrazolyl; pyrazole substituted with —CH$_2$CH$_2$OCH$_3$, or C$_{1-5}$alkyl; isoxazole substituted with two C$_{1-5}$alkyl; —O—CH$_2$—C$_{3-6}$cycloalkyl optionally substituted with halo; piperazine substituted with —CO$_2$tBu; —O-azetidine substituted with —CO$_2$tBu; and 8-quinolyl;
R$^3$ is selected from the group consisting of: H; halo; C$_{1-5}$alkyl; C$_{1-5}$haloalkyl; C$_{1-5}$alkoxy; C$_{1-5}$haloalkoxy; —CN; —CH$_2$CN; CO$_2$C$_{1-5}$alkyl; —N(CH$_3$)$_2$; —(C=O)N(C$_{1-5}$alkyl)$_2$; —(C=O)NH-cyclopropyl; —(C=O)NH-phenyl; —(C=O)morpholine; —O-cyclopropyl; —O—CH$_2$-cyclopropyl substituted with halo; —O-azetidinyl substituted with —CO$_2$tBu; CH$_2$-pyrrolidine; piperidine; piperidine substituted with —OCH$_3$; —CH$_2$-piperidine; —CH$_2$-piperidine substituted with —OH and halo; —CH$_2$-morpholine; CH$_2$-morpholine substituted with one or two C$_{1-5}$alkyl or C$_{1-5}$haloalkyl; CH$_2$-thiomorpholine; CH$_2$-piperazine substituted with —CO$_2$tBu; CH$_2$-azetidine substituted with halo; —CH$_{2-6}$-oxa-3-azabicyclo[3.1.1]heptan-3-yl; pyrazole substituted with C$_{1-5}$alkyl; pyridyl; 3,6-dihydro-2H-pyridine substituted with —CO$_2$tBu; imidazole; oxadiazolyl; and oxadiazole substituted with C$_{1-5}$alkyl, cyclopropyl, pyridyl, or C$_{1-5}$haloalkyl;
R$^4$ is selected from the group consisting of: H, halo, and C$_{1-5}$haloalkoxy;
R$^5$ is selected from the group consisting of: H, halo, C$_{1-5}$alkyl, C$_{1-5}$haloalkyl, —CN, —CO$_2$C$_{1-5}$alkyl, —(C=O)NH-phenyl, —(C=O)pyrrolidine, and —(C=O)piperidine; and
R$^6$ is selected from the group consisting of: H, halo, C$_{1-5}$alkyl, —CH$_2$CN, C$_{1-5}$alkoxy, C$_{1-5}$haloalkyl, and C$_{1-5}$haloalkoxy; and wherein when R$^6$ is H and R$^2$ is C$_{1-5}$alkoxy, R$^3$ is not C$_{1-5}$alkoxy.

An additional embodiment of the invention is a compound of Formula (I) wherein X is NH.
An additional embodiment of the invention is a compound of Formula (I) wherein X is S.
An additional embodiment of the invention is a compound of Formula (I) wherein R$^{1a}$ and R$^{1b}$ are H.
An additional embodiment of the invention is a compound of Formula (I) wherein R$^{1a}$ is H, —Cl, —CH$_3$, —CH$_2$CH$_3$, —CF$_3$, —OCF$_3$, or —CN.
An additional embodiment of the invention is a compound of Formula (I) wherein R$^{1b}$ is H, $^3$H or —F.
An additional embodiment of the invention is a compound of Formula (I) wherein R$^2$ is —OCF$_3$, —OCHF$_2$, —OCH$_2$CF$_3$, —OCH$_2$CHF$_2$, —OCH$_3$, —OCH(CH$_3$)$_2$, —OC(CH$_3$)$_3$, or —OCH$_2$C(CH$_3$)$_3$.
An additional embodiment of the invention is a compound of Formula (I) wherein R$^2$ is —Br, —Cl, —F, —CH$_3$, —CH(CH$_3$)$_2$, —CH$_2$CH(CH$_3$)$_2$, —CH=CH$_2$, —CF$_3$, cyclopropyl, phenyl, —O— phenyl, benzyl, —O-benzyl, —(C=O)H, —CN, —CH$_2$CN, —CH(CH$_3$)CN, —C(CH$_3$)$_2$CN, —OCH$_2$CN, —CO$_2$CH$_3$, —CH$_2$C(=O)NH (CH$_3$),

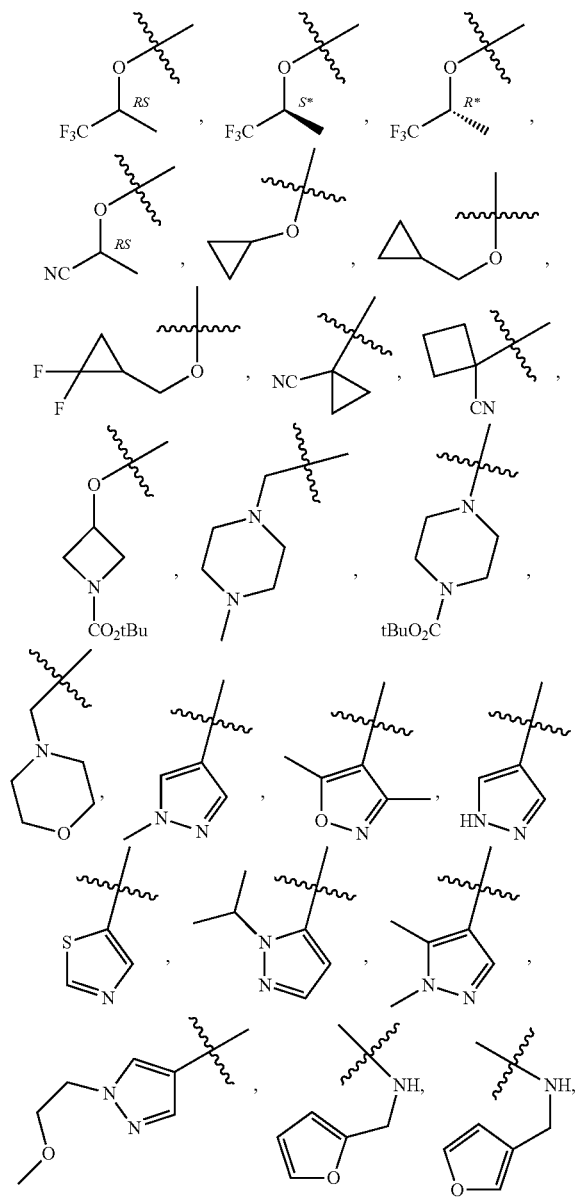

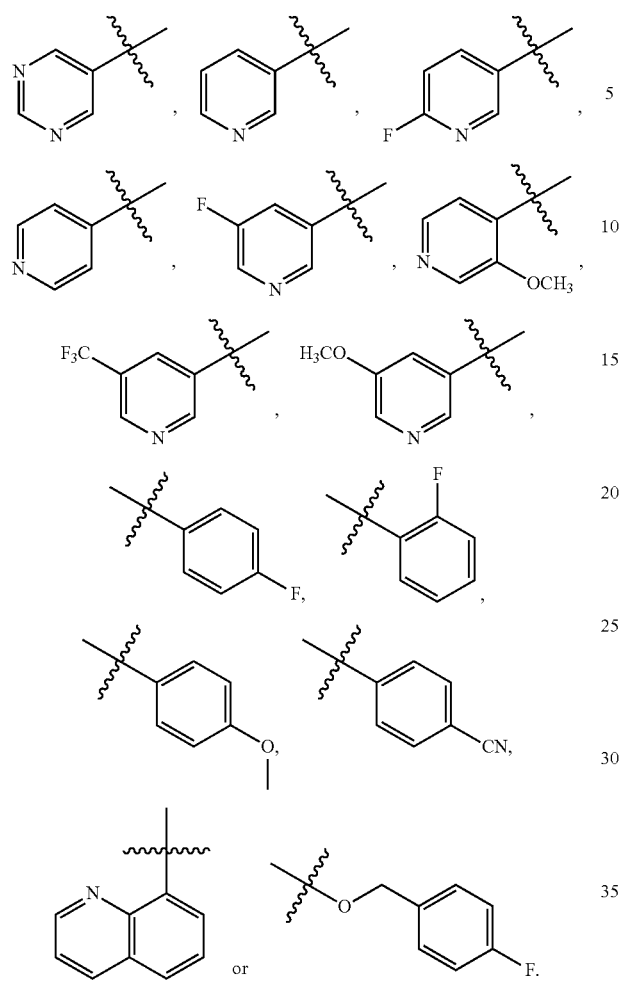

An additional embodiment of the invention is a compound of Formula (I) wherein $R^2$ is —Br, —Cl, —F, —OCF$_3$, —OCHF$_2$, —OCH$_2$CF$_3$, or —OCH$_2$CHF$_2$.

An additional embodiment of the invention is a compound of Formula (I) wherein $R^3$ is H, —Br, —Cl, —CH$_3$, —CF$_3$, —OCH(CH$_3$)$_2$, —OCHF$_2$, —OCH$_2$CHF$_2$, —O-cyclopropyl, —CN, —CH$_2$CN, —CO$_2$CH$_3$, —N(CH$_3$)$_2$, —(C═O)N(CH$_3$)$_2$, —(C═O)NH-cyclopropyl, —(C═O)NH-phenyl, —(C═O)morpholine,

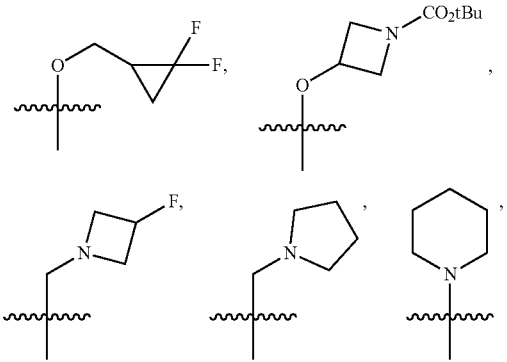

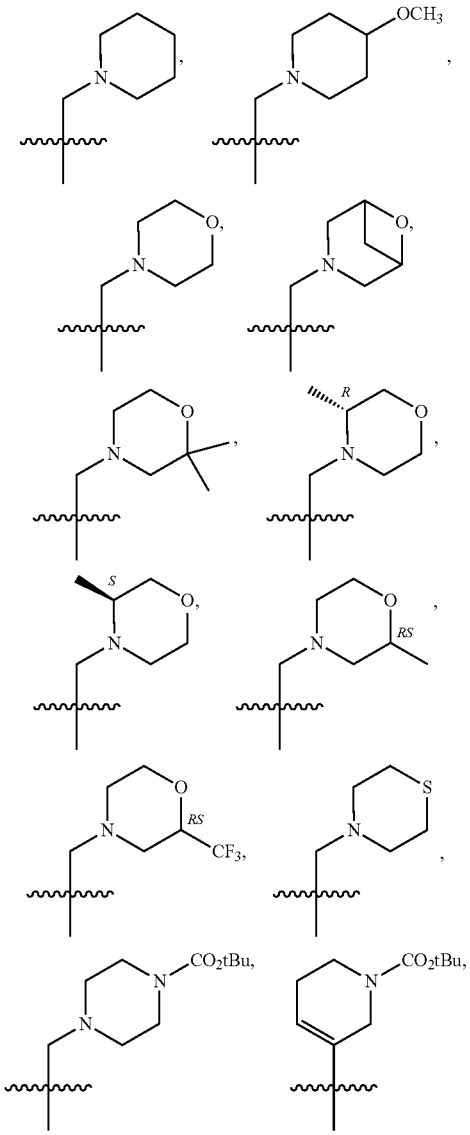

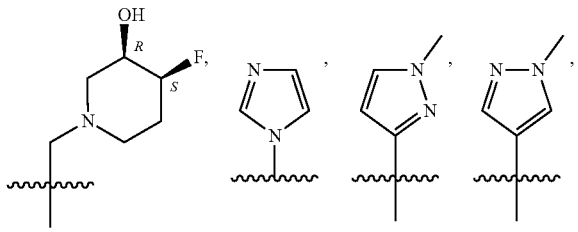

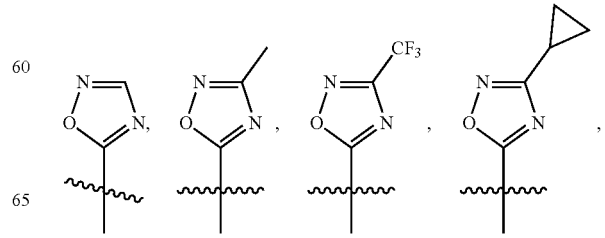

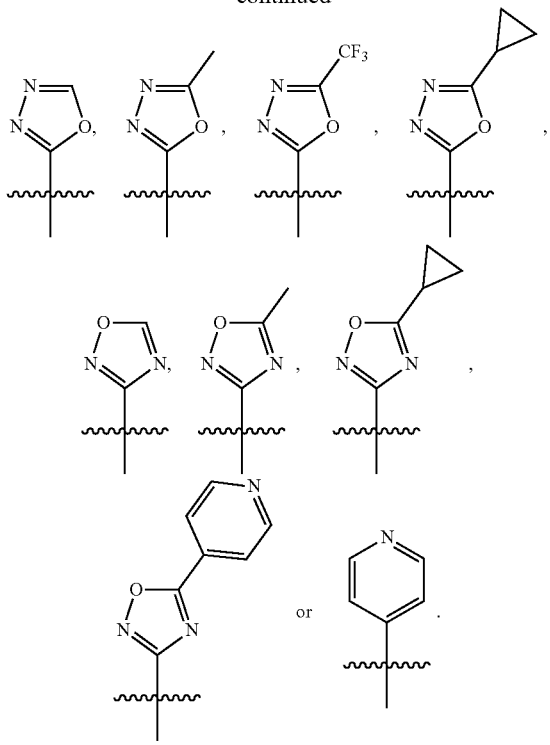

An additional embodiment of the invention is a compound of Formula (I) wherein $R^3$ is —CN or oxadiazolyl optionally substituted with $C_{1-5}$alkyl or $C_{1-5}$haloalkyl.

An additional embodiment of the invention is a compound of Formula (I) wherein $R^4$ is H, —Cl, —F, or —OCF$_3$.

An additional embodiment of the invention is a compound of Formula (I) wherein $R^4$ is H.

An additional embodiment of the invention is a compound of Formula (I) wherein $R^5$ is H, —Cl, —CH$_3$, —CF$_3$, —CN, —CO$_2$CH$_3$, —(C═O)NH-phenyl, —(C═O)pyrrolidine, or —(C═O)piperidine.

An additional embodiment of the invention is a compound of Formula (I) wherein $R^5$ is H or halo.

An additional embodiment of the invention is a compound of Formula (I) wherein $R^6$ is H, halo, $C_{1-5}$alkyl, —CH$_2$CN, $C_{1-5}$alkoxy, $C_{1-5}$haloalkyl, or $C_{1-5}$haloalkoxy, and $R^5$ is H or halo.

An additional embodiment of the invention is a compound of Formula (I) wherein $R^6$ is H, halo, $C_{1-5}$alkyl, or —CH$_2$CN.

An additional embodiment of the invention is a compound of Formula (II), and pharmaceutically acceptable salts, N-oxides, or solvates thereof, (II)

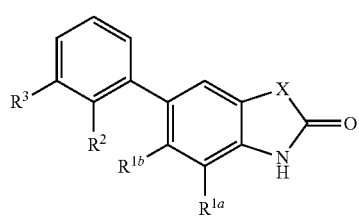

wherein $R^2$ is selected from the group consisting of: halo, $C_{1-5}$alkyl, $C_{1-5}$haloalkyl, —(C═O)H, —CH$_2$C(═O)NH(CH$_3$), —CO$_2$C$_{1-5}$alkyl (CO$_2$CH$_3$), —CN, —CH$_2$CN, -phenyl, —O-phenyl, benzyl, —O—CH$_2$—C$_{3-6}$cycloalkyl, and piperazine substituted with —CO$_2$tBu; and $R^3$ is selected from the group consisting of: H; halo; $C_{1-5}$alkyl; $C_{1-5}$haloalkyl; $C_{1-5}$alkoxy; $C_{1-5}$haloalkoxy; —CN; —CH$_2$CN; CO$_2$C$_{1-5}$alkyl; —N(CH$_3$)$_2$; —(C═O)N(C$_{1-5}$alkyl)$_2$; —(C═O)NH-cyclopropyl; —(C═O)NH-phenyl; —(C═O)morpholine; —O-cyclopropyl; —O—CH$_2$-cyclopropyl substituted with halo; —O-azetidinyl substituted with —CO$_2$tBu; CH$_2$-pyrrolidine; —CH$_2$-piperidine substituted with halo and —OH; piperidine; piperidine substituted with —OCH$_3$; —CH$_2$-piperidine; —CH$_2$-piperidine substituted with —OH and halo; —CH$_2$-morpholine; CH$_2$-morpholine substituted with one or two $C_{1-5}$alkyl, or $C_{1-5}$haloalkyl; CH$_2$-thiomorpholine; CH$_2$-piperazine substituted with —CO$_2$tBu; CH$_2$-azetidine substituted with halo; —CH$_2$-6-oxa-3-azabicyclo[3.1.1]heptan-3-yl; pyrazole substituted with $C_{1-5}$alkyl; pyridyl; 3,6-dihydro-2H-pyridine substituted with —CO$_2$tBu; imidazole; oxadiazolyl; and oxadiazole substituted with $C_{1-5}$alkyl, cyclopropyl, pyridyl, or CF$_3$;

and $R^{1a}$ and $R^{1b}$ are as defined above in Formula (I).

An additional embodiment of the invention is a compound of Formula (II) wherein $R^3$ is H, —Br, —Cl, —CH$_3$, —CF$_3$, —OCH(CH$_3$)$_2$, —OCHF$_2$, —OCH$_2$CHF$_2$, —O-cyclopropyl, —CN, —CH$_2$CN, —CO$_2$CH$_3$, —N(CH$_3$)$_2$, —(C═O)N(CH$_3$)$_2$, —(C═O)NH-cyclopropyl, —(C═O)NH-phenyl, —(C═O)morpholine,

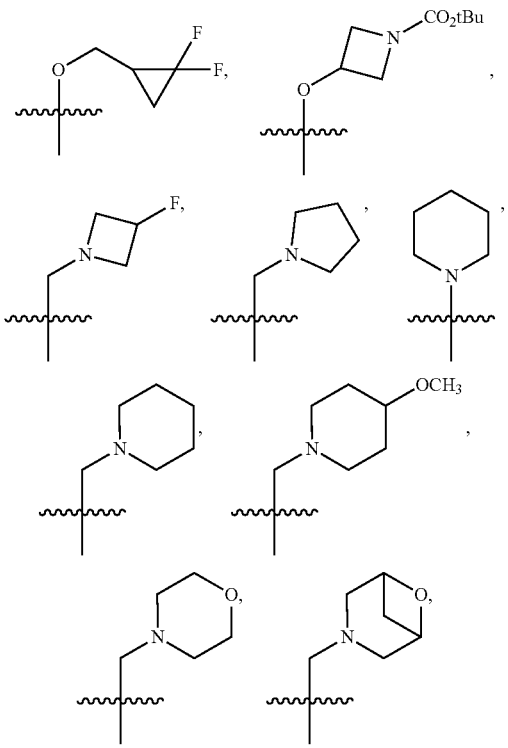

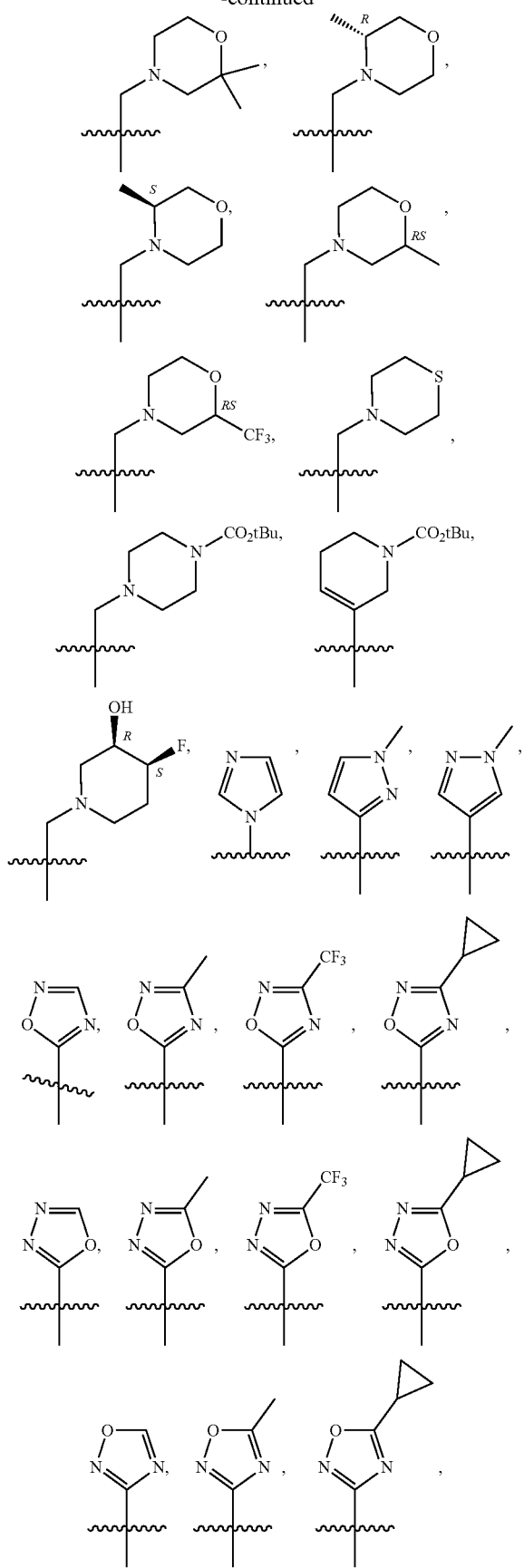

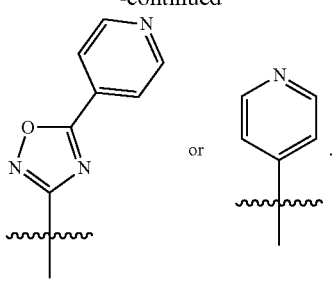

An additional embodiment of the invention is a compound of Formula (II) wherein $R^2$ is halo, $C_{1-5}$alkyl, $C_{1-5}$haloalkyl, —CN, or —CH$_2$—CN.

An additional embodiment of the invention is a compound of Formula (II), and pharmaceutically acceptable salts, N-oxides, or solvates thereof,

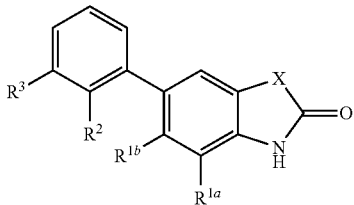

(II)

wherein $R^2$ is $C_{1-5}$alkoxy or $C_{1-5}$haloalkoxy; and $R^3$ is selected from the group consisting of: H; halo; $C_{1-5}$alkyl; $C_{1-5}$haloalkyl; —CN; —CH$_2$CN; —CO$_2$C$_{1-5}$alkyl; —N(CH$_3$)$_2$; —(C=O)N(C$_{1-5}$alkyl)$_2$; —(C=O)NH-cyclopropyl; —(C=O)NH-phenyl; —(C=O)morpholine; —O-cyclopropyl; —O—CH$_2$-cyclopropyl substituted with halo; —O— azetidinyl substituted with —CO$_2$tBu; CH$_2$-pyrrolidine; —CH$_2$-piperidine substituted with halo and —OH; piperidine; piperidine substituted with —OCH$_3$; —CH$_2$-piperidine; —CH$_2$-piperidine substituted with —OH and halo; —CH$_2$-morpholine; CH$_2$-morpholine substituted with one or two $C_{1-5}$alkyl or $C_{1-5}$haloalkyl; CH$_2$-thiomorpholine; CH$_2$-piperazine substituted with —CO$_2$tBu; CH$_2$-azetidine substituted with halo; —CH$_2$-6-oxa-3-azabicyclo[3.1.1]heptan-3-yl; pyrazole substituted with $C_{1-5}$alkyl; pyridyl; 3,6-dihydro-2H-pyridine substituted with —CO$_2$tBu; imidazole; and oxadiazole substituted with $C_{1-5}$alkyl, cyclopropyl, pyridiyl, or —CF$_3$; and $R^{1a}$ and $R^{1b}$ are as defined above as in Formula (I).

An additional embodiment of the invention is a compound of Formula (II) wherein $R^2$ is $C_{1-5}$alkoxy or $C_{1-5}$haloalkoxy, and $R^3$ is selected from: H, —Cl, and —CO$_2$CH$_3$.

An additional embodiment of the invention is a compound of Formula (II) wherein $R^2$ is —OCF$_3$, —OCH$_3$, or —OCH(CH$_3$)$_2$.

An additional embodiment of the invention is a compound of Formula (III) and pharmaceutically acceptable salts, N-oxides, or solvates thereof,

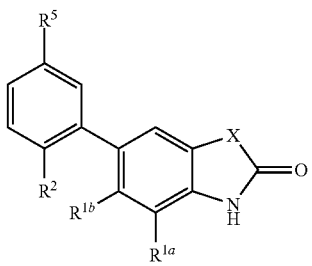

(III)

wherein
R² is halo, C₁₋₅alkyl, C₁₋₅haloalkyl, C₁₋₅alkoxy, C₁₋₅haloalkoxy, —CH₂CN, phenyl, —O-phenyl, benzyl, —OC₃₋₆cycloalkyl, or piperazine substituted with —CO₂tBu; and
R⁵ is H, halo, C₁₋₅alkyl, C₁₋₅haloalkyl, —CN, CO₂C₁₋₅alkyl, —(C=O)NH-phenyl, —(C=O)piperidine, and —(C=O)pyrrolidine;
and R¹ᵃ and R¹ᵇ are as defined above in Formula (I).

An additional embodiment of the invention is a compound of Formula (III) wherein
R² is C₁₋₅alkoxy, or C₁₋₅haloalkoxy;
R⁵ is H, halo, or C₁₋₅alkyl;

An additional embodiment of the invention is a compound of Formula (IV) and pharmaceutically acceptable salts, N-oxides, or solvates thereof,

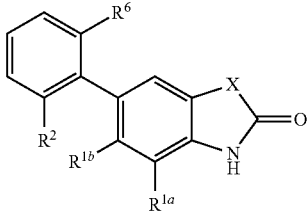

(IV)

wherein
R² is selected from the group consisting of: halo; C₁₋₅alkyl; C₁₋₅alkenyl; C₁₋₅haloalkyl; —(C=O)H; —CO₂C₁₋₅alkyl; —CN; —CH₂CN; —CH(CH₃)CN; —C(CH₃)₂CN; —OCH₂CN; phenyl; phenyl substituted with halo, C₁₋₅alkoxy, or —CN; —O-phenyl; benzyl; benzyl substituted with halo; —O-benzyl; C₃₋₆cycloalkyl; —C₃₋₆cycloalkyl substituted with CN; —OC₃₋₆cycloalkyl; —O-thiazolyl; pyrimidyl; pyridyl; pyridyl substituted with halo, C₁₋₅alkoxy, or C₁₋₅haloalkyl; —NH—CH₂-furyl; —CH₂morpholine; CH₂— piperazine optionally substituted with —CH₃; pyrazole substituted with —CH₂CH₂OCH₃, or C₁₋₅alkyl; isoxazole substituted with two alkyl; —O—CH₂—C₃₋₆cycloalkyl optionally substituted with halo; piperazine substituted with —CO₂tBu; and —O-azetidine substituted with —CO₂tBu; and
R⁶ is H, halo, C₁₋₅alkyl, —CH₂CN, or C₁₋₅haloalkyl.

An additional embodiment of the invention is a compound of Formula (IV) wherein
R² is C₁₋₅alkoxy or C₁₋₅haloalkoxy;
R⁶ is H, halo, C₁₋₅alkyl, —CH₂CN, C₁₋₅alkoxy, C₁₋₅haloalkyl, or C₁₋₅haloalkoxy;
and R¹ᵃ and R¹ᵇ are as defined above in Formula (I).

An additional embodiment of the invention is a compound of Formula (IV), and pharmaceutically acceptable salts, N-oxides, or solvates thereof,

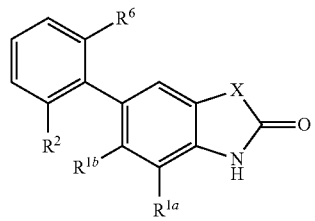

(IV)

wherein
R² is C₁₋₅alkoxy or C₁₋₅haloalkoxy; and
R⁶ is H, halo, C₁₋₅alkyl, —CH₂CN, C₁₋₅alkoxy, C₁₋₅haloalkyl, or C₁₋₅haloalkoxy.

An additional embodiment of the invention is a compound of Formula (IV) wherein R¹ᵇ is ³H.

An additional embodiment of the invention is a compound of Formula (V), and pharmaceutically acceptable salts, N-oxides, or solvates thereof,

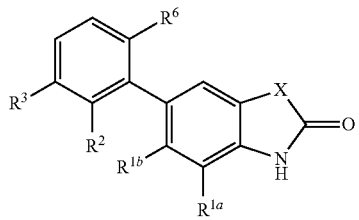

(V)

R² is selected from the group consisting of: halo; C₁₋₅alkyl; C₁₋₅alkenyl; C₁₋₅haloalkyl; —(C=O)H; —CH₂C(=O)NH(CH₃); —CO₂C₁₋₅alkyl; —CN; —CH₂CN; —CH(CH₃)CN; —C(CH₃)₂CN; —OCH₂CN; phenyl; phenyl substituted with halo, C₁₋₅alkoxy, or —CN; —O-phenyl; benzyl; benzyl substituted with halo; —O-benzyl; C₃₋₆cycloalkyl; —OC₃₋₆cycloalkyl; —O-thiazolyl; pyrimidinyl; pyridyl; pyridyl substituted with halo, C₁₋₅alkoxy, or C₁₋₅haloalkyl; —NH—CH₂-furyl; —C₃₋₆cycloalkyl substituted with CN; —CH₂morpholine; CH₂—N-methyl-piperazine; pyrazolyl; pyrazole substituted with —CH₂CH₂OCH₃, or C₁₋₅alkyl; isoxazole substituted with two alkyl; —O—CH₂—C₃₋₆cycloalkyl optionally substituted with halo; piperazine substituted with —CO₂tBu; and —O-azetidine substituted with —CO₂tBu;
R³ is selected from the group consisting of: H; halo; C₁₋₅alkyl; C₁₋₅haloalkyl; C₁₋₅alkoxy; C₁₋₅haloalkoxy; —CN; —CH₂CN; CO₂C₁₋₅alkyl; —N(CH₃)₂; —(C=O)N(C₁₋₅alkyl)₂; —(C=O)NH-cyclopropyl; —(C=O)NH-phenyl; —(C=O)morpholine; —O-cyclopropyl; —O—CH₂-cyclopropyl substituted with halo; —O-azetidinyl substituted with —CO₂tBu; CH₂-pyrrolidine; —CH₂-pyrrolidine substituted with halo and —OH; piperidine; piperidine substituted with —OCH₃; —CH₂-piperidine; —CH₂-piperidine substituted with —OH and halo; —CH₂-morpholine; CH₂-morpholine substituted with one or two C₁₋₅alkyl or C₁₋₅haloalkyl; CH₂-thiomorpholine; CH₂-piperazine substituted with —CO₂tBu; CH₂-azetidine substituted with halo; —CH₂-6-oxa-3- azabicyclo[3.1.1]heptan-3-yl; pyrazole substituted with $C_{1-5}$alkyl; pyridyl; 3,6-dihydro-2H-pyridine substituted with —$CO_2$tBu; imidazole; and oxadiazole substituted with $C_{1-5}$alkyl, cyclopropyl, pyridiyl, or $CF_3$;

$R^6$ is H, halo, $C_{1-5}$alkyl, —$CH_2CN$, or $C_{1-5}$haloalkyl; and $R^{1a}$ and $R^{1b}$ are as defined above in Formula (I).

An additional embodiment of the invention is a compound of Formula (V) wherein $R^2$ is halo, —CN, —$CH_2$—CN, $C_{1-5}$alkyl, or $C_{1-5}$haloalkyl.

An additional embodiment of the invention is a compound of Formula (V) wherein $R^2$ is halo or $C_{1-5}$haloalkoxy.

An additional embodiment of the invention is a compound of Formula (IA), and pharmaceutically acceptable salts, N-oxides, or solvates thereof,

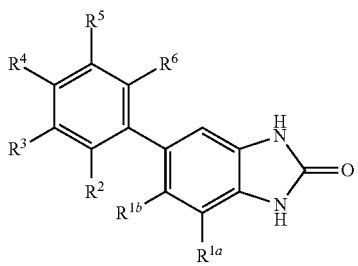

(1A)

wherein
$R^{1a}$ is H or F;
$R^{1b}$ is H;
$R^2$ is halo or $C_{1-5}$haloalkoxy;
$R^3$ is —CN, or oxadizolyl optionally substituted with $C_{1-5}$haloalkyl;
$R^4$ is H;
$R^5$ is H or halo; and
$R^6$ is halo, $C_{1-5}$haloalkoxy, cyclopropyl, —$C(CH_3)_2CN$, or —O—$CH_2$-cyclopropyl.

An additional embodiment of the invention is a compound of Formula (IB), and pharmaceutically acceptable salts, N-oxides, or solvates thereof,

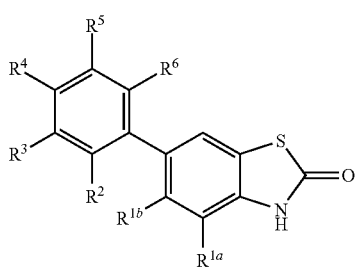

(1B)

wherein
$R^{1a}$ is H or F;
$R^{1b}$ is H;
$R^2$ is halo or $C_{1-5}$haloalkoxy;
$R^3$ is CN, or oxadizolyl optionally substituted with $C_{1-5}$haloalkyl;
$R^4$ is H;
$R^5$ is H or halo; and
$R^6$ is halo, $C_{1-5}$haloalkoxy, cyclopropyl, $C(CH_3)_2CN$, or —O—$CH_2$-cyclopropyl.

An additional embodiment of the invention is a compound of Formula (I) wherein the compound is selected from the group consisting of:

5-(8-quinolyl)-1,3-dihydrobenzimidazol-2-one;

5-(3,5-dichloro-4-pyridyl)-1,3-dihydrobenzimidazol-2-one;

5-(2-chloro-4-methyl-3-pyridyl)-1,3-dihydrobenzimidazol-2-one; and 6-(3,5-dichloro-4-pyridyl)-3H-1,3-benzothiazol-2-one;

and pharmaceutically acceptable salts, N-oxides, or solvates thereof.

An additional embodiment of the invention is a compound selected from the group consisting of compounds of Formula (II), Formula (III), Formula (IV), Formula (V), Formula (IA), and Formula (IB), or a combination thereof.

An additional embodiment of the invention is a compound of Formula (I) wherein the compound is: 6-[2-Chloro-6-(trifluoromethoxy)phenyl]-3H-1,3-benzothiazol-2-one; and pharmaceutically acceptable salts, N-oxides or solvates thereof.

An additional embodiment of the invention is a compound of Formula (I) wherein the compound is: 6-[2-Chloro-6-(trifluoromethoxy)phenyl]-4-methyl-1,3-dihydrobenzimidazol-2-one; and pharmaceutically acceptable salts, N-oxides or solvates thereof.

An additional embodiment of the invention is a compound of Formula (I) wherein the compound is: 5-[2-Chloro-6-(trifluoromethoxy)phenyl]-1,3-dihydrobenzimidazol-2-one; and pharmaceutically acceptable salts, N-oxides or solvates thereof.

An additional embodiment of the invention is a compound of Formula (I) wherein the compound is: 5-(2-Chloro-6-cyclopropyl-phenyl)-1,3-dihydrobenzimidazol-2-one; and pharmaceutically acceptable salts, N-oxides or solvates thereof.

An additional embodiment of the invention is a compound of Formula (I) wherein the compound is: 2-[3-Chloro-2-(2-oxo-1,3-dihydrobenzimidazol-5-yl)phenyl]acetonitrile; and pharmaceutically acceptable salts, N-oxides or solvates thereof.

An additional embodiment of the invention is a compound of Formula (I) wherein the compound is: 5-[2-Chloro-3-(1-piperidyl)phenyl]-1,3-dihydrobenzimidazol-2-one; and pharmaceutically acceptable salts, N-oxides or solvates thereof.

An additional embodiment of the invention is a compound of Formula (I) wherein the compound is: 5-[2-Chloro-6-(cyclopropylmethoxy)phenyl]-1,3-dihydrobenzimidazol-2-one; and pharmaceutically acceptable salts, N-oxides or solvates thereof.

An additional embodiment of the invention is a compound of Formula (I) wherein the compound is: 5-[2-Isopropoxy-6-(trifluoromethoxy)phenyl]-1,3-dihydrobenzimidazol-2-one; and pharmaceutically acceptable salts, N-oxides or solvates thereof.

An additional embodiment of the invention is a compound of Formula (I) wherein the compound is: 5-(2,3,6-Trichlorophenyl)-1,3-dihydrobenzimidazol-2-one; and pharmaceutically acceptable salts, N-oxides or solvates thereof.

A further embodiment of the current invention is a compound as shown below in Table 1.

| Example # | Compound Name |
|---|---|
| 1 | 5-(2,3-Dimethylphenyl)-1,3-dihydrobenzimidazol-2-one; |
| 2 | 5-(2,6-Dimethylphenyl)-1,3-dihydrobenzimidazol-2-one; |
| 3 | 5-(o-Tolyl)-1,3-dihydrobenzimidazol-2-one; |
| 4 | 5-[2-(Trifluoromethyl)phenyl]-1,3-dihydrobenzimidazol-2-one; |
| 5 | 5-(2-Phenylphenyl)-1,3-dihydrobenzimidazol-2-one; |
| 6 | 5-(2-Isopropylphenyl)-1,3-dihydrobenzimidazol-2-one; |
| 7 | 5-(2,6-Dimethoxyphenyl)-1,3-dihydrobenzimidazol-2-one; |
| 8 | 5-(2-Isopropoxyphenyl)-1,3-dihydrobenzimidazol-2-one; |
| 9 | tert-Butyl 4-[2-(2-oxo-1,3-dihydrobenzimidazol-5-yl)phenyl]piperazine-1-carboxylate; |
| 10 | 5-(5-Chloro-2-methyl-phenyl)-1,3-dihydrobenzimidazol-2-one; |
| 11 | 5-(2-Fluoro-6-isopropoxy-phenyl)-1,3-dihydrobenzimidazol-2-one; |
| 12 | 5-[2-Chloro-6-(trifluoromethyl)phenyl]-1,3-dihydrobenzimidazol-2-one; |
| 13 | 5-[2-(Cyclopropylmethoxy)phenyl]-1,3-dihydrobenzimidazol-2-one; |
| 14 | 5-(2-Isobutoxy-6-methoxy-phenyl)-1,3-dihydrobenzimidazol-2-one; |
| 15 | 5-(2-Isobutoxy-5-methyl-phenyl)-1,3-dihydrobenzimidazol-2-one; |
| 16 | 5-(5-Chloro-2-isopropoxy-phenyl)-1,3-dihydrobenzimidazol-2-one; |
| 17 | 5-(2-Chlorophenyl)-1,3-dihydrobenzimidazol-2-one; |
| 18 | 5-(2,5-Dichlorophenyl)-1,3-dihydrobenzimidazol-2-one; |
| 19 | 5-(2-Chloro-5-methyl-phenyl)-1,3-dihydrobenzimidazol-2-one; |
| 20 | 5-(2-Chloro-6-methoxy-phenyl)-1,3-dihydrobenzimidazol-2-one; |
| 21 | 5-(2,5-Dimethylphenyl)-1,3-dihydrobenzimidazol-2-one; |
| 22 | 5-[2-Isopropoxy-5-(trifluoromethyl)phenyl]-1,3-dihydrobenzimidazol-2-one; |
| 23 | 5-(2,6-Dichloro-3-methyl-phenyl)-1,3-dihydrobenzimidazol-2-one; |
| 24 | 5-(2-Phenoxyphenyl)-1,3-dihydrobenzimidazol-2-one; |
| 25 | 5-[2-Chloro-5-(trifluoromethyl)phenyl]-1,3-dihydrobenzimidazol-2-one; |
| 26 | 5-(2-Benzyloxy-6-fluoro-phenyl)-1,3-dihydrobenzimidazol-2-one; |
| 27 | 3-Fluoro-2-(2-oxo-1,3-dihydrobenzimidazol-5-yl)benzaldehyde; |
| 28 | 5-(2-Isopropoxy-6-methoxy-phenyl)-1,3-dihydrobenzimidazol-2-one; |
| 29 | 5-[3-Chloro-2-(trifluoromethoxy)phenyl]-1,3-dihydrobenzimidazol-2-one; |
| 30 | 5-[2-Chloro-4-(trifluoromethoxy)phenyl]-1,3-dihydrobenzimidazol-2-one; |
| 31 | 5-[2-Chloro-6-(trifluoromethoxy)phenyl]-1,3-dihydrobenzimidazol-2-one; |
| 32 | 5-[2-Chloro-6-(trifluoromethoxy)phenyl]-6-tritio-1,3-dihydrobenzimidazol-2-one; |
| 33 | 5-[2-Methoxy-4-(trifluoromethoxy)phenyl]-1,3-dihydrobenzimidazol-2-one; |
| 34 | 5-[3-Chloro-2-(trifluoromethyl)phenyl]-1,3-dihydrobenzimidazol-2-one; |
| 35 | 5-(2-Bromophenyl)-1,3-dihydrobenzimidazol-2-one; |
| 36 | 5-(2-Chloro-6-methyl-phenyl)-1,3-dihydrobenzimidazol-2-one; |
| 37 | 5-(4-Chloro-2,6-dimethyl-phenyl)-1,3-dihydrobenzimidazol-2-one; |
| 38 | 3-Methyl-2-(2-oxo-1,3-dihydrobenzimidazol-5-yl)benzonitrile; |
| 39 | 4-Methyl-3-(2-oxo-1,3-dihydrobenzimidazol-5-yl)benzonitrile; |
| 40 | 4-Chloro-3-(2-oxo-1,3-dihydrobenzimidazol-5-yl)benzonitrile; |
| 41 | 2-[2-(2-Oxo-1,3-dihydrobenzimidazol-5-yl)phenyl]acetonitrile; |
| 42 | Methyl 3-chloro-2-(2-oxo-1,3-dihydrobenzimidazol-5-yl)benzoate; |
| 43 | Methyl 2-chloro-3-(2-oxo-1,3-dihydrobenzimidazol-5-yl)benzoate; |
| 44 | Methyl 4-chloro-3-(2-oxo-1,3-dihydrobenzimidazol-5-yl)benzoate; |
| 45 | Methyl 3-methyl-2-(2-oxo-1,3-dihydrobenzimidazol-5-yl)benzoate; |
| 46 | Methyl 2-methyl-3-(2-oxo-1,3-dihydrobenzimidazol-5-yl)benzoate; |
| 47 | Methyl 4-methyl-3-(2-oxo-1,3-dihydrobenzimidazol-5-yl)benzoate; |
| 48 | Methyl 2-methoxy-3-(2-oxo-1,3-dihydrobenzimidazol-5-yl)benzoate; |
| 49 | 5-(2,6-Dichlorophenyl)-1,3-dihydrobenzimidazol-2-one; |
| 50 | 5-(2,6-Dichloro-4-fluoro-phenyl)-1,3-dihydrobenzimidazol-2-one; |
| 51 | 5-(2,4,6-Trichlorophenyl)-1,3-dihydrobenzimidazol-2-one; |
| 52 | 5-(2,6-Difluorophenyl)-1,3-dihydrobenzimidazol-2-one; |
| 53 | 5-(2-Chloro-6-fluoro-phenyl)-1,3-dihydrobenzimidazol-2-one; |
| 54 | 5-(2-Fluoro-6-methyl-phenyl)-1,3-dihydrobenzimidazol-2-one; |
| 55 | 5-(2-Fluoro-6-methoxy-phenyl)-1,3-dihydrobenzimidazol-2-one; |
| 56 | 3-Chloro-2-(2-oxo-1,3-dihydrobenzimidazol-5-yl)benzonitrile; |
| 57 | 5-[2-Methyl-6-(trifluoromethyl)phenyl]-1,3-dihydrobenzimidazol-2-one; |
| 58 | 5-(8-Quinolyl)-1,3-dihydrobenzimidazol-2-one; |
| 59 | 5-(2-Benzylphenyl)-1,3-dihydrobenzimidazol-2-one; |
| 60 | 5-[2-Methyl-3-(trifluoromethyl)phenyl]-1,3-dihydrobenzimidazol-2-one; |
| 61 | 5-[2-Chloro-3-(trifluoromethyl)phenyl]-1,3-dihydrobenzimidazol-2-one; |
| 62 | 2-Isopropoxy-6-(2-oxo-1,3-dihydrobenzimidazol-5-yl)benzonitrile; |
| 63 | 2-Bromo-6-(2-oxo-1,3-dihydrobenzimidazol-5-yl)benzonitrile; |
| 64 | 5-(2-Chloro-3-methyl-phenyl)-1,3-dihydrobenzimidazol-2-one; |
| 65 | 2-(2-Oxo-1,3-dihydrobenzimidazol-5-yl)-6-(trifluoromethyl)benzonitrile; |
| 66 | 5-(2,3,6-Trichlorophenyl)-1,3-dihydrobenzimidazol-2-one; |
| 67 | 2-Methyl-3-(2-oxo-1,3-dihydrobenzimidazol-5-yl)benzonitrile; |
| 68 | 2-Chloro-3-(2-oxo-1,3-dihydrobenzimidazol-5-yl)benzonitrile; |
| 69 | 5-(3,5-Dichloro-4-pyridyl)-1,3-dihydrobenzimidazol-2-one; |
| 70 | 5-(2-Chloro-4-methyl-3-pyridyl)-1,3-dihydrobenzimidazol-2-one; |
| 71 | 5-[2-Methyl-3-(5-methyl-1,2,4-oxadiazol-3-yl)phenyl]-1,3-dihydrobenzimidazol-2-one; |
| 72 | 6-[2-Methyl-3-(5-methyl-1,2,4-oxadiazol-3-yl)phenyl]-3H-1,3-benzothiazol-2-one; |
| 73 | 5-[3-(5-Cyclopropyl-1,2,4-oxadiazol-3-yl)-2-methyl-phenyl]-1,3-dihydrobenzimidazol-2-one; |
| 74 | 6-[3-(5-Cyclopropyl-1,2,4-oxadiazol-3-yl)-2-methyl-phenyl]-3H-1,3-benzothiazol-2-one; |
| 75 | 5-[2-Methyl-3-[5-(4-pyridyl)-1,2,4-oxadiazol-3-yl]phenyl]-1,3-dihydrobenzimidazol-2-one; |
| 76 | 6-[2-Chloro-6-(trifluoromethoxy)phenyl]-3H-1,3-benzothiazol-2-one; |
| 77 | 6-(2-Isopropoxy-6-methoxy-phenyl)-3H-1,3-benzothiazol-2-one; |
| 78 | N-Methyl-2-[2-(2-oxo-1,3-dihydrobenzimidazol-5-yl)-6-(trifluoromethyl)phenyl]acetamide; |
| 79 | 2-Methyl-3-(2-oxo-1,3-dihydrobenzimidazol-5-yl)-N-phenyl-benzamide; |

-continued

| Example # | Compound Name |
|---|---|
| 80 | N-Cyclopropyl-2-methyl-3-(2-oxo-1,3-dihydrobenzimidazol-5-yl)benzamide; |
| 81 | N,N,2-Trimethyl-3-(2-oxo-1,3-dihydrobenzimidazol-5-yl)benzamide; |
| 82 | 5-[2-Methyl-3-(morpholine-4-carbonyl)phenyl]-1,3-dihydrobenzimidazol-2-one; |
| 83 | 4-Chloro-3-(2-oxo-1,3-dihydrobenzimidazol-5-yl)-N-phenyl-benzamide; |
| 84 | 5-[2-Chloro-5-(pyrrolidine-1-carbonyl)phenyl]-1,3-dihydrobenzimidazol-2-one; |
| 85 | 5-[2-Chloro-5-(piperidine-1-carbonyl)phenyl]-1,3-dihydrobenzimidazol-2-one; |
| 86 | 5-[2-Chloro-6-(2-furylmethylamino)phenyl]-1,3-dihydrobenzimidazol-2-one; |
| 87 | 5-[2-Chloro-6-(3-furylmethylamino)phenyl]-1,3-dihydrobenzimidazol-2-one; |
| 88 | 5-[2-Isopropoxy-6-(trifluoromethoxy)phenyl]-1,3-dihydrobenzimidazol-2-one; |
| 89 | 5-[2-(Cyclopropylmethoxy)-6-(trifluoromethoxy)phenyl]-1,3-dihydrobenzimidazol-2-one; |
| 90 | 5-[2-Chloro-6-(cyclopropoxy)phenyl]-1,3-dihydrobenzimidazol-2-one; |
| 91 | 5-(2-Chloro-6-isopropoxy-phenyl)-1,3-dihydrobenzimidazol-2-one; |
| 92 | 5-[2-Chloro-6-(cyclopropylmethoxy)phenyl]-1,3-dihydrobenzimidazol-2-one; |
| 93 | (±)-5-[2-Chloro-6-[(2,2-difluorocyclopropyl)methoxy]phenyl]-1,3-dihydrobenzimidazol-2-one; |
| 94 | 5-[2-Chloro-6-(difluoromethoxy)phenyl]-1,3-dihydrobenzimidazol-2-one; |
| 95 | 5-[2-Chloro-6-(2,2,2-trifluoroethoxy)phenyl]-1,3-dihydrobenzimidazol-2-one; |
| 96 | 5-[2-Chloro-6-(2,2-difluoroethoxy)phenyl]-1,3-dihydrobenzimidazol-2-one; |
| 97 | 2-[3-Chloro-2-(2-oxo-1,3-dihydrobenzimidazol-5-yl)phenoxy]acetonitrile; |
| 98 | 5-[2-Chloro-6-(2,2-dimethylpropoxy)phenyl]-1,3-dihydrobenzimidazol-2-one; |
| 99 | 5-(2-Benzyloxy-6-chloro-phenyl)-1,3-dihydrobenzimidazol-2-one; |
| 100 | tert-Butyl 3-[3-chloro-2-(2-oxo-1,3-dihydrobenzimidazol-5-yl)phenoxy]azetidine-1-carboxylate; |
| 101 | 5-(2-Chloro-6-thiazol-5-yloxy-phenyl)-1,3-dihydrobenzimidazol-2-one; |
| 102 | 5-[2-(2,2-Difluoroethoxy)-6-methoxy-phenyl]-1,3-dihydrobenzimidazol-2-one; |
| 103 | 5-[2-Methoxy-6-(2,2,2-trifluoroethoxy)phenyl]-1,3-dihydrobenzimidazol-2-one; |
| 104 | 5-[2-(2,2-Dimethylpropoxy)-6-methoxy-phenyl]-1,3-dihydrobenzimidazol-2-one; |
| 105 | 5-(2-Benzyloxy-6-methoxy-phenyl)-1,3-dihydrobenzimidazol-2-one; |
| 106 | 5-[2-[(4-Fluorophenyl)ethoxy]-6-methoxy-phenyl]-1,3-dihydrobenzimidazol-2-one; |
| 107 | 5-(2,6-Diisopropoxyphenyl)-1,3-dihydrobenzimidazol-2-one; |
| 108 | 5-[2-Isopropoxy-6-(trifluoromethyl)phenyl]-1,3-dihydrobenzimidazol-2-one; |
| 109 | 5-[2-Chloro-3-(cyclopropoxy)phenyl]-1,3-dihydrobenzimidazol-2-one; |
| 110 | 5-(2-Chloro-3-isopropoxy-phenyl)-1,3-dihydrobenzimidazol-2-one; |
| 111 | (±)-5-[2-Chloro-3-[(2,2-difluorocyclopropyl)methoxy]phenyl]-1,3-dihydrobenzimidazol-2-one; |
| 112 | 5-[2-Chloro-3-(2,2-difluoroethoxy)phenyl]-1,3-dihydrobenzimidazol-2-one; |
| 113 | 5-[2-Chloro-3-(difluoromethoxy)phenyl]-1,3-dihydrobenzimidazol-2-one; |
| 114 | tert-Butyl 3-[2-chloro-3-(2-oxo-1,3-dihydrobenzimidazol-5-yl)phenoxy]azetidine-1-carboxylate; |
| 115 | 5-(3-Chloro-2-isopropoxy-phenyl)-1,3-dihydrobenzimidazol-2-one; |
| 116 | 5-(2-tert-Butoxy-6-chloro-phenyl)-1,3-dihydrobenzimidazol-2-one; |
| 117 | 5-(2-tert-Butoxy-6-methoxy-phenyl)-1,3-dihydrobenzimidazol-2-one; |
| 118 | (±)-5-[2-Chloro-6-(2,2,2-trifluoro-1-methyl-ethoxy)phenyl]-1,3-dihydrobenzimidazol-2-one; |
| 119 | (R*)-5-[2-Chloro-6-(2,2,2-trifluoro-1-methyl-ethoxy)phenyl]-1,3-dihydrobenzimidazol-2-one; |
| 120 | (S*)-5-[2-Chloro-6-(2,2,2-trifluoro-1-methyl-ethoxy)phenyl]-1,3-dihydrobenzimidazol-2-one; |
| 121 | (±)-5-[2-Methoxy-6-(2,2,2-trifluoro-1-methyl-ethoxy)phenyl]-1,3-dihydrobenzimidazol-2-one; |
| 122 | 2-[3,4-Dichloro-2-(2-oxo-1,3-dihydrobenzimidazol-5-yl)phenyl]acetonitrile; |
| 123 | 2-[2-(2-Oxo-1,3-dihydrobenzimidazol-5-yl)-3-trifluoromethoxy)phenyl]acetonitrile; |
| 124 | 2-[3-Chloro-2-(2-oxo-1,3-dihydrobenzimidazol-5-yl)phenyl]acetonitrile; |
| 125 | 2-[3-Chloro-2-(2-oxo-6-tritio-1,3-dihydrobenzimidazol-5-yl)phenyl]acetonitrile; |
| 126 | (±)-2-[3-Chloro-2-(2-oxo-1,3-dihydrobenzimidazol-5-yl)phenyl]propanenitrile; |
| 127 | 2-[3-Chloro-2-(2-oxo-1,3-dihydrobenzimidazol-5-yl)phenyl]-2-methyl-propanenitrile; |
| 128 | 1-[3-Chloro-2-(2-oxo-1,3-dihydrobenzimidazol-5-yl)phenyl]cyclopropanecarbonitrile; |
| 129 | 1-[3-Chloro-2-(2-oxo-1,3-dihydrobenzimidazol-5-yl)phenyl]cyclobutanecarbonitrile; |
| 130 | 2-[2-Chloro-3-(2-oxo-1,3-dihydrobenzimidazol-5-yl)phenyl]acetonitrile; |
| 131 | 2-[2,4-Dichloro-3-(2-oxo-1,3-dihydrobenzimidazol-5-yl)phenyl]acetonitrile; |
| 132 | 2-[3-Bromo-2-(2-oxo-1,3-dihydrobenzimidazol-5-yl)phenyl]acetonitrile; |
| 133 | 2-[3-Chloro-2-(2-oxo-3H-1,3-benzothiazol-6-yl)phenyl]acetonitrile; |
| 134 | 6-(3,5-Dichloro-4-pyridyl)-3H-1,3-benzothiazol-2-one; |
| 135 | 2-[3-(4-Fluorophenyl)-2-(2-oxo-1,3-dihydrobenzimidazol-5-yl)phenyl]acetonitrile; |
| 136 | 2-[3-(2-Fluorophenyl)-2-(2-oxo-1,3-dihydrobenzimidazol-5-yl)phenyl]acetonitrile; |
| 137 | 2-[3-(4-Methoxyphenyl)-2-(2-oxo-1,3-dihydrobenzimidazol-5-yl)phenyl]acetonitrile; |
| 138 | 2-[3-Cyclopropyl-2-(2-oxo-1,3-dihydrobenzimidazol-5-yl)phenyl]acetonitrile; |
| 139 | 5-[2,6-Dichloro-3-(morpholinomethyl)phenyl]-1,3-dihydrobenzimidazol-2-one; |
| 140 | 5-[2,6-Dichloro-3-(1-piperidylmethyl)phenyl]-1,3-dihydrobenzimidazol-2-one; |
| 141 | 5-[2-Chloro-3-(morpholinomethyl)phenyl]-1,3-dihydrobenzimidazol-2-one; |

| Example # | Compound Name |
|---|---|
| 142 | 5-[2-Chloro-3-(1-piperidylmethyl)phenyl]-1,3-dihydrobenzimidazol-2-one; |
| 143 | 5-[2-Chloro-3-[(2,2-dimethylmorpholin-4-yl)methyl]phenyl]-1,3-dihydrobenzimidazol-2-one; |
| 144 | (±)-5-[2-Chloro-3-[[2-(trifluoromethyl)morpholin-4-yl]methyl]phenyl]-1,3-dihydrobenzimidazol-2-one; |
| 145 | 5-[2-Chloro-6-(morpholinomethyl)phenyl]-1,3-dihydrobenzimidazol-2-one; |
| 146 | 5-[2-Chloro-6-[(4-methylpiperazin-1-yl)methyl]phenyl]-1,3-dihydrobenzimidazol-2-one; |
| 147 | 5-[2-Methyl-3-(1-piperidylmethyl)phenyl]-1,3-dihydrobenzimidazol-2-one; |
| 148 | 5-[2-Methyl-3-(morpholinomethyl)phenyl]-1,3-dihydrobenzimidazol-2-one; |
| 149 | 5-[3-[(2,2-Dimethylmorpholin-4-yl)methyl]-2-methyl-phenyl]-1,3-dihydrobenzimidazol-2-one; |
| 150 | (±)-5-[2-Methyl-3-[(2-methylmorpholin-4-yl)methyl]phenyl]-1,3-dihydrobenzimidazol-2-one; |
| 151 | (±)-5-[2-Methyl-3-[[2-(trifluoromethyl)morpholin-4-yl]methyl]phenyl]-1,3-dihydrobenzimidazol-2-one; |
| 152 | (3R)-5-[2-Methyl-3-[[3-methylmorpholin-4-yl]methyl]phenyl]-1,3-dihydrobenzimidazol-2-one; |
| 153 | (3S)-5-[2-Methyl-3-[[3-methylmorpholin-4-yl]methyl]phenyl]-1,3-dihydrobenzimidazol-2-one; |
| 154 | 5-[2-Methyl-3-(thiomorpholinomethyl)phenyl]-1,3-dihydrobenzimidazol-2-one; |
| 155 | tert-Butyl 4-[[2-methyl-3-(2-oxo-1,3-dihydrobenzimidazol-5-yl)phenyl]methyl]piperazine-1-carboxylate; |
| 156 | 5-[2-Methyl-3-(pyrrolidin-1-ylmethyl)phenyl]-1,3-dihydrobenzimidazol-2-one; |
| 157 | 5-[3-[(3-Fluoroazetidin-1-yl)methyl]-2-methyl-phenyl]-1,3-dihydrobenzimidazol-2-one; |
| 158 | 5-[2-Methyl-3-(6-oxa-3-azabicyclo[3;1;1]heptan-3-ylmethyl)phenyl]-1,3-dihydrobenzimidazol-2-one; |
| 159 | (3R,4S)-5-[3-[[3-Fluoro-4-hydroxy-1-piperidyl]methyl]-2-methyl-phenyl]-1,3-dihydrobenzimidazol-2-one; |
| 160 | 5-(2-Chloro-6-cyclopropyl-phenyl)-1,3-dihydrobenzimidazol-2-one; |
| 161 | 5-(2-Chloro-6-vinyl-phenyl)-1,3-dihydrobenzimidazol-2-one; |
| 162 | 5-(2-Chloro-6-phenyl-phenyl)-1,3-dihydrobenzimidazol-2-one; |
| 163 | 5-[2-Chloro-6-(4-fluorophenyl)phenyl]-1,3-dihydrobenzimidazol-2-one; |
| 164 | 4-[3-Chloro-2-(2-oxo-1,3-dihydrobenzimidazol-5-yl)phenyl]benzonitrile; |
| 165 | 5-[2-Chloro-6-(3-pyridyl)phenyl]-1,3-dihydrobenzimidazol-2-one; |
| 166 | 5-[2-Chloro-6-(5-fluoro-3-pyridyl)phenyl]-1,3-dihydrobenzimidazol-2-one; |
| 167 | 5-[2-Chloro-6-(6-fluoro-3-pyridyl)phenyl]-1,3-dihydrobenzimidazol-2-one; |
| 168 | 5-[2-Chloro-6-(5-methoxy-3-pyridyl)phenyl]-1,3-dihydrobenzimidazol-2-one; |
| 169 | 5-[2-Chloro-6-[5-(trifluoromethyl)-3-pyridyl]phenyl]-1,3-dihydrobenzimidazol-2-one; |
| 170 | 5-[2-Chloro-6-(4-pyridyl)phenyl]-1,3-dihydrobenzimidazol-2-one; |
| 171 | 5-[2-Chloro-6-(3-methoxy-4-pyridyl)phenyl]-1,3-dihydrobenzimidazol-2-one; |
| 172 | 5-[2-Chloro-6-[1-(2-methoxyethyl)pyrazol-4-yl]phenyl]-1,3-dihydrobenzimidazol-2-one; |
| 173 | 5-[2-Chloro-6-(1-methylpyrazol-4-yl)phenyl]-1,3-dihydrobenzimidazol-2-one; |
| 174 | 5-[2-Chloro-6-(3,5-dimethylisoxazol-4-yl)phenyl]-1,3-dihydrobenzimidazol-2-one; |
| 175 | 5-[2-Chloro-6-(2-isopropylpyrazol-3-yl)phenyl]-1,3-dihydrobenzimidazol-2-one; |
| 176 | 5-[2-Chloro-6-(1H-pyrazol-4-yl)phenyl]-1,3-dihydrobenzimidazol-2-one; |
| 177 | 5-[2-Chloro-6-(1,5-dimethylpyrazol-4-yl)phenyl]-1,3-dihydrobenzimidazol-2-one; |
| 178 | 5-(2-Chloro-6-pyrimidin-5-yl-phenyl)-1,3-dihydrobenzimidazol-2-one; |
| 179 | 5-(2-Methyl-6-phenyl-phenyl)-1,3-dihydrobenzimidazol-2-one; |
| 180 | 5-[2-(2-Fluorophenyl)-6-methyl-phenyl]-1,3-dihydrobenzimidazol-2-one; |
| 181 | 5-[2-(4-Fluorophenyl)-6-methyl-phenyl]-1,3-dihydrobenzimidazol-2-one; |
| 182 | 5-[2-Methoxy-6-(8-quinolyl)phenyl]-1,3-dihydrobenzimidazol-2-one; |
| 183 | 5-[2-Chloro-3-(1-methylpyrazol-3-yl)phenyl]-1,3-dihydrobenzimidazol-2-one; |
| 184 | 5-[2-Chloro-3-(4-pyridyl)phenyl]-1,3-dihydrobenzimidazol-2-one; |
| 185 | 5-[2-Chloro-3-(1-methylpyrazol-4-yl)phenyl]-1,3-dihydrobenzimidazol-2-one; |
| 186 | tert-Butyl 5-[2-chloro-3-(2-oxo-1,3-dihydrobenzimidazol-5-yl)phenyl]-3,6-dihydro-2H-pyridine-1-carboxylate; |
| 187 | 5-(2-Chloro-3-imidazol-1-yl-phenyl)-1,3-dihydrobenzimidazol-2-one; |
| 188 | 5-[2-Chloro-3-(1-piperidyl)phenyl]-1,3-dihydrobenzimidazol-2-one; |
| 189 | 5-[2-Chloro-3-(dimethylamino)phenyl]-1,3-dihydrobenzimidazol-2-one; |
| 190 | 5-[2-Chloro-3-(1,3,4-oxadiazol-2-yl)phenyl]-1,3-dihydrobenzimidazol-2-one; |
| 191 | 5-[2-Chloro-3-(5-methyl-1,3,4-oxadiazol-2-yl)phenyl]-1,3-dihydrobenzimidazol-2-one; |
| 192 | 5-[2,6-Dichloro-3-(1,3,4-oxadiazol-2-yl)phenyl]-1,3-dihydrobenzimidazol-2-one; |
| 193 | 5-[2-Bromo-3-(1,3,4-oxadiazol-2-yl)phenyl]-1,3-dihydrobenzimidazol-2-one; |
| 194 | 5-[2-Methyl-3-(1,3,4-oxadiazol-2-yl)phenyl]-1,3-dihydrobenzimidazol-2-one; |
| 195 | 5-[2-Methyl-3-(5-methyl-1,3,4-oxadiazol-2-yl)phenyl]-1,3-dihydrobenzimidazol-2-one; |
| 196 | 5-[2-Chloro-3-(5-cyclopropyl-1,3,4-oxadiazol-2-yl)phenyl]-1,3-dihydrobenzimidazol-2-one; |
| 197 | 5-[3-(5-Cyclopropyl-1,3,4-oxadiazol-2-yl)-2-methyl-phenyl]-1,3-dihydrobenzimidazol-2-one; |
| 198 | 5-[2-Methyl-3-[5-(trifluoromethyl)-1,3,4-oxadiazol-2-yl]phenyl]-1,3-dihydrobenzimidazol-2-one; |

| Example # | Compound Name |
|---|---|
| 199 | 5-[2-Methyl-3-(1,2,4-oxadiazol-5-yl)phenyl]-1,3-dihydrobenzimidazol-2-one; |
| 200 | 6-[2-Methyl-3-(1,2,4-oxadiazol-5-yl)phenyl]-3H-1,3-benzothiazol-2-one; |
| 201 | 5-(3-(3-Cyclopropyl-1,2,4-oxadiazol-5-yl)-2-methylphenyl)-1H-benzo[d]imidazol-2(3H)-one; |
| 202 | 6-[3-(3-Cyclopropyl-1,2,4-oxadiazol-5-yl)-2-methyl-phenyl]-3H-1,3-benzothiazol-2-one; |
| 203 | 5-[2-Methyl-3-(3-methyl-1,2,4-oxadiazol-5-yl)phenyl]-1,3-dihydrobenzimidazol-2-one; |
| 204 | 6-[2-Methyl-3-(3-methyl-1,2,4-oxadiazol-5-yl)phenyl]-3H-1,3-benzothiazol-2-one; |
| 205 | 5-[2-Methyl-3-[3-(trifluoromethyl)-1,2,4-oxadiazol-5-yl]phenyl]-1,3-dihydrobenzimidazol-2-one; |
| 206 | 5-[2-Methyl-3-(1,2,4-oxadiazol-3-yl)phenyl]-1,3-dihydrobenzimidazol-2-one; |
| 207 | 6-[2-Methyl-3-(1,2,4-oxadiazol-3-yl)phenyl]-3H-1,3-benzothiazol-2-one; |
| 208 | 2-Chloro-3-(2-oxo-1,3-dihydrobenzimidazol-5-yl)-4-(trifluoromethoxy)benzonitrile; |
| 209 | 4-Chloro-3-(2-oxo-1,3-dihydrobenzimidazol-5-yl)-2-(trifluoromethoxy)benzonitrile; |
| 210 | 6-[2-Chloro-6-(trifluoromethoxy)phenyl]-5-fluoro-3H-1,3-benzothiazol-2-one; |
| 211 | 6-(2-Chloro-6-(trifluoromethoxy)phenyl)-4-methyl-1H-benzo[d]imidazol-2(3H)-one; |
| 212 | 6-(2-Chloro-3-(1-methyl-1H-pyrazol-4-yl)phenyl)benzo[d]thiazol-2(3H)-one; |
| 213 | 6-(2-Chloro-3-(4-methoxypiperidin-1-yl)phenyl)benzo[d]thiazol-2(3H)-one; |
| 214 | 6-(2-Chloro-6-(trifluoromethoxy)phenyl)-4-fluoro-1,3-dihydro-2H-benzo[d]imidazol-2-one; | and pharmaceutically acceptable salts, N-oxides, or solvates thereof.

A further embodiment of the current invention is a compound as shown below in Table 2.

| Example # | Compound Name |
|---|---|
| 215 | 4-Chloro-6-(2-chloro-6-(trifluoromethoxy)phenyl)-1,3-dihydro-2H-benzo[d]imidazol-2-one; |
| 216 | 6-(2-Chloro-6-(trifluoromethoxy)phenyl)-2-oxo-2,3-dihydro-1H-benzo[d]imidazole-4-carbonitrile; |
| 217 | 6-(2-chloro-6-(trifluoromethoxy)phenyl)-4-ethyl-1,3-dihydro-2H-benzo[d]imidazol-2-one; |
| 218 | 6-(2-chloro-6-(trifluoromethoxy)phenyl)-4-(trifluoromethyl)-1,3-dihydro-2H-benzo[d]imidazol-2-one; |
| 219 | 6-(2-chloro-6-(trifluoromethoxy)phenyl)-4-(trifluoromethoxy)-1,3-dihydro-2H-benzo[d]imidazol-2-one; and |
| 220 | 6-(2-chloro-6-(trifluoromethoxy)phenyl)-4-methoxy-1,3-dihydro-2H-benzo[d]imidazol-2-one; | and pharmaceutically acceptable salts, N-oxides, or solvates thereof.

An additional embodiment of the invention is a pharmaceutical composition comprising:

(A) an effective amount of at least one compound of Formula (I):

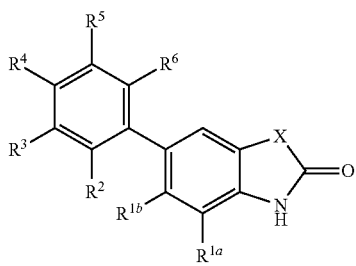

(I)

wherein

X is NH or S;

$R^{1a}$ and $R^{1b}$ are independently selected from the group consisting of H, $^3$H, halo, —CH$_3$, —CH$_2$CH$_3$, —CF$_3$, —OCH$_3$, —OCF$_3$, and —CN;

$R^2$ is selected from the group consisting of: halo; $C_{1-5}$ alkyl; $C_{1-5}$ alkenyl; $C_{1-5}$haloalkyl; $C_{1-5}$alkoxy; $C_{1-5}$haloalkoxy; —(C=O)H; —CH$_2$C(=O)NH(CH$_3$); —CO$_2$C$_{1-5}$ alkyl; —CN; —CH$_2$CN; —CH(CH$_3$)CN; —C(CH$_3$)$_2$CN; —OCH$_2$CN; phenyl; phenyl substituted with halo, $C_{1-5}$ alkoxy, or —CN; —O-phenyl; benzyl; benzyl substituted with halo; —O-benzyl; $C_{3-6}$ cycloalkyl; —OC$_{3-6}$ cycloalkyl; —O-thiazolyl; pyrimidinyl; pyridyl; pyridyl substituted with halo, $C_{1-5}$ alkoxy, or $C_{1-5}$haloalkyl; —NH—CH$_2$-furyl; —C$_{3-6}$ cycloalkyl substituted with CN; -CH$_2$morpholine; CH$_2$—N-methylpiperazine; pyrazolyl; pyrazole substituted with —CH$_2$CH$_2$OCH$_3$, or $C_{1-5}$ alkyl; isoxazole substituted with two $C_{1-5}$ alkyl; —O—CH$_2$—C$_{3-6}$ cycloalkyl optionally substituted with halo; piperazine substituted with —CO$_2$tBu; —O-azetidine substituted with —CO$_2$tBu; and 8-quinolyl;

$R^3$ is selected from the group consisting of: H; halo; $C_{1-5}$ alkyl; $C_{1-5}$haloalkyl; $C_{1-5}$alkoxy; $C_{1-5}$haloalkoxy; —CN; —CH$_2$CN; CO$_2$C$_{1-5}$ alkyl; —N(CH$_3$)$_2$; —(C=O)N(C$_{1-5}$alkyl)$_2$; —(C=O)NH-cyclopropyl; —(C=O)NH-phenyl; —(C=O)morpholine; —O-cyclopropyl; —O—CH$_2$-cyclopropyl substituted with halo; —O-azetidinyl substituted with —CO$_2$tBu; CH$_2$-pyrrolidine; piperidine; piperidine substituted with —OCH$_3$; —CH$_2$-piperidine; —CH$_2$-piperidine substituted with —OH and halo; —CH$_2$-morpholine; CH$_2$-morpholine substituted with one or two $C_{1-5}$alkyl or $C_{1-5}$haloalkyl; CH$_2$-thiomorpholine; CH$_2$-piperazine substituted with —CO$_2$tBu; CH$_2$-azetidine substituted with halo; —CH$_2$-azabicyclo[3.1.1]heptan-3-yl; pyrazole substituted with $C_{1-5}$alkyl; pyridyl; 3,6-dihydro-2H-pyridine substituted with —CO$_2$tBu; imidazole; oxadiazolyl; and oxadiazole substituted with $C_{1-5}$alkyl, cyclopropyl, pyridyl, or $C_{1-5}$haloalkyl;

$R^4$ is selected from the group consisting of: H, halo, and $C_{1-5}$haloalkoxy;

$R^5$ is selected from the group consisting of: H, halo, $C_{1-5}$alkyl, $C_{1-5}$haloalkyl, —CN, —CO$_2$C$_{1-5}$alkyl, —(C=O)NH-phenyl, —(C=O)pyrrolidine, and —(C=O)piperidine; and $R^6$ is selected from the group consisting of: H, halo, $C_{1-5}$alkyl, —CH$_2$CN, $C_{1-5}$alkoxy, —C$_{1-5}$haloalkyl, and $C_{1-5}$haloalkoxy; and wherein when R⁶ is H and R² is C₁₋₅alkoxy, R³ is not C₁₋₅alkoxy;
and pharmaceutically acceptable salts, N-oxides or solvates of compounds of Formula (I);
and (B) at least one pharmaceutically acceptable excipient.

An additional embodiment of the invention is a pharmaceutical composition comprising and effective amount of at least one compound of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA); and at least one pharmaceutically acceptable excipient.

An additional embodiment of the invention is a pharmaceutical composition comprising and effective amount of at least one compound of Formula (IB), as well as pharmaceutically acceptable salts, N-oxides or solvates of compounds of Formula (IB), pharmaceutically acceptable prodrugs of compounds of Formula (IB), and pharmaceutically active metabolites of Formula (IB); and at least one pharmaceutically acceptable excipient.

An additional embodiment of the invention is a pharmaceutical composition comprising and effective amount of at least one compound in Table 1, as well as pharmaceutically acceptable salts, N-oxides or solvates of compounds of Table 1, pharmaceutically acceptable prodrugs of compounds of Table 1, and pharmaceutically active metabolites of Table 1; and at least one pharmaceutically acceptable excipient.

An additional embodiment of the invention is a pharmaceutical composition comprising and effective amount of at least one compound in Table 2, as well as pharmaceutically acceptable salts, N-oxides or solvates of compounds of Table 2, pharmaceutically acceptable prodrugs of compounds of Table 2, and pharmaceutically active metabolites of Table 2; and at least one pharmaceutically acceptable excipient.

Also within the scope of the invention are enantiomers and diastereomers of the compounds of Formula (I) (as well as Formula (II), Formula (III), Formula (IV), Formula (V), Formula (IA), and Formula (IB)). Also within the scope of the invention are the pharmaceutically acceptable salts, N-oxides or solvates of the compounds of Formula (I) (as well Formula (II), Formula (III), Formula (IV), Formula (V), Formula (IA), and Formula (IB)). Also within the scope of the invention are the pharmaceutically acceptable prodrugs of compounds of Formula (I) (as well as Formula (II), Formula (III), Formula (IV), Formula (V), Formula (IA), and Formula (IB)), and pharmaceutically active metabolites of the compounds of Formula (I) (as well as Formula (II), Formula (III), Formula (IV), Formula (V), Formula (IA), and Formula (IB)).

Also within the scope of the invention are isotopic variations of compounds of Formula (I) (as well as Formula (II), Formula (III), Formula (IV), Formula (V), Formula (IA), and Formula (IB)), such as, e.g., deuterated compounds of Formula (I). Also within the scope of the invention are the pharmaceutically acceptable salts, N-oxides or solvates of the isotopic variations of the compounds of Formula (I) (as well Formula (II), Formula (III), Formula (IV), Formula (V), Formula (IA), and Formula (IB)). Also within the scope of the invention are the pharmaceutically acceptable prodrugs of the isotopic variations of the compounds of Formula (I) (as well as Formula (II), Formula (III), Formula (IV), Formula (V), Formula (IA), and Formula (IB)), and pharmaceutically active metabolites of the isotopic variations of the compounds of Formula (I) (as well as Formula (II), Formula (III), Formula (IV), Formula (V), Formula (IA), and Formula (IB)).

An additional embodiment of the invention is a method of treating a subject suffering from or diagnosed with a disease, disorder, or medical condition mediated by AMPA receptor activity, comprising administering to a subject in need of such treatment an effective amount of at least one compound selected from compounds of Formula (I):

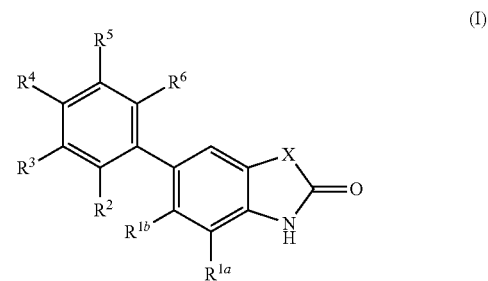

(I)

wherein
X is NH or S;
R$^{1a}$ and R$^{1b}$ are independently selected from the group consisting of H, ³H, halo, —CH₃, —CH₂CH₃, —CF₃, —OCH₃, —OCF₃, and —CN;
R² is selected from the group consisting of: halo; C₁₋₅alkyl; C₁₋₅alkenyl; C₁₋₅haloalkyl; C₁₋₅alkoxy; C₁₋₅haloalkoxy; —(C=O)H; —CH₂C(=O)NH(CH₃); —CO₂C₁₋₅alkyl; —CN; —CH₂CN; —CH(CH₃)CN; —C(CH₃)₂CN; —OCH₂CN; phenyl; phenyl substituted with halo, C₁₋₅alkoxy, or —CN; —O-phenyl; benzyl; benzyl substituted with halo; —O-benzyl; C₃₋₆cycloalkyl; —OC₃₋₆cycloalkyl; —O-thiazolyl; pyrimidinyl; pyridyl; pyridyl substituted with halo, C₁₋₅alkoxy, or C₁₋₅haloalkyl; —NH—CH₂-furyl; —C₃₋₆cycloalkyl substituted with CN; —CH₂morpholine; CH₂—N-methylpiperazine; pyrazolyl; pyrazole substituted with —CH₂CH₂OCH₃, or C₁₋₅alkyl; isoxazole substituted with two C₁₋₅alkyl; —O—CH₂—C₃₋₆cycloalkyl optionally substituted with halo; piperazine substituted with —CO₂tBu; —O-azetidine substituted with —CO₂tBu; and 8-quinolyl;
R³ is selected from the group consisting of: H; halo; C₁₋₅alkyl; C₁₋₅haloalkyl; C₁₋₅alkoxy; C₁₋₅haloalkoxy; —CN; —CH₂CN; CO₂C₁₋₅alkyl; —N(CH₃)₂; —(C=O)N(C₁₋₅alkyl)₂; —(C=O)NH-cyclopropyl; —(C=O)NH-phenyl; —(C=O)morpholine; —O-cyclopropyl; —O—CH₂-cyclopropyl substituted with halo; —O-azetidinyl substituted with —CO₂tBu; CH₂-pyrrolidine; piperidine; piperidine substituted with —OCH₃; —CH₂-piperidine; —CH₂-piperidine substituted with —OH and halo; —CH₂-morpholine; CH₂-morpholine substituted with one or two C₁₋₅alkyl or C₁₋₅haloalkyl; CH₂-thiomorpholine; CH₂-piperazine substituted with —CO₂tBu; CH₂-azetidine substituted with halo; —CH₂-6-oxa-3-azabicyclo[3.1.1]heptan-3-yl; pyrazole substituted with C₁₋₅alkyl; pyridyl; 3,6-dihydro-2H-pyridine substituted with —CO₂tBu; imidazole; oxadiazolyl; and oxadiazole substituted with C₁₋₅alkyl, cyclopropyl, pyridyl, or C₁₋₅haloalkyl;
R⁴ is selected from the group consisting of: H, halo, and C₁₋₅haloalkoxy;

$R^5$ is selected from the group consisting of: H, halo, $C_{1-5}$alkyl, $C_{1-5}$haloalkyl, —CN, —$CO_2C_{1-5}$alkyl, —(C=O)NH-phenyl, —(C=O)pyrrolidine, and —(C=O)piperidine; and $R^6$ is selected from the group consisting of: H, halo, $C_{1-5}$alkyl, —$CH_2$CN, $C_{1-5}$alkoxy, $C_{1-5}$haloalkyl, and $C_{1-5}$haloalkoxy; and wherein when $R^6$ is H and $R^2$ is $C_{1-5}$alkoxy, $R^3$ is not $C_{1-5}$alkoxy;

and pharmaceutically acceptable salts, N-oxides, or solvates thereof, to a subject in need thereof.

The AMPA subtype of glutamate receptors are glutamate-gated ion channels expressed primarily on postsynaptic membranes of excitatory synapses in the central nervous system. AMPA receptors assemble as tetramers of subunits. Mammals express four AMPA-receptor subunits, called GluA1-GluA4. In their native environment, the pore-forming GluA tetramers directly or indirectly associate with numerous auxiliary proteins. The wide variety of proteins which can participate in AMPA receptor complexes vastly increases the ability of a neuron to tune the response characteristics of its synapses.

AMPA receptors mediate the majority of fast neurotransmission across synaptic gaps. However, since AMPA receptor activity is so ubiquitous within CNS, general antagonism affects most areas of the CNS resulting in undesired effects, such as ataxia, sedation, and/or dizziness, which are shared by all known general AMPA receptor antagonists.

In order to circumvent the problems with side-effects noted above, it is hereby proposed that selective modulation of TARP γ8-associated AMPA receptor complexes provides effective therapeutic agents which also avoid or reduce the side-effects associated with the administration of non-selective AMPA receptor modulators. TARP γ8 is primarily expressed in the hippocampus and the cortex, while TARP γ2 is primarily expressed in the cerebellum. In one aspect, selective modulation of TARP γ8 potentially avoids modulation of TARP γ2-associated AMPA receptor complexes, which are more prevalent in the cerebellum, thereby reducing side effects associated with general (non-TARP dependent/non-selective) AMPA antagonism.

For instance, selective modulation of TARP γ8-associated AMPA receptor complexes is contemplated as an effective anti-seizure/anti-epileptic therapeutic with reduced the side effects (e.g. sedation, ataxis, and/or dizziness) associated with general (non-TARP dependent/non-selective) AMPA antagonists. Similarly, reduction of hippocampal over-excitability, using selective modulation of TARP γ8-associated AMPA receptor complexes may lead to normalization of the symptoms of schizophrenia, and it may protect against the subsequent decline in hippocampal volume. In a further instance, selectively attenuating hippocampal excitability, via selective modulation of TARP γ8-associated AMPA receptor complexes, could provide therapeutic benefit to patients with bipolar disorder. Likewise, selective modulation of TARP γ8-associated AMPA receptor complexes within the hippocampus may provide an effective anxiolytic.

Accordingly, provided herein are compounds which are selective modulators of TARP γ8-associated AMPA receptor complexes. Compounds which are selective modulators of TARP γ8-associated AMPA receptor complexes ameliorate and/or eliminate the side effects (e.g. sedation, ataxis, and/or dizziness) of general (non-TARP dependent/non-selective) AMPA receptor modulators.

In some embodiments, provided herein are compounds which selectively modulate the activity of complexes comprising GluA1 receptors associated with the protein TARP γ8.

In one embodiment, selective modulation of TARP γ8-associated AMPA receptor complexes refers to selective antagonism of TARP γ8-associated AMPA receptor complexes. In another embodiment, selective modulation of TARP γ8-associated AMPA receptor complexes refers to selective partial inhibition of TARP γ8-associated AMPA receptor complexes. In a further embodiment, selective antagonism of TARP γ8-associated AMPA receptor complexes refers to negative allosteric modulation of TARP γ8-associated AMPA receptor complexes.

The invention relates to methods of using the compounds described herein to treat subjects diagnosed with or suffering from a disease, disorder, or condition mediated by AMPA receptor activity. These methods are accomplished by administering to the subject a compound of the invention. In some embodiments, the compounds described herein are selective for modulation of TARP γ8 associated AMPA receptor complexes.

An AMPA receptor mediated disease, disorder or condition includes and is not limited to cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain, diabetic neuropathy, encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder (for example, CNS lupus erythematodes, polyarteritis nodosa, Sjogren syndrome, sarcoidosis, isolated cerebral vasculitis, etc.), schizophrenia, depression, and bipolar disorder. In some embodiments, the AMPA mediated disease, disorder or condition is depression, anxiety disorders, anxious depression, post traumatic stress disorder, epilepsy, schizophrenia, prodromal schizophrenia, or a cognitive disorder.

In one group of embodiments, an AMPA receptor mediated disease, disorder or condition is a condition related to hippocampal hyperexcitability. In one embodiment, provided herein are methods to selectively dampen hippocampal activity in the brain comprising administration of compounds described herein to a subject in need thereof. In one embodiment, provided herein are methods for the treatment of an AMPA receptor mediated disease, disorder or condition which is depression comprising administration of compounds described herein to a subject in need thereof. As used herein, depression includes and is not limited to major depression, psychotic depression, persistent depressive disorder, post-partum depression, seasonal affective disorder, depression which is resistant to other anti-depressants, manic-depression associated with bipolar disorder, post traumatic stress disorder, and the like. In another embodiment, provided herein are methods for the treatment of an AMPA receptor mediated disease, disorder or condition which is post traumatic stress disorder (PTSD) comprising administration of compounds described herein to a subject in need thereof. In another embodiment, provided herein are methods for the treatment of an AMPA receptor mediated disease, disorder or condition which is epilepsy, schizophrenia, or prodromal schizophrenia comprising administration of compounds described herein to a subject in need thereof. In yet another embodiment, provided herein are methods for the treatment of an AMPA receptor mediated disease, disorder or condition which is a cognitive disorder comprising administration of compounds described herein to a subject in need thereof. As used herein, cognitive disorder includes and is not limited to mild cognitive impairment, amnesia, dementia, delirium, cognitive impairment associated with anxiety disorders, mood disorders, psychotic disorders and the like.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

Certain Definitions

As used herein, the terms "including", "containing" and "comprising" are used herein in their open, non-limiting sense.

The term "alkyl" refers to a straight- or branched-chain alkyl group having from 1 to 12 carbon atoms in the chain. In some embodiments, an alkyl group is a $C_{1-6}$alkyl group.

In some embodiments, an alkyl group is a $C_{1-5}$alkyl group. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "haloalkyl" refers to a straight- or branched-chain alkyl group having from 1 to 12 carbon atoms in the chain and having at least one of the hydrogens replaced with a halogen. In some embodiments, a haloalkyl group is a $C_{1-6}$haloalkyl group. In some embodiments, a haloalkyl group is a $C_{1-5}$haloalkyl group. One exemplary substitutent is fluoro. Preferred substituted alkyl groups of the invention include trihalogenated alkyl groups such as trifluoromethyl groups. Haloalkyl includes and is not limited to —$CF_3$, —$CH_2F$, —$CHF_2$, —$CH_2Cl$, —$CH_2$—$CF_3$, and the like.

The term "cycloalkyl" refers to monocyclic, non-aromatic hydrocarbon groups having from 3 to 8 carbon atoms. Examples of cycloalkyl groups include, for example, cyclopropyl, cyclobutyl, cyclopentyl, cyclohexyl, and the like.

The term "alkoxy" includes a straight chain or branched alkyl group with a terminal oxygen linking the alkyl group to the rest of the molecule. In some embodiments, an alkoxy group is a $C_{1-6}$alkoxy group. In some embodiments, an alkoxy group is a $C_{1-5}$alkoxy group. Alkoxy includes methoxy, ethoxy, propoxy, isopropoxy, butoxy, t-butoxy, pentoxy and so on.

The term "haloalkoxy" includes a straight chain or branched alkyl group with a terminal oxygen linking the alkyl group to the rest of the molecule and having at least one of the hydrogens replaced with a halogen. In some embodiments, a haloalkoxy group is a $C_{1-6}$haloalkoxy group. In some embodiments, a haloalkoxy group is a $C_{1-5}$haloalkoxy group. Haloalkoxy includes and is not limited to —$OCF_3$, —$OCH_2F$, —$OCHF_2$, —$OCH_2Cl$, —O—$CH_2$—$CF_3$, and the like.

The term "thiophenyl" and "thienyl" are used interchangeably.

The term "halogen" represents chlorine, fluorine, bromine, or iodine. The term "halo" represents chloro, fluoro, bromo, or iodo.

The term "benzyl" and —$CH_2$-phenyl are used interchangeably

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

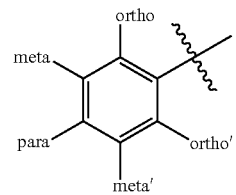

When referring to substituents on a pyridyl group, the terms "para", "meta", and "ortho" refer to the placement of a substituent relative to the point of attachment of the pyridyl ring. For example the structure below is described as 3-pyridyl with the $X^1$ substituent in the ortho position, the $X^2$ substituent in the meta position, and $X^3$ substituent in the para position:

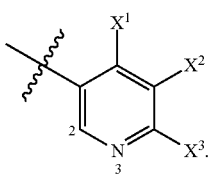

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, $5^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers." Isomers that differ in the arrangement of their atoms in space are termed "."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enatiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

Compounds of the invention may also exist as "rotamers," that is, conformational isomers that occur when the rotation leading to different conformations is hindered, resulting a rotational energy barrier to be overcome to convert from one conformational isomer to another.

The symbols  are used as meaning the same spatial arrangement in chemical structures shown herein. Analogously, the symbols ||||||||||| and ······|||||| are used as meaning the same spatial arrangement in chemical structures shown herein.

A wavy line "⌇" indicates the point of attachment to the rest of the molecule.

Additionally, any formula given herein is intended to refer also to hydrates, solvates, and polymorphs of such compounds, and mixtures thereof, even if such forms are not listed explicitly. Certain compounds of Formula (I) (as well as Formula (II), Formula (III), Formula (IV), Formula (V), Formula (IA), and Formula (IB)), or pharmaceutically acceptable salts of Formula (I) (as well as Formula (II), Formula (III), Formula (IV), Formula (V), Formula (IA), and Formula (IB))) may be obtained as solvates. Solvates include those formed from the interaction or complexation of compounds of the invention with one or more solvents, either in solution or as a solid or crystalline form. In some embodiments, the solvent is water andthe solvates are hydrates. In addition, certain crystalline forms of compounds of Formula (I) (as well as Formula (II), Formula (III), Formula (IV), Formula (V), Formula (IA), and Formula (IB)) or pharmaceutically acceptable salts of compounds of Formula (I) (as well as Formula (II), Formula (III), Formula (IV), Formula (V), Formula (IA), and Formula (IB)) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R-COO$^-$$_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R-COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R-COO$^-$$_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion+H$_3$NCH$_2$COO$^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium or tritium (i.e., $^2$H, $^3$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent S$^1$$_{example}$ is one of S$_1$ and S$_2$, and substituent S$^2$$_{example}$ is one of S$_3$ and S$_4$, then these assignments refer to embodiments of this invention given according to the choices S$^1$$_{example}$ is S$_1$ and S$^2$$_{example}$ is S$_3$; S$^1$$_{example}$ is S$_1$ and S$^2$$_{example}$ is S$_4$; S$^1$$_{example}$ is S$_2$ and S$^2$$_{example}$ is S$_3$; S$^1$$_{example}$ is S$_2$ and S$^2$$_{example}$ is S$_4$; and equivalents of each one of such choices. The shorter terminology "S$_{example}$ is one of S$_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^{1a}$, $R^{1b}$, $R^2$, $R^{2a}$, $R^3$, $R^{3a}$, $R^4$, $R^{4a}$, $R^5$, $R^{5a}$, $R^6$, $R^{6a}$, X, Z, PG, Hal$^1$, and Hal$^2$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein.

The foregoing convention given herein for substituents extends, when applicable, to members such as $R^{1a}$, $R^{1b}$, $R^2$, $R^{2a}$, $R^3$, $R^{3a}$, $R^4$, $R^{4a}$, $R^5$, $R^{5a}$, $R^6$, $R^{6a}$, X, Z, PG, Hal$^1$, and Hal$^2$ and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The invention includes also pharmaceutically acceptable salts of the compounds of Formula (I) (as well as Formula (II), Formula (III), Formula (IV), Formula (V), Formula (IA), and Formula (IB)), preferably of those described above and of the specific compounds exemplified herein, and methods of treatment using such salts.

The term "pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

A "pharmaceutically acceptable salt" is intended to mean a salt of a free acid or base of compounds represented by Formula (I) (as well as Formula (II), Formula (III), Formula (IV), Formula (V), Formula (IA), and Formula (IB)) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) (as well as Formula (II), Formula (III), Formula (IV), Formula (V), Formula (IA), and Formula (IB)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I) (as well as Formula (II), Formula (III), Formula (IV), Formula (V), Formula (IA), and Formula (IB)) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) (as well as Formula (II), Formula (III), Formula (IV), Formula (V), Formula (IA), and Formula (IB)) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of Formula (I) (as well as Formula (II), Formula (III), Formula (IV), Formula (V), Formula (IA), and Formula (IB)), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I) (as well as Formula (II), Formula (III), Formula (IV), Formula (V), Formula (IA), and Formula (IB)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I) (as well as Formula (II), Formula (III), Formula (IV), Formula (V), Formula (IA), and Formula (IB)). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) (as well as Formula (II), Formula (III), Formula (IV), Formula (V), Formula (IA), and Formula (IB)) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl) amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., Adv. Drug Delivery Rev. 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., J Med Chem. 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) (as well as Formula (II), Formula (III), Formula (IV), Formula (V), Formula (IA), and Formula (IB)), which may also be used in the methods of the invention. A "pharmaceutically active metabolite" means a pharmacologically active product of metabolism in the body of a compound of Formula (I) (as well as Formula (II), Formula (III), Formula (IV), Formula (V), Formula (IA), and Formula (IB)) (as applicable) or salt thereof. Prodrugs and active metabolites of a compound may be determined using routine techniques known or available in the art. See, e.g., Bertolini, et al., J Med Chem. 1997, 40, 2011-2016; Shan, et al., J Pharm Sci. 1997, 86 (7), 765-767; Bagshawe, Drug Dev Res. 1995, 34, 220-230; Bodor, Adv Drug Res. 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) (as well as Formula (II), Formula (III), Formula (IV), Formula (V), Formula (IA), and Formula (IB)) and their pharmaceutically acceptable salts, pharmaceutically acceptable prodrugs, and pharmaceutically active metabolites of the present invention are useful as modulators of the AMPA receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the AMPA receptor expression or activity, and "activators" are compounds that increase, activate, facilitate, sensitize, or up-regulate AMPA receptor expression or activity.

The term "pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

The term "subject" includes humans. The terms "human," "patient," and "subject" are used interchangeably herein.

The term "treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 10 mg to about 2.5 g/day.

"Compounds of the present invention," and equivalent expressions, are meant to embrace compounds of the Formula (I) as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. The additional active ingredients may be coadministered separately with a compound of the invention or included with such an agent in a pharmaceutical composition according to the invention. In an exemplary embodiment, additional active ingredients are those that are known or discovered to be effective in the treatment of conditions, disorders, or diseases mediated by orexin activity, such as another orexin modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The compounds of the invention are used, alone or in combination with one or more additional active ingredients, to formulate pharmaceutical compositions of the invention. A pharmaceutical composition of the invention comprises: (a) an effective amount of at least one compound in accordance with the invention; and (b) a pharmaceutically acceptable excipient.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semisolid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol. Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 .mu.g/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I), as well as Formulas (IA)-(IB). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations

Table 3. Abbreviations and acronyms used herein include the following.

| Term | Acronym/Abbreviation |
| --- | --- |
| 2-Methyltetrahydrofuran | 2-Me—THF |
| 1,1'-Azobis(cyclohexanecarbonitrile) | ABCN |
| Acetic anhydride | $Ac_2O$ |
| Acetonitrile | ACN, MeCN |
| Acetic acid | AcOH |
| Azobisisobutyronitirile | AIBN |
| 2,2'-Bis(diphenylphosphino)-1,1'-binaphthyl | BINAP |
| 5-(Di-tert-butylphosphino)-1',3',5'-triphenyl-1'H-[1,4']bipyrazole | BippyPhos |
| tert-Butylcarbamoyl | BOC |
| Benzotriazol-1-yloxytris(dimethylamino)-phosphonium hexafluorophosphate | BOP |
| [2-(Di-1-adamantylphosphino)-2',4',6'-triisopropyl-3,6-dimethoxybiphenyl][2-(2'-amino-1,1'-biphenyl)]palladium(II) methanesulfonate | BrettPhos Pd third-generation pre-catalyst |
| 1,1'-Carbonyldiimidazole | CDI |
| Diatomaceous Earth | Celite 545, Celite ® |
| Copper(II) acetate | $Cu(OAc)_2$ |
| (Diethylamino)sulfur trifluoride | DAST |
| 2-Dicyclohexylphosphino-2'-(N,N-dimethylamino)biphenyl | DavePhos |
| Di-tert-butyl azodicarboxylate | DBAD |
| N,N'-Dicyclohexylcarbodiimide | DCC |
| Dichlorethane | DCE |
| Methylene chloride, dichloromethane | DCM |
| Bis(2-methoxyethyl)aminosulfur trifluoride | Deoxo-Fluor ® |
| 1,1,1-Triacetoxy-1,1-dihydro-1,2-benziodoxol-3(1H)-one | Dess-Martin periodinane |
| Diisobutylaluminium hydride | DIBAL, DIBAL-H |
| N,N-Diisopropylethylamine | DIPEA, DIEA, Hunig's base |
| N,N-Dimethylformamide | DMF |
| Dimethyl sulfoxide | DMSO |
| Deutero-dimethyl sulfoxide | $DMSO-d_6$ |
| Diphenylphosphino ferrocene | dppf |
| Di-tert-butylphosphino ferrocene | dtbpf |
| 1-Ethyl-3-(3-dimethylaminopropyl)carbodiimide | EDCI, EDC, EDAC |
| Electrospray Ionisation | ESI |
| Ethyl magnesium bromide | EtMgBr |
| Ethyl Acetate | EtOAc, or EA, or AcOEt |
| Ethanol | EtOH |
| Flash Column Chromatography | FCC |
| Diethyl 1,4-dihydro-2,6-dimethyl-3,5-pyridinecarboxylate | Hantzsch Ester |
| 2-(1H-9-Azobenzotriazole-1-yl)-1,1,3,3-tetramethylaminium hexafluorophosphate | HATU |

| Term | Acronym/Abbreviation |
|---|---|
| Acetic Acid | HOAc |
| 1-Hydroxy-7-azabenzotriazole | HOAT, HOAt |
| 1-Hydroxy-benzotriazole | HOBt |
| High-pressure liquid chromatography | HPLC |
| Isopropyl Alcohol | IPA |
| Isopropyl magnesium bromide | i-PrMgBr |
| Potassium acetate | KOAc |
| Lithium aluminum hydride | LAH |
| Lithium hexamethyldisilylazide | LHMDS |
| meta-Chloroperoxybenzoic acid | mCPBA or MCPBA |
| Methyl magnesium bromide | MeMgBr |
| Deteromethanol | MeOD-$d_4$ |
| Methanol | MeOH |
| Mesyl chloride, Methanesulfonyl chloride | MsCl |
| Sodium dithionite | $Na_2S_2O_4$ |
| Sodium tert-butoxide | NaOtBu |
| N-Bromosuccinimide | NBS |
| N-Methylmorpholine | NMM |
| Tetrakis(triphenylphosphine)palladium(0) | $Pd(PPh_3)_4$ |
| Tris(dibenzylideneacetone(dipalladium (0) | $Pd_2(dba)_3$ |
| [1,1'-Bis(di-tert-butylphosphino)ferrocene]dichloropalladium(II) | $PdCl_2(dtbpf)$ |
| Palladium(II)bis(triphenylphosphine) dichloride, bis(triphenylphosphine)palladium(II) dichloride | $PdCl_2(PPh_3)_2$ |
| Phosphorous oxychloride | $POCl_3$ |
| Triphenylphosphine | $PPh_3$ |
| Precipitate | ppt |
| p-Toluenesulfonic acid | p-TsOH, PTSA |
| Pyridinium tribromide | $Py^+Br_3^-$ |
| Sodium potassium L(+)-tartrate tetrahydrate | Rochelle salt |
| Room temperature | rt |
| 2-Dicyclohexylphosphino-2',6'-diisopropoxybiphenyl | Ru-Phos |
| N-Chloromethyl-N-fluorotriethylenediammonium bis(tetrafluoroborate) | Selectfluor ® |
| 2-(TriMethsilyl)-ethoxyMethyl chloride | SEM-Cl |
| [2-(Trimethylsilyl)ethoxy]methyl acetal | SEM |
| Supercritical Fluid Chromatography | SFC |
| Thionyl chloride | $SOCl_2$ |
| Tetrabutylammonium fluoride | TBAF |
| Triethyl amine | TEA |
| Trifluoroacetic acid | TFA |
| Trifluoroacetic anhydride | TFAA |
| Tetrahydrofuran | THF |
| Tetrahydropyran | THP |
| 4,5-bis(diphenylphosphino)-9,9-dimethylxanthene | XantPhos |
| 2-Dicyclohexylphosphino-2',4',6'-triisopropylbiphenyl | XPhos |

PREPARATIVE EXAMPLES

Exemplary compounds useful in methods of the invention will now be described by reference to the illustrative synthetic schemes for their general preparation below and the specific examples to follow.

SCHEME A

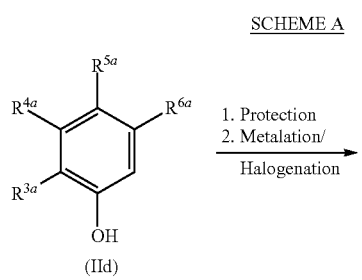

(IId)

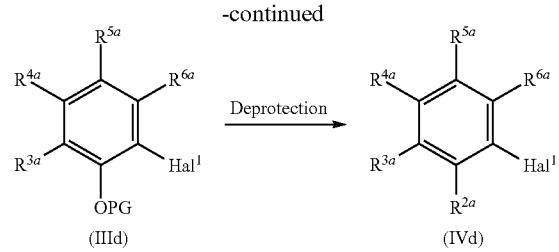

According to SCHEME A, a phenol compound of formula (IId), is protected with a protecting group (PG), where PG is a conventional phenol protecting group, such as methoxymethyl ether (MOM), under conditions known to one skilled in the art. Subsequent metalation followed by halogenation provides a compound of formula (IIId). For example, reaction of a protected phenol with a strong base such as n-butyllithium (n-BuLi), and the like, at a temperature such as −78° C., in a suitable solvent such as THF, and the like, and an electrophilic halogen source such as iodine provides a compound of formula (IIId), where $Hal^1$ is —I, and PG is methoxymethyl ether. Removal of the protecting group in a compound of formula (IIId) using conditions known to one skilled in the art affords a compound of formula (IVd), where $R^{2a}$ is —OH. For example, reaction with an acid such as HCl, in a solvent such as dioxane, ether and the like, at temperatures ranging from 20-50° C., affords a compound of formula (IVd). In a preferred method, the acid is HCl in dioxane.

SCHEME B

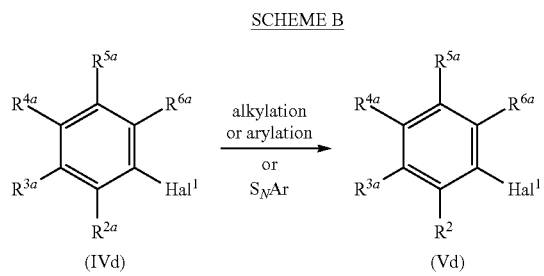

(IVd)    (Vd)

According to SCHEME B, a compound of formula (IVd), where $R^{2a}$, $R^{3a}$, or $R^{6a}$ is —OH, is treated with an alkylating reagent such as an optionally substituted alkylhalide or an arylating reagent such as a optionally substituted heteroaromatic halide, in the presence of a suitable base such as cesium carbonate ($Cs_2CO_3$), potassium carbonate ($K_2CO_3$), sodium hydride (NaH), with our without an additive such as potassium iodide, and the like, in a suitable solvent such as DMF, employing conventional or microwave heating, at temperatures ranging from rt to 150° C., to provide a compound of formula (Vd), where $R^2$ $R^3$ or $R^6$ is $C_{1-5}$alkoxy, $C_{1-5}$haloalkoxy, —O—$CH_2CN$, —$OC_{3-6}$cycloalkyl, —$OCH_2C_{3-6}$cycloalkyl, azetidinyl substituted with —BOC, thiazolyl, or —O-benzyl optionally substituted with —$OCH_3$, or F. For example, reaction of a compound of formula (IVd), where $R^{2a}$ is —OH, $R^{6a}$ is —$OC_{1-5}$haloalkyl, and Hal is —I, is reacted with an alkylhalide such as 2-iodopropane, (bromomethyl)cyclopropane, and the like, a base such as $Cs_2CO_3$, in DMF, at room temperature, for a period of a 1-3 h, to provide a compound of formula (V). In another example, a compound of formula (IVd), where $R^{2a}$ is —Cl, $R^{3a}$ is —OH, Hal is —Br, is reacted as described above with an alkylating agent such as tert-butyl 3-bromoazetidine-1-carboxylate, $K_2CO_3$, in DMF, at 150° C., employing microwave conditions, to afford a compound of formula (Vd), where $R^{2a}$ is —Cl, $R^{3a}$ is —O-azetidinyl substituted with —BOC, and, Hal is Br.

A compound of formula (IVd), where $R^{2a}$ is —F, $R^{6a}$ is —Cl, or $C_{1-5}$alkoxy, and $Hal^1$ is —Cl, —Br, or —I, is reacted in an SNAr (nucleophilic aromatic substitution) reaction with a suitably substituted alcohol, to provide a compound of formula (Vd), where $R^2$ is $C_{1-5}$haloalkoxy. For example, a compound of formula (IVd), where $R^{2a}$ is —F, $R^{6a}$ is —Cl, and $Hal^1$ is —Cl, —Br, or —I, is reacted with an alcohol such as 1,1,1-trifluoro-2-propanol, in the presence of a suitable base such as sodium tert-butoxide (NaOtBu), NaH, $K_2CO_3$, and the like, in a suitable solvent such as THF, DMF, and the like, employing conventional heating, at a temperature ranging from 50 to 80° C., to provide a compound of formula (Vd), where $R^2$ is —$OC_{1-5}$haloalkyl, $R^{6a}$ is —Cl, or $C_{1-5}$alkoxy, and $Hal^1$ is —Br.

SCHEME C

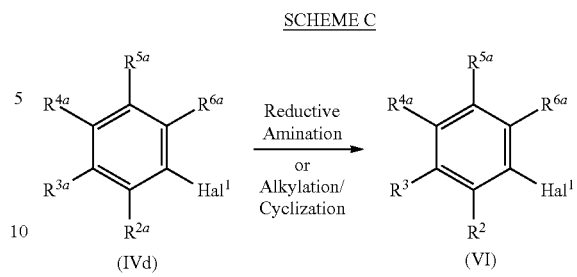

(IVd)    (VI)

According to SCHEME C, a commercially available or synthetically accessible compound of formula (IVd), where $R^{2a}$ or $R^{3a}$ is —$NH_2$, and $Hal^1$ is —I, —Br, or —Cl, is reacted in a reductive amination reaction with a commercially available or synthetically accessible suitable aldehyde or aldehyde equivalent, a reducing agent such as $NaBH_4$, $NaCNBH_4$, formic acid, and the like, in a suitable solvent such as MeOH, $CH_2Cl_2$, THF, and the like, at temperatures ranging from 0° C. to 70° C., for a period of 6 to 12 h. For example, a compound of formula (IVd), where $R^{2a}$ is —$NH_2$, $Hal^1$ is —I, and $R^{6a}$ is —Cl, is reacted with 2-furaldehyde, in the presence of a reducing agent such as $NaBH_4$, in a solvent such as MeOH, at temperatures ranging from 0° C. to rt, for a period of 10-16 h, provides a compound of formula (VI), where $R^2$ is —NH—$CH_2$-furyl, $Hal^1$ is —I, and $R^{6a}$ is —Cl. Alkyl, haloalkyl, cycloalkyl, aryl aldehydes may be reacted under reductive amination conditions described above, with a compound of formula (IVd), where $R^{2a}$ or $R^{3a}$ are —$NH_2$ to provide a compound of formula (VI), where $R^2$ or $R^3$ are —NH-alkyl, —NH-haloalkyl, —NH-cycloalkyl, or —NH-aryl.

A compound of formula (IVd), where $R^{2a}$ is —Cl, $R^{3a}$ is —$NH_2$, and $Hal^1$ is —Br, is reacted with a dihaloalkane of formula HAL-$(CH_2)_n$-HAL, where HAL is iodide, bromide, and chloride, and n=4-6, in the presence of a base such as $K_2CO_3$, and the like, an additive such as NaI, in a suitable solvent such as DMF, and the like, employing microwave heating at temperatures ranging from 120-150° C., for a period of about 50-70 minutes, to provide a compound of formula (VI), where $R^3$ is piperidinyl, and $Hal^1$ is —Br. In a preferred method, the dihaloaklane is 1,5-dibromopentane and the base is $K_2CO_3$.

SCHEME D

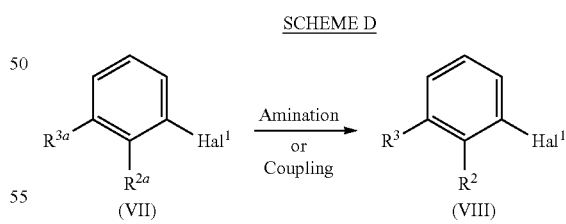

(VII)    (VIII)

According to SCHEME D, a compound of formula (VII), where $R^{2a}$ is —Cl, $R^{3a}$ is —Br, and $Hal^1$ is —Br, is aminated under conditions known to one of skill in the art, to provide a compound of formula (VIII). For example, a compound of formula (VII), where $R^{2a}$ is —Cl, $R^{3a}$ is —Br, and $Hal^1$ is —Br, is treated with a suitable primary or secondary cyclic or acyclic amine, in the presence of a palladium catalyst such as $Pd_2(dba)_3$, and the like, a phosphine ligand such as BINAP, and the like, a suitable base such as NaOt-Bu, and the like, in a solvent such as toluene, and the like, employing conventional or microwave heating, at a temperature such as 140° C., to provide a compound of formula (VIII), where $R^{2a}$ is —Cl, $R^{3a}$ is 4-methoxypiperdinyl, and $Hal^1$ is —Br. In a preferred method, the catalyst is $Pd_2(dba)_3$.

A compound of formula (VII), where $R^{2a}$ is —Cl, $R^{3a}$ is —Br, and $Hal^1$ is —Br is coupled under Suzuki reaction conditions known to one skilled in the art with a commercially available or synthetically accessible suitable aryl heteroaryl boronic acid or boronic ester, in the presence of a palladium catalyst such as $PdCl_2(dppf)$-$CH_2Cl_2$, and the like, a suitable base such a potassium phosphate, and the like, in a solvent such as dioxane, water, or a mixture thereof, employing conventional or microwave heating, at a temperature such as 100° C., to provide a compound of formula (VIII), where $R^{2a}$ is —Cl, $R^{3a}$ is 1-methyl-1H-pyrazolyl, and $Hal^1$ is —Br.

SCHEME E

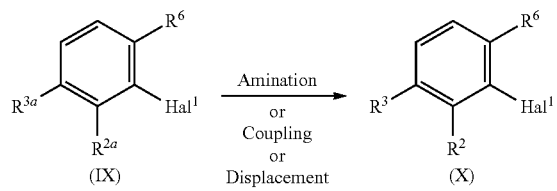

According to SCHEME E, a compound of formula (IX), where $R^{2a}$ or $R^{3a}$ is —$CH_3$, $R^6$ is —H, —Br, or —Cl, and $Hal^1$ is —I or —Br, is treated with a brominating reagent such as NBS, in the presence of a suitable catalyst such as AIBN, ABCN, and the like, in a suitable solvent such as carbon tetrachloride, employing conventional heating, at a temperature such as 90° C., to provide a methylbromide compound where $R^{2a}$ or $R^{3a}$ is —$CH_2Br$. Subsequent reaction of a methylbromide compound, where $R^{2a}$ or $R^{3a}$ is —$CH_2Br$, with a cyanide source such as potassium cyanide, in a suitable solvent such as DMF and water, employing conventional heating, at a temperature such as 40° C., provides a compound of formula (X), where $R^2$ or $R^3$ is —$CH_2CN$.

A compound of formula (X), where $R^2$ or $R^3$ is —$CH_2CN$, is reacted with an alkylating agent such as iodomethane, 1,2-dibromoethane, 1,3-dibromopropane, and the like, in the presence of a base such as lithium diisopropylamide (LDA), NaH, and the like, in a suitable solvent such as DMF or THF, employing conventional cooling at temperatures ranging from −78° C. to rt, to provide a compound of formula (X), where $R^2$ or $R^3$ is —$CH(CH_3)CN$, —$C(CH_3)_2CN$, —$C_{3-6}$cycloalkyl substituted with CN.

SCHEME F

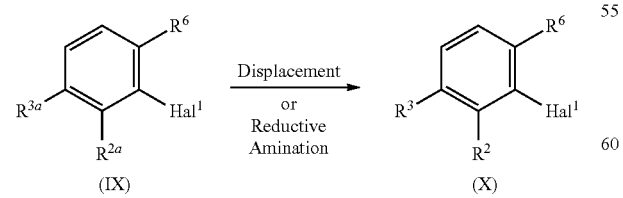

A methylbromide compound of formula (IX) where $R^{2a}$ is —Cl, $R^{3a}$ is —$CH_2Br$, $R^6$ is H or —Cl, and $Hal^1$ is —Br, or —I, is reacted in a displacement reaction with a commercially available or synthetically accessible optionally substituted 5-6 membered heterocyclic amine, such as morpholine, piperidine, N-methylpiperazine, and the like, in the presence of base such as triethylamine, in a suitable solvent such as DCM to afford a compound of formula (X), where $R^2$ is —Cl, $R^3$ is an optionally substituted 5-6 membered heterocyclic amine, such as morpholinyl, piperidinyl, or N-methylpiperazinyl, $R^6$ is H or —Cl, and $Hal^1$ is —Br, or —I.

A benzaldehyde compound of formula (IX) where $R^{2a}$ is $C_{1-5}$alkyl, $R^{3a}$ is —C(=O)H, $R^6$ is H, and $Hal^1$ is —Br, is reacted in a reductive amination reaction with a commercially available or synthetically accessible optionally substituted 5-6 membered heterocyclic amine, such as morpholine, piperidine, N-methylpiperazine, and the like, in the presence of a reducing agent such as $NaBH_4$, $NaCNBH_4$, formic acid, $Na(CH_3COO)_3BH$, and the 15 like, in a suitable solvent such as MeOH, $CH_2C_{012}$, THF, and the like, at temperatures ranging from 0° C. to 70° C., for a period of 6-12 h, to provide a compound of formula (X), where $R^2$ is $C_{1-5}$alkyl, $R^3$ is an optionally substituted 5-6 membered heterocyclic amine, such as morpholinyl, piperidinyl, or N-methylpiperazinyl, $R^6$ is H, and $Hal^1$ is —Br. In a preferred method, the amine is piperidine and the reducing agent is $Na(CH_3COO)_3BH$.

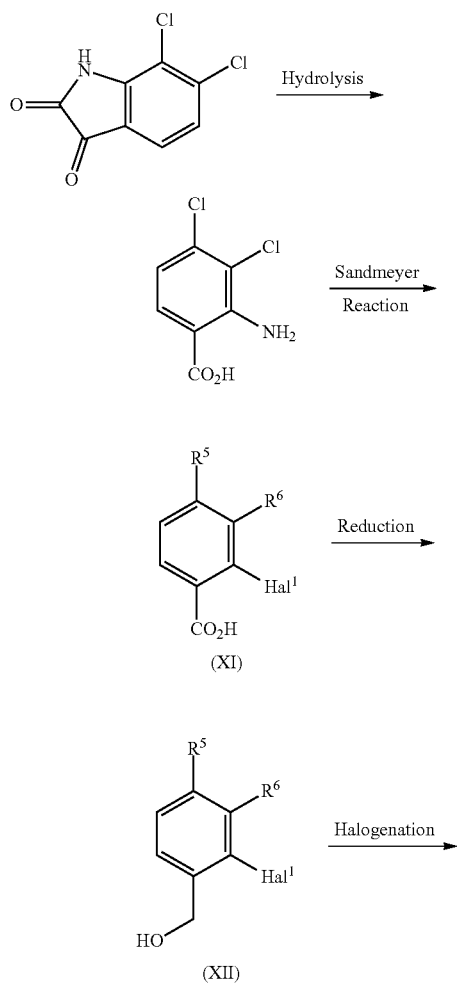

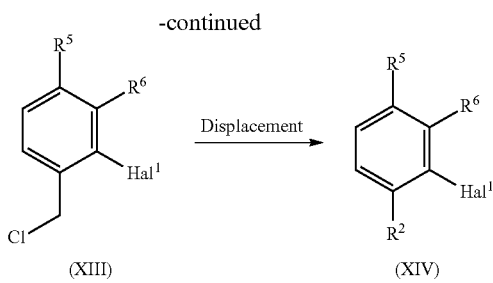

According to SCHEME G, commercially available or synthetically accessible 6,7-dichloroindoline-2,3-dione is hydrolyzed under basic aqueous conditions, such as potassium hydroxide and hydrogen peroxide in water, to provide 2-amino-3,4-dichlorobenzoic acid. 2-Amino-3,4-dichlorobenzoic acid is treated with sodium nitrite in the presence of an acid, such as sulfuric acid, followed by the addition of a nucleophilic halide source, such as potassium iodide, in suitable solvents such as DMSO and water, employing conventional cooling at temperatures ranging from 0° C. to rt, to provide a compound of formula (XI), where $R^5$ and $R^6$ are —Cl and $Hal^1$ is —I. An acid compound of formula (XI), $R^5$ is —H or Cl, $R^6$ is $C_{1-5}$haloalkoxy, or —Cl, and $Hal^1$ is —I, is reduced to an alcohol with a reducing agent such as borane-THF, in a suitable solvent such as THF, employing conventional heating, at temperatures ranging from rt to 50° C., to provide an alcohol compound of formula (XII) where $R^5$ is —H or Cl, $R^6$ is $C_{1-5}$haloalkoxy, or —Cl, and $Hal^1$ is —I. An alcohol compound of formula (XII) is converted to a suitable leaving group such as an alkyl chloride by treatment with thionyl chloride, a catalytic DMF, in a suitable solvent such as DCM, employing conventional cooling, at temperatures ranging from 0° C. to rt, followed by displacement with a cyanide source, such as potassium cyanide, in a suitable solvent such as DMF, to afford a compound of formula (XIV), where $R^2$ is —CH$_2$CN, $R^5$ is —H or Cl, $R^6$ is $C_{1-5}$haloalkoxy, or —Cl, and $Hal^1$ is —I.

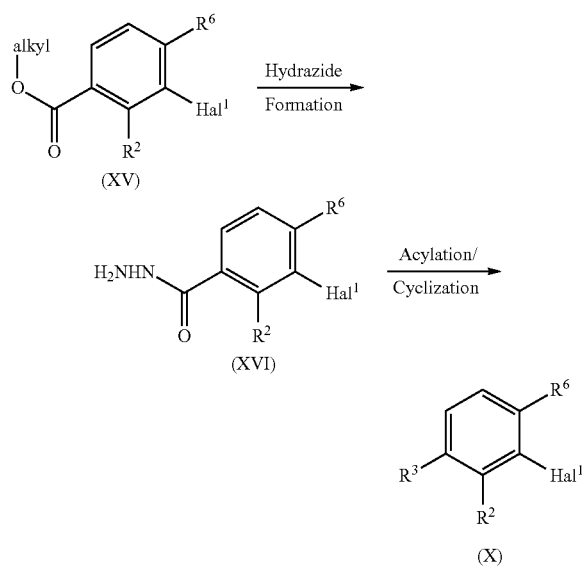

According to SCHEME H, an ester compound of formula (XV), where alkyl is $C_{1-5}$alkyl, $R^2$ is —Cl, —Br, or $C_{1-5}$alkyl, $R^6$ is H or —Cl, and $Hal^1$ is —Br or —I, is treated with hydrazine monohydrate, in a suitable solvent such as EtOH, employing conventional heating, at temperatures ranging from rt to 80° C., to provide a compound of formula (XVI). A hydrazide compound of formula (XVI) is treated with triethyl orthoacetate, triethyl orthoformate, and the like, employing conventional heating, at a temperature such as 145° C., to provide a compound of formula (X), where $R^2$ is —Cl, —Br, or $C_{1-5}$alkyl, $R^3$ is 1,3,4-oxadiazol-2-yl, or 5-methyl-1,3,4-oxadiazol-2-yl, $R^6$ is H or —Cl, and $Hal^1$ is —Br or —I.

Alternately, a compound of formula (XVI) is treated with an acid chloride compound of formula $C_{1-5}$alkyl-(C=O)Cl, $C_{1-5}$haloalkyl-(C=O)Cl, or —$C_{3-6}$cycloalkyl-(C=O)Cl, aryl, or heteroaryl acid chlorides, in the presence of a hindered base such as TEA, in a suitable solvent such as DCM, followed by cyclization with POCl$_3$, employing conventional or microwave heating, at a temperature such as 100° C., to provide a compound of formula (X), where $R^2$ is —Cl, —Br, or $C_{1-5}$alkyl, $R^3$ is 5-cyclopropyl-1,3,4-oxadiazol-2-yl, 5-(trifluoromethyl)-1,3,4-oxadiazol-2-yl, $R^6$ is H or —Cl, and $Hal^1$ is —Br or —I.

SCHEME I

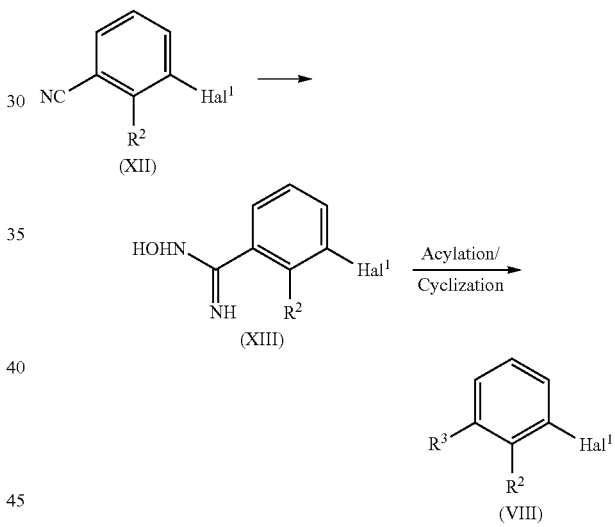

According to SCHEME I, a nitrile compound of formula (XII), where $R^2$ is $C_{1-5}$alkyl and $Hal^1$ is —Br, is treated with aqueous hydroxylamine, in a solvent such as water, EtOH, tBuOH, and the like, employing conventional heating, at temperatures ranging from rt to 80° C., to provide a compound of formula (XIII). Alternately, trimethylamine is added in the previously described conditions if hydroxylamine hydrochloride is used. A compound of formula (XIII) is treated with trimethylorthoformate in the presence of BF$_3$-OEt$_2$, in a suitable solvent such as DMSO, employing conventional heating, at temperatures ranging from rt to 80° C., to provide a compound of formula (VIII), $R^2$ is $C_{1-5}$alkyl, $R^3$ is 1,2,4-oxadiazol-3-yl and $Hal^1$ is —Br.

Alternately, a compound of formula (XIII) is treated with an acid chloride compound of formula $C_{1-5}$alkyl-(C=O)Cl, $C_{1-5}$haloalkyl-(C=O)Cl, or $C_{3-6}$cycloalkyl-(C=O)Cl, 4-pyridyl-C(=O)Cl, in the presence of a base such as pyridine, in a suitable solvent such as dioxane, employing conventional heating, at a temperature such as 100° C., to provide a compound of formula (VIII), where $R^2$ is $C_{1-5}$alkyl, $R^3$ is methyl-1,2,4-oxadiazol-3-yl, 5-cyclopropyl-1,2,4-oxadiazol-3-yl, or 5-(4-pyridyl)-1,2,4-oxadiazol-3-yl, and $Hal^1$-Br.

SCHEME J

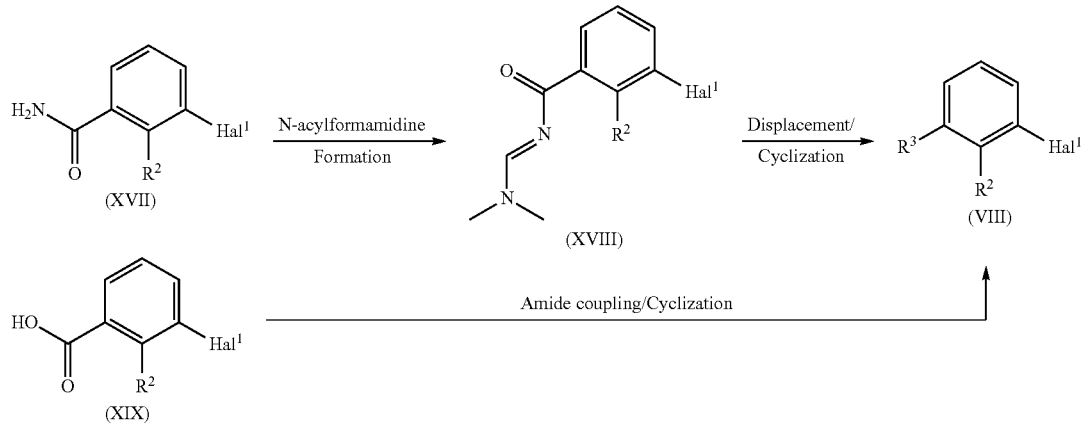

According to Scheme I, a compound of formula (XVII), where $R^2$ is $C_{1-5}$alkyl, and $Hal^1$ is —Br, is reacted with N,N-dimethylformamide dimethyl acetal, employing conventional heating, at a temperature such as 120° C., to provide an N-acylformamidine compound of formula (XVIII). An N-acylformamidine compound of formula (XVIII), is treated with aqueous hydroxylamine, in a suitable solvent such as acetic acid, employing conventional heating, at a temperature such as 90° C., to provide a compound of (VIII), where $R^2$ is $C_{1-5}$alkyl, $R^3$ is 1,2,4-oxadiazol-5-yl and $Hal^1$ is —Br.

A benzoic acid compound of formula (XIX), where $R^2$ is $C_{1-5}$alkyl, and $Hal^1$ is —Br, is reacted with N'-hydroxy-acetimidamide, N'-hydroxytrifluoroacetimidamide, N'-hydroxycyclopropanecarboximidamide, and the like, in the presence of an amide coupling reagent such as propylphosphonic anhydride (T3P®), a hindered base such as TEA, in a suitable solvent such as EtOAc, employing conventional heating, at a temperature such as 80° C., to provide a compound of formula (VIII), where $R^2$ is $C_{1-5}$alkyl, $R^3$ is 3-methyl-1,2,4-oxadiazol-5-yl, 3-cyclopropyl-1,2,4-oxadiazol-5-yl, or 3-(trifluoromethyl)-1,2,4-oxadiazol-5-yl, and $Hal^1$ is —Br.

SCHEME K

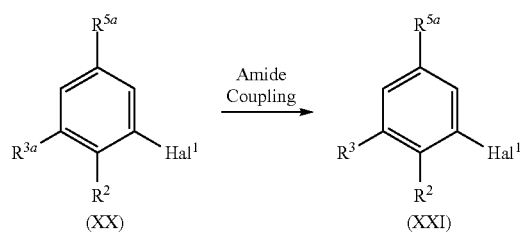

According to SCHEME K, a compound of formula (XX), where $R^2$ is $C_{1-5}$alkyl, $R^{3a}$ is —$CO_2H$, and $Hal^1$ is —I, is reacted under amide bond formation conditions known to one skilled in the art, to provide a compound of formula (XXI), where $R^3$ is —(C=O)NH-phenyl, —(C=O)NHC$_{3-6}$cycloalkyl, —(C=O)N(CH$_3$)$_2$, —(C=O)morpholine. For example, a compound of formula (XX), where $R^2$ is $C_{1-5}$alkyl, $R^{3a}$ is —$CO_2H$, and $Hal^1$ is —I, is reacted with an suitable amine, in the presence of an amide coupling reagent such as T3P®, a hindered base such DIEA, and the like, with our without 4-dimethylaminopyridine (DMAP), in a suitable solvent such as THF, EtOAc, and the like, to provide a compound of formula (XXI), where $R^3$ is —(C=O)NH-phenyl, —(C=O)NHC$_{3-6}$cycloalkyl, —(C=O)N(CH$_3$)$_2$, or —(C=O)morpholine.

In an analogous manner, a compound of formula (XX), where $R^2$ is —Cl, and $R^{5a}$ is —$CO_2H$, and $Hal^1$ is —I, is reacted under amide bond formation conditions known to one skilled in the art, to provide a compound of formula (XXI), $R^2$ is —Cl, and $R^5$ is —(C=O)NHpyrrolidyl, —(C=O)NHpiperidinyl, —(C=O)NHphenyl, and $Hal^1$ is —I.

SCHEME L

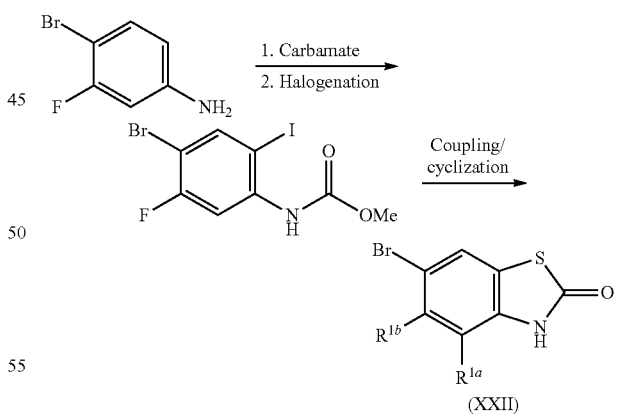

According to SCHEME L, 4-bromo-3-fluoroaniline is reacted with methylchloroformate, in the presence of a base such as aq. NaHCO$_3$, in a solvent such as DCM, and the like, at room temperature, for a period of 3-5 h, to afford methyl (4-bromo-3-fluorophenyl)carbamate. Methyl (4-bromo-3-fluorophenyl)carbamate is treated with an electrophilic halogen source such as NIS, a suitable acid such as trifluoromethanesulfonic acid (TfOH), in a suitable solvent such as ACN, to provide methyl (4-bromo-5-fluoro-2-iodophenyl)

carbamate. Methyl (4-bromo-5-fluoro-2-iodophenyl)carbamate is treated with a nucleophilic sulfur source such as Na₂S, in the presence of a copper (I) catalyst such as CuI, in a suitable solvent such as DMF, employing conventional heating at a temperature such as 80° C., followed by the addition of an acid source such as AcOH, employing additional heating at a temperature such as 130° C. to provide a benzothiazolone compound of formula (XXII), where $R^{1a}$ is H and $R^{1b}$ is —F. A compound of formula (XXII), where $R^{1a}$ is H and $R^{1b}$ is —H or —F is further protected with a suitable nitrogen protecting group, such as —BOC, under conditions known to one skilled in the art.

SCHEME M

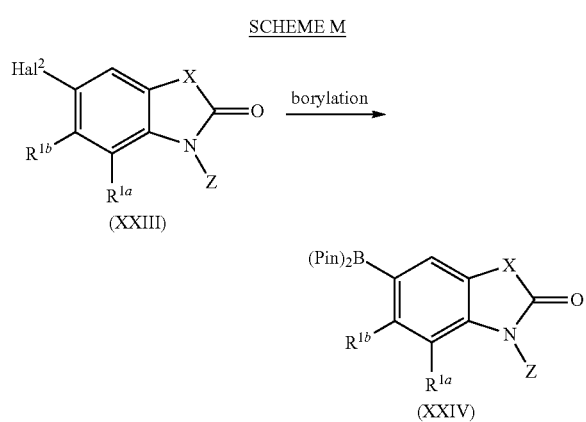

According to SCHEME M, a commercially available or synthetically accessible compound of formula (XXIII), where $R^{1a}$ is —H or —F, $R^{1b}$ is H, $Hal^2$ is —Br, X is S or NH, and Z is H or a suitable nitrogen protecting group such as —BOC, -acetyl, -SEM, is treated with bis(pinacolato)diboron in the presence of a palladium catalyst such as PdCl₂(dppf)-CH₂Cl₂, Pd₂(dba)₃, and the like, a base such as potassium acetate, in a suitable solvent such as dioxane, DMF, and the like, employing conventional heating, at a temperature ranging from 60-85° C., for a period of about 12-18 h, to provide a compound of formula (XXIV).

SCHEME N

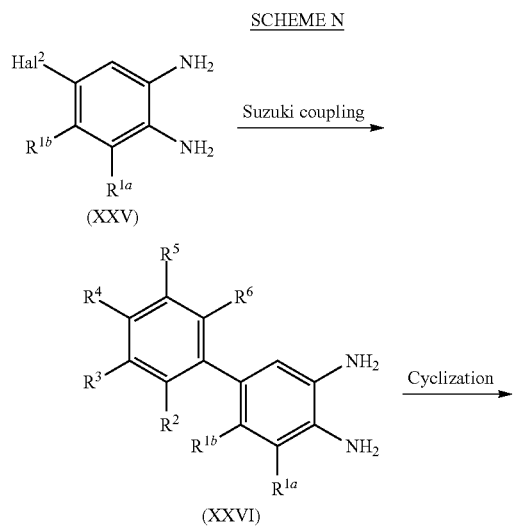

According to SCHEME N, a commercially available or synthetically accessible compound of formula (XXV), where $Hal^2$ is —Br, $R^{1a}$ is —H or —CH₃, $R^{1b}$ is H, is coupled in a Suzuki reaction, with a suitable commercially available or synthetically accessible aryl boronic acid or aryl boronic ester, a palladium catalyst such as PdCl₂(dtbpf), and the like, a base such as potassium phosphate, in a solvent such as dioxane and water, or a mixture thereof, employing conventional or microwave heating at a temperature such as 100° C. to provide a compound of formula (XXVI), where $R^2$ is $C_{1-5}$haloalkoxy and $R^6$ is —Cl. A compound of formula (XXVI) is treated with 1,1'-carbonyldiimidazole (CDI), in a solvent such as THF, and the like, to provide a compound of Formula (I), where X is NH, $R^{1a}$ is —H or —CH₃, $R^{1b}$ is H, $R^2$ is $C_{1-5}$haloalkoxy, and $R^6$ is —Cl. In addition, a compound of Formula (I), where $R^{1a}$ is —Cl, —CN, -Et, —CF₃, —OCH₃, or —OCF₃, $R^{1b}$ is H, $R^2$ is —$C_{1-5}$haloalkoxy, and $R^6$ is —Cl, may be prepared according to Scheme N from commercially available starting materials of formula (XXV).

SCHEME O

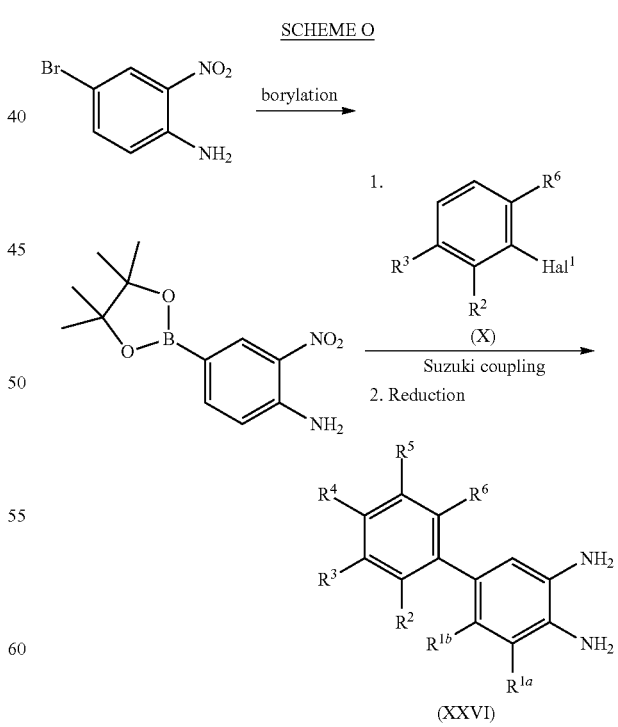

According to SCHEME O, 4-bromo-2-nitroaniline is borylated, under conditions previously described, to provide 2-nitro-4-(4,4,5,5-tetramethyl-1,3,2-dioxaborolan-2-yl)aniline. 2-Nitro-4-(4,4,5,5-tetramethyl-1,3,2-dioxaborolan-2-yl)aniline is reacted under Suzuki coupling conditions, for example, reaction with a halo compound of formula (X), where $R^2$ is halo, and $R^6$ is $C_{1-5}$haloalkoxy, a palladium catalyst such as Pd(dppf)Cl$_2$, PdCl$_2$(dtbpf), and the like, a base such as sodium carbonate, potassium phosphate, and the like, in a solvent such as dioxane and water, or a mixture thereof, employing conventional or microwave heating, at a temperature ranging from 80-100° C. Subsequent reduction of the nitro group employing conditions known to one skilled in the art, provides a compound of formula (XXVI). In a preferred method, the reduction conditions are employing iron powder, in a solvent such as EtOH, water, or a mixture thereof, concentrated HCl.

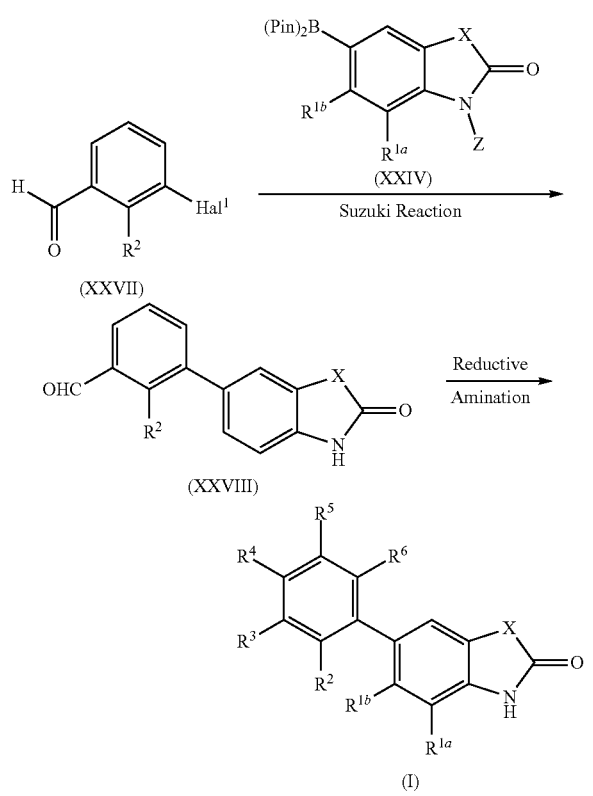

According to SCHEME P, a compound of formula (XXVII), where $R^2$ is $C_{1-5}$alkyl, and Hal$^1$ is —Br, is coupled with a commercially available or synthetically accessible boronic ester compound of formula (XXIV), where X=NH or S, Z is H or a suitable nitrogen protecting group, and $R^{1a}$ and $R^{1b}$ are H, in the presence of a suitable palladium catalyst such as PdCl$_2$(dtbpf), a base such a potassium phosphate, in a solvent such as dioxane, water, or a mixture thereof, employing conventional or microwave heating, at a temperature such as 100° C., to provide a compound of formula (XXVIII). A compound of formula (XXVIII) is treated with a commercially available or synthetically accessible optionally substituted amine such as morpholine or thiomorpholine optionally substituted with one or two —CH$_3$, tert-butyl piperazine-1-carboxylate, pyrrolidine, 3-fluoroazetidine, (3R,4S)-3-fluoropiperidin-4-ol, or 6-oxa-3-azabicyclo[3.1.1]heptane, a reducing agent such as Na(OAc)$_3$BH, and the like, in a suitable solvent such as DCM, MeOH, AcOH, and mixtures thereof, to provide a compound of Formula (I). Where Z is a protecting group, a deprotection step, employing conditions known to one skilled in the art, is necessary to form a compound of Formula (I).

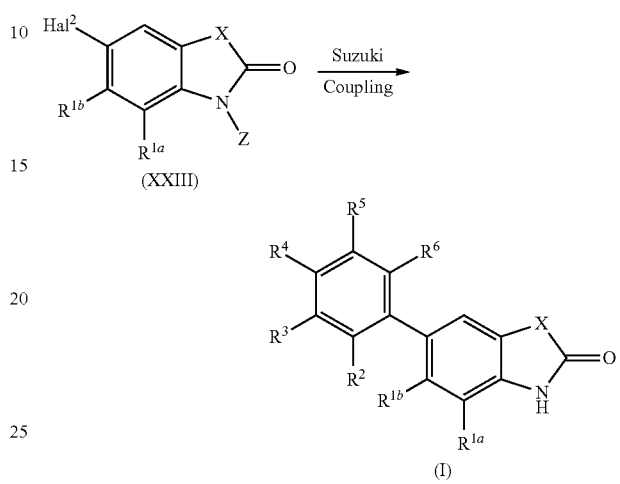

According to SCHEME Q, a compound of formula (XXIII), where Hal$^2$ is —Br, $R^{1a}$ and $R^{1b}$ are selected from H and F, is coupled in a Suzuki reaction, employing methods previously described, with a commercially available suitably substituted phenyl boronic acid or ester, to provide a compound of Formula (I).

A compound of Formula (I), where $R^2$ is —Br, and $R^6$ is —CH$_2$CN, is coupled in a Suzuki reaction, employing methods previously described, with a commercially available suitably substituted phenyl boronic acid or ester, to provide a compound of Formula (I), where $R^2$ is a phenyl ring optionally substituted with —F, —OCH$_3$, or $C_{3-6}$cycloalkyl, and $R^6$ is —CH$_2$CN.

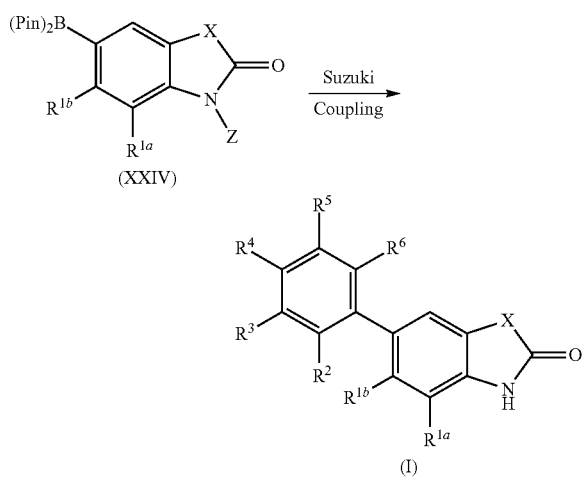

According to SCHEME R, a compound of formula (XXIV), where $R^{1a}$ and $R^{1b}$ are H is coupled in Suzuki reaction, employing methods previously described, with a commercially available or synthetically accessible suitably substituted compound of formula (VI), (VIII), (X), (XIV), (XXI) as previously described in the schemes above, to provide a compound of Formula (I).

A compound of Formula (I), where $R^2$ is —Br, and $R^6$ is —Cl, $C_{1-5}$alkyl, or $C_{1-5}$alkoxy, is coupled in Suzuki reaction, employing methods previously described, with a commercially available suitably substituted boronic acid or ester, to provide a compound of Formula (I), where $R^2$ is —$C_{3-6}$cycloalkyl, —CH=CH$_2$, pyridyl, pyridiyl substituted with —F, —OCH$_3$, or —CF$_3$, phenyl, phenyl substituted with —F, or —CN, 2-methoxyethyl)pyrazol-4-yl, 1-methylpyrazol-4-yl, 3,5-dimethylisoxazol-4-yl, 2-isopropylpyrazol-3-yl, 1H-pyrazol-4-yl, 1,5-dimethylpyrazol-4-yl, pyrimidin-5-yl, or 8-quinolyl.

A compound of Formula (I), where $R^2$ is —Cl, and $R^3$ is —Br, is coupled in Suzuki reaction, employing methods previously described, with a commercially available suitably substituted boronic acid or ester, to provide a compound of Formula (I), where $R^2$ is —Cl, and $R^3$ is 1-methylpyrazol-3-yl, 1-methylpyrazol-4-yl, 4-pyridyl, or dihydro-2H-pyridine-1-carboxylate.

Compounds of Formula (I) may be converted to their corresponding salts using methods known to one of ordinary skill in the art. For example, an amine of Formula (I) is treated with trifluoroacetic acid, HCl, or citric acid in a solvent such as Et$_2$O, CH$_2$Cl$_2$, THF, CH$_3$OH, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at rt (rt) under a nitrogen atmosphere. Where solutions were "dried," they were generally dried over a drying agent such as Na$_2$SO$_4$ or MgSO$_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via 1/16" PTFE (PolyTetraFluoroEthylene) tubing to a LTF-VS mixer (Little Things Factory GmbH (http://www.ltf-gmbh.com), unless otherwise indicated.

Normal-phase silica gel chromatography (FCC) was performed on silica gel (SiO$_2$) using prepacked cartridges.

Preparative reverse-phase high performance liquid chromatography (RP HPLC) was performed on either:

An Agilent HPLC with an Xterra Prep RP18 column (5 μM, 30×100 or 50×150 mm) or an XBridge $^{18}$C OBD column (5 μM, 30×100 or 50×150 mm), and a mobile phase of 5% ACN in 20 mM NH$_4$OH was held for 2 min, then a gradient of 5-99% ACN over 15 min, then held at 99% ACN for 5 min, with a flow rate of 40 or 80 mL/min.

or

A Shimadzu LC-8A Series HPLC with an Inertsil ODS-3 column (3 μm, 30×100 mm, T=45° C.), mobile phase of 5% ACN in H$_2$O (both with 0.05% TFA) was held for 1 min, then a gradient of 5-99% ACN over 6 min, then held at 99% ACN for 3 min, with a flow rate of 80 mL/min.

or

A Shimadzu LC-8A Series HPLC with an XBridge C18 OBD column (5 μm, 50×100 mm), mobile phase of 5% ACN in H$_2$O (both with 0.05% TFA) was held for 1 min, then a gradient of 5-99% ACN over 14 min, then held at 99% ACN for 10 min, with a flow rate of 80 mL/min.

or

A Gilson HPLC with an XBridge C18 column (5 μm, 100×50 mm), mobile phase of 5-99% ACN in 20 mM NH$_4$OH over 10 min and then hold at 99 ACN for 2 min, at a flow rate of 80 mL/min.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100-150 bar with a flow rate ranging from 40-60 mL/min. The column was heated to 35-40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, Mass.) or ACD/Name Version 10.01 (Advanced Chemistry).

Compounds designated as R* or S* are enantiopure compounds where the absolute configuration was not determined.

Intermediate 1. tert-Butyl 6-bromo-2-oxobenzo[d]thiazole-3(2H)-carboxylate

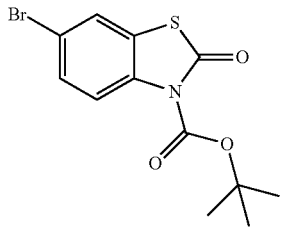 [SMILES: CC(C)(C)OC(=O)n1c(=O)sc2cc(Br)ccc21]

To a cooled (0° C.) solution of 6-bromobenzo[d]thiazol-2(3H)-one (200 mg, 0.87 mmol) in DMF (4.0 mL) was added 60 wt % sodium hydride in mineral oil (42 mg, 1.04 mmol). The mixture was warmed to rt for 2 h, followed by the addition of di-tert-butyl dicarbonate (285 mg, 1.30 mmol). After an additional 16 h at rt, water was added, and the mixture was extracted with EtOAc (3×) The combined organic extracts were dried (Na$_2$SO$_4$), filtered and concentrated in vacuo to afford the title compound as a waxy solid (283 mg, 95% yield). $^1$H NMR (400 MHz, CDCl$_3$) δ 7.79 (d, J=8.9 Hz, 1H), 7.50 (d, J=2.1 Hz, 1H), 7.42 (dd, J=8.9, 2.1 Hz, 1H), 1.65 (s, 9H).

Intermediate 2: 6-(4,4,5,5-Tetramethyl-1,3,2-dioxaborolan-2-yl)benzo[d]thiazol-2(3H)-one

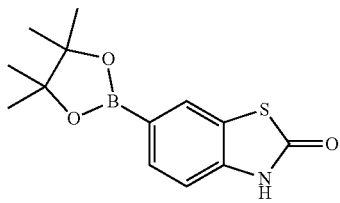 [SMILES: CC1(C)OB(c2ccc3[nH]c(=O)sc3c2)OC1(C)C]

To a solution of 6-bromobenzo[d]thiazol-2(3H)-one (1.0 g, 4.4 mmol) in DME (4.0 mL) were added bis(pinacoloato)diboron (1.1 g, 4.3 mmol), Pd$_2$(dba)$_3$ (119 mg, 0.13 mmol), butyldi-1-adamantylphosphine (140 mg, 0.39 mmol) and potassium acetate (1.3 g, 13 mmol). The reaction mixture was purged with nitrogen for 10 minutes and then heated at 65° C. for 16 h. After cooling to rt, the solvent was removed in vacuo. The crude residue was triturated with DCM and the filtrate was purified by FCC (SiO$_2$; 0-30% EtOAc/hexanes) to afford the title compound as a yellow solid (150 mg, 13% yield). MS (ESI): mass calcd. for C$_{13}$H$_{16}$BNO$_3$S, 277.1; m/z found, 278.2 [M+H]. $^1$H NMR (500 MHz, CDCl$_3$) δ 12.02 (s, 1H), 7.90-7.73 (m, 1H), 7.57 (dd, J=7.9, 1.2 Hz, 1H), 7.12 (dd, J=7.9, 0.6 Hz, 1H), 1.29 (s, 12H).

Intermediate 3: 3-Acetyl-6-(4,4,5,5-tetramethyl-1,3,2-dioxaborolan-2-yl)benzo[d]thiazol-2(3H)-one

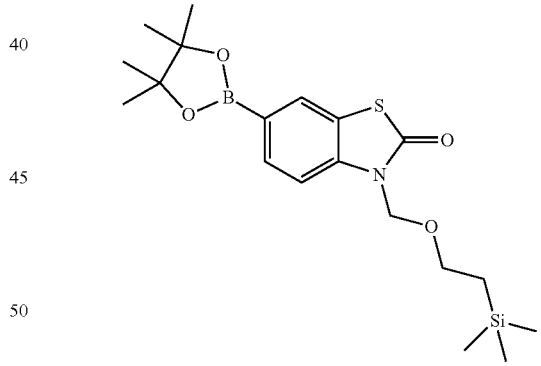

To a solution of Intermediate 1, tert-butyl 6-bromo-2-oxobenzo[d]thiazole-3(2H)-carboxylate, (1.0 g, 3.0 mmol) in dioxane (10 mL) was added potassium acetate (590 mg, 6.1 mmol), bis(pinacolato)diboron (920 mg, 3.6 mmol) and PdCl$_2$(dppf)-CH$_2$Cl$_2$ (443 mg, 0.61 mmol). The reaction mixture was degassed with nitrogen and then heated at 85° C. for 16 h. After cooling to rt, brine was added and the mixture was extracted with EtOAc (×2). The combined organic extracts were dried (Na$_2$SO$_4$), filtered and concentrated to give a brown solid. Purification (FCC, SiO$_2$; 0-20% EtOAc/hexanes) afforded the title compound (524 mg, 54% yield). MS (ESI): mass calcd. for C$_{15}$H$_{18}$BNO$_4$S, 319.1; m/z found, 320.2 [M+H]. $^1$H NMR (500 MHz, DMSO-d$_6$) δ 8.21 (dd, J=8.3, 2.1 Hz, 1H), 7.97 (d, J=1.6 Hz, 1H), 7.72-7.57 (m, 1H), 2.67 (s, 3H), 1.30 (s, 12H).

Intermediate 4: 6-(4,4,5,5-Tetramethyl-1,3,2-dioxaborolan-2-yl)-3-((2-(trimethylsilyl)ethoxy)methyl)benzo[d]thiazol-2(3H)-one

Step A: 6-Bromo-3-((2-(trimethylsilyl)ethoxy)methyl)benzo[d]thiazol-2(3H)-one To a cooled (0° C.) solution of 6-bromobenzo[d]thiazol-2(3H)-one (1.0 g, 4.4 mmol) in THF (8.9 mL) was added 60 wt % sodium hydride in mineral oil (209 mg, 5.2 mmol) portionwise. After 20 minutes, 2-(trimethylsilyl)ethoxymethyl chloride (0.77 mL, 4.4 mmol) was added dropwise. The resulting yellow solution was allowed to warm to rt and stirred for a total of 2 h. Brine was added and the mixture was extracted with EtOAc (×3). The combined organic extracts were dried (Na$_2$SO$_4$), filtered and concentrated in vacuo. Purification (FCC, SiO$_2$; 0-30% EtOAc/hexanes)

afforded the desired product as a white solid (1.2 g, 77% yield). $^1$H NMR (400 MHz, CDCl$_3$) δ 8.10-7.99 (m, 1H), 7.64 (ddd, J=7.7, 2.9, 1.5 Hz, 1H), 7.38 (dd, J=8.3, 2.8 Hz, 1H), 5.42 (d, J=2.7 Hz, 2H), 3.63 (t, J=7.8 Hz, 2H), 0.92 (t, J=7.8 Hz, 2H), 0.00 (s, 9H).

Step B: 6-(4,4,5,5-Tetramethyl-1,3,2-dioxaborolan-2-yl)-3-((2-(trimethylsilyl)ethoxy)methyl)benzo[d]thiazol-2(3H)-one To a solution of 6-bromo-3-((2-(trimethylsilyl)ethoxy)methyl)benzo[d]thiazol-2(3H)-one (960 mg, 2.7 mmol) in dioxane (14 mL) was added potassium acetate (523 mg, 5.3 mmol), bis(pinacolato)diboron (812 mg, 3.2 mmol) and PdCl$_2$(dppf) (194 mg, 0.27 mmol). The reaction mixture was degassed with nitrogen and then heated at 90° C. for 2 h. After cooling to rt, brine was added and the mixture was extracted with EtOAc (×2). The combined organic extracts were dried (Na$_2$SO$_4$), filtered and concentrated to remove solvent. Purification (FCC, SiO$_2$; 0-50% EtOAc/hexanes) afforded the title compound (922 mg, 85% yield). $^1$H NMR (400 MHz, DMSO-d$_6$) δ 8.02 (d, J=1.1 Hz, 1H), 7.74 (dd, J=8.1, 1.2 Hz, 1H), 7.45 (d, J=8.1 Hz, 1H), 5.43 (s, 2H), 3.64 (dd, J=8.4, 7.5 Hz, 2H), 1.38 (s, 12H), 0.97-0.89 (m, 2H), 0.00 (s, 9H).

Intermediate 5: tert-Butyl 6-bromo-5-fluoro-2-oxobenzo[d]thiazole-3(2H)-carboxylate

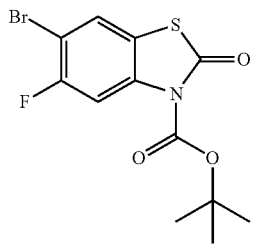 [SMILES: CC(C)(C)OC(=O)n1c(=O)sc2cc(Br)c(F)cc21]

Step A: Methyl (4-bromo-3-fluorophenyl)carbamate

To a solution of 4-bromo-3-fluoroaniline (1.0 g, 5.23 mmol) in DCM (8.0 mL) was added a solution of NaHCO$_3$ (464 mg, 5.5 mmol) in water (10.0 mL). Methylchloroformate (0.61 mL, 7.90 mmol) was added dropwise to the vigorously stirred biphasic mixture over a period of 30 minutes. The resulting mixture was stirred at rt for 4 h. The organic phase was separated, washed twice with water and the aqueous phase was extracted with DCM. The combined organic extracts were dried (Na$_2$SO$_4$), filtered and concentrated to obtain the product as a white solid (1.4 g, 92% yield). $^1$H NMR (500 MHz, CDCl$_3$) δ 7.49-7.36 (m, 2H), 7.01-6.90 (m, 1H), 6.70 (s, 1H), 3.80 (s, 3H).

Step B: Methyl (4-bromo-5-fluoro-2-iodophenyl)carbamate

To a solution of methyl (4-bromo-3-fluorophenyl)carbamate (1.1 g, 4.4 mmol) in acetonitrile (11.0 mL) were added N-iodosuccinimide (980 mg, 4.4 mmol) followed by trifluoromethanesulfonic acid (0.04 mL, 0.43 mmol). The resulting solution was stirred at rt under nitrogen for 16 h. The reaction mixture was then poured into saturated aqueous NaHCO$_3$ and extracted with EtOAc (×3). The combined organic phases were washed with 1N Na$_2$S$_2$O$_3$ and the aqueous phase was backextracted with EtOAc. The combined organic extracts were dried (Na$_2$SO$_4$), filtered and concentrated in vacuo. Purification (FCC, SiO$_2$; 0-20% EtOAc/hexanes) afforded the title compound as a white solid (1.3 g, 77% yield). $^1$H NMR (400 MHz, DMSO-d$_6$) δ 9.00 (s, 1H), 8.17 (d, J=7.7 Hz, 1H), 7.52 (d, J=10.5 Hz, 1H), 3.67 (s, 3H).

Step C: 6-Bromo-5-fluorobenzo[d]thiazol-2(3H)-one

To a solution of methyl (4-bromo-5-fluoro-2-iodophenyl)carbamate (400 mg, 1.1 mmol) in DMF (2.0 mL) were added sodium sulfide nonahydrate (770 mg, 3.2 mmol) and copper (I) iodide (20 mg, 0.1 mmol) in a pressure vial. The mixture was degassed with nitrogen for 10 minutes and heated at 80° C. for 16 h. Acetic acid (3.0 mL) was added to the cooled reaction mixture and then heated at 130° C. for 72 h in the same vial. After cooling to rt, saturated aqueous NaHCO$_3$ was added, and the mixture was extracted with EtOAc. The combined organic extracts were dried (Na$_2$SO$_4$), filtered and concentrated in vacuo. The crude product was purified by reverse-phase HPLC (XBridge C18 column (5 μm, 100×4.6 mm), mobile phase of 10-100% ACN in 20 mM NH$_4$OH) to afford the title compound as a white solid (50 mg, 19% yield). $^1$H NMR (400 MHz, DMSO-d$_6$) δ 12.17 (s, 1H), 8.00 (d, J=6.8 Hz, 1H), 7.09 (d, J=9.1 Hz, 1H).

Step D: tert-Butyl 6-bromo-5-fluoro-2-oxobenzo[d]thiazole-3(2H)-carboxylate

To a 0° C. solution of 6-bromo-5-fluorobenzo[d]thiazol-2(3H)-one (48 mg, 0.19 mmol) in DMF (0.82 mL), was added NaH (60% dispersion in mineral oil, 9.2 mg, 0.23 mmol). The reaction mixture was stirred at rt for 2 h. Di-tert-butyl dicarbonate (63 mg, 0.29 mmol) was added and the reaction mixture stirred at room temperature overnight. The reaction mixture was diluted with water, extracted with EtOAc. The combined organics were dried (Na$_2$SO$_4$), filtered and concentrated under reduced pressure to afford the title compound which was used without further purification (69 mg, 100%).

Intermediate 6: 2-Iodo-1-isopropoxy-3-(trifluoromethoxy)benzene

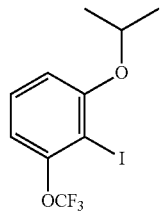 [SMILES: CC(C)Oc1cccc(OC(F)(F)F)c1I]

Step A: 1-(Methoxymethoxy)-3-(trifluoromethoxy)benzene

To a solution of 3-(trifluoromethoxy) phenol (4.0 g, 23 mmol) in dry THF (16 mL) at 0° C. was added potassium tert-butoxide, portionwise (10 g, 90 mmol) over 15 minutes with vigorous stirring. The reaction was then warmed to 0° C. and stirred for 30 min. The reaction was cooled to 0° C. and chloromethyl methyl ether (4.3 mL, 56 mmol) was added dropwise. After the addition, the stirring was continued for another 4 h at rt. The reaction mixture was diluted with water and extracted with EtOAc, dried (Na$_2$SO$_4$), filtered and concentrated. Purification (FCC, SiO$_2$; 0-10% EtOAc/hexanes) afforded the title compound as an oil (5.0 g, 62% yield). $^1$H NMR (400 MHz, CDCl$_3$): δ 7.32-7.24 (m, 1H), 7.01-6.94 (m, 1H), 6.94-6.90 (m, 1H), 6.89-6.82 (m, 1H), 5.17 (s, 2H).

Step B: 2-Iodo-1-(methoxymethoxy)-3-(trifluoromethoxy)benzene

To a solution of 1-(methoxymethoxy)-3-(trifluoromethoxy)benzene (1.0 g, 4.5 mmol) in THF (5 mL), precooled to −78° C. was added n-BuLi (2.5 M in hexanes, 3.0 mL, 33 mmol) dropwise over 30 min, maintaining the inner temperature below −70° C. After the addition, the resulting mixture was stirred for 2 h at −78° C. and a solution of iodine (1.5 g, 5.9 mmol) in THF (5 mL) was added dropwise over 1 h. The reaction mixture was then warmed to rt for another hour and quenched with saturated aqueous Na$_2$S$_2$O$_3$. The crude mixture was extracted with EtOAc and the combined organic extracts were dried (Na$_2$SO$_4$), concentrated and purified by FCC (SiO$_2$; 0-5% hexanes—5% EtOAc/hexanes) to afford the title compound as an oil (911 mg, 58% yield). $^1$H NMR (400 MHz, CDCl$_3$): δ 7.35-7.21 (m, 1H), 7.00 (dd, J=8.4, 1.2 Hz, 1H), 6.97-6.93 (m, 1H), 5.16 (s, 2H), 3.52 (s, 3H).

Step C: 2-Iodo-3-(trifluoromethoxy)phenol

To a flask containing 2-iodo-1-(methoxymethoxy)-3-(trifluoromethoxy)benzene (320 mg, 0.92 mmol) was added 4.0 M HCl in dioxane (4.0 mL). Stirring was maintained at rt for 40 min. The reaction mixture was diluted with DCM (10 mL) and concentrated in vacuo. The process was repeated with EtOAc (10 mL) to remove any excess HCl, to provide the title compound (255 mg, 91% yield). $^1$H NMR (400 MHz, CDCl$_3$): δ 7.30-7.22 (m, 1H), 6.94 (d, J=8.3 Hz, 1H), 6.88-6.83 (m, 1H), 5.56 (s, 1H).

Step D: 2-Iodo-1-isopropoxy-3-(trifluoromethoxy)benzene

To a suspension of 2-iodo-3-(trifluoromethoxy)phenol (255 mg, 0.84 mmol), and cesium carbonate (546 mg, 1.7 mmol) in DMF (3.0 mL) was added 2-iodopropane (0.21 mL, 2.1 mmol). The resulting mixture was stirred at rt for 1 h. The crude reaction mixture was diluted with water and extracted with EtOAc (×2). The organic extracts were dried (Na$_2$SO$_4$), and concentrated under reduced pressure to afford the title compound as an oil (285 mg, 98% yield). $^1$H NMR (400 MHz, CDCl$_3$): δ 7.33-7.22 (m, 1H), 6.93-6.83 (m, 1H), 6.77-6.66 (m, 1H), 4.67-4.51 (m, 1H), 1.44-1.35 (d, J=6.1 Hz, 6H).

Intermediate 7: 1-(Cyclopropylmethoxy)-2-iodo-3-(trifluoromethoxy)benzene

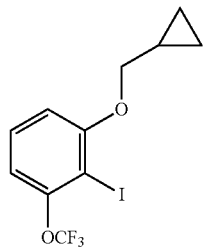 [SMILES: FC(F)(F)Oc1cccc(OCC2CC2)c1I]

The title compound was prepared in a manner analogous to Intermediate 6, substituting (bromomethyl)cyclopropane for 2-iodopropane in Step D. $^1$H NMR (400 MHz, DMSO-d$_6$): δ 7.45 (t, J=8.3 Hz, 1H), 7.05-6.91 (m, 2H), 3.97 (d, J=6.7 Hz, 2H), 1.33-1.18 (m, 1H), 0.64-0.55 (m, 2H), 0.44-0.35 (m, 2H).

Intermediate 8: 2-(3-chloro-2-iodophenyl)acetonitrile

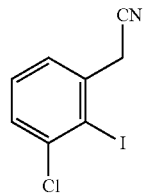 [SMILES: N#CCc1cccc(Cl)c1I]

Step A: 1-(Bromomethyl)-3-chloro-2-iodobenzene

To a solution of 1-chloro-2-iodo-3-methylbenzene (4.0 g, 16 mmol) in CCl$_4$ (12 mL), were added N-bromosuccinimide (NBS) (5.6 g, 32 mmol) and 1,1'-azobis(cyclohexanecarbonitrile) (AIBN) (3.9 g, 16 mmol). The mixture was degassed with nitrogen and then heated at 90° C. for 1 h. After cooling to rt, silica gel was added, and the solvent was removed in vacuo. Purification (FCC, SiO$_2$; 0-5% EtOAc/hexanes) provided the title compound as an oil (3.7 g, 70% yield). $^1$H NMR (400 MHz, CDCl$_3$): δ 7.37 (m, 2H), 7.29-7.23 (m, 1H), 4.65 (s, 2H).

Step B: 2-(3-Chloro-2-iodophenyl)acetonitrile

To a solution of 1-(bromomethyl)-3-chloro-2-iodobenzene (1.0 g, 3.0 mmol) in DMF (13 mL) was added a solution of potassium cyanide (236 mg, 3.6 mmol) in water (1.3 mL). The mixture was stirred at 40° C. for 1 h. The reaction mixture was cooled to rt, diluted with water, and extracted with EtOAc (2×). The organic extracts were dried (Na$_2$SO$_4$), and concentrated to obtain the product as white solid (770 mg, 92% yield). $^1$H NMR (500 MHz, CDCl$_3$) δ 7.44 (m, 2H), 7.36-7.33 (m, 1H), 3.93-3.83 (m, 2H).

Intermediate 9: 2-(3-bromo-2-chlorophenyl)acetonitrile

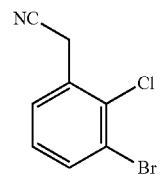

The title compound was prepared in a manner analogous to Intermediate 8, substituting 1-bromo-2-chloro-3-methylbenzene for 1-chloro-2-iodo-3-methylbenzene in Step A and sodium cyanide for potassium cyanide in Step B. $^1$H NMR (400 MHz, DMSO-d$_6$) δ 7.80 (dd, J=8.1, 1.5 Hz, 1H), 7.60-7.56 (m, 1H), 7.40-7.31 (m, 1H), 4.20 (s, 2H).

Intermediate 10:
2-(3-bromo-2,4-dichlorophenyl)acetonitrile

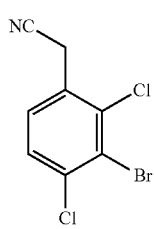

The title compound was prepared in a manner analogous to Intermediate 8, substituting 2-bromo-1,3-dichloro-4-methylbenzene for 1-chloro-2-iodo-3-methylbenzene in Step A and sodium cyanide for potassium cyanide in Step B. $^1$H NMR (400 MHz, DMSO-$d_6$) δ 7.78-7.67 (m, 1H), 7.59 (t, J=9.7 Hz, 1H), 4.19 (s, 2H).

Intermediate 11:
2-(3-bromo-2-iodophenyl)acetonitrile

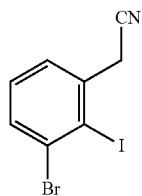

The title compound was prepared in a manner analogous to Intermediate 8, substituting 1-bromo-2-iodo-3-methylbenzene for 1-chloro-2-iodo-3-methylbenzene in Step A. $^1$H NMR (400 MHz, DMSO-$d_6$) δ 7.80-7.68 (m, 1H), 7.58-7.47 (m, 1H), 7.42-7.35 (m, 1H), 4.18 (s, 2H).

Intermediate 12.
2-(3-Chloro-2-iodophenyl)-2-methylpropanenitrile

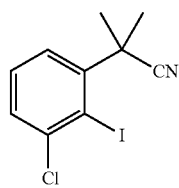

To an ice cold solution of 60 wt % sodium hydride/mineral oil (180 mg, 4.5 mmol) in DMF (5.0 mL) was added 2-(3-chloro-2-iodophenyl)acetonitrile (Intermediate 8, 250 mg, 0.90 mmol), in THF (2.5 mL) dropwise. The reaction mixture was stirred for 20 minutes at 0° C., and then iodomethane (0.06 mL, 0.90 mmol) was added. After stirring at rt for 16 h, the reaction mixture was quenched with water (1.0 mL), and the solvents were removed in vacuo. The crude residue was partitioned between EtOAc and 1N HCl. The organic layer was dried (Na$_2$SO$_4$), filtered and concentrated to obtain the product as an oil (370 mg, 90% yield), which was used directly in the next reaction without further purification.

Intermediate 13.
4-(3-Bromo-2,4-dichlorobenzyl)morpholine

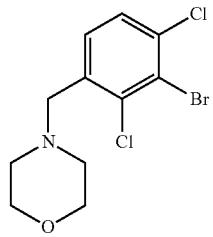 [SMILES: Clc1ccc(CN2CCOCC2)c(Cl)c1Br]

Step A:
2-Bromo-4-(bromomethyl)-1,3-dichlorobenzene

A solution of 3-bromo-2,4-dichlorotoluene (2 g, 8.3 mmol), N-bromosuccinimide (3.0 g, 17 mmol), and 1,1'-azobis(cyanocyclohexane) (2.0 g, 8.3 mmol) in carbon tetrachloride (6.4 mL) was degassed with nitrogen for 10 minutes. The reaction mixture was heated at 90° C. under nitrogen for 3 h. After cooling to rt, DCM and 15 g of silica gel were added. The slurry was concentrated in vacuo and then purified by FCC (SiO$_2$; hexanes—10% EtOAc/hexanes) to afford the desired product (1.5 g, 58% yield). $^1$H NMR (400 MHz, CDCl$_3$) δ 7.42-7.31 (m, 2H), 4.59 (s, 2H).

Step B: 4-(3-Bromo-2,4-dichlorobenzyl)morpholine

To a solution of 2-bromo-4-(bromomethyl)-1,3-dichlorobenzene (250 mg, 0.78 mmol) and triethylamine (0.22 mL, 1.6 mmol) in DCM (2.6 mL) was added morpholine (0.14 mL, 1.6 mmol). The reaction mixture was stirred at rt for 40 min. Water was added, the layers were separated, and the aqueous layer was extracted three times with EtOAc. The combined organic extracts were dried (Na$_2$SO$_4$), filtered and concentrated to give an oil, which was used directly without further purification. MS (ESI): mass calcd. for C$_{11}$H$_{12}$BrCl$_2$NO, 323.0; m/z found, 324.0 [M+H]$^+$. $^1$H NMR (400 MHz, CDCl$_3$) δ 7.67-7.58 (m, 1H), 7.58-7.50 (m, 1H), 3.65-3.53 (m, 6H), 2.48-2.37 (m, 4H).

Intermediate 14. 3,4-Dichloro-2-iodobenzoic acid

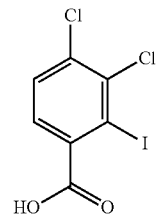

Step A: 2-Amino-3,4-dichlorobenzoic acid

To a cooled (0° C.) suspension of potassium hydroxide (370 mg, 6.6 mmol) and potassium chloride (920 mg, 12.3 mmol) in water (10.5 mL) was added 6,7-dichloroindoline-2,3-dione (1 g, 4.6 mmol), followed by dropwise addition of 30 wt % aqueous hydrogen peroxide (1.1 mL, 35 mmol).

The resulting mixture was stirred for 30 minutes at rt. Acetic acid (4.0 mL) was added and the resulting yellow precipitate was filtered, washed with water and dried in vacuo to afford the desired product (910 mg, 95% yield). $^1$H NMR (400 MHz, DMSO-$d_6$) δ 13.16 (s, 1H), 7.73 (d, J=8.6 Hz, 1H), 7.11 (s, 2H), 6.81 (d, J=8.6 Hz, 1H).

Step B: 3,4-Dichloro-2-iodobenzoic acid

To a cooled (0° C.) solution of 2-amino-3,4-dichlorobenzoic acid (900 mg, 4.4 mmol) in DMSO (4.0 mL) was added conc. $H_2SO_4$ (8.0 mL), and the mixture was stirred for 10 minutes. To this ice cold solution was added sodium nitrite (452 mg, 6.5 mmol) in water (3.0 mL) dropwise. After 1 h at 0° C., a solution of potassium iodide (1.80 g, 10.9 mmol) in water (3.0 mL) was added and stirring was maintained at rt for an additional 2 h. The reaction mixture was diluted with EtOAc and washed with 2 N sodium sulfite solution. The organic layer was dried ($Na_2SO_4$), filtered, and concentrated to afford the title compound as yellow solid (940 mg, 67% yield). $^1$H NMR (400 MHz, DMSO-$d_6$) δ 13.71 (s, 1H), 7.74 (d, J=8.4 Hz, 1H), 7.50 (d, J=8.3 Hz, 1H).

Intermediate 15.
2-(3,4-Dichloro-2-iodophenyl)acetonitrile

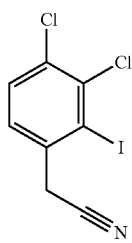 [SMILES: N#CCc1ccc(Cl)c(Cl)c1I]

Step A. (3,4-Dichloro-2-iodophenyl)methanol

To a solution of 3,4-dichloro-2-iodobenzoic acid (Intermediate 14, 450 mg, 1.42 mmol) in THF (2.5 mL) was added borane-THF (1 M/THF, 4.0 mL, 4.0 mmol). The resulting solution was heated at 50° C. for 1 h. After cooling to rt, the reaction mixture was cautiously quenched with methanol (1.0 mL) and the solvent was removed in vacuo to afford a white solid (455 mg, 98%). The title compound was used crude in the next step without further purification.

Step B.
1,2-Dichloro-4-(chloromethyl)-3-iodobenzene

A solution of (3,4-dichloro-2-iodophenyl)methanol (450 mg, 1.49 mmol) in DCM (2.0 mL) and DMF (0.15 mL) was cooled to 0° C. Thionyl chloride (0.2 mL, 2.9 mmol) was added dropwise, and the reaction was stirred for 10 minutes at rt. The solvents were removed in vacuo. The residue was diluted with aqueous $NaHCO_3$ and extracted with ether (×2). The combined organic extracts were dried over $Na_2SO_4$, and concentrated in vacuo (455 mg, 95%). The title compound was used crude in the next step without further purification.

Step C. 2-(3,4-Dichloro-2-iodophenyl)acetonitrile

To a solution of 1,2-dichloro-4-(chloromethyl)-3-iodobenzene (450 mg, 1.4 mmol) in DMF (2.0 mL) was added sodium cyanide (137 mg, 2.8 mmol). After stirring the reaction mixture at rt for 2 h, ice was added and the aqueous layer was extracted with EtOAc (×2). The organic extracts were dried ($Na_2SO_4$), filtered, and concentrated to obtain the title compound as an oil (410 mg, 94% yield). $^1$H NMR (400 MHz, DMSO-$d_6$) δ 7.75 (d, J=8.3 Hz, 1H), 7.51 (m, 1H), 4.18 (s, 2H).

Intermediate 16.
2-(2-Bromo-3-(trifluoromethoxy)phenyl)acetonitrile

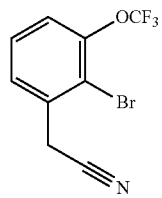 [SMILES: N#CCc1cccc(OC(F)(F)F)c1Br]

The title compound was prepared in a manner analogous to Intermediate 15, substituting 2-bromo-3-(trifluoromethoxy)benzoic acid for 3,4-dichloro-2-iodobenzoic acid. $^1$H NMR (400 MHz, $CDCl_3$) b 7.54-7.48 (m, 1H), 7.45-7.38 (m, 1H), 7.36-7.27 (m, 1H), 3.91 (s, 2H).

Intermediate 17.
2-(3-Chloro-2-iodophenyl)propanenitrile

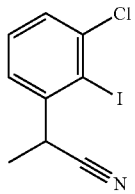

To a cooled (−78° C.) solution of LDA (1.0 M/THF, 1.4 mL, 1.4 mmol) in THF (2.5 mL) was added a solution of 2-(3-chloro-2-iodophenyl)acetonitrile (Intermediate 8, 316 mg, 1.1 mmol), in THF (2.5 mL). The resulting yellow solution was stirred at −78° C. for 1 h. Iodomethane (0.1 mL, 1.3 mmol) was added dropwise, and the mixture was slowly warmed to rt over 2 h. The reaction mixture was then treated with aqueous solution of $NH_4Cl$ and extracted with EtOAc (×2). The organic layers were dried over $Na_2SO_4$, filtered, and concentrated. Purification (FCC, $SiO_2$; 0-20% EtOAc/hexanes) provided the title compound as an oil (120 mg, 36%). $^1$H NMR (500 MHz, $CDCl_3$) δ 7.54-7.41 (m, 2H), 7.39-7.31 (m, 1H), 4.45-4.36 (m, 1H), 1.68-1.56 (m, 3H).

Intermediate 18.
1-(3-Chloro-2-iodophenyl)cyclopropanecarbonitrile

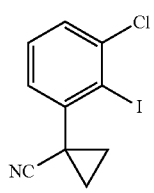

The title compound was prepared in a manner analogous to Intermediate 17, substituting 1,2-dibromoethane for iodomethane. ¹H NMR (400 MHz, DMSO-d₆) δ 7.67-7.56 (m, 1H), 7.50-7.36 (m, 2H), 1.88-1.75 (m, 2H), 1.54-1.35 (m, 2H).

Intermediate 19.
1-(3-Chloro-2-iodophenyl)cyclobutanecarbonitrile

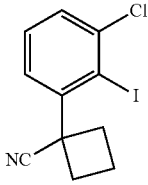

The title compound was prepared in a manner analogous to Intermediate 17, substituting 1,3-dibromopropane for iodomethane to afford a crude product which was used without further purification.

Intermediate 20.
1-(3-Bromo-2,4-dichloro-benzyl)piperidine

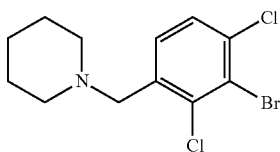 [SMILES: Clc1ccc(CN2CCCCC2)c(Cl)c1Br]

The title compound was prepared in a manner analogous to Intermediate 13, substituting piperidine for morpholine in Step B. MS (ESI): mass calcd. for C₁₂H₁₄BrCl₂N, 321.0; m/z found, 322.0 [M+H]⁺.

Intermediate 21.
4-(3-Bromo-2-chlorobenzyl)morpholine

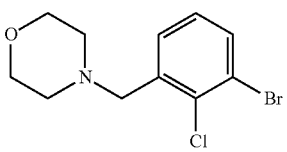 [SMILES: Clc1c(Br)cccc1CN1CCOCC1]

The title compound was prepared in a manner analogous to Intermediate 13, substituting 3-bromo-2-chlorotoluene for 3-bromo-2,4-dichlorotoluene in Step A ¹H NMR (400 MHz, DMSO-d₆) δ 7.69 (dd, J=8.0, 1.6 Hz, 1H), 7.51 (dd, J=7.7, 1.6 Hz, 1H), 7.28 (t, J=7.8 Hz, 1H), 3.64-3.52 (m, 6H), 2.47-2.36 (m, 4H).

Intermediate 22.
1-(3-Bromo-2-chlorobenzyl)piperidine

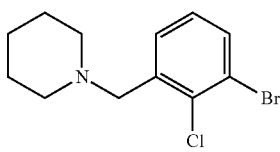 [SMILES: Clc1c(Br)cccc1CN1CCCCC1]

The title compound was prepared in a manner analogous to Intermediate 13, substituting 3-bromo-2-chlorotoluene for 3-bromo-2,4-dichlorotoluene in Step A and piperidine for morpholine in Step B. ¹H NMR (400 MHz, DMSO-d₆) 7.67 (dd, J=8.0, 1.6 Hz, 1H), 7.51 (dd, J=7.7, 1.5 Hz, 1H), 7.28 (t, J=7.8 Hz, 1H), 3.53 (s, 2H), 2.38 (t, J=5.2 Hz, 4H), 1.56-1.45 (m, 4H), 1.45-1.28 (m, 2H).

Intermediate 23.
4-(3-Bromo-2-chlorobenzyl)-2,2-dimethylmorpholine

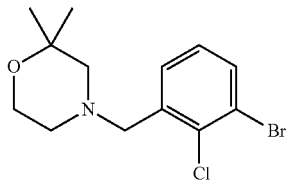 [SMILES: CC1(C)CN(Cc2cccc(Br)c2Cl)CCO1]

To a flask containing 3-bromo-2-chlorobenzaldehyde (250 mg, 1.14 mmol) and 2,2-dimethylmorpholine (157 mg, 1.37 mmol) in DCM (3.8 mL) was added acetic acid (6.5 μL, 0.11 mmol), followed by sodium triacetoxyborohydride (290 mg, 1.37 mmol). The reaction mixture was stirred at rt for 1 h, diluted with water, and then extracted twice with EtOAc. The combined organic extracts were dried over Na₂SO₄, filtered, and concentrated in vacuo to provide the title compound as an oil. ¹H NMR (400 MHz, DMSO-d₆) δ 7.68 (dd, J=8.0, 1.6 Hz, 1H), 7.53 (ddd, J=7.6, 1.6, 0.8 Hz, 1H), 7.28 (t, J=7.8 Hz, 1H), 3.62 (dd, J=5.7, 4.0 Hz, 2H), 3.53 (s, 2H), 2.40-2.27 (m, 2H), 2.21 (s, 2H), 1.20-1.09 (s, 6H).

Intermediate 24. 4-(3-Bromo-2-chlorobenzyl)-2-(trifluoromethyl)morpholine

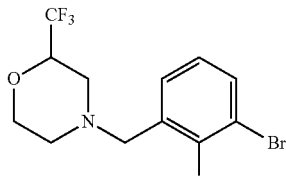

The title compound was prepared in a manner analogous to Intermediate 23, substituting 2-(trifluoromethyl)morpholine hydrochloride for 2,2-dimethylmorpholine. ¹H NMR (400 MHz, DMSO-d₆) δ 7.72 (dd, J=8.0, 1.5 Hz, 1H), 7.53 (dd, J=7.7, 1.6 Hz, 1H), 7.29 (t, J=7.8 Hz, 1H), 4.26-4.12 (m, 1H), 3.92 (ddd, J=11.3, 3.3, 1.6 Hz, 1H), 3.70 (s, 2H), 3.67-3.57 (m, 1H), 2.94-2.83 (m, 1H), 2.72-2.61 (m, 1H), 2.32-2.19 (m, 2H).

Intermediate 25.
3-Bromo-2-chloro-N,N-dimethylaniline

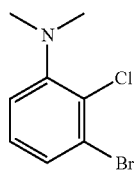

A solution of 3-bromo-2-chloroaniline (500 mg, 2.0 mmol) and 37 wt % aqueous formaldehyde (3 mL) in formic acid (3 mL) was heated at 70° C. for 16 h. After cooling to rt, the reaction mixture was filtered and the filtrate was concentrated in vacuo. The residue was dissolved in water (5 mL) and then adjusted to pH 8 with solid NaHCO$_3$. The solution was extracted with DCM (3×10 mL), and the combined organic extracts were dried (Na$_2$SO$_4$), filtered and concentrated in vacuo to afford the crude product (430 mg, 30%), which was used without further purification.

Intermediate 26: 5-(4,4,5,5-Tetramethyl-1,3,2-dioxaborolan-2-yl)-1H-benzo[d]imidazol-2(3H)-one

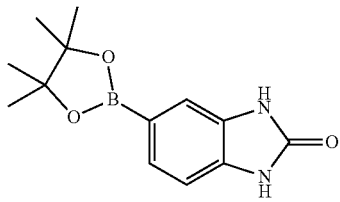 [SMILES: CC1(C)OB(c2ccc3[nH]c(=O)[nH]c3c2)OC1(C)C]

To a round-bottomed flask containing DMF (35 mL) was added 5-bromo-1,3-dihydro-benzimidazol-2-one (5.0 g, 23 mmol), and the resulting solution was purged with nitrogen for 15 minutes. To this solution were added successively bis(pinacolato)diboron (7.2 g, 28 mmol), potassium acetate (6.9 g, 70 mmol), and PdCl$_2$(dppf)-CH$_2$Cl$_2$ (1.7 g, 2.4 mmol). After heating at 95° C. for 16 h, the black mixture was cooled to rt and diluted with brine (50 mL) and EtOAc (75 mL). The resulting precipitate was removed by filtration and washed with EtOAc. The filtrate was transferred to a separatory funnel and the layers separated. The organic layer was washed with water (3×50 mL), dried (Na$_2$SO$_4$), filtered and concentrated in vacuo. Trituration of the crude residue with DCM provided the desired product as a white solid (2.5 g, 41% yield). MS (ESI): mass calcd. for C$_{13}$H$_{17}$BN$_2$O$_3$, 260.1; m/z found, 261.2 [M+H]$^+$. 1H NMR (400 MHz, DMSO-d$_6$) δ 10.76 (s, 1H), 10.65 (s, 1H), 7.29 (dd, J=7.7, 1.0 Hz, 1H), 7.18 (s, 1H), 6.92 (d, J=7.5 Hz, 1H), 1.27 (s, 12H).

Intermediate 27. 1-Chloro-2-iodo-3-(trifluoromethoxy)benzene

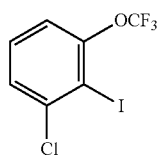 [SMILES: FC(F)(F)Oc1cccc(Cl)c1I]

To a cooled (−78° C.) solution of 1-chloro-3-(trifluoromethoxy)benzene (100 g, 510 mmol) in THF (500 mL) was added n-butyllithium (2.5 M/hexanes, 205 mL, 510 mmol) dropwise over a period of 10 minutes. Stirring was maintained at −78° C. for 1 h, and then a solution of iodine (130 g, 510 mmol) in THF (500 mL) was added dropwise at −78° C. over a period of 30 minutes. After the addition, the temperature was maintained at −78° C. for 1 h and then allowed to warm to rt and stirred for a total of 18 h. The reaction mixture was poured into saturated aqueous Na$_2$SO$_3$ and extracted with EtOAc (2×1000 mL). The combined organic extracts were dried over Na$_2$SO$_4$ and concentrated in vacuo to give the title compound as an oil (159 g, 96% yield). $^1$H NMR (500 MHz, CDCl$_3$) δ 7.40 (dd, J=8.1, 1.4 Hz, 1H), 7.32 (t, J=8.1 Hz, 1H), 7.16 (dt, J=8.2, 1.4 Hz, 1H).

Intermediate 28. 2'-Chloro-6'-(trifluoromethoxy)-[1,1'-biphenyl]-3,4-diamine

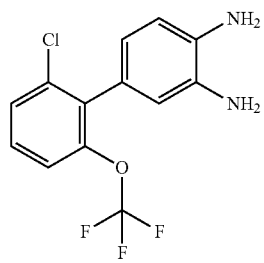 [SMILES: Nc1ccc(-c2c(Cl)cccc2OC(F)(F)F)cc1N]

Step A: 2-Nitro-4-(4,4,5,5-tetramethyl-1,3,2-dioxaborolan-2-yl)aniline

To a reaction vessel containing 4-bromo-2-nitroaniline (150 g, 693 mmol) and bis(pinacolato) diboron (352 g, 1.39 mol) in DMF (1.5 L) were added Pd(dppf)Cl$_2$ (5.07 g, 6.93 mmol) and potassium acetate (34.1 g, 3.47 mol) sequentially. The reaction mixture was heated at 80° C. under an N$_2$ atmosphere for 18 h. After cooling to rt, water (7.5 L) and EtOAc (1.8 L) were added. The layers were separated, and the aqueous layer was extracted with EtOAc (900 mL). The combined organic layers were washed with brine (6 L), dried over Na$_2$SO$_4$, and concentrated in vacuo. The crude product was slurried with methanol (900 mL) and filtered to provide the desired product as a yellow powder (147 g, 80% yield). $^1$H NMR (400 MHz, CDCl$_3$) δ 8.61 (d, J=1.2 Hz, 1H), 7.75 (dd, J=8.4 Hz, 1.2 Hz, 1H), 6.79 (d, J=8.4 Hz, 1H), 6.22 (bs, 2H), 1.35 (s, 12H).

Step B: 2'-Chloro-3-nitro-6'-(trifluoromethoxy)-[1,1'-biphenyl]-4-amine

To a reaction vessel containing 2-nitro-4-(4,4,5,5-tetramethyl-1,3,2-dioxaborolan-2-yl)aniline (159 g, 602 mmol) and 1-chloro-2-iodo-3-(trifluoromethoxy)benzene (194 g, 602 mmol) in dioxane (850 mL) and water (170 mL) were added Pd(dppf)Cl$_2$ (13.2 g, 18 mmol) and sodium carbonate (128 g, 1.2 mol) sequentially. The reaction mixture was heated at 80° C. under an N$_2$ atmosphere for 16 h. After cooling to rt, the reaction mixture was poured into water (2.8 L) and extracted with EtOAc (2×600 mL). The combined organic layers were concentrated in vacuo, and the crude product was purified by flash column chromatography (SiO$_2$; 11-17% EtOAc/petroleum ether) to provide the desired product as a yellow oil (110 g, 67% yield). $^1$H NMR (400 MHz, CDCl$_3$) δ 8.11 (d, J=2.0 Hz, 1H), 7.44 (d, J=1.2 Hz, 1H), 7.35-7.26 (m, 3H), 6.89 (d, J=8.4 Hz, 1H), 6.20 (bs, 2H).

Step C: 2'-Chloro-6'-(trifluoromethoxy)-[1,1'-biphenyl]-3,4-diamine

To a mixture of 2'-chloro-3-nitro-6'-(trifluoromethoxy)-[1,1'-biphenyl]-4-amine (110 g, 332 mmol) and iron powder (92.4 g, 1.66 mol) in ethanol (1900 mL) and water (300 mL). Concentrated HCl (11 mL) was added at once and the resulting mixture was heated at reflux for 2 h. After cooling to rt, the reaction mixture was filtered, and the filtrate was concentrated in vacuo to provide the crude product. Purification by flash column chromatography (SiO$_2$; 17-25% EtOAc/petroleum ether) provided the title compound as a brown solid (100 g, 99% yield). $^1$H NMR (400 MHz, CDCl$_3$) δ 7.43 (dd, J=7.6, 2.0 Hz, 1H), 7.29-7.27 (m, 2H), 6.79 (d, J=8.4 Hz, 1H), 6.66-6.65 (m, 2H), 1.65 (bs, 4H).

Example 1: 5-(2,3-Dimethylphenyl)-1,3-dihydrobenzimidazol-2-one

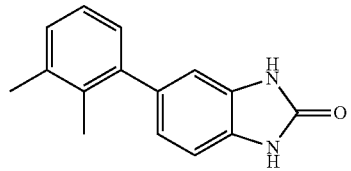 [SMILES: Cc1cccc(-c2ccc3[nH]c(=O)[nH]c3c2)c1C]

To a solution of (2,3-dimethylphenyl)boronic acid (85 mg, 0.56 mmol) and 5-bromo-1H-benzo[d]imidazol-2(3H)-one (100 mg, 0.45 mmol) in 4:1 dioxane:water (2.0 mL) were added potassium phosphate (199 mg, 0.94 mmol) and PdCl$_2$(dppf)-CH$_2$Cl$_2$ (19 mg, 0.02 mmol). The mixture was degassed with nitrogen and then heated at 100° C. for 16 h. After cooling to rt, the reaction mixture was diluted with water and extracted with DCM (2×). The combined organic extracts were dried (Na$_2$SO$_4$), filtered, and concentrated. Purification (FCC, SiO$_2$; 0-50% EtOAc/hexanes) afforded the title compound as a white solid (71 mg, 63% yield). MS (ESI): mass calcd. for C$_{15}$H$_{14}$N$_2$O, 238.1; m/z found, 239.1 [M+H]$^+$. $^1$H NMR (400 MHz, DMSO-d$_6$) δ 10.64 (s, 2H), 7.20-7.07 (m, 2H), 6.98 (dd, J=16.2, 7.3 Hz, 2H), 6.88-6.73 (m, 2H), 2.28 (s, 3H), 2.10 (s, 3H).

Example 2: 5-(2,6-Dimethylphenyl)-1,3-dihydrobenzimidazol-2-one

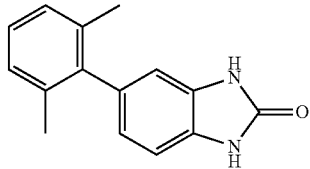 [SMILES: Cc1cccc(C)c1-c1ccc2[nH]c(=O)[nH]c2c1]

Step A: 5-(4,4,5,5-Tetramethyl-1,3,2-dioxaborolan-2-yl)-1H-benzo[d]imidazol-2(3H)-one To a round-bottomed flask containing DMF (35 mL) was added 5-bromo-1,3-dihydro-benzimidazol-2-one (5.0 g, 23 mmol), and the resulting solution was purged with nitrogen for 15 minutes. To this solution were added successively bis(pinacolato)diboron (7.2 g, 28 mmol), potassium acetate (6.9 g, 70 mmol), and PdCl$_2$(dppf)-CH$_2$Cl$_2$ (1.7 g, 2.4 mmol). After heating at 95° C. for 16 h, the black mixture was cooled to rt and diluted with brine (50 mL) and EtOAc (75 mL). The resulting precipitate was removed by filtration and washed with EtOAc. The filtrate was transferred to a separatory funnel and the layers separated. The organic layer was washed with water (3×50 mL), dried (Na$_2$SO$_4$), filtered and concentrated in vacuo. Trituration of the crude residue with DCM provided the desired product as a white solid (2.5 g, 41% yield). MS (ESI): mass calcd. for C$_{13}$H$_{17}$BN$_2$O$_3$, 260.1; m/z found, 261.2 [M+H]$^+$. $^1$H NMR (400 MHz, DMSO-d$_6$) δ 10.76 (s, 1H), 10.65 (s, 1H), 7.29 (dd, J=7.7, 1.0 Hz, 1H), 7.18 (s, 1H), 6.92 (d, J=7.5 Hz, 1H), 1.27 (s, 12H).

Step B: 5-(2,6-Dimethylphenyl)-1,3-dihydrobenzimidazol-2-one

To a solution of 5-(4,4,5,5-tetramethyl-1,3,2-dioxaborolan-2-yl)-1H-benzo[d]imidazol-2(3H)-one (Intermediate 28, 100 mg, 0.38 mmol), potassium phosphate (204 mg, 0.96 mmol), and PdCl$_2$(dtbpf) (13 mg, 0.019 mmol) in 4:1 dioxane:water (2.0 mL) was added 2,6-dimethyliodobenzene at once (178 mg, 0.77 mmol). The mixture was degassed with nitrogen for 10 minutes and then heated at 100° C. for 16 h. After cooling to rt, the reaction mixture was diluted with water and extracted with EtOAc (×3). The combined organic extracts were dried (Na$_2$SO$_4$), filtered and concentrated under reduced pressure. Purification (FCC, SiO$_2$; 0-100% EtOAc/hexanes) afforded the title compound as a white solid (22 mg, 24% yield). MS (ESI): mass calcd. for C$_{15}$H$_{14}$N$_2$O, 238.1; m/z found, 239.0 [M+H]$^+$. $^1$H NMR (400 MHz, CD$_3$OD) δ 7.13-7.02 (m, 4H), 6.86-6.80 (m, 1H), 6.76 (dd, J=8.0, 1.4 Hz, 1H), 2.00 (s, 6H).

Example 3: 5-(o-Tolyl)-1,3-dihydrobenzimidazol-2-one

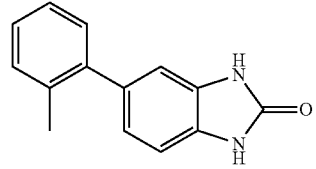 [SMILES: Cc1ccccc1-c1ccc2[nH]c(=O)[nH]c2c1]

The title compound was prepared in a manner analogous to Example 1, substituting o-tolylboronic acid for (2,3-dimethylphenyl)boronic acid. The crude product was purified by trituration with DCM to afford the title compound (43 mg, 41%). MS (ESI): mass calcd. for C$_{14}$H$_{12}$N$_2$O, 224.1; m/z found, 225.1 [M+H]$^+$. $^1$H NMR (400 MHz, DMSO-d$_6$) δ 10.83 (d, J=145.8 Hz, 2H), 7.45-7.13 (m, 4H), 7.08-6.65 (m, 3H), 2.22 (s, 3H).

Example 4: 5-[2-(Trifluoromethyl)phenyl]-1,3-dihydrobenzimidazol-2-one

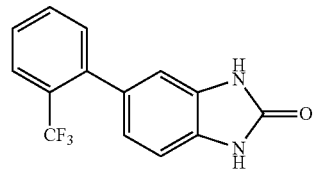 [SMILES: O=c1[nH]c2ccc(-c3ccccc3C(F)(F)F)cc2[nH]1]

The title compound was prepared in a manner analogous to Example 1, substituting (2-(trifluoromethyl)phenyl)boronic acid for (2,3-dimethylphenyl)boronic acid. The crude product was purified by trituration with DCM to afford the title compound (10 mg, 15%) MS (ESI): mass calcd. for $C_{14}H_9F_3N_2O$, 278.1; m/z found, 279.1 [M+H]+. 1H NMR (400 MHz, DMSO-$d_6$) δ 10.70 (s, 2H), 7.80 (dd, J=7.9, 1.4 Hz, 1H), 7.69 (dt, J=7.4, 1.3 Hz, 1H), 7.63-7.52 (m, 1H), 7.40 (d, J=7.6 Hz, 1H), 6.97 (d, J=7.9 Hz, 1H), 6.89-6.81 (m, 2H).

Example 5: 5-(2-Phenylphenyl)-1,3-dihydrobenzimidazol-2-one

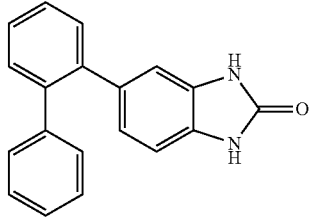 [SMILES: O=c1[nH]c2ccc(-c3ccccc3-c3ccccc3)cc2[nH]1]

The title compound was prepared in a manner analogous to Example 1, substituting [1,1'-biphenyl]-2-ylboronic acid for (2,3-dimethylphenyl)boronic acid. The crude product was purified by trituration with DCM to afford title compound (43 mg, 32% yield). MS (ESI): mass calcd. for $C_{19}H_{14}N_2O$, 286.1; m/z found, 287.1 [M+H]+. 1H NMR (400 MHz, DMSO-$d_6$) δ 10.52 (s, 2H), 7.46-7.35 (m, 4H), 7.28-7.17 (m, 3H), 7.15-7.07 (m, 2H), 6.78 (d, J=8.0 Hz, 1H), 6.71-6.57 (m, 2H).

Example 6: 5-(2-Isopropylphenyl)-1,3-dihydrobenzimidazol-2-one

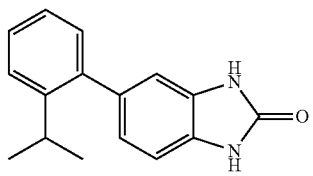 [SMILES: CC(C)c1ccccc1-c1ccc2[nH]c(=O)[nH]c2c1]

The title compound was prepared in a manner analogous to Example 1, substituting (2-isopropylphenyl)boronic acid for (2,3-dimethylphenyl)boronic acid. The crude product was purified by trituration with DCM to afford title compound (22 mg, 25% yield). MS (ESI): mass calcd. for $C_{16}H_{16}N_2O$, 252.3; m/z found, 253.3 [M+H]+. 1H NMR (400 MHz, DMSO-$d_6$) δ 10.54 (s, 2H), 7.44-7.37 (m, 1H), 7.32 (td, J=7.5, 1.5 Hz, 1H), 7.19 (td, J=7.4, 1.3 Hz, 1H), 7.11 (dd, J=7.9, 1.5 Hz, 1H), 6.97 (d, J=7.9 Hz, 1H), 6.85-6.75 (m, 2H), 3.03 (hept, J=6.9 Hz, 1H), 1.11 (d, J=6.8 Hz, 6H).

Example 7: 5-(2,6-Dimethoxyphenyl)-1,3-dihydrobenzimidazol-2-one

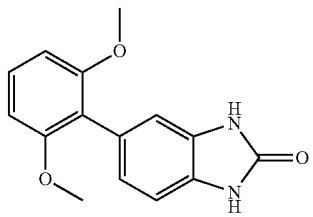 [SMILES: COc1cccc(OC)c1-c1ccc2[nH]c(=O)[nH]c2c1]

The title compound was prepared in a manner analogous to Example 1, substituting (2,6-dimethoxyphenyl)boronic acid for (2,3-dimethylphenyl)boronic acid. The crude product was purified by trituration with DCM to afford the title compound (45 mg, 35% yield). MS (ESI): mass calcd. for $C_{15}H_{14}N_2O_3$, 270.1; m/z found, 271.1 [M+H]+. 1H NMR (400 MHz, DMSO-$d_6$) δ 10.55 (s, 1H), 10.49 (s, 1H), 7.27 (t, J=8.3 Hz, 1H), 6.96-6.86 (m, 1H), 6.81-6.66 (m, 4H), 3.64 (s, 6H).

Example 8: 5-(2-Isopropoxyphenyl)-1,3-dihydrobenzimidazol-2-one

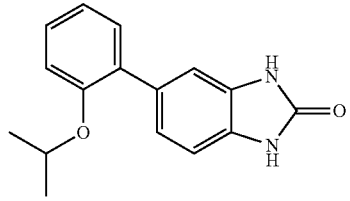 [SMILES: CC(C)Oc1ccccc1-c1ccc2[nH]c(=O)[nH]c2c1]

The title compound was prepared in a manner analogous to Example 1, substituting (2-isopropoxyphenyl)boronic acid for (2,3-dimethylphenyl)boronic acid. The crude product was purified by trituration with DCM to afford the title compound (53 mg, 42% yield). MS (ESI): mass calcd. for $C_{16}H_{16}N_2O_2$, 268.1; m/z found, 269.1 [M+H]+. 1H NMR (400 MHz, DMSO-$d_6$) δ 10.61 (s, 2H), 7.25 (t, J=7.6 Hz, 2H), 7.14-7.04 (m, 3H), 7.03-6.87 (m, 2H), 4.52 (hept, J=6.1 Hz, 1H), 1.19 (d, J=6.0 Hz, 6H).

Example 9: tert-Butyl 4-[2-(2-oxo-1,3-dihydrobenzimidazol-5-yl)phenyl]piperazine-1-carboxylate

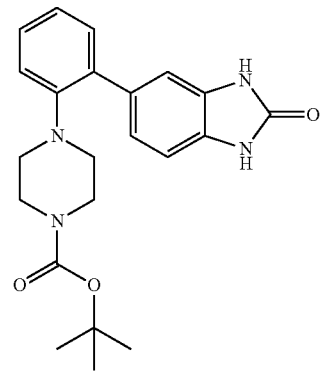 [SMILES: CC(C)(C)OC(=O)N1CCN(c2ccccc2-c2ccc3[nH]c(=O)[nH]c3c2)CC1]

The title compound was prepared in a manner analogous to Example 1, substituting tert-butyl 4-(2-(4,4,5,5-tetramethyl-1,3,2-dioxaborolan-2-yl)phenyl)piperazine-1-carboxylate for (2,3-dimethylphenyl)boronic acid. The crude product was purified by reverse-phase HPLC (XBridge C18 column (5 μm, 100×4.6 mm), mobile phase of 10-100% ACN in 20 mM NH4OH) to afford the title compound (13 mg, 9% yield). MS (ESI): mass calcd. for $C_{22}H_{26}N_4O_3$, 394.2; m/z found, 395.2 [M+H]+. 1H NMR (500 MHz, DMSO-$d_6$) δ 10.58 (s, 2H), 7.32-7.17 (m, 4H), 7.08-7.01 (m, 2H), 6.97 (d, J=8.0 Hz, 1H), 3.22 (t, J=4.7 Hz, 4H), 2.70 (s, 4H), 1.37 (s, 9H).

Example 10: 5-(5-Chloro-2-methyl-phenyl)-1,3-dihydrobenzimidazol-2-one

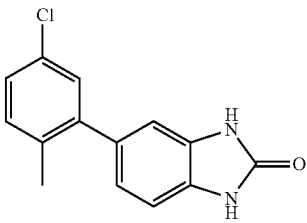 [SMILES: Cc1ccc(Cl)cc1-c1ccc2[nH]c(=O)[nH]c2c1]

The title compound was prepared in a manner analogous to Example 1, substituting (5-chloro-2-methylphenyl)boronic acid for (2,3-dimethylphenyl)boronic acid. The crude product was purified by reverse-phase HPLC (XBridge C18 column (5 μm, 100×4.6 mm), mobile phase of 10-100% ACN in 20 mM NH$_4$OH) to afford the title compound (17 mg, 19% yield). MS (ESI): mass calcd. for C$_{14}$H$_{11}$ClN$_2$O, 258.1; m/z found, 259.2 [M+H]$^+$. $^1$H NMR (400 MHz, CD$_3$OD): δ 7.25-7.17 (m, 3H), 7.12-7.07 (m, 1H), 7.02-6.92 (m, 2H), 2.21 (s, 3H).

Example 11: 5-(2-Fluoro-6-isopropoxy-phenyl)-1,3-dihydrobenzimidazol-2-one

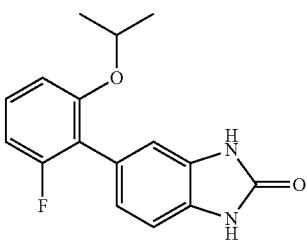 [SMILES: CC(C)Oc1cccc(F)c1-c1ccc2[nH]c(=O)[nH]c2c1]

The title compound was prepared in a manner analogous to Example 1, substituting (2-fluoro-6-isopropoxyphenyl)boronic acid for (2,3-dimethylphenyl)boronic acid. The crude product was purified by trituration with DCM to afford the title compound (8.1 mg, 8% yield). MS (ESI): mass calcd. for C$_{16}$H$_{15}$FN$_2$O$_2$, 286.1; m/z found, 287.1 [M+H]$^+$. $^1$H NMR (400 MHz, DMSO-d$_6$) δ 10.71 (s, 2H), 7.20-6.97 (m, 6H), 4.70-4.58 (m, 1H), 1.31 (d, J=5.9 Hz, 5H).

Example 12: 5-[2-Chloro-6-(trifluoromethyl)phenyl]-1,3-dihydrobenzimidazol-2-one

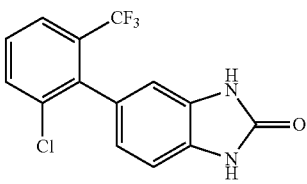 [SMILES: O=c1[nH]c2ccc(-c3c(Cl)cccc3C(F)(F)F)cc2[nH]1]

The title compound was prepared in a manner analogous to Example 1, substituting (2-chloro-6-(trifluoromethyl)phenyl)boronic acid for (2,3-dimethylphenyl)boronic acid. The crude product was purified by trituration with DCM to afford the title compound (18 mg, 12% yield). MS (ESI): mass calcd. for C$_{14}$H$_{18}$ClF$_3$N$_2$O, 312.0; m/z found, 313.1 [M+H]$^+$. $^1$H NMR (400 MHz, DMSO-d$_6$) δ 10.86-10.69 (m, 2H), 7.98-7.92 (m, 1H), 7.79-7.73 (m, 1H), 7.64 (d, J=7.9 Hz, 1H), 7.08-6.96 (m, 3H).

Example 13: 5-[2-(Cyclopropylmethoxy)phenyl]-1,3-dihydrobenzimidazol-2-one

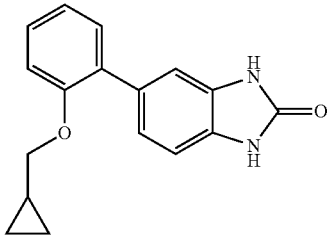 [SMILES: O=c1[nH]c2ccc(-c3ccccc3OCC3CC3)cc2[nH]1]

The title compound was prepared in a manner analogous to Example 1, substituting (2-(cyclopropylmethoxy)phenyl)boronic acid for (2,3-dimethylphenyl)boronic acid. The crude product was purified by reverse-phase HPLC (XBridge C18 column (5 μm, 100×4.6 mm), mobile phase of 10-100% ACN in 20 mM NH$_4$OH) to afford the title compound (10 mg, 8% yield). MS (ESI): mass calcd. for C$_{17}$H$_{16}$N$_2$O$_2$, 280.1; m/z found, [M=H]=281.1 [M+H]$^+$. $^1$H NMR (400 MHz, DMSO-d$_6$) δ 10.62 (s, 2H), 7.32-7.22 (m, 2H), 7.16-7.03 (m, 3H), 7.03-6.90 (m, 2H), 3.89-3.80 (m, 2H), 1.20-1.08 (m, 1H), 0.57-0.47 (m, 2H), 0.27 (dt, J=6.0, 4.2 Hz, 2H).

Example 14: 5-(2-Isobutoxy-6-methoxy-phenyl)-1,3-dihydrobenzimidazol-2-one

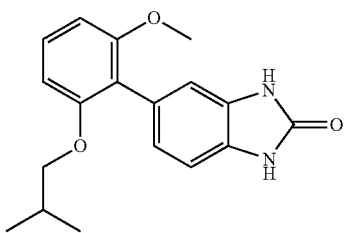 [SMILES: COc1cccc(OCC(C)C)c1-c1ccc2[nH]c(=O)[nH]c2c1]

The title compound was prepared in a manner analogous to Example 1, substituting (2-isobutoxy-6-methoxyphenyl)boronic acid for (2,3-dimethylphenyl)boronic acid. The crude product was purified by reverse-phase HPLC (XBridge C18 column (5 μm, 100×4.6 mm), mobile phase of 10-100% ACN in 20 mM NH$_4$OH) to afford the title compound (20 mg, 14% yield). MS (ESI): mass calcd. for C$_{18}$H$_{20}$N$_2$O$_3$, 312.1; m/z found, 313.2 [M+H]. $^1$H NMR (400 MHz, DMSO-d$_6$) δ 10.52 (s, 2H), 7.23 (t, J=8.3 Hz, 1H), 6.91-6.86 (m, 1H), 6.82-6.75 (m, 2H), 6.75-6.64 (m, 3H), 3.71-3.62 (m, 5H), 1.78 (dt, J=13.2, 6.6 Hz, 1H), 0.78 (d, J=6.7 Hz, 6H).

Example 15: 5-(2-Isobutoxy-5-methyl-phenyl)-1,3-dihydrobenzimidazol-2-one

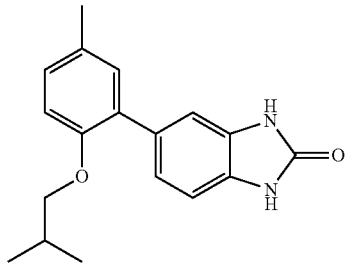 [SMILES: Cc1ccc(OCC(C)C)c(-c2ccc3[nH]c(=O)[nH]c3c2)c1]

The title compound was prepared in a manner analogous to Example 1, substituting (2-isobutoxy-5-methylphenyl)boronic acid for (2,3-dimethylphenyl)boronic acid. The crude product was purified by reverse-phase HPLC (XBridge C18 column (5 μm, 100×4.6 mm), mobile phase of 10-100% ACN in 20 mM NH$_4$OH) to afford the title compound (47 mg, 34% yield). MS (ESI): mass calcd. for C$_{18}$H$_{20}$N$_2$O$_2$, 296.2; m/z found, 297.2 [M+H]$^+$. $^1$H NMR (400 MHz, DMSO-d$_6$) δ 10.61 (s, 2H), 7.10-7.01 (m, 4H), 6.93 (dd, J=8.1, 3.9 Hz, 2H), 3.69 (d, J=6.4 Hz, 2H), 2.27 (s, 3H), 1.95-1.85 (m, 1H), 0.89 (d, J=6.7 Hz, 6H).

Example 16: 5-(5-Chloro-2-isopropoxy-phenyl)-1,3-dihydrobenzimidazol-2-one

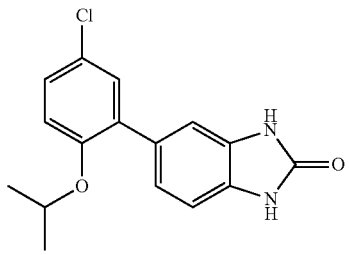 [SMILES: CC(C)Oc1ccc(Cl)cc1-c1ccc2[nH]c(=O)[nH]c2c1]

The title compound was prepared in a manner analogous to Example 1, substituting (5-chloro-2-isopropoxyphenyl)boronic acid for (2,3-dimethylphenyl)boronic acid. The crude product was purified by reverse-phase HPLC (XBridge C18 column (5 μm, 100×4.6 mm), mobile phase of 10-100% ACN in 20 mM NH$_4$OH) to afford the title compound (53 mg, 38% yield). MS (ESI): mass calcd. for C$_{16}$H$_{15}$ClN$_2$O$_2$, 302.1; m/z found, 303.1 [M+H]$^+$. $^1$H NMR (400 MHz, DMSO-d$_6$) δ 10.66 (s, 1H), 10.63 (s, 1H), 7.31-7.26 (m, 2H), 7.15-7.04 (m, 3H), 6.95 (d, J=8.0 Hz, 1H), 4.53 (hept, J=6.0 Hz, 1H), 1.19 (d, J=6.0 Hz, 6H).

Example 17: 5-(2-Chlorophenyl)-1,3-dihydrobenzimidazol-2-one

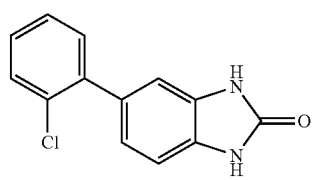 [SMILES: O=c1[nH]c2ccc(-c3ccccc3Cl)cc2[nH]1]

The title compound was prepared in a manner analogous to Example 1, substituting (2-chlorophenyl)boronic acid for (2,3-dimethylphenyl)boronic acid. The crude product was purified by reverse-phase HPLC (XBridge C18 column (5 μm, 100×4.6 mm), mobile phase of 10-100% ACN in 20 mM NH$_4$OH) to afford the title compound (11 mg, 9% yield). MS (ESI): mass calcd. for C$_{13}$H$_9$ClN$_2$O, 244.0; m/z found, 245.1 [M+H]$^+$. $^1$H NMR (400 MHz, DMSO-d$_6$) δ 10.73 (s, 1H), 10.69 (s, 1H), 7.54 (dt, J=7.3, 1.1 Hz, 1H), 7.42-7.36 (m, 3H), 7.01-6.94 (m, 3H).

Example 18: 5-(2,5-Dichlorophenyl)-1,3-dihydrobenzimidazol-2-one

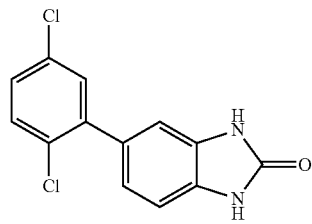 [SMILES: O=c1[nH]c2ccc(-c3cc(Cl)ccc3Cl)cc2[nH]1]

The title compound was prepared in a manner analogous to Example 1, substituting (2,5-dichlorophenyl)boronic acid for (2,3-dimethylphenyl)boronic acid. The crude product was purified by reverse-phase HPLC (XBridge C18 column (5 μm, 100×4.6 mm), mobile phase of 10-100% ACN in 20 mM NH$_4$OH) to afford the title compound (5 mg, 4% yield). MS (ESI): mass calcd. for C$_{13}$H$_9$ClN$_2$O, 244.0; m/z found, 245.1 [M+H]$^+$. $^1$H NMR (400 MHz, DMSO-d$_6$) δ 10.73 (s, 1H), 10.69 (s, 1H), 7.54 (dt, J=7.3, 1.1 Hz, 1H), 7.42-7.36 (m, 3H), 7.01-6.94 (m, 3H).

Example 19: 5-(2-Chloro-5-methyl-phenyl)-1,3-dihydrobenzimidazol-2-one

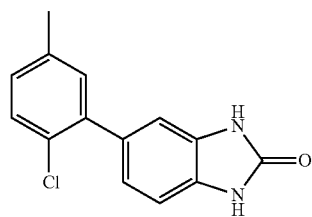 [SMILES: Cc1ccc(Cl)c(-c2ccc3[nH]c(=O)[nH]c3c2)c1]

The title compound was prepared in a manner analogous to Example 1, substituting (2-chloro-5-methylphenyl)boronic acid for (2,3-dimethylphenyl)boronic acid. Purification of the crude product by reverse-phase HPLC (XBridge C18 column (5 μm, 100×4.6 mm), mobile phase of 10-100% ACN in 20 mM NH$_4$OH) afforded the title compound (12 mg, 10% yield). MS (ESI): mass calcd. for C$_{14}$H$_{11}$ClN$_2$O, 258.1; m/z found, 259.2 [M+H]$^+$. $^1$H NMR (400 MHz, CD$_3$OD): δ 7.33 (d, J=8.1 Hz, 1H), 7.19-7.02 (m, 5H), 2.34 (s, 3H).

Example 20: 5-(2-Chloro-6-methoxy-phenyl)-1,3-dihydrobenzimidazol-2-one

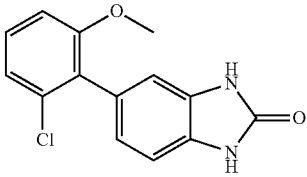 [SMILES: COc1cccc(Cl)c1-c1ccc2[nH]c(=O)[nH]c2c1]

The title compound was prepared in a manner analogous to Example 1, substituting (2-chloro-6-methoxyphenyl)boronic acid for (2,3-dimethylphenyl)boronic acid. The crude product was purified by reverse-phase HPLC (XBridge C18 column (5 μm, 100×4.6 mm), mobile phase of 10-100% ACN in 20 mM NH$_4$OH) to afford the title product (6 mg, 5% yield). MS (ESI): mass calcd. for $C_{14}H_{11}ClN_2O_2$, 274.1; m/z found, 275.1 [M+H]$^+$. $^1$H NMR (400 MHz, CD$_3$OD): δ 7.34-7.24 (m, 1H), 7.10-6.97 (m, 3H), 6.91-6.83 (m, 2H), 3.70 (s, 3H).

Example 21: 5-(2,5-Dimethylphenyl)-1,3-dihydrobenzimidazol-2-one

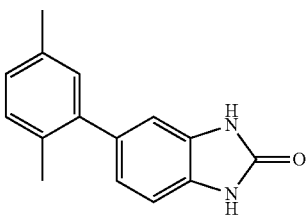

The title compound was prepared in a manner analogous to Example 1, substituting (2,5-dimethylphenyl)boronic acid for (2,3-dimethylphenyl)boronic acid. MS (ESI): mass calcd. for $C_{15}H_{14}N_2O$, 238.1; m/z found, 239.1 [M+H]$^+$. $^1$H NMR (500 MHz, CDCl$_3$) δ 10.33 (s, 1H), 10.29 (s, 1H), 7.11 (dd, J=18.3, 7.9 Hz, 2H), 7.07-7.00 (m, 3H), 6.98 (d, J=8.0 Hz, 1H), 2.32 (s, 3H), 2.19 (s, 3H).

Example 22: 5-[2-Isopropoxy-5-(trifluoromethyl)phenyl]-1,3-dihydrobenzimidazol-2-one

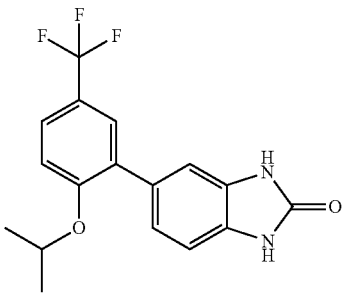 [SMILES: CC(C)Oc1ccc(C(F)(F)F)cc1-c1ccc2[nH]c(=O)[nH]c2c1]

The title compound was prepared in a manner analogous to Example 1, substituting (2-isopropoxy-5-(trifluoromethyl)phenyl)boronic acid for (2,3-dimethylphenyl)boronic acid and PdCl$_2$(dtbpf) for PdCl$_2$(dppf)-CH$_2$Cl$_2$. MS (ESI): mass calcd. for $C_{17}H_{15}F_3N_2O_2$, 336.1; m/z found, 337.1 [M+H]$^+$. $^1$H NMR (400 MHz, DMSO-d$_6$) δ 10.68 (s, 1H), 10.63 (s, 1H), 7.66-7.62 (m, 1H), 7.53 (dd, J=2.2, 0.9 Hz, 1H), 7.28 (d, J=8.6 Hz, 1H), 7.19-7.07 (m, 2H), 6.97 (d, J=8.0 Hz, 1H), 4.74 (hept, J=6.1 Hz, 1H), 1.26 (d, J=6.0 Hz, 6H).

Example 23: 5-(2,6-Dichloro-3-methyl-phenyl)-1,3-dihydrobenzimidazol-2-one

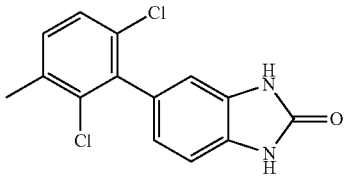 [SMILES: Cc1ccc(Cl)c(-c2ccc3[nH]c(=O)[nH]c3c2)c1Cl]

The title compound was prepared in a manner analogous to Example 1, substituting (2,6-dichloro-3-methylphenyl)boronic acid for (2,3-dimethylphenyl)boronic acid and PdCl$_2$(dtbpf) for PdCl$_2$(dppf)-CH$_2$Cl$_2$. MS (ESI): mass calcd. for $C_{14}H_{10}Cl_2N_2O$, 292.0; m/z found, 293.0 [M+H]$^+$. $^1$H NMR (400 MHz, CD$_3$OD) δ 7.39-7.29 (m, 1H), 7.30-7.24 (m, 1H), 7.12 (dd, J=7.9, 0.7 Hz, 1H), 6.90-6.79 (m, 2H), 2.39 (d, J=0.7 Hz, 3H).

Example 24: 5-(2-Phenoxyphenyl)-1,3-dihydrobenzimidazol-2-one

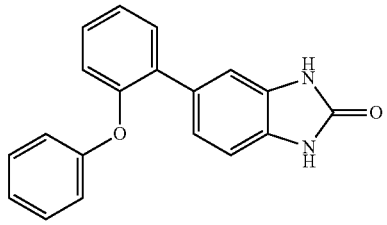 [SMILES: O=c1[nH]c2ccc(-c3ccccc3Oc3ccccc3)cc2[nH]1]

The title compound was prepared in a manner analogous to Example 1, substituting (2-phenoxyphenyl)boronic acid for (2,3-dimethylphenyl)boronic acid and PdCl$_2$(dtbpf) for PdCl$_2$(dppf)-CH$_2$Cl$_2$. MS (ESI): mass calcd. for $C_{19}H_{14}N_2O_2$, 302.1; m/z found, 303.1 [M+H]$^+$. $^1$H NMR (400 MHz, DMSO-d$_6$) δ 10.62 (s, 2H), 7.47 (dd, J=7.6, 1.8 Hz, 1H), 7.38-7.21 (m, 4H), 7.11-6.96 (m, 4H), 6.95-6.83 (m, 3H).

Example 25: 5-[2-Chloro-5-(trifluoromethyl)phenyl]-1,3-dihydrobenzimidazol-2-one

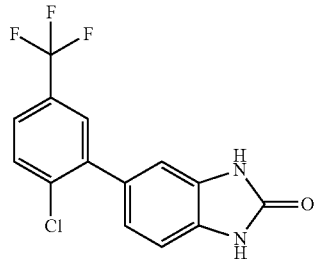 [SMILES: O=c1[nH]c2ccc(-c3cc(C(F)(F)F)ccc3Cl)cc2[nH]1]

The title compound was prepared in a manner analogous analogous to Example 1, substituting (2-chloro-5-(trifluoromethyl)phenyl)boronic acid for (2,3-dimethylphenyl)boronic acid and PdCl$_2$(dtbpf) for PdCl$_2$(dppf)-CH$_2$Cl$_2$. The crude product was purified by reverse-phase HPLC (XBridge C18 column (5 μm, 100×4.6 mm), mobile phase of 10-100% ACN in 20 mM NH$_4$OH) to afford the title compound (65 mg, 44% yield). MS (ESI): mass calcd. for C$_{14}$H$_8$ClF$_3$N$_2$O, 312.0; m/z found, 313.1 [M+H]$^+$. $^1$H NMR (400 MHz, DMSO-d$_6$): δ 10.79 (s, 1H), 10.76 (s, 1H), 7.84-7.78 (m, 1H), 7.77-7.69 (m, 2H), 7.07-7.00 (m, 3H).

Example 26: 5-(2-Benzyloxy-6-fluoro-phenyl)-1,3-dihydrobenzimidazol-2-one

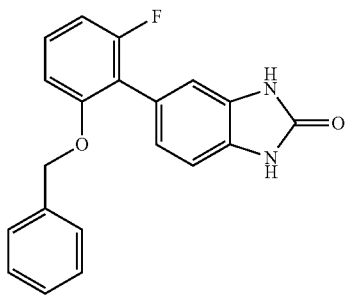 [SMILES: O=c1[nH]c2ccc(-c3c(F)cccc3OCc3ccccc3)cc2[nH]1]

The title compound was prepared in a manner analogous to Example 1, substituting (2-(benzyloxy)-6-fluorophenyl)boronic acid for (2,3-dimethylphenyl)boronic acid and PdCl$_2$(dtbpf) for PdCl$_2$(dppf)-CH$_2$Cl$_2$. The crude product was purified by trituration with DCM to afford the title compound (53 mg, 34% yield). MS (ESI): mass calcd. for C$_{20}$H$_{15}$FN$_2$O$_2$, 334.1; m/z found, 335.1 [M+H]$^+$. $^1$H NMR (400 MHz, DMSO-d$_6$): δ 10.67 (s, 1H), 7.39-7.25 (m, 3H), 7.07-6.84 (m, 3H), 5.11 (s, 1H).

Example 27: 3-Fluoro-2-(2-oxo-1,3-dihydrobenzimidazol-5-yl)benzaldehyde

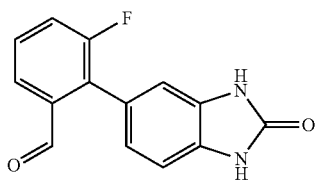 [SMILES: O=Cc1cccc(F)c1-c1ccc2[nH]c(=O)[nH]c2c1]

The title compound was prepared in a manner analogous to Example 1, substituting (2-fluoro-6-formylphenyl)boronic acid for (2,3-dimethylphenyl)boronic acid and PdCl$_2$(dtbpf) for PdCl$_2$(dppf)-CH$_2$Cl$_2$. The crude product was purified by trituration with DCM to afford the title compound (84 mg, 70% yield). MS (ESI): mass calcd. for C$_{14}$H$_9$FN$_2$O$_2$, 256.1; m/z found, 257.2 [M+H]$^+$. $^1$H NMR (400 MHz, DMSO-d$_6$) δ 10.69 (s, 2H), 9.72 (s, 1H), 7.73 (dd, J=7.4, 1.7 Hz, 1H), 7.68-7.56 (m, 2H), 7.06 (d, J=7.9 Hz, 1H), 7.03-6.91 (m, 2H), 11.19-10.19 (m, 2H).

Example 28: 5-(2-Isopropoxy-6-methoxy-phenyl)-1,3-dihydrobenzimidazol-2-one

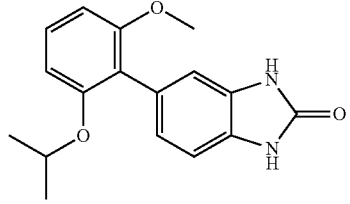 [SMILES: COc1cccc(OC(C)C)c1-c1ccc2[nH]c(=O)[nH]c2c1]

The title compound was prepared in a manner analogous to Example 1, substituting (2-isopropoxy-6-methoxyphenyl)boronic acid for (2,3-dimethylphenyl)boronic acid and PdCl$_2$(dtbpf) for PdCl$_2$(dppf)-CH$_2$Cl$_2$. The crude product was purified by trituration with DCM to afford the title compound (583 mg, 69%). MS (ESI): mass calcd. for C$_{17}$H$_{18}$N$_2$O$_3$, 298.1; m/z found, 299.1 [M+H]$^+$. $^1$H NMR (400 MHz, DMSO-d$_6$) δ 10.53 (s, 1H), 10.47 (s, 1H), 7.22 (t, J=8.3 Hz, 1H), 6.89 (d, J=7.9 Hz, 1H), 6.81-6.64 (m, 4H), 4.40 (hept, J=6.0 Hz, 1H), 3.64 (s, 3H), 1.08 (d, J=6.0 Hz, 6H).

Example 29: 5-[3-Chloro-2-(trifluoromethoxy)phenyl]-1,3-dihydrobenzimidazol-2-one

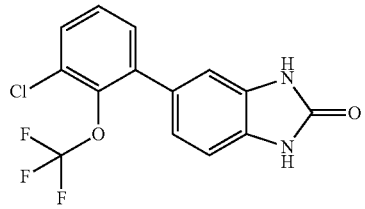 [SMILES: O=c1[nH]c2ccc(-c3cccc(Cl)c3OC(F)(F)F)cc2[nH]1]

The title compound was prepared in a manner analogous to Example 1, substituting (3-chloro-2-(trifluoromethoxy)phenyl)boronic acid for (2,3-dimethylphenyl)boronic acid and PdCl$_2$(dtbpf) for PdCl$_2$(dppf)-CH$_2$Cl$_2$. The crude product was purified by reverse-phase HPLC (XBridge C18 column (5 μm, 100×4.6 mm), mobile phase of 10-100% ACN in 20 mM NH$_4$OH) to afford the title compound (43 mg, 19%). MS (ESI): mass calcd. for C$_{14}$H$_8$ClF$_3$N$_2$O$_2$, 328.0; m/z found, 329.0 [M+H]$^+$. $^1$H NMR (400 MHz, DMSO-d$_6$): δ 10.77 (s, 1H), 10.73 (s, 1H), 7.59-7.48 (m, 2H), 7.49-7.42 (m, 1H), 7.04-6.96 (m, 3H).

Example 30: 5-[2-Chloro-4-(trifluoromethoxy)phenyl]-1,3-dihydrobenzimidazol-2-one

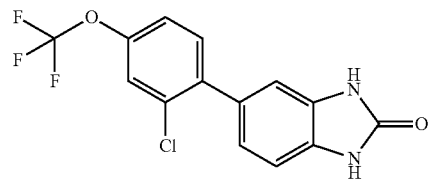 [SMILES: O=c1[nH]c2ccc(-c3ccc(OC(F)(F)F)cc3Cl)cc2[nH]1]

The title compound was prepared in a manner analogous to Example 1, substituting (2-chloro-4-(trifluoromethoxy)

phenyl)boronic acid for (2,3-dimethylphenyl)boronic acid and PdCl$_2$(dtbpf) for PdCl$_2$(dppf)-CH$_2$Cl$_2$. The crude product was purified by reverse-phase HPLC (XBridge C18 column (5 μm, 100×4.6 mm), mobile phase of 10-100% ACN in 20 mM NH$_4$OH) to afford the title compound (11 mg, 7% yield). MS (ESI): mass calcd. for C$_{14}$H$_8$ClF$_3$N$_2$O$_2$, 328.0; m/z found, 329.1 [M+H]$^+$. $^1$H NMR (400 MHz, DMSO-d$_6$) δ 10.75 (s, 2H), 7.66 (d, J=2.3 Hz, 1H), 7.57-7.51 (m, 1H), 7.44 (m, J=8.6, 2.5, 1.3 Hz, 1H), 7.04-6.92 (m, 3H).

Example 31: 5-[2-Chloro-6-(trifluoromethoxy)phenyl]-1,3-dihydrobenzimidazol-2-one

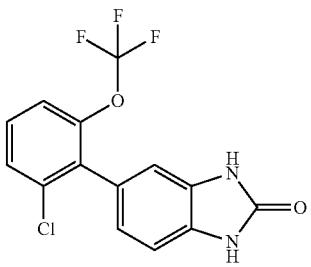 [SMILES: O=c1[nH]c2ccc(-c3c(Cl)cccc3OC(F)(F)F)cc2[nH]1]

Method A

To a solution of (2-chloro-6-(trifluoromethoxy)phenyl)boronic acid (4.5 g, 19 mmol) and 5-bromo-1H-benzo[d]imidazol-2(3H)-one (2.0 g, 9.4 mmol) in 4:1 dioxane:water (20 ml) were added potassium phosphate (4.0 g, 19 mmol) and 1,1'-bis(di-tert-butylphosphino)ferrocene palladium (II) chloride (Pd(DTBPF)Cl$_2$) (612 mg, 0.94 mmol). The mixture was degassed with nitrogen and then heated at 100° C. for 16 h. After cooling to room temperature, the reaction mixture was filtered through Celite® and washed successively with EtOAc and DCM. The filtrate was combined with silica gel, concentrated in vacuo, and dry-loaded onto an 80 g silica gel cartridge. Purification by FCC (0-10% MeOH in DCM) afforded a solid. The solid was dissolved in hot EtOH (60° C.), and water was added to initiate precipitation. After cooling to room temperature, the precipitate was filtered and dried under high vacuum for 4 h to provide the desired product as a white solid (918 mg, 30% yield). MS (ESI): mass calcd. for C$_{14}$H$_8$ClF$_3$N$_2$O$_2$, 328.0; m/z found, 329.1 [M+H]$^+$. $^1$H NMR (400 MHz, DMSO-d$_6$): δ 10.75 (s, 1H), 10.69 (s, 1H), 7.69-7.60 (m, 1H), 7.59-7.43 (m, 2H), 7.08-6.98 (m, 1H), 6.86-6.77 (m, 2H).

Method B

The title compound is also prepared in a manner analogous to Example 211, using 2'-chloro-6'-(trifluoromethoxy)-[1,1'-biphenyl]-3,4-diamine (Intermediate 28).

Example 32: 5-[2-Chloro-6-(trifluoromethoxy)phenyl]-6-tritio-1,3-dihydrobenzimidazol-2-one

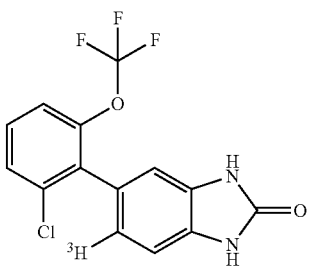 [SMILES: [3H]c1cc2[nH]c(=O)[nH]c2cc1-c1c(Cl)cccc1OC(F)(F)F]

Step A: 5-Bromo-6-[2-chloro-6-(trifluoromethoxy)phenyl]-1,3-dihydrobenzimidazol-2-one To a solution of 5-[2-chloro-6-(trifluoromethoxy)phenyl]-1,3-dihydrobenzimidazol-2-one (140 mg, 0.43 mmol) in TFA (4.3 mL) was added N-bromosuccinimide (76 mg, 0.43 mmol). After stirring at rt for 4 h, the solvent was removed in vacuo. DCM (10 mL) was added and then concentrated under reduced pressure. The residue was diluted with saturated aqueous NaHCO$_3$ and extracted twice with EtOAc. The combined organic extracts were dried (Na$_2$SO$_4$), filtered and concentrated to provide the title compound (65 mg, 37% yield). MS (ESI): mass calcd. for C$_{14}$H$_7$BrClF$_3$N$_2$O$_2$, 405.9; m/z found, 406.7 [M+H]$^+$. $^1$H NMR (400 MHz, DMSO-d$_6$): δ 10.97 (s, 1H), 10.84 (s, 1H), 7.67-7.55 (m, 2H), 7.52-7.45 (m, 1H), 7.24 (s, 1H), 6.81 (s, 1H).

Step B: 5-[2-Chloro-6-(trifluoromethoxy)phenyl]-6-tritio-1,3-dihydrobenzimidazol-2-one To a flask containing 5-bromo-6-[2-chloro-6-(trifluoromethoxy)phenyl]-1,3-dihydrobenzimidazol-2-one (3 mg), 10 wt % Pd/C (3 mg) was added methanol (0.5 mL) and tritium gas (10 Ci). The mixture was stirred for 30 minutes at rt. The crude product was dissolved in ethanol and filtered. The labile tritium was exchanged as the ethanol was removed in vacuo. This was repeated 2 additional times. The crude product was purified by reverse-phase HPLC (Gemini 5 μm C-18 column, 50% aq acetonitrile containing 0.01% NH$_4$OH) to afford the title compound. The specific activity was determined to be 24.2 Ci/mmol, and the product was stored at −20° C. in EtOH at a concentration of 1.0 mCi/mL. MS (ESI): mass calcd. for C$_{14}$H$_{7T}$ClF$_3$N$_2$O, 330.0; m/z found, 331.6 [M+H]$^+$.

Example 33: 5-[2-Methoxy-4-(trifluoromethoxy)phenyl]-1,3-dihydrobenzimidazol-2-one

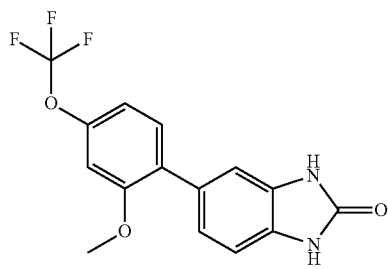 [SMILES: COc1cc(OC(F)(F)F)ccc1-c1ccc2[nH]c(=O)[nH]c2c1]

The title compound was prepared in a manner analogous to Example 1, substituting (2-methoxy-4-(trifluoromethoxy)phenyl)boronic acid for (2,3-dimethylphenyl)boronic acid and PdCl$_2$(dtbpf) for PdCl$_2$(dppf)-CH$_2$Cl$_2$. The crude product was purified by reverse-phase HPLC (XBridge C18 column (5 μm, 100×4.6 mm), mobile phase of 10-100% ACN in 20 mM NH$_4$OH) to afford the title compound (20 mg, 13% yield). MS (ESI): mass calcd. for C$_{15}$H$_{11}$F$_3$N$_2$O$_3$, 324.1; m/z found, 325.1 [M+H]$^+$. $^1$H NMR (400 MHz, DMSO-d$_6$) δ 10.66 (s, 1H), 10.63 (s, 1H), 7.36 (d, J=8.4 Hz, 1H), 7.11-6.94 (m, 5H), 3.79 (s, 3H).

Example 34: 5-[3-Chloro-2-(trifluoromethyl)phenyl]-1,3-dihydrobenzimidazol-2-one

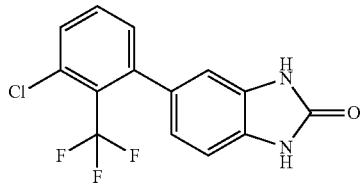 [SMILES: O=c1[nH]c2ccc(-c3cccc(Cl)c3C(F)(F)F)cc2[nH]1]

The title compound was prepared in a manner analogous to Example 1, substituting (3-chloro-2-(trifluoromethyl)phenyl)boronic acid for (2,3-dimethylphenyl)boronic acid and PdCl$_2$(dtbpf) for PdCl$_2$(dppf)-CH$_2$Cl$_2$. The crude product was purified by reverse-phase HPLC (XBridge C18 column (5 μm, 100×4.6 mm), mobile phase of 10-100% ACN in 20 mM NH$_4$OH) to afford the title compound (10 mg, 7% yield). MS (ESI): mass calcd. for C$_{14}$H$_8$ClF$_3$N$_2$O, 312.0; m/z found, 313.0 [M+H]$^+$. $^1$H NMR (400 MHz, CD$_3$OD) δ 7.63-7.59 (m, 1H), 7.57-7.50 (m, 1H), 7.28 (dt, J=7.8, 1.2 Hz, 1H), 7.09-7.05 (m, 1H), 6.95-6.89 (m, 2H).

Example 35: 5-(2-Bromophenyl)-1,3-dihydrobenzimidazol-2-one

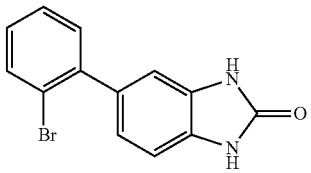 [SMILES: O=c1[nH]c2ccc(-c3ccccc3Br)cc2[nH]1]

The title compound was prepared in a manner analogous to Example 2, substituting 1-bromo-2-iodobenzene for 2,6-dimethyliodobenzene in Step B. The crude product was purified by reverse-phase HPLC (XBridge C18 column (5 μm, 100×4.6 mm), mobile phase of 10-100% ACN in 20 mM NH$_4$OH) to afford the title compound (9 mg, 11% yield). MS (ESI): mass calcd. for C$_{13}$H$_9$BrN$_2$O, 288.0; m/z found, 288.1 [M+H]$^+$. $^1$H NMR (400 MHz, CDCl$_3$) δ 10.66 (s, 2H), 7.68 (dd, J=8.0, 1.2 Hz, 1H), 7.43-7.31 (m, 2H), 7.28-7.19 (m, 1H), 6.98-6.93 (m, 1H), 6.93-6.86 (m, 2H).

Example 36: 5-(2-Chloro-6-methyl-phenyl)-1,3-dihydrobenzimidazol-2-one

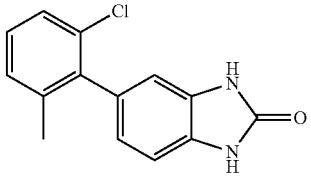 [SMILES: Cc1cccc(Cl)c1-c1ccc2[nH]c(=O)[nH]c2c1]

The title compound was prepared in a manner analogous to Example 2, substituting 1-chloro-2-iodo-3-methylbenzene for 2,6-dimethyliodobenzene in Step B. MS (ESI): mass calcd. for C$_{14}$H$_{11}$ClN$_2$O, 258.1; m/z found, 259.1 [M+H]$^+$. $^1$H NMR (400 MHz, DMSO-d$_6$): δ 10.69 (s, 1H), 10.65 (s, 1H), 7.41-7.31 (m, 1H), 7.31-7.21 (m, 2H), 7.06-6.95 (m, 1H), 6.77-6.63 (m, 2H), 2.04 (s, 3H).

Example 37: 5-(4-Chloro-2,6-dimethyl-phenyl)-1,3-dihydrobenzimidazol-2-one

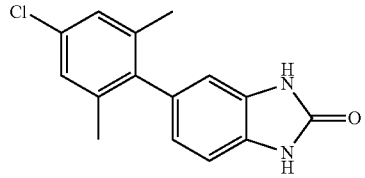 [SMILES: Cc1cc(Cl)cc(C)c1-c1ccc2[nH]c(=O)[nH]c2c1]

The title compound was prepared in a manner analogous to Example 2, substituting 2-bromo-5-chloro-1,3-dimethyl-benzene for 2,6-dimethyliodobenzene in Step B. MS (ESI): mass calcd. for C$_{15}$H$_{13}$ClN$_2$O, 272.1; m/z found, 273.1 [M+H]$^+$. $^1$H NMR (400 MHz, CD$_3$OD): δ 7.22-7.04 (m, 3H), 6.84-6.72 (m, 2H), 2.00 (s, 6H).

Example 38: 3-Methyl-2-(2-oxo-1,3-dihydrobenzimidazol-5-yl)benzonitrile

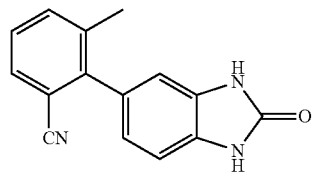 [SMILES: Cc1cccc(C#N)c1-c1ccc2[nH]c(=O)[nH]c2c1]

The title compound was prepared in a manner analogous to Example 2, substituting 2-iodo-3-methylbenzonitrile for 2,6-dimethyliodobenzene and PdCl$_2$(dppf)-CH$_2$Cl$_2$ for PdCl$_2$(dtbpf) in Step B. MS (ESI): mass calcd. for C$_{15}$H$_{11}$N$_3$O, 249.1; m/z found, 250.1 [M+H]$^+$. $^1$H NMR (500 MHz, DMSO-d$_6$) δ 10.78 (s, 2H), 7.72 (d, J=7.7 Hz, 1H), 7.63 (d, J=7.7 Hz, 1H), 7.45 (t, J=7.7 Hz, 1H), 7.04 (d, J=7.8 Hz, 1H), 6.85 (d, J=9.5 Hz, 2H), 2.14 (s, 3H).

Example 39: 4-Methyl-3-(2-oxo-1,3-dihydrobenzimidazol-5-yl)benzonitrile

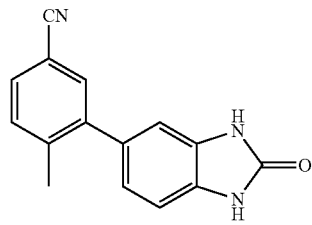 [SMILES: Cc1ccc(C#N)cc1-c1ccc2[nH]c(=O)[nH]c2c1]

The title compound was prepared in a manner analogous to Example 2, substituting 3-bromo-4-methylbenzonitrile for 2,6-dimethyliodobenzene and PdCl$_2$(dppf)-CH$_2$Cl$_2$ for PdCl$_2$(dtbpf) in Step B. MS (ESI): mass calcd. for C$_{15}$H$_{11}$N$_3$O, 249.1; m/z found, 250.1 [M+H]$^+$. $^1$H NMR (500 MHz, CDCl$_3$) δ 10.55 (s, 1H), 10.49 (s, 1H), 7.50 (dd, J=7.8, 1.8 Hz, 1H), 7.45-7.37 (m, 1H), 7.34 (d, J=7.9 Hz, 1H), 7.14 (d, J=8.0 Hz, 1H), 6.98 (d, J=1.5 Hz, 1H), 6.93 (dd, J=8.0, 1.6 Hz, 1H).

Example 40: 4-Chloro-3-(2-oxo-1,3-dihydrobenzimidazol-5-yl)benzonitrile

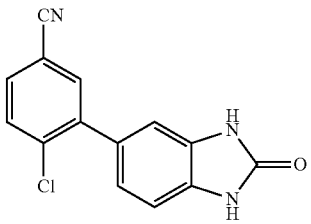

The title compound was prepared in a manner analogous to Example 2, substituting 3-bromo-4-chlorobenzonitrile for 2,6-dimethyliodobenzene and PdCl$_2$(dppf)-CH$_2$Cl$_2$ for PdCl$_2$(dtbpf) in Step B. MS (ESI): mass calcd. for C$_{14}$H$_8$ClN$_3$O, 269.0; m/z found, 270.0 [M+H]$^+$. $^1$H NMR (500 MHz, DMSO-d$_6$) δ 10.79 (bs, 2H), 7.90 (d, J=2.1 Hz, 1H), 7.84 (dd, J=8.3, 2.1 Hz, 1H), 7.78 (d, J=8.3 Hz, 1H), 7.02 (d, J=3.8 Hz, 2H), 6.92 (s, 1H).

Example 41: 2-[2-(2-Oxo-1,3-dihydrobenzimidazol-5-yl)phenyl]acetonitrile

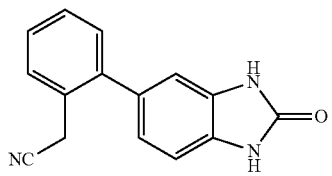 [SMILES: N#CCc1ccccc1-c1ccc2[nH]c(=O)[nH]c2c1]

The title compound was prepared in a manner analogous to Example 2, substituting 2-(2-iodophenyl)acetonitrile for 2,6-dimethyliodobenzene and PdCl$_2$(dppf)-CH$_2$Cl$_2$ for PdCl$_2$(dtbpf) in Step B. MS (ESI): mass calcd. for C$_{15}$H$_{11}$N$_3$O, 249.1; m/z found, 250.1 [M+H]$^+$. $^1$H NMR (400 MHz, DMSO-d$_6$) δ 10.71 (s, 2H), 7.57-7.47 (m, 1H), 7.47-7.35 (m, 2H), 7.33-7.25 (m, 1H), 7.01 (d, J=7.9 Hz, 1H), 6.94-6.82 (m, 2H), 3.88 (s, 2H).

Example 42: Methyl 3-chloro-2-(2-oxo-1,3-dihydrobenzimidazol-5-yl)benzoate

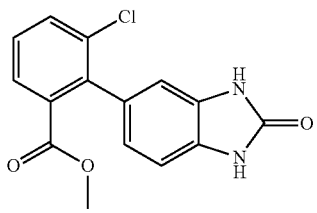 [SMILES: COC(=O)c1cccc(Cl)c1-c1ccc2[nH]c(=O)[nH]c2c1]

The title compound was prepared in a manner analogous to Example 2, substituting methyl 2,3-dichlorobenzoate for 2,6-dimethyliodobenzene and PdCl$_2$(dppf)-CH$_2$Cl$_2$ for PdCl$_2$(dtbpf) in Step B. MS (ESI): mass calcd. for C$_{15}$H$_{11}$ClN$_2$O$_3$, 302.0; m/z found, 303.1 [M+H]$^+$. $^1$H NMR (400 MHz, DMSO-d$_6$) δ 10.68 (s, 2H), 7.74 (dd, J=8.0, 1.3 Hz, 1H), 7.69-7.60 (m, 1H), 7.52-7.42 (m, 1H), 7.00-6.84 (m, 1H), 6.76-6.67 (m, 2H), 3.49 (s, 3H).

Example 43: Methyl 2-chloro-3-(2-oxo-1,3-dihydrobenzimidazol-5-yl)benzoate

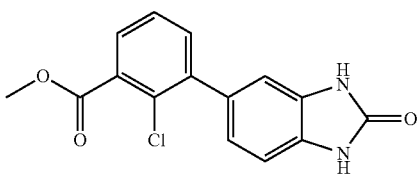 [SMILES: COC(=O)c1cccc(-c2ccc3[nH]c(=O)[nH]c3c2)c1Cl]

Step A: Methyl 3-bromo-2-chlorobenzoate

To a cooled (0° C.) solution of 3-bromo-2-chlorobenzoic acid (2 g, 8.5 mmol) in THF (22 mL) and MeOH (6.7 mL) was added (trimethylsilyl)diazomethane (2M in hexanes, 8.5 mL, 17 mmol) dropwise. The reaction mixture was stirred at 0° C. for 2 h and then quenched dropwise with AcOH until the yellow color disappeared. The solvent was removed in vacuo. The residue was diluted with saturated aq. NaHCO$_3$ and extracted with EtOAc (×3). The combined organic extracts were dried (Na$_2$SO$_4$), filtered and concentrated to afford the desired product as a clear oil (2.0 g, 92% yield). $^1$H NMR (400 MHz, DMSO-d$_6$) δ 7.89-7.83 (m, 1H), 7.65 (dd, J=7.7, 1.6 Hz, 1H), 7.29 (t, J=7.9 Hz, 1H), 3.75 (s, 3H).

Step B: Methyl 2-chloro-3-(2-oxo-1,3-dihydrobenzimidazol-5-yl)benzoate

The title compound was prepared in a manner analogous to Example 2, substituting methyl 3-bromo-2-chlorobenzoate for 2,6-dimethyliodobenzene and PdCl$_2$(dppf)-CH$_2$Cl$_2$ for PdCl$_2$(dtbpf) in Step B. MS (ESI): mass calcd. for C$_{15}$H$_{11}$ClN$_2$O$_3$, 302.0; m/z found, 302.9 [M+H]$^+$. $^1$H NMR (500 MHz, DMSO-d$_6$) δ 10.62 (s, 1H), 10.59 (s, 1H), 7.55 (dd, J=7.5, 1.8 Hz, 1H), 7.42 (dd, J=7.7, 1.9 Hz, 1H), 7.37 (t, J=7.6 Hz, 1H), 6.89 (d, J=7.9 Hz, 1H), 6.86-6.81 (m, 1H), 6.80 (s, 1H), 3.76 (s, 3H).

Example 44: Methyl 4-chloro-3-(2-oxo-1,3-dihydrobenzimidazol-5-yl)benzoate

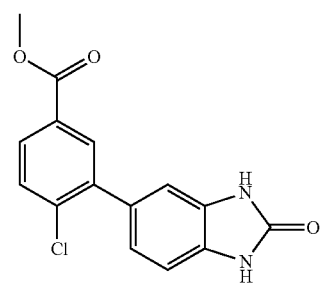 [SMILES: COC(=O)c1ccc(Cl)c(-c2ccc3[nH]c(=O)[nH]c3c2)c1]

The title compound was prepared in a manner analogous to Example 2, substituting methyl 4-chloro-3-iodobenzoate for 2,6-dimethyliodobenzene and PdCl$_2$(dppf)-CH$_2$Cl$_2$ for PdCl$_2$(dtbpf) in Step B. MS (ESI): mass calcd. for C$_{15}$H$_{11}$ClN$_2$O$_3$, 302.0; m/z found, 302.9 [M+H]$^+$. $^1$H NMR (500 MHz, DMSO-d$_6$) δ 10.78 (s, 1H), 10.73 (s, 1H), 7.91 (d, J=8.6 Hz, 2H), 7.71 (d, J=8.1 Hz, 1H), 7.12-6.97 (m, 3H), 3.87 (s, 3H).

Example 45: Methyl 3-methyl-2-(2-oxo-1,3-dihydrobenzimidazol-5-yl)benzoate

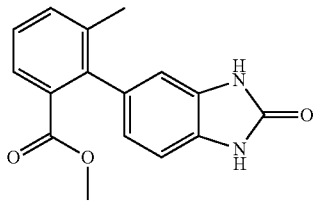 [SMILES: COC(=O)c1cccc(C)c1-c1ccc2[nH]c(=O)[nH]c2c1]

The title compound was prepared in a manner analogous to Example 2, substituting methyl 2-iodo-3-methylbenzoate for 2,6-dimethyliodobenzene and PdCl$_2$(dppf)-CH$_2$Cl$_2$ for PdCl$_2$(dtbpf) in Step B. MS (ESI): mass calcd. for C$_{16}$H$_{14}$N$_2$O$_3$, 282.1; m/z found, 283.1 [M+H]$^+$. $^1$H NMR (400 MHz, CD$_3$OD) δ 7.59-7.53 (m, 1H), 7.49-7.40 (m, 1H), 7.38-7.29 (m, 1H), 7.07 (d, J=8.0 Hz, 1H), 6.86-6.75 (m, 2H), 3.50 (s, 3H), 2.12 (s, 3H).

Example 46: Methyl 2-methyl-3-(2-oxo-1,3-dihydrobenzimidazol-5-yl)benzoate

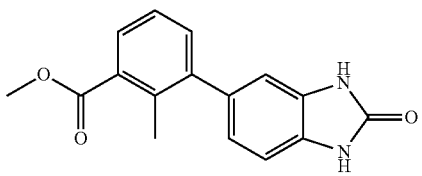 [SMILES: COC(=O)c1cccc(-c2ccc3[nH]c(=O)[nH]c3c2)c1C]

The title compound was prepared in a manner analogous to Example 2, substituting methyl 3-iodo-2-methylbenzoate for 2,6-dimethyliodobenzene and PdCl$_2$(dppf)-CH$_2$Cl$_2$ for PdCl$_2$(dtbpf) in Step B. MS (ESI): mass calcd. for C$_{16}$H$_{14}$N$_2$O$_3$, 282.1; m/z found, 283.0 [M+H]$^+$. $^1$H NMR (500 MHz, DMSO-d$_6$) δ 10.56 (s, 1H), 10.54 (s, 1H), 7.57 (dd, J=7.6, 1.6 Hz, 1H), 7.31-7.12 (m, 2H), 6.87 (d, J=7.9 Hz, 1H), 6.75-6.63 (m, 2H), 3.72 (s, 3H), 2.19 (s, 3H).

Example 47: Methyl 4-methyl-3-(2-oxo-1,3-dihydrobenzimidazol-5-yl)benzoate

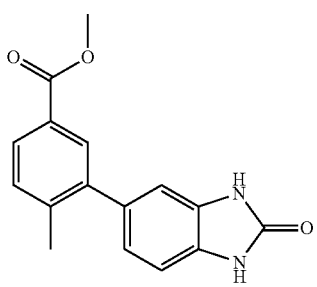 [SMILES: COC(=O)c1ccc(C)c(-c2ccc3[nH]c(=O)[nH]c3c2)c1]

The title compound was prepared in a manner analogous to Example 2, substituting methyl 3-bromo-4-methylbenzoate for 2,6-dimethyliodobenzene and PdCl$_2$(dppf)-CH$_2$Cl$_2$ for PdCl$_2$(dtbpf) in Step B. MS (ESI): mass calcd. for C$_{16}$H$_{14}$N$_2$O$_3$, 282.1; m/z found, 283.1 [M+H]$^+$. $^1$H NMR (400 MHz, CD$_3$OD): δ 7.91-7.80 (m, 2H), 7.43-7.34 (m, 1H), 7.15-7.08 (m, 1H), 7.03-6.93 (m, 2H), 3.89 (s, 3H), 2.31 (s, 3H).

Example 48: Methyl 2-methoxy-3-(2-oxo-1,3-dihydrobenzimidazol-5-yl)benzoate

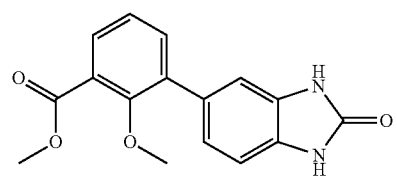 [SMILES: COC(=O)c1cccc(-c2ccc3[nH]c(=O)[nH]c3c2)c1OC]

The title compound was prepared in a manner analogous to Example 2, substituting methyl 3-bromo-2-methoxybenzoate for 2,6-dimethyliodobenzene and PdCl$_2$(dppf)-CH$_2$Cl$_2$ for PdCl$_2$(dtbpf) in Step B. MS (ESI): mass calcd. for C$_{16}$H$_{14}$N$_2$O$_4$, 298.1; m/z found, 299.0 [M+H]$^+$. $^1$H NMR (600 MHz, CD$_3$OD) δ 7.68 (dd, J=7.7, 1.8 Hz, 1H), 7.53 (dd, J=7.6, 1.8 Hz, 1H), 7.31-7.18 (m, 3H), 7.12 (d, J=8.1 Hz, 1H), 3.91 (s, 3H), 3.44 (s, 3H).

Example 49: 5-(2,6-Dichlorophenyl)-1,3-dihydrobenzimidazol-2-one

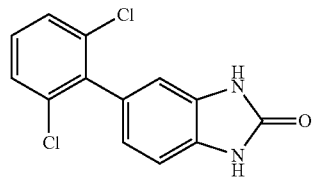 [SMILES: O=c1[nH]c2ccc(-c3c(Cl)cccc3Cl)cc2[nH]1]

The title compound was prepared in a manner analogous to Example 2, substituting 1,3-dichloro-2-iodobenzene for 2,6-dimethyliodobenzene and PdCl$_2$(dppf)-CH$_2$Cl$_2$ for PdCl$_2$(dtbpf) in Step B. MS (ESI): mass calcd. for C$_{13}$H$_8$Cl$_2$N$_2$O, 278.0; m/z found, 279.0 [M+H]$^+$. $^1$H NMR (400 MHz, CD$_3$OD) δ 7.46 (d, J=8.1 Hz, 2H), 7.34-7.27 (m, 1H), 7.12 (dd, J=7.7, 0.9 Hz, 1H), 6.91-6.85 (m, 2H).

Example 50: 5-(2,6-Dichloro-4-fluoro-phenyl)-1,3-dihydrobenzimidazol-2-one

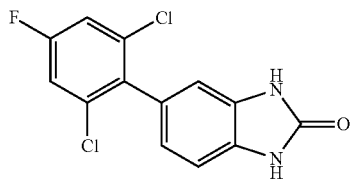 [SMILES: O=c1[nH]c2ccc(-c3c(Cl)cc(F)cc3Cl)cc2[nH]1]

The title compound was prepared in a manner analogous to Example 2, substituting 2-bromo-1,3-dichloro-5-fluorobenzene for 2,6-dimethyliodobenzene and PdCl$_2$(dppf)-CH$_2$Cl$_2$ for PdCl$_2$(dtbpf) in Step B. MS (ESI): mass calcd. for C$_{13}$H$_7$Cl$_2$FN$_2$O, 296.0; m/z found, 297.0 [M+H]$^+$. $^1$H NMR (500 MHz, CDCl$_3$) δ 9.74 (m, 2H), 7.17 (d, J=8.1 Hz, 3H), 7.02-6.94 (m, 1H), 6.92 (dd, J=8.0, 1.6 Hz, 1H).

Example 51: 5-(2,4,6-Trichlorophenyl)-1,3-dihydrobenzimidazol-2-one

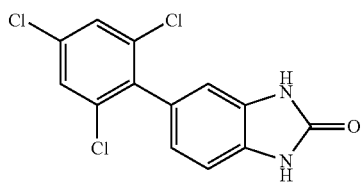 [SMILES: O=c1[nH]c2ccc(-c3c(Cl)cc(Cl)cc3Cl)cc2[nH]1]

The title compound was prepared in a manner analogous to Example 2, substituting 2-bromo-1,3,5-trichlorobenzene for 2,6-dimethyliodobenzene and PdCl$_2$(dppf)-CH$_2$Cl$_2$ for PdCl$_2$(dtbpf) in Step B. The crude product was purified by reverse-phase HPLC (XBridge C18 column (5 μm, 100×4.6 mm), mobile phase of 10-100% ACN in 20 mM NH$_4$OH) to afford the title compound (28 mg, 23% yield). MS (ESI): mass calcd. for C$_{13}$H$_7$Cl$_3$N$_2$O, 312.0; m/z found, 313.1 [M+H]$^+$. $^1$H NMR (400 MHz, DMSO-d$_6$): δ 10.77 (s, 1H), 10.72 (s, 1H), 7.73-7.65 (m, 3H), 7.08-6.98 (m, 1H), 6.79-6.76 (m, 1H).

Example 52: 5-(2,6-Difluorophenyl)-1,3-dihydrobenzimidazol-2-one

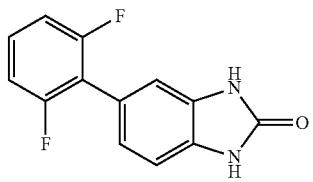 [SMILES: O=c1[nH]c2ccc(-c3c(F)cccc3F)cc2[nH]1]

The title compound was prepared in a manner analogous to Example 2, substituting 1,3-difluoro-2-iodobenzene for 2,6-dimethyliodobenzene and PdCl$_2$(dppf)-CH$_2$Cl$_2$ for PdCl$_2$(dtbpf) in Step B. MS (ESI): mass calcd. for C$_{13}$H$_8$F$_2$N$_2$O, 246.1; m/z found, 247.2 [M+H]$^+$. $^1$H NMR (400 MHz, DMSO-d$_6$) δ 10.75 (s, 2H), 7.43 (tt, J=8.4, 6.5 Hz, 1H), 7.19 (t, J=7.9 Hz, 2H), 7.06-6.95 (m, 3H).

Example 53: 5-(2-Chloro-6-fluoro-phenyl)-1,3-dihydrobenzimidazol-2-one

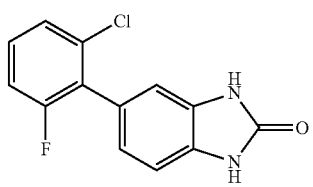

The title compound was prepared in a manner analogous to Example 2, substituting 1-chloro-3-fluoro-2-iodobenzene for 2,6-dimethyliodobenzene and PdCl$_2$(dppf)-CH$_2$Cl$_2$ for PdCl$_2$(dtbpf) in Step B. MS (ESI): mass calcd. for C$_{13}$H$_8$ClFN$_2$O, 262.0; m/z found, 263.1 [M+H]$^+$. $^1$H NMR (400 MHz, DMSO-d$_6$) δ 10.77 (s, 1H), 10.72 (s, 1H), 7.46-7.40 (m, 2H), 7.36-7.26 (m, 1H), 7.02 (d, J=7.8 Hz, 1H), 6.94-6.85 (m, 2H).

Example 54: 5-(2-Fluoro-6-methyl-phenyl)-1,3-dihydrobenzimidazol-2-one

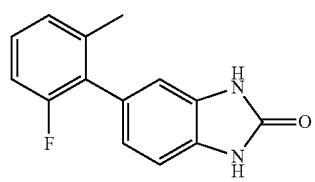 [SMILES: Cc1cccc(F)c1-c1ccc2[nH]c(=O)[nH]c2c1]

The title compound was prepared in a manner analogous to Example 2, substituting 2-bromo-1-fluoro-3-methylbenzene for 2,6-dimethyliodobenzene and PdCl$_2$(dppf)-CH$_2$Cl$_2$ for PdCl$_2$(dtbpf) in Step B. MS (ESI): mass calcd. for C$_{14}$H$_{11}$FN$_2$O, 242.1; m/z found, 243.1 [M+H]$^+$. $^1$H NMR (400 MHz, DMSO-d$_6$) δ 10.64 (s, 2H), 7.33-7.23 (m, 1H), 7.16-7.03 (m, 2H), 7.02-6.96 (d, J=7.9 Hz, 1H), 6.84-6.74 (m, 2H), 2.09 (s, 3H).

Example 55: 5-(2-Fluoro-6-methoxy-phenyl)-1,3-dihydrobenzimidazol-2-one

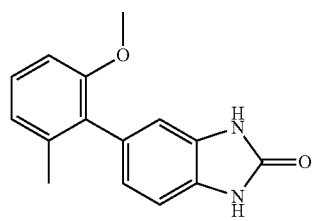 [SMILES: COc1cccc(C)c1-c1ccc2[nH]c(=O)[nH]c2c1]

The title compound was prepared in a manner analogous to Example 2, substituting 2-bromo-1-methoxy-3-methylbenzene for 2,6-dimethyliodobenzene and PdCl$_2$(dppf)-CH$_2$Cl$_2$ for PdCl$_2$(dtbpf) in Step B. MS (ESI): mass calcd. for C$_{15}$H$_{14}$N$_2$O$_2$, 254.1; m/z found, 255.1 [M+H]$^+$. $^1$H NMR (400 MHz, DMSO-d$_6$) δ 10.63-10.49 (m, 2H), 7.20 (t, J=7.9 Hz, 1H), 6.98-6.81 (m, 3H), 6.72-6.60 (m, 2H), 3.62 (s, 3H), 2.00 (s, 3H).

Example 56: 3-Chloro-2-(2-oxo-1,3-dihydrobenzimidazol-5-yl)benzonitrile

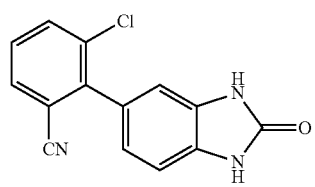 [SMILES: N#Cc1cccc(Cl)c1-c1ccc2[nH]c(=O)[nH]c2c1]

The title compound was prepared in a manner analogous to Example 2, substituting 2-bromo-3-chlorobenzonitrile for 2,6-dimethyliodobenzene and PdCl$_2$(dppf)-CH$_2$Cl$_2$ for PdCl$_2$(dtbpf) in Step B. MS (ESI): mass calcd. for C$_{14}$H$_8$ClN$_3$O, 269.0; m/z found, [M+H]270.1 [M+H]$^+$. $^1$H NMR (400 MHz, DMSO-d$_6$) δ 10.84 (s, 1H), 10.80 (s, 1H), 7.92 (ddd, J=8.3, 4.0, 1.2 Hz, 2H), 7.58 (dd, J=8.3, 7.7 Hz, 1H), 7.08-7.03 (m, 1H), 6.98-6.92 (m, 2H).

Example 57: 5-[2-Methyl-6-(trifluoromethyl)phenyl]-1,3-dihydrobenzimidazol-2-one

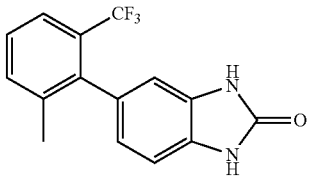 [SMILES: Cc1cccc(C(F)(F)F)c1-c1ccc2[nH]c(=O)[nH]c2c1]

The title compound was prepared in a manner analogous to Example 2, substituting 2-bromo-1-methyl-3-(trifluoromethyl)benzene for 2,6-dimethyliodobenzene and PdCl$_2$(dppf)-CH$_2$Cl$_2$ for PdCl$_2$(dtbpf) in Step B. The crude product was purified by trituration with DCM to afford the title compound (16 mg, 19% yield). MS (ESI): mass calcd. for C$_{15}$H$_{11}$F$_3$N$_2$O, 292.1; m/z found, 293.1 [M+H]$^+$. $^1$H NMR (400 MHz, DMSO-d$_6$) δ 10.70 (s, 1H), 10.64 (s, 1H), 7.67-7.56 (m, 2H), 7.54-7.41 (m, 1H), 6.98 (dd, J=7.8, 0.7 Hz, 1H), 6.75-6.60 (m, 2H), 1.98 (s, 3H).

Example 58: 5-(8-Quinolyl)-1,3-dihydrobenzimidazol-2-one

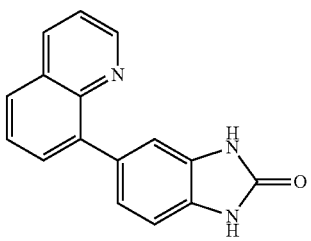 [SMILES: O=c1[nH]c2ccc(-c3cccc4cccnc34)cc2[nH]1]

The title compound was prepared in a manner analogous to Example 2, substituting 8-bromoquinoline for 2,6-dimethyliodobenzene in Step B. The crude product was purified by reverse-phase HPLC (XBridge C18 column (5 µm, 100×4.6 mm), mobile phase of 10-100% ACN in 20 mM NH$_4$OH) to afford the title compound (5 mg, 7% yield). MS (ESI): mass calcd. for C$_{16}$H$_{11}$N$_3$O, 261.1; m/z found, 262.2 [M+H]$^+$. $^1$H NMR (500 MHz, CD$_3$OD) δ 8.80 (dd, J=4.2, 1.8 Hz, 1H), 8.39 (dd, J=8.3, 1.8 Hz, 1H), 7.92 (dd, J=8.2, 1.5 Hz, 1H), 7.74 (dd, J=7.1, 1.6 Hz, 1H), 7.65 (dd, J=8.1, 7.1 Hz, 1H), 7.53 (dd, J=8.3, 4.2 Hz, 1H), 7.34-7.26 (m, 2H), 7.16 (d, J=8.0 Hz, 1H).

Example 59: 5-(2-Benzylphenyl)-1,3-dihydrobenzimidazol-2-one

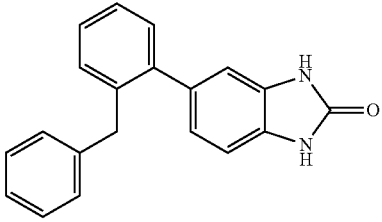 [SMILES: O=c1[nH]c2ccc(-c3ccccc3Cc3ccccc3)cc2[nH]1]

The title compound was prepared in a manner analogous to Example 2, substituting 1-benzyl-2-bromobenzene for 2,6-dimethyliodobenzene and PdCl$_2$(dppf)-CH$_2$Cl$_2$ for PdCl$_2$(dtbpf) in Step B. MS (ESI): mass calcd. for C$_{20}$H$_{16}$N$_2$O, 300.1; m/z found, 301.1 [M+H]$^+$. $^1$H NMR (400 MHz, DMSO-d$_6$) δ 10.65 (s, 1H), 10.62 (s, 1H), 7.35-7.09 (m, 7H), 7.00-6.89 (m, 3H), 6.86-6.71 (m, 2H), 3.94 (s, 2H).

Example 60: 5-[2-Methyl-3-(trifluoromethyl)phenyl]-1,3-dihydrobenzimidazol-2-one

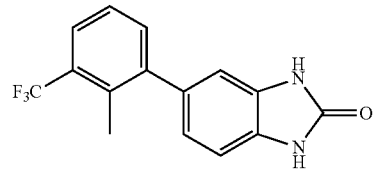 [SMILES: Cc1c(-c2ccc3[nH]c(=O)[nH]c3c2)cccc1C(F)(F)F]

The title compound was prepared in a manner analogous to Example 2, substituting 1-bromo-2-methyl-3-(trifluoromethyl)benzene for 2,6-dimethyliodobenzene and PdCl$_2$(dppf)-CH$_2$Cl$_2$ for PdCl$_2$(dtbpf) in Step B. The crude product was purified by reverse-phase HPLC (XBridge C18 column (5 µm, 100×4.6 mm), mobile phase of 10-100% ACN in 20 mM NH$_4$OH) to afford the title compound (2 mg, 2% yield). MS (ESI): mass calcd. for C$_{15}$H$_{11}$F$_3$N$_2$O, 292.1; m/z found, 293.2 [M+H]$^+$. $^1$H NMR (400 MHz, CD$_3$OD) δ 7.65 (dd, J=7.5, 1.3 Hz, 1H), 7.46-7.42 (m, 1H), 7.40-7.34 (m, 1H), 7.11 (d, J=8.4 Hz, 1H), 6.97-6.92 (m, 2H).

Example 61: 5-[2-Chloro-3-(trifluoromethyl)phenyl]-1,3-dihydrobenzimidazol-2-one

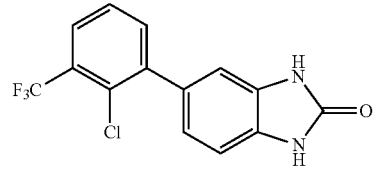 [SMILES: O=c1[nH]c2ccc(-c3cccc(C(F)(F)F)c3Cl)cc2[nH]1]

The title compound was prepared in a manner analogous to Example 2, substituting 1-bromo-2-chloro-3-(trifluoromethyl)benzene for 2,6-dimethyliodobenzene and PdCl$_2$(dppf)-CH$_2$Cl$_2$ for PdCl$_2$(dtbpf) in Step B. The crude product was purified by reverse-phase HPLC (XBridge C18 column (5 μm, 100×4.6 mm), mobile phase of 10-100% ACN in 20 mM NH₄OH) to afford the title compound (4 mg, 3% yield). MS (ESI): mass calcd. for C₁₄H₈ClF₃N₂O, 312.0; m/z found, 313.1 [M+H]⁺. ¹H NMR (400 MHz, CD₃OD) δ 7.78 (dd, J=7.9, 1.6 Hz, 1H), 7.62 (dd, J=7.8, 1.6 Hz, 1H), 7.55-7.49 (m, 1H), 7.15-7.09 (m, 1H), 7.09-7.03 (m, 2H).

Example 62: 2-Isopropoxy-6-(2-oxo-1,3-dihydrobenzimidazol-5-yl)benzonitrile

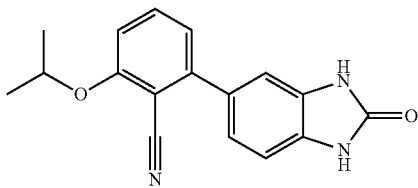 [SMILES: CC(C)Oc1cccc(-c2ccc3[nH]c(=O)[nH]c3c2)c1C#N]

The title compound was prepared in a manner analogous to Example 2, substituting 2-bromo-6-isopropoxybenzonitrile for 2,6-dimethyliodobenzene and PdCl₂(dppf)-CH₂Cl₂ for PdCl₂(dtbpf) in Step B. MS (ESI): mass calcd. for C₁₇H₁₅N₃O₂, 293.1; m/z found, 294.1 [M+H]⁺. ¹H NMR (400 MHz, DMSO-d₆) δ 10.79 (s, 2H), 7.64 (dd, J=8.5, 7.7 Hz, 1H), 7.23 (d, J=8.5 Hz, 1H), 7.14-7.01 (m, 4H), 4.82 (dt, J=12.1, 6.1 Hz, 1H), 1.34 (d, J=6.0 Hz, 6H).

Example 63: 2-Bromo-6-(2-oxo-1,3-dihydrobenzimidazol-5-yl)benzonitrile

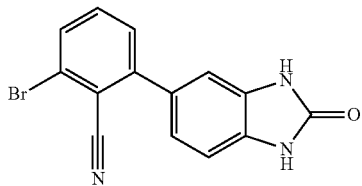 [SMILES: N#Cc1c(Br)cccc1-c1ccc2[nH]c(=O)[nH]c2c1]

The title compound was prepared in a manner analogous to Example 2, substituting 2-bromo-6-iodobenzonitrile for 2,6-dimethyliodobenzene and PdCl₂(dppf)-CH₂Cl₂ for PdCl₂(dtbpf) in Step B. The crude product was purified by reverse-phase HPLC (XBridge C18 column (5 μm, 100×4.6 mm), mobile phase of 10-100% ACN in 20 mM NH₄OH) to afford the title compound (2 mg, 3% yield). MS (ESI): mass calcd. for C₁₄H₈BrN₃O, 313.0; m/z found, 314.1 [M+H]⁺. ¹H NMR (400 MHz, CD₃OD) δ 7.77 (dd, J=7.8, 1.3 Hz, 1H), 7.62-7.52 (m, 2H), 7.26-7.21 (m, 2H), 7.19-7.14 (m, 1H).

Example 64: 5-(2-Chloro-3-methyl-phenyl)-1,3-dihydrobenzimidazol-2-one

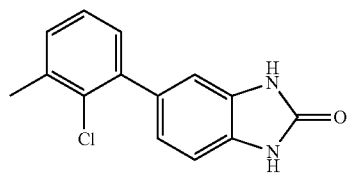 [SMILES: Cc1cccc(-c2ccc3[nH]c(=O)[nH]c3c2)c1Cl]

The title compound was prepared in a manner analogous to Example 2, substituting 1-bromo-2-chloro-3-methylbenzene for 2,6-dimethyliodobenzene and PdCl₂(dppf)-CH₂Cl₂ for PdCl₂(dtbpf) in Step B. The crude product was purified by reverse-phase HPLC (XBridge C18 column (5 μm, 100×4.6 mm), mobile phase of 10-100% ACN in 20 mM NH₄OH) to afford the title compound (5 mg, 5% yield). MS (ESI): mass calcd. for C₁₄H₁₁ClN₂O, 258.1; m/z found, 259.1 [M+H]⁺. ¹H NMR (400 MHz, CD₃OD): δ 7.31-7.16 (m, 3H), 7.10-7.02 (m, 3H), 2.43 (s, 3H).

Example 65: 2-(2-Oxo-1,3-dihydrobenzimidazol-5-yl)-6-(trifluoromethyl)benzonitrile

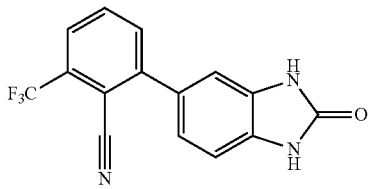 [SMILES: N#Cc1c(-c2ccc3[nH]c(=O)[nH]c3c2)cccc1C(F)(F)F]

The title compound was prepared in a manner analogous to Example 2, substituting 2-bromo-6-(trifluoromethyl)benzonitrile for 2,6-dimethyliodobenzene in Step B. The crude product was purified by reverse-phase HPLC (XBridge C18 column (5 μm, 100×4.6 mm), mobile phase of 10-100% ACN in 20 mM NH₄OH) to afford the title compound (5 mg, 4% yield). MS (ESI): mass calcd. for C₁₅H₈F₃N₃O, 303.1; m/z found, M+H]=304.2 [M+H]⁺. ¹H NMR (400 MHz, CD₃OD): δ 8.03-7.66 (m, 3H), 7.33-7.06 (m, 3H).

Example 66: 5-(2,3,6-Trichlorophenyl)-1,3-dihydrobenzimidazol-2-one

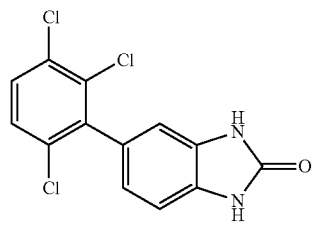 [SMILES: O=c1[nH]c2ccc(-c3c(Cl)ccc(Cl)c3Cl)cc2[nH]1]

The title compound was prepared in a manner analogous to Example 2, substituting 2-bromo-1,3,4-trichlorobenzene for 2,6-dimethyliodobenzene and PdCl₂(dppf)-CH₂Cl₂ for PdCl₂(dtbpf) in Step B. The crude product was purified by reverse-phase HPLC (XBridge C18 column (5 μm, 100×4.6 mm), mobile phase of 10-100% ACN in 20 mM NH₄OH) to afford the title compound (41 mg, 14% yield). MS (ESI): mass calcd. for C₁₃H₇Cl₃N₂O, 312.0; m/z found, 312.9 [M+H]⁺. ¹H NMR (400 MHz, DMSO-d₆) δ 6.67-6.63 (m, 1H), 6.59-6.55 (m, 1H), 6.24 (dd, J=7.8, 0.8 Hz, 1H), 6.00-5.95 (m, 2H).

Example 67: 2-Methyl-3-(2-oxo-1,3-dihydrobenz-imidazol-5-yl)benzonitrile

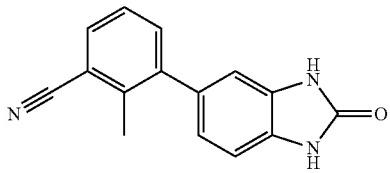 [SMILES: Cc1c(C#N)cccc1-c1ccc2[nH]c(=O)[nH]c2c1]

The title compound was prepared in a manner analogous to Example 2, substituting 3-bromo-2-methylbenzonitrile for 2,6-dimethyliodobenzene and PdCl$_2$(dppf)-CH$_2$Cl$_2$ for PdCl$_2$(dtbpf) in Step B. The crude product was purified by reverse-phase HPLC (XBridge C18 column (5 µm, 100×4.6 mm), mobile phase of 10-100% ACN in 20 mM NH$_4$OH) to afford the title product (8 mg, 8% yield). MS (ESI): mass calcd. for C$_{15}$H$_{11}$N$_3$O, 249.1; m/z found, 250.1 [M+H]$^+$. $^1$H NMR (500 MHz, CD$_3$OD) δ 7.66 (dd, J=7.7, 1.4 Hz, 1H), 7.50 (dd, J=7.7, 1.4 Hz, 1H), 7.39 (t, J=7.7 Hz, 1H), 7.12 (d, J=8.4 Hz, 1H), 7.02-6.93 (m, 2H), 2.43 (s, 3H).

Example 68: 2-Chloro-3-(2-oxo-1,3-dihydrobenz-imidazol-5-yl)benzonitrile

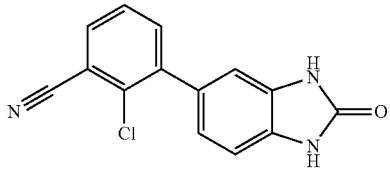 [SMILES: N#Cc1cccc(-c2ccc3[nH]c(=O)[nH]c3c2)c1Cl]

The title compound was prepared in a manner analogous to Example 2, substituting 3-bromo-2-chlorobenzonitrile for 2,6-dimethyliodobenzene and PdCl$_2$(dppf)-CH$_2$Cl$_2$ for PdCl$_2$(dtbpf) in Step B. The crude product was purified by reverse-phase HPLC (XBridge C18 column (5 µm, 100×4.6 mm), mobile phase of 10-100% ACN in 20 mM NH$_4$OH) to afford the title compound (15 mg, 14% yield). MS (ESI): mass calcd. for C$_{14}$H$_8$ClN$_3$O, 269.0; m/z found, 270.1 [M+H]$^+$. $^1$H NMR (500 MHz, DMSO) δ 10.80 (s, 1H), 10.77 (s, 1H), 7.97 (dd, J=7.7, 1.6 Hz, 1H), 7.75 (dd, J=7.8, 1.6 Hz, 1H), 7.60 (t, J=7.7 Hz, 1H), 7.06-6.96 (m, 3H).

Example 69: 5-(3,5-Dichloro-4-pyridyl)-1,3-dihyd-robenzimidazol-2-one

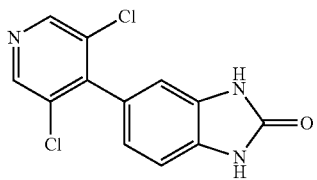 [SMILES: O=c1[nH]c2ccc(-c3c(Cl)cncc3Cl)cc2[nH]1]

The title compound was prepared in a manner analogous to Example 2, substituting 3,5-dichloro-4-iodopyridine for 2,6-dimethyliodobenzene and PdCl$_2$(dppf)-CH$_2$Cl$_2$ for PdCl$_2$(dtbpf) in Step B. MS (ESI): mass calcd. for C$_{12}$H$_7$Cl$_2$N$_3$O, 280.1; m/z found, 281.1 $^1$H NMR (400 MHz, DMSO-d$_6$) δ 10.85 (s, 1H), 10.81 (s, 1H), 8.72 (s, 2H), 7.12-7.01 (m, 1H), 6.93-6.85 (m, 2H).

Example 70: 5-(2-Chloro-4-methyl-3-pyridyl)-1,3-dihydrobenzimidazol-2-one

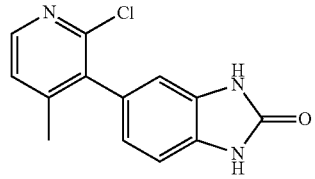 [SMILES: Cc1ccnc(Cl)c1-c1ccc2[nH]c(=O)[nH]c2c1]

The title compound was prepared in a manner analogous to Example 2, substituting 3-bromo-2-chloro-4-methylpyridine for 2,6-dimethyliodobenzene and PdCl$_2$(dppf)-CH$_2$Cl$_2$ for PdCl$_2$(dtbpf) in Step B. The crude product was purified by reverse-phase HPLC (XBridge C18 column (5 µm, 100×4.6 mm), mobile phase of 10-100% ACN in 20 mM NH$_4$OH) to afford the title product (2 mg, 3% yield). MS (ESI): mass calcd. for C$_{13}$H$_{10}$ClN$_3$O, 259.7; m/z found, 260.7 [M+H]$^+$. $^1$H NMR (400 MHz, CD$_3$OD) δ 8.20 (d, J=5.1 Hz, 1H), 7.34 (dd, J=5.0, 0.8 Hz, 1H), 7.15 (dd, J=7.9, 0.7 Hz, 1H), 6.92-6.84 (m, 2H), 2.15 (d, J=0.6 Hz, 3H).

Example 71: 5-[2-Methyl-3-(5-methyl-1,2,4-oxadi-azol-3-yl)phenyl]-1,3-dihydrobenzimidazol-2-one

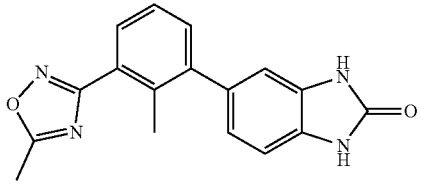 [SMILES: Cc1nc(-c2cccc(-c3ccc4[nH]c(=O)[nH]c4c3)c2C)no1]

Step A: 3-(3-Bromo-2-methylphenyl)-5-methyl-1,2,4-oxadiazole

To a stirred solution of 3-bromo-2-methyl-benzonitrile (569 mg, 2.9 mmol) in tBuOH (7 mL) was added 50 wt % aqueous hydroxylamine (0.27 mL, 4.4 mmol). The mixture was heated at 60° C. for 3 h. After cooling to rt, the solvent was removed in vacuo, and to the resulting residue was added dioxane (8 mL), pyridine (16 mL), and acetyl chloride (0.25 mL, 3.5 mmol). The reaction mixture was heated at 100° C. for 16 h. After cooling to rt, the solvent was removed in vacuo. The residue was diluted with water and extracted with EtOAc. The organic layer was dried over MgSO$_4$ and concentrated under vacuum. The crude was purified by FCC (SiO$_2$; 0-10% EtOAc/heptanes) to afford the desired product (161 mg, 22% yield). MS (ESI): mass calcd. for C$_{10}$H$_9$BrN$_2$O, 252.0 m/z found, 253.0 [M+H]$^+$.

Step B: 5-[2-Methyl-3-(5-methyl-1,2,4-oxadiazol-3-yl)phenyl]-1,3-dihydrobenzimidazol-2-one To a solution of 5-(4,4,5,5-tetramethyl-1,3,2-dioxaboro-lan-2-yl)-1H-benzo[d]imidazol-2(3H)-one (Intermediate 28, 69 mg, 0.27 mmol), sodium bicarbonate (60 mg, 0.71 mmol), PdCl₂(dtbpf) (12 mg, 0.02 mmol) in 3:1 dioxane: water (6 mL) was 3-(3-bromo-2-methylphenyl)-5-methyl-1, 2,4-oxadiazole (45 mg, 0.18 mmol) at once. The mixture was degassed with nitrogen for 10 minutes and then heated at 70° C. for 3 h. After cooling to rt, the reaction mixture was diluted with water and extracted with EtOAc (×3). The combined organic extracts were dried (Na₂SO₄), filtered and concentrated. Purification (FCC, SiO₂; 0-50% EtOAc/heptanes) afforded the title compound as a white solid (11 mg, 20% yield). MS (ESI): mass calcd. for C₁₇H₁₄N₄O₂, 306.1; m/z found, 307.0 [M+H]⁺. ¹H NMR (300 MHz, DMSO-d₆) δ 10.69 (bs, 1H), 10.67 (bs, 1H), 9.15 (s, 1H), 7.97 (dd, J=6.9, 1.9 Hz, 1H), 7.55-7.42 (m, 2H), 7.01 (d, J=7.8 Hz, 1H), 6.90 (dd, J=8.0, 2.0 Hz, 1H), 6.87 (s, 1H), 2.46 (s, 3H).

Example 72: 6-[2-Methyl-3-(5-methyl-1,2,4-oxadiazol-3-yl)phenyl]-3H-1,3-benzothiazol-2-one

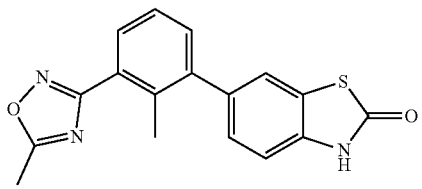 [SMILES: Cc1nc(-c2cccc(-c3ccc4[nH]c(=O)sc4c3)c2C)no1]

The title compound was prepared in a manner analogous to Example 71, substituting Intermediate 2, (6-(4,4,5,5-tetramethyl-1,3,2-dioxaborolan-2-yl)benzo[d]thiazol-2 (3H)-one), for 5-(4,4,5,5-tetramethyl-1,3,2-dioxaborolan-2-yl)-1H-benzo[d]imidazol-2(3H)-one in Step B. MS (ESI): mass calcd. for C₁₇H₁₃N₃O₂S, 323.1; m/z found, 324.0 [M+H]⁺. ¹H NMR (300 MHz, DMSO-d₆) δ 11.95 (bs, 1H), 7.80 (dd, J=2.5, 6.6 Hz, 1H), 7.60 (d, J=1.2 Hz, 1H), 7.46-7.36 (m, 2H), 7.26 (dd, J=8.2, 1.5 Hz, 1H), 7.19 (d, J=8.1 Hz, 1H), 2.68 (s, 3H), 2.36 (s, 3H).

Example 73: 5-[3-(5-Cyclopropyl-1,2,4-oxadiazol-3-yl)-2-methyl-phenyl]-1,3-dihydrobenzimidazol-2-one

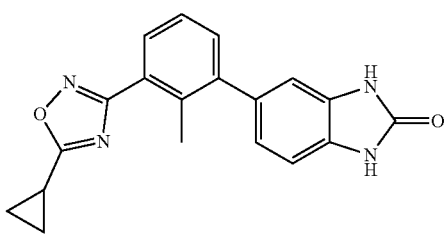 [SMILES: Cc1c(-c2ccc3[nH]c(=O)[nH]c3c2)cccc1-c1noc(C2CC2)n1]

The title compound was prepared in a manner analogous to Example 71, substituting cyclopropanecarbonyl chloride for acetyl chloride in Step A. MS (ESI): mass calcd. for C₁₉H₁₆N₄O₂, 332.1; m/z found, 333.0 [M+H]⁺. ¹H NMR (300 MHz, DMSO-d₆) δ 10.67 (bs, 1H), 10.65 (bs, 1H), 7.80-7.68 (m, 1H), 7.43-7.31 (m, 2H), 6.99 (d, J=7.8 Hz, 1H), 6.88 (dd, J=8.1, 1.4 Hz, 1H), 6.84 (s, 1H), 2.45-2.36 (m, 1H), 2.32 (s, 3H), 1.35-1.13 (m, 4H).

Example 74: 6-[3-(5-Cyclopropyl-1,2,4-oxadiazol-3-yl)-2-methyl-phenyl]-3H-1,3-benzothiazol-2-one

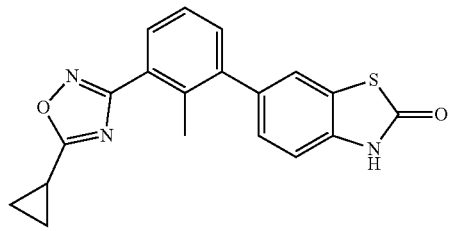 [SMILES: Cc1c(-c2ccc3[nH]c(=O)sc3c2)cccc1-c1noc(C2CC2)n1]

The title compound was prepared in a manner analogous to Example 71, substituting cyclopropanecarbonyl chloride for acetyl chloride in Step A, and 6-(4,4,5,5-tetramethyl-1,3,2-dioxaborolan-2-yl)benzo[d]thiazol-2(3H)-one (Intermediate 2), for 5-(4,4,5,5-tetramethyl-1,3,2-dioxaborolan-2-yl)-1H-benzo[d]imidazol-2(3H)-one in Step B. MS (ESI): mass calcd. for C₁₉H₁₅N₃O₂S, 349.1; m/z found, 349.9 [M+H]⁺. ¹H NMR (300 MHz, DMSO-d₆) δ 11.96 (bs 1H), 7.76 (dd, J=6.0, 2.8 Hz, 1H), 7.59 (s, 1H), 7.45-7.35 (m, 2H), 7.25 (dd, J=8.0, 1.0 Hz, 1H), 7.19 (d, J=8.1 Hz, 1H), 2.46-2.36 (m, 1H), 2.33 (s, 3H), 1.35-1.25 (m, 2H), 1.22-1.13 (m, 2H).

Example 75: 5-[2-Methyl-3-[5-(4-pyridyl)-1,2,4-oxadiazol-3-yl]phenyl]-1,3-dihydrobenzimidazol-2-one

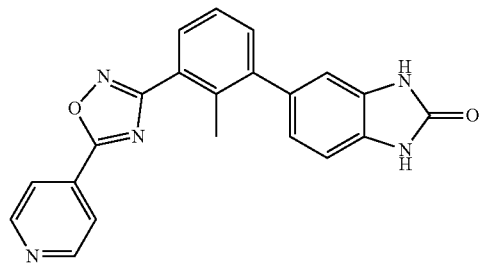 [SMILES: Cc1c(-c2ccc3[nH]c(=O)[nH]c3c2)cccc1-c1noc(-c2ccncc2)n1]

The title compound was prepared in a manner analogous to Example 71, substituting isonicotinoyl chloride for acetyl chloride in Step A. MS (ESI): mass calcd. for C₂₁H₁₅N₅O₂, 369.1; m/z found, 370.1 [M+H]⁺. ¹H NMR (300 MHz, DMSO-d₆) δ 9.53 (br s, 2H), 8.96-8.89 (m, 2H), 8.15-8.09 (m, 2H), 7.90 (dd, J=6.0, 3.2 Hz, 1H), 7.51-7.40 (m, 2H), 7.02 (d, J=8.0 Hz, 1H), 6.92 (dd, J=8.1, 1.4 Hz, 1H), 6.88 (s, 1H), 2.42 (s, 3H).

Example 76: 6-[2-Chloro-6-(trifluoromethoxy)phenyl]-3H-1,3-benzothiazol-2-one

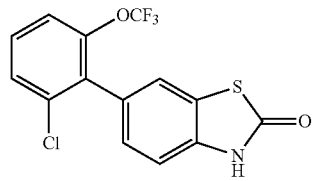 [SMILES: O=c1[nH]c2ccc(-c3c(Cl)cccc3OC(F)(F)F)cc2s1]

The title compound was prepared in a manner analogous to Example 1, substituting (2-chloro-6-(trifluoromethoxy)phenyl)boronic acid for (2,3-dimethylphenyl)boronic acid, 6-[2-chloro-6-(trifluoromethoxy)phenyl]-3H-1,3-benzothiazol-2-one for 5-bromo-1H-benzo[d]imidazol-2(3H)-one, and PdCl$_2$(dtbpf) for PdCl$_2$(dppf)-CH$_2$Cl$_2$. MS (ESI): mass calcd. for C$_{14}$H$_7$ClF$_3$NO$_2$S, 345.0; m/z found, 345.9 [M+H]$^+$. $^1$H NMR (400 MHz, CDCl$_3$): δ 9.12 (s, 1H), 7.49-7.43 (m, 1H), 7.39-7.28 (m, 3H), 7.23-7.17 (m, 2H).

Example 77: 6-(2-Isopropoxy-6-methoxy-phenyl)-3H-1,3-benzothiazol-2-one

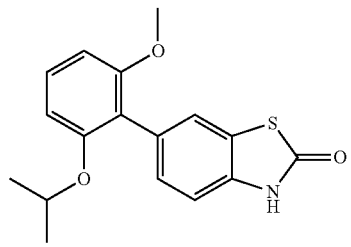 [SMILES: COc1cccc(OC(C)C)c1-c1ccc2[nH]c(=O)sc2c1]

The title compound was prepared in a manner analogous to Example 1, substituting (2-isopropoxy-6-methoxyphenyl)boronic acid for (2,3-dimethylphenyl)boronic acid, tert-butyl 6-bromo-2-oxobenzo[d]thiazole-3(2H)-carboxylate (Intermediate 1) for 5-bromo-1H-benzo[d]imidazol-2(3H)-one, and PdCl$_2$(dtbpf) for PdCl$_2$(dppf)-CH$_2$Cl$_2$. MS (ESI): mass calcd. for C$_{17}$H$_{17}$NO$_3$S, 315.1; m/z found, 316.1 [M+H]$^+$. $^1$H NMR (500 MHz, CD$_3$OD) δ 7.33 (d, J=1.6 Hz, 1H), 7.25 (t, J=8.4 Hz, 1H), 7.21-7.16 (m, 1H), 7.16-7.09 (m, 1H), 6.74-6.65 (m, 2H), 4.41 (hept, J=6.1 Hz, 1H), 3.71 (s, 3H), 1.14 (d, J=6.0 Hz, 6H).

Example 78: N-Methyl-2-[2-(2-oxo-1,3-dihydrobenzimidazol-5-yl)-6-(trifluoromethyl)phenyl] acetamide

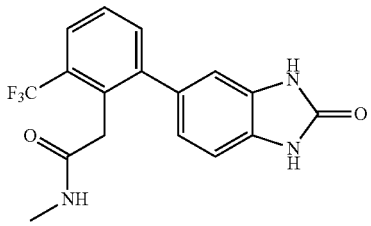 [SMILES: CNC(=O)Cc1c(-c2ccc3[nH]c(=O)[nH]c3c2)cccc1C(F)(F)F]

Step A: 2-(2-Bromo-6-(trifluoromethyl)phenyl)-N-methylacetamide

To a solution of 2-(2-bromo-6-(trifluoromethyl)phenyl)acetic acid (40 mg, 0.14 mmol) in DMF (1.0 mL) were added HATU (107 mg, 0.28 mmol), DIEA (0.05 mL, 0.28 mmol) and methylamine (6.2 μL, 0.15 mmol) sequentially. The reaction mixture was stirred at rt for 15 minutes, diluted with water, and extracted with EtOAc (×3). The combined organic extracts were dried (Na$_2$SO$_4$), filtered and concentrated to obtain the title compound, which was used without further purification.

Step B: N-Methyl-2-[2-(2-oxo-1,3-dihydrobenzimidazol-5-yl)-6-(trifluoromethyl)phenyl]acetamide The title compound was prepared in a manner analogous to Example 2, substituting 2-(2-bromo-6-(trifluoromethyl)phenyl)-N-methylacetamide for 2,6-dimethyliodobenzene and PdCl$_2$(dppf)-CH$_2$Cl$_2$ for PdCl$_2$(dtbpf) in Step B. The crude product was purified by reverse-phase HPLC (XBridge C18 column (5 μm, 100×4.6 mm), mobile phase of 10-100% ACN in 20 mM NH$_4$OH) to afford the title compound (11 mg, 20% yield). MS (ESI): mass calcd. for C$_{17}$H$_{14}$F$_3$N$_3$O$_2$, 349.1; m/z found, 350.1 [M+H]$^+$. $^1$H NMR (400 MHz, CD$_3$OD): δ 7.78-7.69 (m, 1H), 7.53-7.43 (m, 2H), 7.11-7.04 (m, 1H), 7.02-6.90 (m, 2H), 3.65 (s, 2H), 2.60 (s, 3H).

Example 79: 2-Methyl-3-(2-oxo-1,3-dihydrobenzimidazol-5-yl)-N-phenyl-benzamide

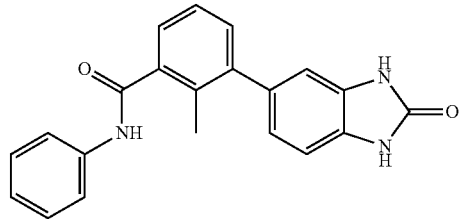 [SMILES: Cc1c(C(=O)Nc2ccccc2)cccc1-c1ccc2[nH]c(=O)[nH]c2c1]

Step A: 3-Iodo-2-methyl-N-phenylbenzamide

To a cooled (0° C.) solution of 3-iodo-2-methylbenzoic acid (300 mg, 1.1 mmol), aniline (0.16 mL, 1.7 mmol), N,N-diisopropylethylamine (DIEA) (0.61 mL, 3.4 mmol), and DMAP (28 mg, 0.23 mmol) in THF (3 mL) was added dropwise a 50 wt % solution of propylphosphonic anhydride (T3P®) in EtOAc (1.0 mL, 1.7 mmol). Following the addition, the ice bath was removed and the reaction mixture was stirred at 23° C. for 1 h. 1N HCl was added and the mixture was extracted with EtOAc (3×). The combined organic extracts were dried (Na$_2$SO$_4$), filtered and concentrated to afford the title compound as a white solid, which was used without further purification. MS (ESI): mass calcd. for C$_{14}$H$_{12}$INO, 337.0; m/z found, 337.8 [M+H]$^+$.

Step B: 5-[2-Methyl-3-(1,2,4-oxadiazol-3-yl)phenyl]-1,3-dihydrobenzimidazol-2-one The title compound was prepared in a manner analogous to Example 2, substituting 3-iodo-2-methyl-N-phenylbenzamide for 2,6-dimethyliodobenzene and PdCl$_2$(dppf)-CH$_2$Cl$_2$ for PdCl$_2$(dtbpf) in Step B. MS (ESI): mass calcd. for C$_{21}$H$_{17}$N$_3$O$_2$, 343.1; m/z found, 344.0 [M+H]$^+$. $^1$H NMR (400 MHz, DMSO-d$_6$) δ 10.70 (s, 1H), 10.67 (s, 1H), 10.39 (s, 1H), 7.75 (dd, J=8.3, 1.2 Hz, 2H), 7.46-7.23 (m, 5H), 7.17-7.05 (m, 1H), 7.01 (d, J=7.9 Hz, 1H), 6.97-6.80 (m, 2H), 2.23 (s, 3H).

Example 80: N-Cyclopropyl-2-methyl-3-(2-oxo-1,3-dihydrobenzimidazol-5-yl)benzamide

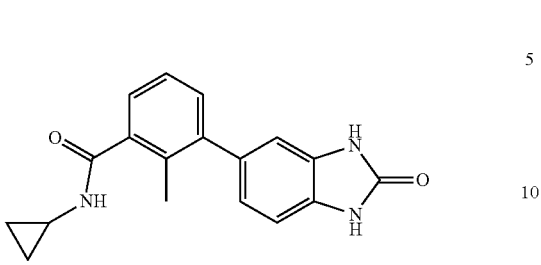

The title compound was prepared in a manner analogous to Example 79, substituting cyclopropylamine for aniline in Step A. MS (ESI): mass calcd. for $C_{18}H_{17}N_3O_2$, 307.1; m/z found, 308.0 [M+H]$^+$. $^1$H NMR (500 MHz, DMSO-d$_6$) δ 10.66 (d, J=16.1 Hz, 2H), 8.34 (d, J=4.6 Hz, 1H), 7.32-7.16 (m, 3H), 6.98 (d, J=7.9 Hz, 1H), 6.90-6.74 (m, 2H), 2.88-2.79 (m, 1H), 2.15 (s, 3H), 0.72-0.65 (m, 2H), 0.55-0.49 (m, 2H).

Example 81: N,N,2-Trimethyl-3-(2-oxo-1,3-dihydrobenzimidazol-5-yl)benzamide

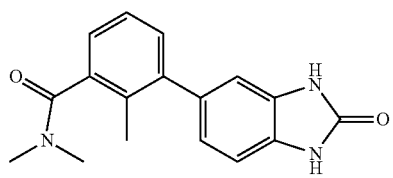 [SMILES: Cc1c(C(=O)N(C)C)cccc1-c1ccc2[nH]c(=O)[nH]c2c1]

The title compound was prepared in a manner analogous to Example 79, substituting 2 M dimethylamine in THF for aniline in Step A. MS (ESI): mass calcd. for $C_{17}H_{17}N_3O_2$, 295.1; m/z found, 296.0 [M+H]$^+$. $^1$H NMR (500 MHz, DMSO-d$_6$) δ 10.68 (s, 1H)), 10.65 (s, 1H), 7.27 (t, J=7.5 Hz, 1H), 7.23-7.17 (m, 1H), 7.13-7.08 (m, 1H), 6.99 (d, J=7.9 Hz, 1H), 6.90-6.82 (m, 2H), 3.01 (s, 3H), 2.79 (s, 3H), 2.05 (s, 3H).

Example 82: 5-[2-Methyl-3-(morpholine-4-carbonyl)phenyl]-1,3-dihydrobenzimidazol-2-one

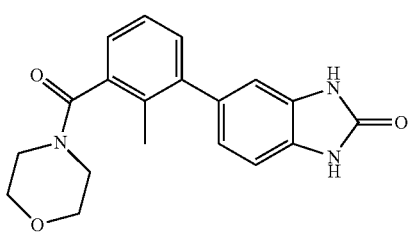 [SMILES: Cc1c(C(=O)N2CCOCC2)cccc1-c1ccc2[nH]c(=O)[nH]c2c1]

The title compound was prepared in a manner analogous to Example 79, substituting morpholine for aniline in Step A. MS (ESI): mass calcd. for $C_{19}H_{19}N_3O_3$, 337.1; m/z found, 338.0 [M+H]$^+$. $^1$H NMR (500 MHz, DMSO-d$_6$) δ 10.68 (s, 1H), 10.65 (s, 1H), 7.29 (t, J=7.5 Hz, 1H), 7.22 (d, J=6.5 Hz, 1H), 7.16 (d, J=7.4 Hz, 1H), 6.98 (d, J=7.9 Hz, 1H), 6.94-6.80 (m, 2H), 3.58-3.46 (m, 4H), 3.26-3.12 (m, 4H), 2.09 (s, 3H).

Example 83: 4-Chloro-3-(2-oxo-1,3-dihydrobenzimidazol-5-yl)-N-phenyl-benzamide

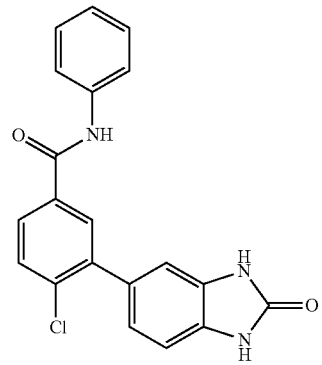

The title compound was prepared in a manner analogous to Example 79, substituting 4-chloro-3-iodobenzoic acid for 3-iodo-2-methylbenzoic acid in Step A. MS (ESI): mass calcd. for $C_{20}H_{14}ClN_3O_2$, 363.1; m/z found, 363.9 [M+H]$^+$. $^1$H NMR (500 MHz, DMSO-d$_6$) δ 10.76 (s, 1H), 10.75 (s, 1H), 10.32 (s, 1H), 8.01 (d, J=2.3 Hz, 1H), 7.94 (dd, J=8.3, 2.3 Hz, 1H), 7.83-7.74 (m, 2H), 7.71 (d, J=8.3 Hz, 1H), 7.42-7.28 (m, 2H), 7.20-6.99 (m, 4H).

Example 84: 5-[2-Chloro-5-(pyrrolidine-1-carbonyl)phenyl]-1,3-dihydrobenzimidazol-2-one

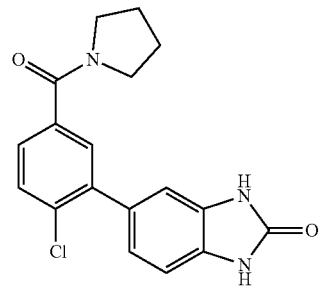

The title compound was prepared in a manner analogous to Example 79, substituting 4-chloro-3-iodobenzoic acid for 3-iodo-2-methylbenzoic acid and pyrrolidine for aniline in Step A. MS (ESI): mass calcd. for $C_{18}H_{16}ClN_3O_2$, 341.1; m/z found, 341.9 [M+H]$^+$. $^1$H NMR (500 MHz, CDCl$_3$) δ10.77-10.60 (m, 1H), 10.54 (s, 1H), 7.52 (d, J=2.0 Hz, 1H), 7.47-7.31 (m, 2H), 7.02-6.86 (m, 3H), 3.65 (t, J=6.9 Hz, 2H), 3.43 (t, J=6.6 Hz, 2H), 2.00-1.80 (m, 4H).

Example 85: 5-[2-Chloro-5-(piperidine-1-carbonyl)phenyl]-1,3-dihydrobenzimidazol-2-one

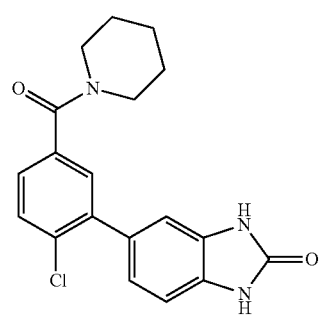

The title compound was prepared in a manner analogous to Example 79, substituting 4-chloro-3-iodobenzoic acid for 3-iodo-2-methylbenzoic acid and piperidine for aniline in Step A. MS (ESI): mass calcd. for $C_{19}H_{18}ClN_3O_2$, 355.1; m/z found, 355.9 [M+H]$^+$. $^1$H NMR (400 MHz, CDCl$_3$) δ 10.78 (s, 1H), 10.65 (s, 1H), 7.49-7.32 (m, 2H), 7.34-7.17 (m, 1H), 7.02-6.89 (m, 3H), 3.77-3.65 (m, 2H), 3.43-3.31 (m, 2H), 2.53-2.45 (m, 1H), 2.10-2.01 (m, 1H), 1.71-1.59 (m, 4H).

Example 86: 5-[2-Chloro-6-(2-furylmethylamino) phenyl]-1,3-dihydrobenzimidazol-2-one

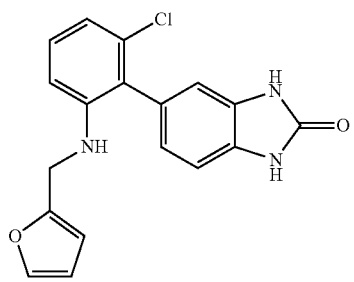

Step A:
3-Chloro-N-(furan-2-ylmethyl)-2-iodoaniline

To a solution of 3-chloro-2-iodoaniline (500 mg, 2.0 mmol) in MeOH (4 mL) was added 2-furaldehyde (0.2 mL, 2.4 mmol). The reaction mixture was stirred at rt for 12 h and then cooled to 0° C. Sodium borohydride (157 mg, 4.1 mmol) was added portionwise. Once the bubbling ceased, the ice bath was removed and stirring was maintained at rt for 2 h. The reaction was concentrated in vacuo, diluted with water, and extracted with EtOAc (×3). The combined organic extracts were dried (Na$_2$SO$_4$), filtered and concentrated. Purification (FCC, SiO$_2$; 0-30% DCM/hexanes) afforded the title compound as an oil (384 mg, 58% yield). MS (ESI): mass calcd. for $C_{11}H_9ClINO$, 332.9; m/z found, 333.8 [M+H]$^+$. $^1$H NMR (400 MHz, CDCl$_3$) δ 7.37 (dd, J=1.9, 0.8 Hz, 1H), 7.10 (t, J=8.0 Hz, 1H), 6.84 (dd, J=7.9, 1.4 Hz, 1H), 6.47 (dd, J=8.2, 1.3 Hz, 1H), 6.32 (dd, J=3.2, 1.8 Hz, 1H), 6.28-6.19 (m, 1H), 4.87 (t, J=5.6 Hz, 1H), 4.36 (dd, J=5.6, 0.7 Hz, 2H).

Step B: 5-[2-Chloro-6-(2-furylmethylamino)phenyl]-1,3-dihydrobenzimidazol-2-one

The title compound was prepared in a manner analogous to Example 2, substituting 3-chloro-N-(furan-2-ylmethyl)-2-iodoaniline for 2,6-dimethyliodobenzene and PdCl$_2$(dppf)-CH$_2$Cl$_2$ for PdCl$_2$(dtbpf). MS (ESI): mass calcd. for $C_{18}H_{14}ClN_3O_2$, 339.1; m/z found, 339.9 [M+H]$^+$. $^1$H NMR (400 MHz, DMSO) δ 10.72 (s, 1H), 10.68 (s, 1H), 7.58-7.49 (m, 1H), 7.11 (t, J=8.1 Hz, 1H), 7.05 (d, J=7.9 Hz, 1H), 6.79-6.69 (m, 3H), 6.67 (d, J=8.2 Hz, 1H), 6.35 (dd, J=3.1, 1.9 Hz, 1H), 6.18 (d, J=3.1 Hz, 1H), 4.82-4.75 (m, 1H), 4.24 (d, J=6.1 Hz, 2H).

Example 87: 5-[2-Chloro-6-(3-furylmethylamino) phenyl]-1,3-dihydrobenzimidazol-2-one

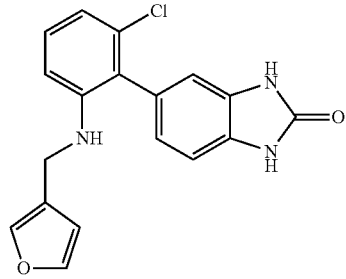

The title compound was prepared in a manner analogous to Example 86, substituting 3-furaldehyde for 2-furaldehyde in Step A. MS (ESI): mass calcd. for $C_{18}H_{14}ClN_3O_2$, 339.1; m/z found, 339.9 [M+H]$^+$. $^1$H NMR (400 MHz, CDCl$_3$) δ 10.52 (s, 1H), 10.31 (s, 1H), 7.27 (t, J=1.7 Hz, 1H), 7.22 (t, J=1.2 Hz, 1H), 7.16 (d, J=8.0 Hz, 1H), 7.11 (t, J=8.1 Hz, 1H), 7.00 (s, 1H), 6.92 (dd, J=8.0, 1.5 Hz, 1H), 6.81 (dd, J=8.1, 0.9 Hz, 1H), 6.60 (dd, J=8.4, 1.0 Hz, 1H), 6.29-6.16 (m, 1H), 4.07 (d, J=5.5 Hz, 2H), 3.87-3.80 (m, 1H).

Example 88: 5-[2-Isopropoxy-6-(trifluoromethoxy) phenyl]-1,3-dihydrobenzimidazol-2-one

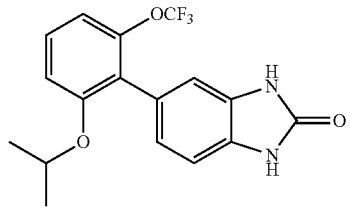

The title compound was prepared in a manner analogous to Example 2, substituting 2-iodo-1-isopropoxy-3-(trifluoromethoxy)benzene (Intermediate 6) for 2,6-dimethyliodobenzene in Step B. The crude product was purified by reverse-phase HPLC (XBridge C18 column (5 μm, 100×4.6 mm), mobile phase of 10-100% ACN in 20 mM NH$_4$OH) to afford the title compound (27 mg, 20% yield). MS (ESI): mass calcd. for $C_{17}H_{15}F_3N_2O_3$, 353.1 m/z found, 352.3 [M+H]$^+$. $^1$H NMR (400 MHz, DMSO): δ 10.64 (s, 1H), 10.56 (s, 1H), 7.46-7.34 (m, 1H), 7.15 (d, J=8.9 Hz, 1H), 7.06-6.91 (m, 2H), 6.87-6.73 (m, 2H), 4.60-4.48 (m, 1H), 1.19-1.09 (d, J=6.0 Hz, 6H).

Example 89: 5-[2-(Cyclopropylmethoxy)-6-(trifluoromethoxy)phenyl]-1,3-dihydrobenzimidazol-2-one

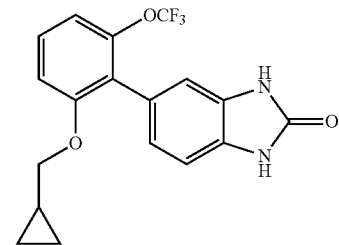

The title compound was prepared in a manner analogous to Example 2, substituting 1-(cyclopropylmethoxy)-2-iodo-3-(trifluoromethoxy)benzene (Intermediate 7) for 2,6-dimethyliodobenzene in Step B. MS (ESI): mass calcd. for $C_{18}H_{15}F_3N_2O_3$, 364.3; m/z found, 365.1 [M+H]$^+$. $^1$H NMR (400 MHz, DMSO-d$_6$): δ 10.65 (s, 1H), 10.57 (s, 1H), 7.49-7.27 (m, 1H), 7.13 (dd, J=8.6, 1.0 Hz, 1H), 7.07-6.91 (m, 2H), 6.90-6.74 (m, 2H), 3.85 (d, J=6.6 Hz, 2H), 1.15-0.94 (m, 1H), 0.52-0.38 (m, 2H), 0.27-0.12 (m, 2H).

Example 90: 5-[2-Chloro-6-(cyclopropoxy)phenyl]-1,3-dihydrobenzimidazol-2-one

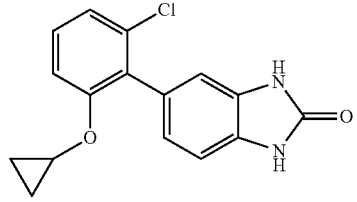

Step A: 2-Bromo-1-chloro-3-cyclopropoxybenzene

A mixture of 2-bromo-3-chlorophenol (200 mg, 0.96 mmol), bromocyclopropane (96 µL, 1.2 mmol), and potassium carbonate (138 mg, 0.96 mmol) in DMF (1.0 mL) was heated at 150° C. in a microwave oven for 30 minutes. The reaction mixture was cooled to rt, diluted with water, and extracted with EtOAc (×2). The organic extracts were dried (Na$_2$SO$_4$), filtered and concentrated in vacuo to obtain the desired product as an oil (180 mg, 75%). $^1$H NMR (400 MHz, DMSO-d$_6$): δ 7.46-7.31 (m, 2H), 7.27-7.18 (dd, J=7.7, 1.7 Hz, 1H), 4.04-3.91 (m, 1H), 0.91-0.79 (m, 2H), 0.78-0.63 (m, 2H).

Step B: 5-[2-Chloro-6-(cyclopropoxy)phenyl]-1,3-dihydrobenzimidazol-2-one

The title compound was prepared in a manner analogous to Example 2, substituting 2-bromo-1-chloro-3-cyclopropoxybenzene for 2,6-dimethyliodobenzene and PdCl$_2$(dppf)-CH$_2$Cl$_2$ for PdCl$_2$(dtbpf). The crude product was purified by reverse-phase HPLC (XBridge C18 column (5 m, 100×4.6 mm), mobile phase of 0-100% ACN in 20 mM NH$_4$OH) to afford the title compound (12 mg, 10% yield). MS (ESI): mass calcd. for $C_{16}H_{13}ClN_2O_2$, 300.1; m/z found, 301.0 [M+H]$^+$. $^1$H NMR (400 MHz, CD$_3$OD) δ 7.36-7.21 (m, 2H), 7.12-6.99 (m, 2H), 6.86-6.77 (m, 2H), 3.78-3.67 (tt, J=6.0, 2.9 Hz, 1H), 0.75-0.65 (m, 2H), 0.58-0.48 (m, 2H).

Example 91: 5-(2-Chloro-6-isopropoxy-phenyl)-1,3-dihydrobenzimidazol-2-one

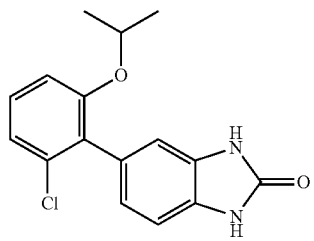

Step A: 2-Bromo-1-chloro-3-isopropoxybenzene

A mixture of 2-bromo-3-chlorophenol (200 mg, 0.96 mmol), 2-iodopropane (0.24 mL, 2.4 mmol), cesium carbonate (628 mg, 1.9 mmol), and potassium iodide (20 mg, 0.12 mmol) in DMF (1.0 mL) was stirred at rt for 4 h. The reaction mixture was diluted with water, and extracted with EtOAc (×2). The organic extracts were dried (Na$_2$SO$_4$), filtered and concentrated in vacuo to obtain the desired product as an oil which was used without further purification (230 mg, 96%). $^1$H NMR (500 MHz, DMSO-d$_6$): δ 7.37-7.29 (m, 1H), 7.18 (dd, J=8.1, 1.3 Hz, 1H), 7.13-7.07 (m, 1H), 4.74-4.65 (m, 1H), 0.91-0.79 (m, 2H), 1.20 (d, J=6.0 Hz, 6H).

Step B: 5-[2-Chloro-6-(cyclopropoxy)phenyl]-1,3-dihydrobenzimidazol-2-one

The title compound was prepared in a manner analogous to Example 2, substituting 2-bromo-1-chloro-3-isopropoxy-benzene for 2,6-dimethyliodobenzene and PdCl$_2$(dppf)-CH$_2$Cl$_2$ for PdCl$_2$(dtbpf) in Step B. The crude product was purified by reverse-phase HPLC (XBridge C18 column (5 m, 100×4.6 mm), mobile phase of 0-100% ACN in 20 mM NH$_4$OH) to afford the title compound (10 mg, 8% yield). MS (ESI): mass calcd. for $C_{16}H_{15}ClN_2O_2$, 302.1; m/z found, 303.1 [M+H]$^+$. $^1$H NMR (600 MHz, CD$_3$OD) δ 7.27-7.20 (m, 1H), 7.06 (d, J=8.0 Hz, 2H), 6.99 (d, J=8.1 Hz, 1H), 6.93-6.85 (m, 2H), 4.48-4.37 (m, 1H), 1.18-1.05 (d, J=6.0 Hz, 6H).

Example 92: 5-[2-Chloro-6-(cyclopropylmethoxy)phenyl]-1,3-dihydrobenzimidazol-2-one

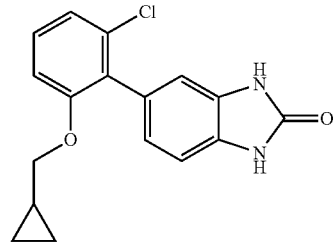

The title compound was prepared in a manner analogous to Example 90, substituting (bromomethyl)cyclopropane for bromocyclopropane in Step A. MS (ESI): mass calcd. for $C_{17}H_{15}ClN_2O_2$, 314.1; m/z found, 315.1 [M+H]$^+$. $^1$H NMR (400 MHz, CD$_3$OD) δ 7.24 (t, J=8.2 Hz, 1H), 7.15-7.04 (m, 2H), 7.02-6.86 (m, 3H), 3.77 (d, J=6.4 Hz, 2H), 1.08-0.98 (m, 1H), 0.48-0.35 (m, 2H), 0.20-0.11 (m, 2H).

Example 93: (±)-5-[2-Chloro-6-[(2,2-difluorocyclopropyl)methoxy]phenyl]-1,3-dihydrobenzimidazol-2-one

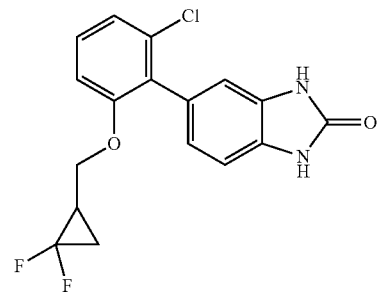

The title compound was prepared in analogous manner to Example 90, substituting sodium 2-chloro-2,2-difluoroacetate for bromocyclopropane in Step A. MS (ESI): mass calcd. for $C_{17}H_{13}ClF_2N_2O_2$, 350.1; m/z found, 351.1 [M+H]$^+$. $^1$H NMR (400 MHz, CD$_3$OD) δ 7.34-7.21 (m, 1H), 7.16-7.04 (m, 2H), 7.01 (dd, J=8.3, 0.8 Hz, 1H), 6.95-6.85 (m, 2H), 4.06-3.89 (m, 2H), 1.96-1.81 (m, 1H), 1.52-1.38 (m, 1H), 1.18-1.05 (m, 1H).

Example 94: 5-[2-Chloro-6-(difluoromethoxy)phenyl]-1,3-dihydrobenzimidazol-2-one

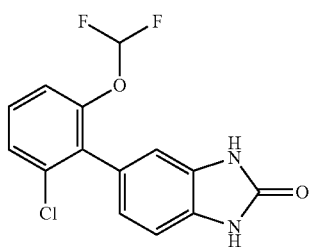 [SMILES: O=c1[nH]c2ccc(-c3c(Cl)cccc3OC(F)F)cc2[nH]1]

The title compound was prepared in a manner analogous to Example 90, substituting sodium 2-chloro-2,2-difluoroacetate for bromocyclopropane in Step A. MS (ESI): mass calcd. for $C_{14}H_9ClF_2N_2O_2$, 310.0; m/z found, 311.0 [M+H]$^+$. $^1$H NMR (500 MHz, DMSO-d$_6$): δ 10.71 (s, 1H), 10.66 (s, 1H), 7.50-7.42 (m, 2H), 7.31-7.23 (m, 1H), 7.11-6.93 (m, 2H), 6.83-6.76 (m, 2H).

Example 95: 5-[2-Chloro-6-(2,2,2-trifluoroethoxy)phenyl]-1,3-dihydrobenzimidazol-2-one

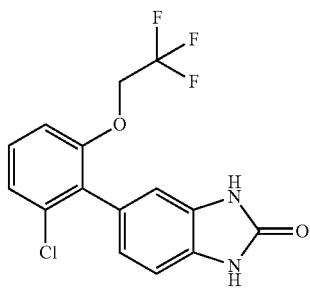 [SMILES: O=c1[nH]c2ccc(-c3c(Cl)cccc3OCC(F)(F)F)cc2[nH]1]

The title compound was prepared in a manner analogous to Example 90, substituting 1,1,1-trifluoro-2-iodoethane for bromocyclopropane and heating at 50° C. instead of 150° C. in Step A. MS (ESI): mass calcd. for $C_{15}H_{10}ClF_3N_2O_2$, 342.0; m/z found, 343.0 [M+H]$^+$. $^1$H NMR (400 MHz, DMSO-d$_6$) δ 10.62 (bs, 2H), 7.43-7.31 (m, 1H), 7.28-7.19 (m, 2H), 6.95 (dd, J=7.9, 0.5 Hz, 1H), 6.84-6.71 (m, 2H), 4.69 (q, J=8.9 Hz, 2H).

Example 96: 5-[2-Chloro-6-(2,2-difluoroethoxy)phenyl]-1,3-dihydrobenzimidazol-2-one

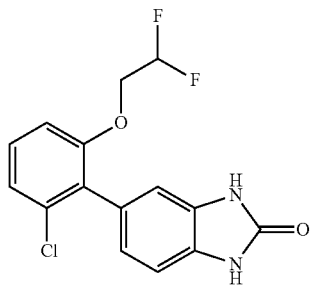 [SMILES: O=c1[nH]c2ccc(-c3c(Cl)cccc3OCC(F)F)cc2[nH]1]

The title compound was prepared in analogous manner to Example 90, substituting 2-bromo-1,1-difluoroethane for bromocyclopropane and heating at 50° C. instead of 150° C. in Step A. MS (ESI): mass calcd. for $C_{15}H_{11}ClF_2N_2O_2$, 324.0; m/z found, 325.7 [M+H]$^+$. $^1$H NMR (400 MHz, CD$_3$OD) δ 7.31 (t, J=8.2 Hz, 1H), 7.18 (d, J=8.0 Hz, 1H), 7.07 (dd, J=12.0, 8.2 Hz, 2H), 6.95-6.89 (m, 2H), 6.07-5.72 (m, 1H), 4.20-4.07 (m, 2H).

Example 97: 2-[3-Chloro-2-(2-oxo-1,3-dihydrobenzimidazol-5-yl)phenoxy]acetonitrile

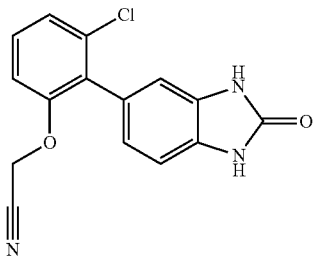 [SMILES: N#CCOc1cccc(Cl)c1-c1ccc2[nH]c(=O)[nH]c2c1]

The title compound was prepared in a manner analogous to Example 90, substituting bromoacetonitrile for bromocyclopropane and heating at 40° C. instead of 150° C. in Step A. MS (ESI): mass calcd. for $C_{15}H_{10}ClN_3O_2$, 299.0; m/z found, 301.0 [M+H]$^+$. $^1$H NMR (400 MHz, DMSO-d$_6$) δ 10.66 (br s, 2H), 7.49-7.36 (m, 1H), 7.33-7.18 (m, 2H), 7.05-6.94 (d, J=7.9 Hz, 1H), 6.81-6.69 (m, 2H), 5.10 (s, 2H).

Example 98: 5-[2-Chloro-6-(2,2-dimethylpropoxy)phenyl]-1,3-dihydrobenzimidazol-2-one

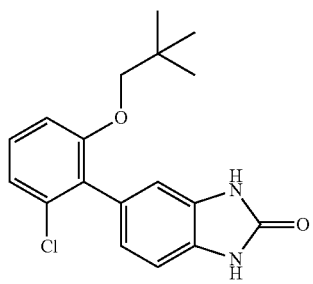 [SMILES: CC(C)(C)COc1cccc(Cl)c1-c1ccc2[nH]c(=O)[nH]c2c1]

The title compound was prepared in a manner analogous to Example 90, substituting 1-bromo-2,2-dimethylpropane for bromocyclopropane in Step A and PdCl$_2$(dtbpf) for PdCl$_2$(dppf)-CH$_2$Cl$_2$ in Step B. MS (ESI): mass calcd. for C$_{18}$H$_{19}$ClN$_2$O$_2$, 330.1; m/z found, 331.1 [M+H]$^+$. $^1$H NMR (400 MHz, DMSO-d$_6$) δ 10.64 (s, 1H), 10.61 (s, 1H), 7.37-7.25 (m, 1H), 7.12 (dd, J=8.1, 1.0 Hz, 1H), 7.06-6.89 (m, 2H), 6.83-6.69 (m, 2H), 3.59 (m, 2H), 0.80 (s, 9H).

Example 99: 5-(2-Benzyloxy-6-chloro-phenyl)-1,3-dihydrobenzimidazol-2-one

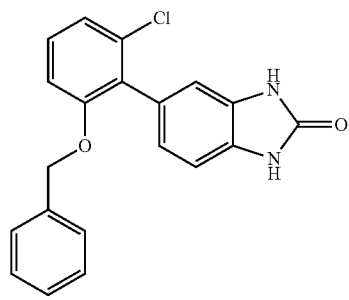 [SMILES: O=c1[nH]c2ccc(-c3c(Cl)cccc3OCc3ccccc3)cc2[nH]1]

The title compound was prepared in a manner analogous to Example 90, substituting benzyl bromide for bromocyclopropane and heating at 70° C. instead of 150° C. in Step A. MS (ESI): mass calcd. for C$_{20}$H$_{15}$ClN$_2$O$_2$, 350.1; m/z found, 351.1 [M+H]$^+$. $^1$H NMR (400 MHz, DMSO-d$_6$) δ 10.69 (s, 1H), 10.65 (s, 1H), 7.35-7.19 (m, 6H), 7.17-7.08 (m, 2H), 7.02 (d, J=7.9 Hz, 1H), 6.86-6.79 (m, 2H), 5.11 (s, 2H).

Example 100: tert-Butyl 3-[3-chloro-2-(2-oxo-1,3-dihydrobenzimidazol-5-yl)phenoxy]azetidine-1-carboxylate

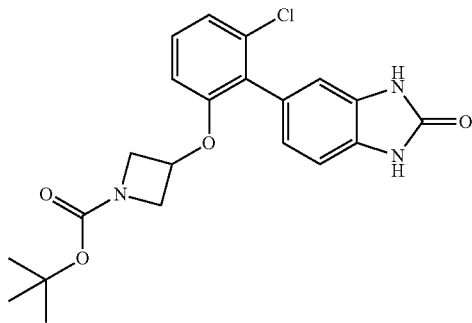 [SMILES: CC(C)(C)OC(=O)N1CC(Oc2cccc(Cl)c2-c2ccc3[nH]c(=O)[nH]c3c2)C1]

The title compound was prepared in analogous manner to Example 91, substituting tert-butyl 3-bromoazetidine-1-carboxylate for 2-iodopropane in Step A and PdCl$_2$(dtbpf) for PdCl$_2$(dppf)-CH$_2$Cl$_2$ in Step B. MS (ESI): mass calcd. for C$_{21}$H$_{22}$ClN$_3$O$_4$, 415.1; m/z found, 416.1 [M+H]$^+$. $^1$H NMR (500 MHz, CD$_3$OD) δ 7.31-7.19 (m, 1H), 7.18-7.06 (m, 2H), 6.97-6.89 (m, 2H), 6.76 (d, J=7.7 Hz, 1H), 4.92 (ddd, J=10.3, 6.4, 4.0 Hz, 1H), 4.22 (t, J=7.9 Hz, 2H), 3.70 (dd, J=9.5, 3.3 Hz, 2H), 1.46 (s, 9H).

Example 101: 5-(2-Chloro-6-thiazol-5-yloxy-phenyl)-1,3-dihydrobenzimidazol-2-one

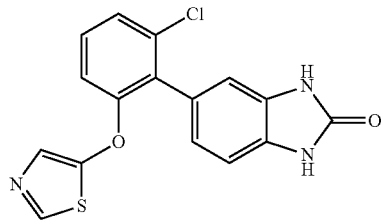 [SMILES: O=c1[nH]c2ccc(-c3c(Cl)cccc3Oc3cncs3)cc2[nH]1]

The title compound was prepared in a manner analogous to Example 90, substituting 5-bromothiazole for bromocyclopropane in Step A and PdCl$_2$(dtbpf) for PdCl$_2$(dppf)-CH$_2$Cl$_2$ in Step B. MS (ESI): mass calcd. for C$_{16}$H$_{10}$ClN$_3$O$_2$S, 343.0; m/z found, 344.0 [M+H]$^+$. $^1$H NMR (400 MHz, DMSO-d$_6$) δ 10.70 (s, 1H), 10.64 (s, 1H), 8.65 (d, J=0.9 Hz, 1H), 7.51-7.35 (m, 3H), 7.19 (dd, J=7.0, 2.4 Hz, 1H), 6.98 (d, J=7.9 Hz, 1H), 6.90-6.80 (m, 2H).

Example 102: 5-[2-(2,2-Difluoroethoxy)-6-methoxy-phenyl]-1,3-dihydrobenzimidazol-2-one

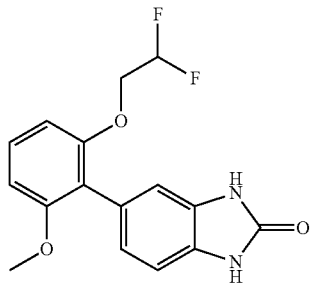 [SMILES: COc1cccc(OCC(F)F)c1-c1ccc2[nH]c(=O)[nH]c2c1]

The title compound was prepared in a manner analogous to Example 90, substituting 2-bromo-1,1-difluoroethane for bromocyclopropane and 2-bromo-3-methoxyphenol for 2-bromo-3-chlorophenol in Step A; as well as PdCl$_2$(dtbpf) for PdCl$_2$(dppf)-CH$_2$Cl$_2$ in Step B. MS (ESI): mass calcd. for C$_{15}$H$_{11}$ClF$_2$N$_2$O$_2$, 32010; m/z found, 321.1 [M+H]$^+$. $^1$H NMR (400 MHz, DMSO-d$_6$) δ 10.57 (s, 1H), 10.51 (s, 1H), 7.27 (t, J=8.3 Hz, 1H), 6.88 (d, J=8.0 Hz, 1H), 6.82-6.75 (m, 4H), 6.14 (tt, J=54.7, 3.7 Hz, 1H), 4.26-4.12 (m, 2H), 3.65 (s, 3H).

Example 103: 5-[2-Methoxy-6-(2,2,2-trifluoroethoxy)phenyl]-1,3-dihydrobenzimidazol-2-one

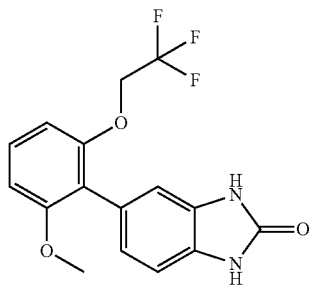 [SMILES: COc1cccc(OCC(F)(F)F)c1-c1ccc2[nH]c(=O)[nH]c2c1]

The title compound was prepared in a manner analogous to Example 90, substituting 1,1,1-trifluoro-2-iodoethane for bromocyclopropane and 2-bromo-3-methoxyphenol for 2-bromo-3-chlorophenol in Step A, as well as PdCl$_2$(dtbpf) for PdCl$_2$(dppf)-CH$_2$Cl$_2$ in Step B. MS (ESI): mass calcd. for C$_{16}$H$_{13}$F$_3$N$_2$O$_3$, 338.1; m/z found, 339.1 [M+H]$^+$. $^1$H NMR (400 MHz, DMSO-d$_6$) δ 10.56 (s, 1H), 10.51 (s, 1H), 7.30 (t, J=8.4 Hz, 1H), 6.90 (dd, J=7.9, 0.7 Hz, 1H), 6.87-6.73 (m, 4H), 4.61 (q, J=8.9 Hz, 2H), 3.62 (s, 3H).

Example 104: 5-[2-(2,2-Dimethylpropoxy)-6-methoxy-phenyl]-1,3-dihydrobenzimidazol-2-one

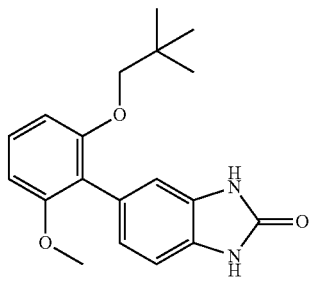 [SMILES: COc1cccc(OCC(C)(C)C)c1-c1ccc2[nH]c(=O)[nH]c2c1]

The title compound was prepared in analogous manner to Example 90, substituting 1-bromo-2,2-dimethylpropane for bromocyclopropane and 2-bromo-3-methoxyphenol for 2-bromo-3-chlorophenol in Step A, as well as PdCl$_2$(dtbpf) for PdCl$_2$(dppf)-CH$_2$Cl$_2$ in Step B. MS (ESI): mass calcd. for C$_{19}$H$_{22}$N$_2$O$_3$, 326.2; m/z found, 327.1 [M+H]$^+$. $^1$H NMR (400 MHz, CD$_3$OD) δ 7.23 (t, J=8.3 Hz, 1H), 7.05-6.99 (m, 1H), 6.97-6.90 (m, 2H), 6.72-6.60 (m, 2H), 3.73 (s, 3H), 3.54 (s, 2H), 0.84 (s, 9H).

Example 105: 5-(2-Benzyloxy-6-methoxy-phenyl)-1,3-dihydrobenzimidazol-2-one

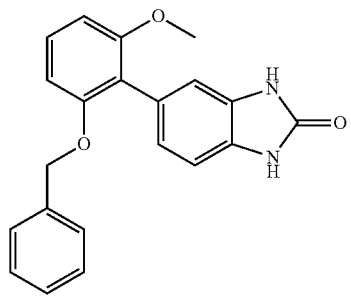 [SMILES: COc1cccc(OCc2ccccc2)c1-c1ccc2[nH]c(=O)[nH]c2c1]

The title compound was prepared in a manner analogous to Example 90, substituting benzyl bromide for bromocyclopropane, 2-bromo-3-methoxyphenol for 2-bromo-3-chlorophenol, and heating at 70° C. instead of 150° C. in Step A. MS (ESI): mass calcd. for C$_{21}$H$_{18}$N$_2$O$_3$, 346.1; m/z found, 347.1 [M+H]$^+$. $^1$H NMR (400 MHz, DMSO-d$_6$): δ 10.59 (s, 1H), 10.54 (s, 1H), 7.33-7.20 (m, 6H), 6.94-6.68 (m, 5H), 5.07 (s, 2H), 3.68 (s, 3H).

Example 106: 5-[2-[(4-Fluorophenyl) ethoxy]-6-methoxy-phenyl]-1,3-dihydrobenzimidazol-2-one

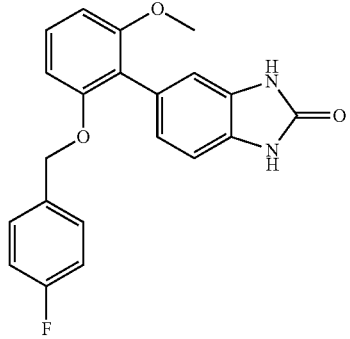 [SMILES: COc1cccc(OCc2ccc(F)cc2)c1-c1ccc2[nH]c(=O)[nH]c2c1]

The title compound was prepared in a manner analogous to Example 90, substituting 1-(bromomethyl)-4-fluorobenzene for bromocyclopropane, 2-bromo-3-methoxyphenol for 2-bromo-3-chlorophenol, and heating at 70° C. instead of 150° C. in Step A. MS (ESI): mass calcd. for C$_{21}$H$_{17}$FN$_2$O$_3$, 364.1; m/z found, 365.1 [M+H]$^+$. $^1$H NMR (400 MHz, DMSO-d$_6$) δ 10.45 (s, 2H), 7.34-7.20 (m, 3H), 7.16-7.07 (m, 2H), 6.93-6.85 (m, 1H), 6.85-6.68 (m, 4H), 4.97 (s, 2H), 3.64 (s, 3H).

Example 107: 5-(2,6-Diisopropoxyphenyl)-1,3-dihydrobenzimidazol-2-one

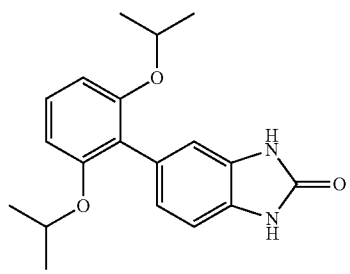 [SMILES: CC(C)Oc1cccc(OC(C)C)c1-c1ccc2[nH]c(=O)[nH]c2c1]

The title compound was prepared in a manner analogous to Example 91, substituting 2-bromobenzene-1,3-diol for 2-bromo-3-chlorophenol in Step A. MS (ESI): mass calcd. for C$_{19}$H$_{22}$N$_2$O$_3$, 326.2; m/z found, 327.2 [M+H]$^+$. $^1$H NMR (400 MHz, DMSO-d$_6$) δ 10.50 (s, 1H), 10.45 (s, 1H), 7.17 (t, J=8.3 Hz, 1H), 6.90-6.84 (m, 1H), 6.85-6.78 (m, 2H), 6.68 (d, J=8.4 Hz, 2H), 4.38 (hept, J=6.1 Hz, 2H), 1.09 (d, J=6.0 Hz, 12H).

Example 108: 5-[2-Isopropoxy-6-(trifluoromethyl)phenyl]-1,3-dihydrobenzimidazol-2-one

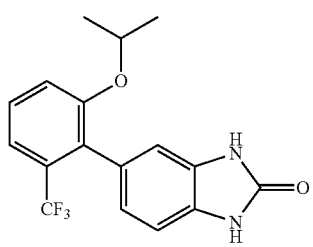

The title compound was prepared in a manner analogous to Example 90, substituting 2-iodopropane for bromocyclopropane and 2-bromo-3-(trifluoromethyl)phenol for 2-bromo-3-chlorophenol in Step A. MS (ESI): mass calcd. for $C_{17}H_{15}F_3N_2O_2$, 336.1; m/z found, 337.3 [M+H]. $^1$H NMR (500 MHz, $CD_3OD$) δ 7.46 (t, J=8.1 Hz, 1H), 7.32 (dd, J=17.0, 8.1 Hz, 2H), 7.04 (d, J=8.0 Hz, 1H), 6.89-6.79 (m, 2H), 4.53-4.40 (hept, J=6.0 Hz, 1H), 1.14-1.05 (m, 6H).

Example 109: 5-[2-Chloro-3-(cyclopropoxy)phenyl]-1,3-dihydrobenzimidazol-2-one

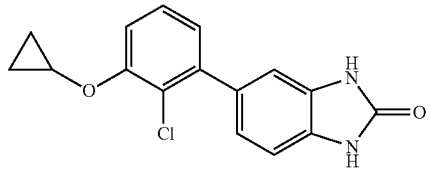 [SMILES: O=c1[nH]c2ccc(-c3cccc(OC4CC4)c3Cl)cc2[nH]1]

The title compound was prepared in a manner analogous to Example 90, substituting 3-bromo-2-chlorophenol for 2-bromo-3-chlorophenol in Step A. MS (ESI): mass calcd. for $C_{16}H_{13}ClN_2O_2$, 300.1; m/z found, 301.1 [M+H]$^+$. $^1$H NMR (400 MHz, DMSO-$d_6$): δ 10.66 (s, 2H), 7.48-7.25 (m, 2H), 7.03-6.83 (m, 4H), 4.03-3.88 (m, 1H), 0.90-0.78 (m, 2H), 0.77-0.65 (m, 2H).

Example 110: 5-(2-Chloro-3-isopropoxy-phenyl)-1,3-dihydrobenzimidazol-2-one

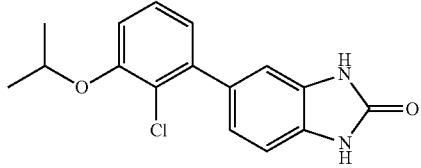 [SMILES: CC(C)Oc1cccc(-c2ccc3[nH]c(=O)[nH]c3c2)c1Cl]

The title compound was prepared in a manner analogous to Example 91, substituting 3-bromo-2-chlorophenol for 2-bromo-3-chlorophenol in Step A. MS (ESI): mass calcd. for $C_{16}H_{15}ClN_2O_2$, 302.1; m/z found, 303.1 [M+H]$^+$. $^1$H NMR (600 MHz, $CD_3OD$) δ 7.25 (t, J=7.9 Hz, 1H), 7.13-6.99 (m, 4H), 6.93 (dd, J=7.6, 1.4 Hz, 1H), 4.70-4.59 (m, 1H), 1.41 (d, J=6.1 Hz, 6H).

Example 111: (±)-5-[2-Chloro-3-[(2,2-difluorocyclopropyl)methoxy]phenyl]-1,3-dihydrobenzimidazol-2-one

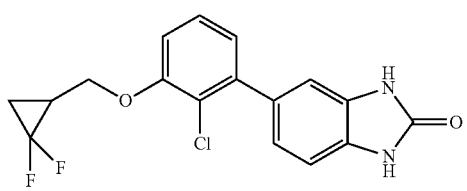 [SMILES: O=c1[nH]c2ccc(-c3cccc(OCC4CC4(F)F)c3Cl)cc2[nH]1]

The title compound was prepared in a manner analogous to Example 90, substituting 2-(bromomethyl)-1,1-difluorocyclopropane for bromocyclopropane and 3-bromo-2-chlorophenol for 2-bromo-3-chlorophenol in Step A. MS (ESI): mass calcd. for $C_{17}H_{13}ClF_2N_2O_2$, 350.1; m/z found, 351.1 [M+H]$^+$. $^1$H NMR (600 MHz, $CD_3OD$) δ 7.28 (t, J=8.0 Hz, 1H), 7.12-7.02 (m, 4H), 6.97 (dd, J=7.7, 1.4 Hz, 1H), 4.24-4.08 (m, 2H), 2.25-2.11 (m, 1H), 1.68-1.58 (m, 1H), 1.45-1.33 (m, 1H).

Example 112: 5-[2-Chloro-3-(2,2-difluoroethoxy)phenyl]-1,3-dihydrobenzimidazol-2-one

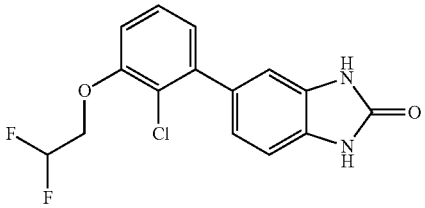 [SMILES: O=c1[nH]c2ccc(-c3cccc(OCC(F)F)c3Cl)cc2[nH]1]

The title compound was prepared in a manner analogous to Example 90, substituting 2-bromo-1,1-difluoroethane for bromocyclopropane and 3-bromo-2-chlorophenol for 2-bromo-3-chlorophenol in Step A. MS (ESI): mass calcd. for $C_{15}H_{11}ClF_2N_2O_2$, 324.0; m/z found, 325.2 [M+H]$^+$. $^1$H NMR (400 MHz, DMSO-$d_6$) δ 10.72 (s, 1H), 10.67 (s, 1H), 7.40-7.31 (m, 1H), 7.21 (dd, J=8.3, 1.4 Hz, 1H), 7.07-7.00 (m, 1H), 7.01-6.90 (m, 3H), 6.61-6.26 (m, 1H), 4.53-4.39 (m, 2H).

Example 113: 5-[2-Chloro-3-(difluoromethoxy)phenyl]-1,3-dihydrobenzimidazol-2-one

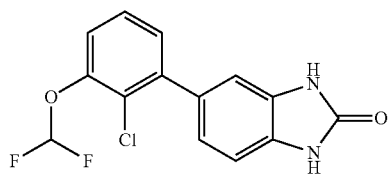 [SMILES: O=c1[nH]c2ccc(-c3cccc(OC(F)F)c3Cl)cc2[nH]1]

The title compound was prepared in a manner analogous to Example 91, substituting sodium 2-chloro-2,2-difluoroacetate for bromocyclopropane and 3-bromo-2-chlorophenol for 2-bromo-3-chlorophenol in Step A. The reaction was also heated conventionally at 100° C. for 1 h. MS (ESI): mass calcd. for $C_{14}H_9ClF_2N_2O_2$, 310.0; m/z found, 311.0 [M+H]$^+$. $^1$H NMR (500 MHz, DMSO-$d_6$): δ 10.74 (s, 1H), 10.71 (s, 1H), 7.48-7.41 (m, 1H), 7.38-7.26 (m, 3H), 7.04-6.92 (m, 3H).

Example 114: tert-Butyl 3-[2-chloro-3-(2-oxo-1,3-dihydrobenzimidazol-5-yl)phenoxy]azetidine-1-carboxylate

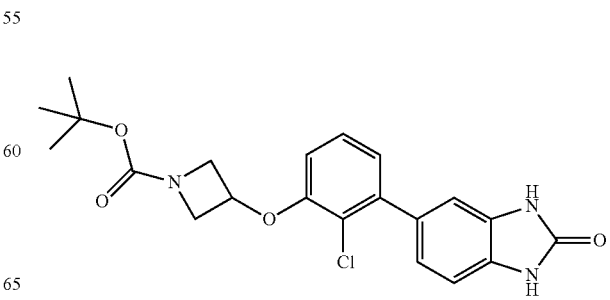

The title compound was prepared in a manner analogous to Example 91, substituting tert-butyl 3-bromoazetidine-1-carboxylate for 2-iodopropane and 3-bromo-2-chlorophenol for 2-bromo-3-chlorophenol in Step A. MS (ESI): mass calcd. for $C_{21}H_{22}ClN_3O_4$, 415.1; m/z found, 416.1 [M+H]+. $^1$H NMR (400 MHz, DMSO-$d_6$) δ10.78 (s, 2H), 7.41-7.22 (m, 1H), 7.06-6.89 (m, 4H), 6.84 (dd, J=8.3, 1.4 Hz, 1H), 5.15-4.98 (m, 1H), 4.42-4.29 (m, 2H), 3.84 (dd, J=9.8, 3.6 Hz, 2H), 1.47 (s, 9H).

Example 115: 5-(3-Chloro-2-isopropoxy-phenyl)-1,3-dihydrobenzimidazol-2-one

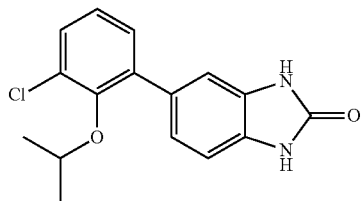 [SMILES: CC(C)Oc1c(Cl)cccc1-c1ccc2[nH]c(=O)[nH]c2c1]

The title compound was prepared in a manner analogous to Example 90, substituting 2-iodopropane for bromocyclopropane and 2-bromo-6-chlorophenol for 2-bromo-3-chlorophenol in Step A. MS (ESI): mass calcd. for $C_{16}H_{15}ClN_2O_2$, 302.1; m/z found, [M+H]+=303.1. $^1$H NMR (400 MHz, CD$_3$OD) δ 7.36 (dd, J=8.0, 1.7 Hz, 1H), 7.29-7.24 (m, 2H), 7.22-7.18 (m, 1H), 7.14-7.08 (m, 2H), 3.95 (hept, J=6.2 Hz, 1H), 1.17-0.72 (m, 6H).

Example 116: 5-(2-tert-Butoxy-6-chloro-phenyl)-1,3-dihydrobenzimidazol-2-one

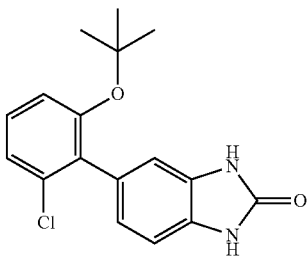 [SMILES: CC(C)(C)Oc1cccc(Cl)c1-c1ccc2[nH]c(=O)[nH]c2c1]

Step A: 2-Bromo-1-(tert-butoxy)-3-chlorobenzene

To a solution of 2-bromo-3-chlorophenol (250 mg, 1.2 mmol) in toluene (2.0 mL) was added 1,1-di-tert-butoxy-N,N-dimethylmethanamine (1.6 mL, 6.5 mmol), and the mixture was heated at 80° C. for 24 h. The reaction mixture was then cooled to rt, diluted with EtOAc, and washed with 1M NaOH. The organic layer was dried over Na$_2$SO$_4$, filtered, and concentrated. Purification (FCC, SiO$_2$; 0-10% EtOAc/hexanes) afforded the title compound as a colorless oil (106 mg, 34% yield). $^1$H NMR (400 MHz, CDCl$_3$) δ 7.19 (m, 2H), 7.04-6.97 (m, 1H), 1.45 (s, 9H).

Step B: 5-(2-tert-Butoxy-6-chloro-phenyl)-1,3-dihydrobenzimidazol-2-one

The title compound was prepared in a manner analogous to Example 2, substituting 2-bromo-1-(tert-butoxy)-3-chlorobenzene for 2,6-dimethyliodobenzene. The crude product was purified by reverse-phase HPLC (XBridge C18 column (5 μm, 100×4.6 mm), mobile phase of 10-100% ACN in 20 mM NH$_4$OH) afforded the title product (46 mg, 44% yield). MS (ESI): mass calcd. for $C_{17}H_{17}ClN_2O_2$, 316.1; m/z found, 317.1 [M+H]+. $^1$H NMR (400 MHz, DMSO-$d_6$) δ 10.65 (s, 1H), 10.63 (s, 1H), 7.32-7.18 (m, 2H), 7.14 (dd, J=7.7, 1.6 Hz, 1H), 6.95 (dd, J=7.9, 0.6 Hz, 1H), 6.84-6.73 (m, 2H), 1.04 (s, 9H).

Example 117: 5-(2-tert-Butoxy-6-methoxy-phenyl)-1,3-dihydrobenzimidazol-2-one

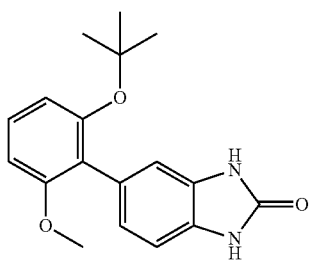 [SMILES: COc1cccc(OC(C)(C)C)c1-c1ccc2[nH]c(=O)[nH]c2c1]

The title compound was prepared in a manner analogous to Example 116, substituting 2-bromo-3-methoxyphenol for 2-bromo-3-chlorophenol in Step A. MS (ESI): mass calcd. for $C_{18}H_{20}N_2O_3$, 312.1; m/z found, 313.2 [M+H]+. $^1$H NMR (400 MHz, DMSO-$d_6$) δ 10.53 (s, 1H), 10.47 (s, 1H), 7.20 (t, J=8.2 Hz, 1H), 6.93-6.87 (m, 1H), 6.85-6.72 (m, 5H), 3.66 (s, 3H), 1.01 (s, 9H).

Example 118: (±)-5-[2-Chloro-6-(2,2,2-trifluoro-1-methyl-ethoxy)phenyl]-1,3-dihydrobenzimidazol-2-one

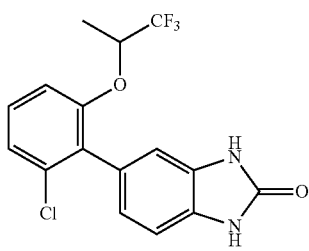 [SMILES: CC(Oc1cccc(Cl)c1-c1ccc2[nH]c(=O)[nH]c2c1)C(F)(F)F]

Step A: 2-Bromo-1-chloro-3-((1,1,1-trifluoropropan-2-yl)oxy)benzene

To a mixture of sodium tert-butoxide (138 mg, 1.4 mmol) in THF (1.0 mL) was added 1,1,1-trifluoro-2-propanol (0.14 mL, 1.5 mmol) and 2-bromo-1-chloro-3-fluorobenzene (200 mg, 0.96 mmol) in DMF (2.0 mL). The reaction mixture was heated at 80° C. for 24 h. After cooling to rt, EtOAc (5.0 mL) was added to the reaction mixture and washed sequentially with 1M HCl (2.5 mL), saturated aqueous NaHCO$_3$, and brine. The aqueous layers were extracted with EtOAc, and the combined organic extracts were dried (Na$_2$SO$_4$), filtered and concentrated. Purification by FCC (0-10% EtOAc/hexanes) afforded the title compound as an oil (87 mg, 30% yield). ¹H NMR (400 MHz, CDCl₃) δ 7.23 (m, 2H), 6.86 (dd, J=7.3, 2.4 Hz, 1H), 4.72-4.58 (m, 1H), 1.62-1.49 (m, 3H).

Step B: (±)-5-[2-Chloro-6-(2,2,2-trifluoro-1-methyl-ethoxy)phenyl]-1,3-dihydrobenzimidazol-2-one The title compound was prepared in a manner analogous to Example 2, substituting (±)-2-bromo-1-chloro-3-((1,1,1-trifluoropropan-2-yl)oxy)benzene for 2,6-dimethyliodobenzene in Step B. The crude product was purified by reverse-phase HPLC (XBridge C18 column (5 µm, 100×4.6 mm), mobile phase of 10-100% ACN in 20 mM NH₄OH) afforded the title product (26.5 mg, 32% yield). MS (ESI): mass calcd. for C₁₆H₁₂ClF₃N₂O₂, 356.1; m/z found, 357.1 [M+H]⁺. ¹H NMR (500 MHz, DMSO-d₆) δ 10.65 (s, 2H), 7.36 (m, 1H), 7.30-7.21 (m, 2H), 6.97 (dd, J=8.3, 1.8 Hz, 1H), 6.76 (s, 2H), 5.15-5.04 (m, 1H), 1.21 (dd, J=6.5, 1.8 Hz, 3H).

Example 119: (R*)-5-[2-Chloro-6-(2,2,2-trifluoro-1-methyl-ethoxy)phenyl]-1,3-dihydrobenzimidazol-2-one

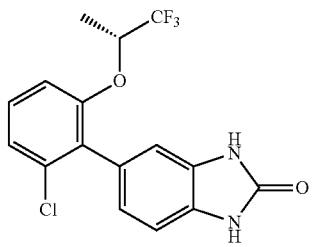 [SMILES: C[C@@H](Oc1cccc(Cl)c1-c1ccc2[nH]c(=O)[nH]c2c1)C(F)(F)F]

Chiral SFC separation of Example 118, (±)-5-[2-chloro-6-(2,2,2-trifluoro-1-methyl-ethoxy)phenyl]-1,3-dihydrobenzimidazol-2-one on a Chiralpak AD-H column (5 µm, 250×21 mm), using 85% CO₂/15% EtOH provided 4.1 mg of the title compound as the first eluting enantiomer. MS (ESI): mass calcd. for C₁₆H₁₂ClF₃N₂O₂, 356.1; m/z found, 357.1 [M+H]⁺. ¹H NMR (400 MHz, CD₃OD) δ 7.35-7.26 (m, 1H), 7.24-7.17 (m, 1H), 7.15-7.04 (m, 2H), 6.94-6.84 (m, 2H), 4.79-4.67 (m, 1H), 1.27 (d, J=6.4 Hz, 3H).

Example 120: (S*)-5-[2-Chloro-6-(2,2,2-trifluoro-1-methyl-ethoxy)phenyl]-1,3-dihydrobenzimidazol-2-one

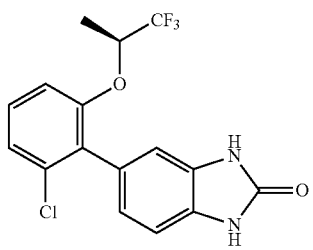 [SMILES: C[C@H](Oc1cccc(Cl)c1-c1ccc2[nH]c(=O)[nH]c2c1)C(F)(F)F]

Chiral SFC separation of Example 118, (±)-5-[2-chloro-6-(2,2,2-trifluoro-1-methyl-ethoxy)phenyl]-1,3-dihydrobenzimidazol-2-one on a Chiralpak AD-H column (5 µm, 250×21 mm), using 85% CO₂/15% EtOH provided 3.8 mg of the title compound as the second eluting enantiomer. MS (ESI): mass calcd. for C₁₆H₁₂ClF₃N₂O₂, 356.1; m/z found, 357.1 [M+H]⁺. ¹H NMR (400 MHz, CD₃OD) δ 7.35-7.26 (m, 1H), 7.24-7.17 (m, 1H), 7.15-7.04 (m, 2H), 6.94-6.84 (m, 2H), 4.79-4.67 (m, 1H), 1.27 (d, J=6.4 Hz, 3H).

Example 121: (±)-5-[2-Methoxy-6-(2,2,2-trifluoro-1-methyl-ethoxy)phenyl]-1,3-dihydrobenzimidazol-2-one

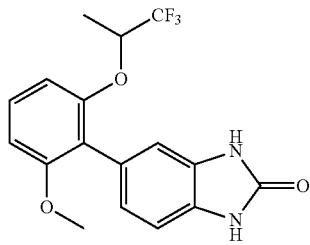 [SMILES: COc1cccc(OC(C)C(F)(F)F)c1-c1ccc2[nH]c(=O)[nH]c2c1]

The title compound was prepared analogous to Example 118, substituting 2-bromo-1-fluoro-3-methoxybenzene for 2-bromo-1-chloro-3-fluorobenzene in Step A. MS (ESI): mass calcd. for C₁₇H₁₅F₃N₂O₃, 352.1; m/z found, 353.1 [M+H]⁺. ¹H NMR (500 MHz, DMSO-d₆) δ 10.56 (s, 1H), 10.51 (s, 1H), 7.28 (t, J=8.4 Hz, 1H), 6.88 (dd, J=14.2, 8.1 Hz, 2H), 6.84-6.72 (m, 3H), 4.97 (hept, J=6.5 Hz, 1H), 3.66 (s, 3H), 1.19 (d, J=6.3 Hz, 3H).

Example 122: 2-[3,4-Dichloro-2-(2-oxo-1,3-dihydrobenzimidazol-5-yl)phenyl]acetonitrile

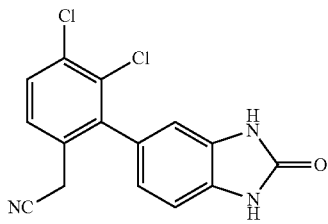 [SMILES: N#CCc1ccc(Cl)c(Cl)c1-c1ccc2[nH]c(=O)[nH]c2c1]

The title compound was prepared in a manner analogous to Example 2, substituting 2-(3,4-dichloro-2-iodophenyl)acetonitrile (Intermediate 15) for 2,6-dimethyl iodobenzene. The crude residue was purified by reverse-phase HPLC (XBridge C18 column (5 µm, 100×4.6 mm), mobile phase of 10-100% ACN in 20 mM NH₄OH) to afford the title compound (26 mg, 21% yield). MS (ESI): mass calcd. for C₁₅H₉O₁₂N₃O, 317.0; m/z found, 318.1 [M+H]⁺. ¹H NMR (500 MHz, DMSO-d₆) δ 10.77 (s, 2H), 7.73 (d, J=8.4 Hz, 1H), 7.53 (d, J=8.4 Hz, 1H), 7.07-7.02 (m, 1H), 6.80-6.73 (m, 2H), 3.67 (s, 2H).

Example 123: 2-[2-(2-Oxo-1,3-dihydrobenzimidazol-5-yl)-3-trifluoromethoxy)phenyl]acetonitrile

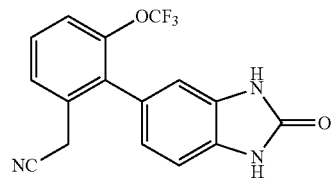 [SMILES: N#CCc1cccc(OC(F)(F)F)c1-c1ccc2[nH]c(=O)[nH]c2c1]

The title compound was prepared in a manner analogous to Example 122, using 2-(2-iodo-3-(trifluoromethoxy)phenyl)acetonitrile (Intermediate 16). MS (ESI): mass calcd. for $C_{16}H_{10}F_3N_3O_2$, 333.1; m/z found, 334.1 [M+H]$^+$. $^1$H NMR (400 MHz, DMSO-d$_6$) δ 10.77 (s, 1H), 10.74 (s, 1H), 7.60-7.56 (m, 2H), 7.52-7.44 (m, 1H), 7.06-7.00 (m, 1H), 6.82-6.75 (m, 2H), 3.75 (s, 2H)

Example 124: 2-[3-Chloro-2-(2-oxo-1,3-dihydrobenzimidazol-5-yl)phenyl]acetonitrile

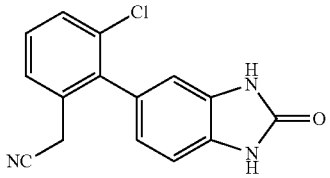 [SMILES: N#CCc1cccc(Cl)c1-c1ccc2[nH]c(=O)[nH]c2c1]

The title compound was prepared in a manner analogous to Example 2, substituting 2-(3-chloro-2-iodophenyl)acetonitrile (Intermediate 8) for 2,6-dimethyliodobenzene and PdCl$_2$(dppf)-CH$_2$Cl$_2$ for PdCl$_2$(dtbpf) in Step B. MS (ESI): mass calcd. for $C_{15}H_{10}ClN_3O$, 283.1; m/z found, 285.1 [M+H]$^+$. $^1$H NMR (400 MHz, DMSO-d$_6$) δ 10.74 (s, 1H), 10.72 (s, 1H), 7.56 (dd, J=7.9, 1.4 Hz, 1H), 7.53-7.49 (m, 1H), 7.48-7.40 (m, 1H), 7.06-7.00 (m, 1H), 6.78-6.72 (m, 2H), 3.69 (s, 2H).

Example 125: 2-[3-Chloro-2-(2-oxo-6-tritio-1,3-dihydrobenzimidazol-5-yl)phenyl]acetonitrile

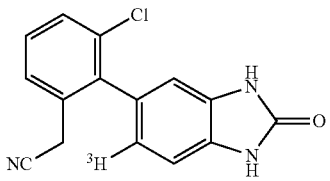 [SMILES: [3H]c1cc2[nH]c(=O)[nH]c2cc1-c1c(Cl)cccc1CC#N]

The title compound was prepared in a manner analogous to Example 32, substituting 2-[3-chloro-2-(2-oxo-1,3-dihydrobenzimidazol-5-yl)phenyl]acetonitrile (Example 124) for 5-[2-chloro-6-(trifluoromethoxy)phenyl]-1,3-dihydrobenzimidazol-2-one and stirring was maintained for 6 h instead of 30 minutes. The crude product was purified by reverse-phase HPLC (Gemini 5 μm C-18 column, 35% aq acetonitrile containing 0.01% NH$_4$OH) to afford the title compound. The specific activity was determined to be 22.3 Ci/mmol, and the product was stored at −20° C. in EtOH at a concentration of 1.0 mCi/mL. MS (FTMS+c NSI SIM): mass calcd. for $C_{15}H_9TClN_3O$, 285.1; m/z found, 286.1 [M+H]$^+$.

Example 126: (±)-2-[3-Chloro-2-(2-oxo-1,3-dihydrobenzimidazol-5-yl)phenyl]propanenitrile

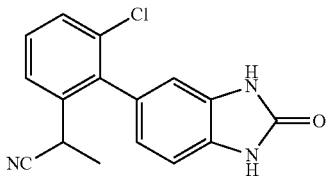 [SMILES: CC(C#N)c1cccc(Cl)c1-c1ccc2[nH]c(=O)[nH]c2c1]

The title compound was prepared in a manner analogous to Example 2, substituting 2-(3-chloro-2-iodophenyl)propanenitrile (Intermediate 17) for 2,6-dimethyliodobenzene and PdCl$_2$(dppf)-CH$_2$Cl$_2$ for PdCl$_2$(dtbpf) in Step B. MS (ESI): mass calcd. for $C_{16}H_{12}ClN_3O$, 297.1; m/z found, 298.1 [M+H]$^+$. $^1$H NMR (400 MHz, DMSO-d$_6$): δ 10.79-10.70 (m, 2H), 7.62-7.54 (m, 2H), 7.52-7.47 (m, 1H), 7.07-7.01 (m, 1H), 6.79-6.73 (m, 2H), 3.83-3.75 (m, 1H), 1.42-1.38 (m, 3H).

Example 127: 2-[3-Chloro-2-(2-oxo-1,3-dihydrobenzimidazol-5-yl)phenyl]-2-methyl-propanenitrile

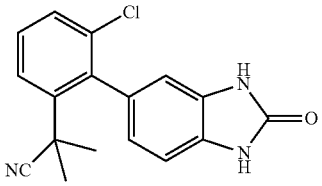 [SMILES: CC(C)(C#N)c1cccc(Cl)c1-c1ccc2[nH]c(=O)[nH]c2c1]

The title compound was prepared in a manner analogous to Example 2 (Step B), substituting 2-(3-chloro-2-iodophenyl)-2-methylpropanenitrile (Intermediate 12) for 2,6-dimethyliodobenzene and PdCl$_2$(dppf)-CH$_2$Cl$_2$ for PdCl$_2$(dtbpf) in Step B. MS (ESI): mass calcd. for $C_{17}H_{14}ClN_3O$, 311.1; m/z found, 313.1 $^1$H NMR (400 MHz, CD$_3$OD) δ 7.61 (dd, J=8.1, 1.2 Hz, 1H), 7.51 (dd, J=8.0, 1.2 Hz, 1H), 7.45-7.37 (m, 1H), 7.11 (dd, J=8.0, 0.7 Hz, 1H), 6.95-6.85 (m, 2H), 1.66 (s, 3H), 1.61 (s, 3H).

Example 128: 1-[3-Chloro-2-(2-oxo-1,3-dihydrobenzimidazol-5-yl)phenyl]cyclopropanecarbonitrile

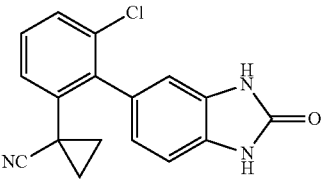 [SMILES: N#CC1(c2cccc(Cl)c2-c2ccc3[nH]c(=O)[nH]c3c2)CC1]

The title compound was prepared in a manner analogous to Example 2 (Step B.), using 1-(3-chloro-2-iodophenyl)cyclopropanecarbonitrile (Intermediate 18). MS (ESI): mass calcd. for $C_{17}H_{12}ClN_3O$, 309.1; m/z found, 311.1 [M+H]$^+$. $^1$H NMR (400 MHz, DMSO-d$_6$) δ 10.73 (s, 2H), 7.59 (dd, J=8.0, 1.3 Hz, 1H), 7.54-7.47 (m, 1H), 7.46-7.38 (m, 1H), 7.04 (d, J=8.3 Hz, 1H), 6.88-6.80 (m, 2H), 1.37-1.18 (m, 4H).

Example 129: 1-[3-Chloro-2-(2-oxo-1,3-dihydrobenzimidazol-5-yl)phenyl]cyclobutanecarbonitrile

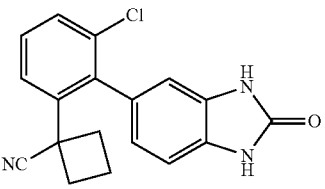 [SMILES: N#CC1(c2cccc(Cl)c2-c2ccc3[nH]c(=O)[nH]c3c2)CCC1]

The title compound was prepared in a manner analogous to Example 2 (Step B.), using 1-(3-chloro-2-iodophenyl)cyclobutanecarbonitrile (Intermediate 19). MS (ESI): mass calcd. for $C_{18}H_{14}ClN_3O$, 323.1; m/z found, 324.1 [M+H]$^+$. $^1$H NMR (400 MHz, DMSO-d$_6$) δ 10.74 (s, 2H), 7.57 (dd, J=8.0, 1.2 Hz, 1H), 7.45 (t, J=7.9 Hz, 1H), 7.32 (dd, J=7.8, 1.3 Hz, 1H), 7.00 (d, J=8.3 Hz, 1H), 6.85-6.74 (m, 2H), 2.35 (dd, J=12.3, 5.7 Hz, 2H), 2.09-1.58 (m, 4H).

Example 130: 2-[2-Chloro-3-(2-oxo-1,3-dihydrobenzimidazol-5-yl)phenyl]acetonitrile

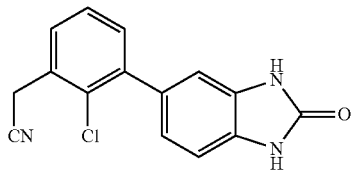 [SMILES: N#CCc1cccc(-c2ccc3[nH]c(=O)[nH]c3c2)c1Cl]

The title compound was prepared in a manner analogous to Example 2 (Step B), substituting 2-(3-bromo-2-chlorophenyl)acetonitrile (Intermediate 9) for 2,6-dimethyliodobenzene and PdCl$_2$(dppf)-CH$_2$Cl$_2$ for PdCl$_2$(dtbpf) in Step B. MS (ESI): mass calcd. for $C_{15}H_{10}ClN_3O$, 283.1; m/z found, 284.1 [M+H]$^+$. $^1$H NMR (400 MHz, DMSO-d$_6$) δ 10.74 (s, 1H), 10.70 (s, 1H), 7.54 (dd, J=7.6, 1.8 Hz, 1H), 7.49-7.43 (m, 1H), 7.43-7.36 (m, 1H), 7.05-6.88 (m, 3H), 4.16 (s, 2H).

Example 131: 2-[2,4-Dichloro-3-(2-oxo-1,3-dihydrobenzimidazol-5-yl)phenyl]acetonitrile

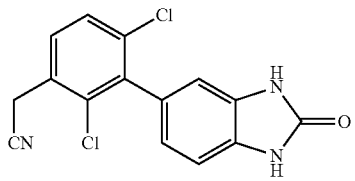 [SMILES: N#CCc1ccc(Cl)c(-c2ccc3[nH]c(=O)[nH]c3c2)c1Cl]

The title compound was prepared in a manner analogous to Example 2 (Step B), substituting 2-(3-bromo-2,4-dichlorophenyl)acetonitrile (Intermediate 10) for 2,6-dimethyliodobenzene and PdCl$_2$(dppf)-CH$_2$Cl$_2$ for PdCl$_2$(dtbpf) in Step B. MS (ESI): mass calcd. for $C_{15}H_9Cl_2N_3O$, 317.0; m/z found, 318.0 [M+H]$^+$. $^1$H NMR (400 MHz, CD$_3$OD) δ 7.54 (s, 2H), 7.14 (dd, J=7.8, 0.9 Hz, 1H), 6.98-6.84 (m, 2H), 4.02 (s, 2H).

Example 132: 2-[3-Bromo-2-(2-oxo-1,3-dihydrobenzimidazol-5-yl)phenyl]acetonitrile

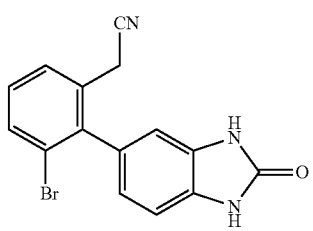 [SMILES: N#CCc1cccc(Br)c1-c1ccc2[nH]c(=O)[nH]c2c1]

The title compound was prepared in manner analogous to Example 2 (Step B), substituting 2-(3-bromo-2-iodophenyl)acetonitrile (Intermediate 11) for 2,6-dimethyliodobenzene and PdCl$_2$(dppf)-CH$_2$Cl$_2$ for PdCl$_2$(dtbpf) in Step B. MS (ESI): mass calcd. for $C_{15}H_{10}BrN_3O$, 327.0; m/z found, 328.2 [M+H]$^+$. $^1$H NMR (500 MHz, CD$_3$OD) δ 7.69 (dd, J=8.1, 1.1 Hz, 1H), 7.56-7.50 (m, 1H), 7.31 (t, J=7.9 Hz, 1H), 7.16 (dd, J=8.0, 0.7 Hz, 1H), 6.90-6.79 (m, 2H), 3.60 (s, 2H).

Example 133: 2-[3-Chloro-2-(2-oxo-3H-1,3-benzothiazol-6-yl)phenyl]acetonitrile

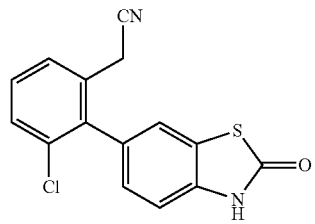 [SMILES: N#CCc1cccc(Cl)c1-c1ccc2[nH]c(=O)sc2c1]

The title compound was prepared in an analogous to manner to Example 2 (Step B), substituting 2-(3-chloro-2-iodophenyl)acetonitrile (Intermediate 8) for 2,6-dimethyliodobenzene, 6-(4,4,5,5-tetramethyl-1,3,2-dioxaborolan-2-yl)benzo[d]thiazol-2(3H)-one (Intermediate 2) for 5-(4,4,5,5-tetramethyl-1,3,2-dioxaborolan-2-yl)-1H-benzo[d]imidazol-2(3H)-one, and PdCl$_2$(dppf)-CH$_2$Cl$_2$ for PdCl$_2$(dtbpf) in Step B. MS (ESI): mass calcd. for $C_{15}H_9ClN_2OS$, 300.0; m/z found, 301.0 [M+H]$^+$. $^1$H NMR (500 MHz, CDCl$_3$) δ 7.51-7.46 (m, 2H), 7.40-7.35 (m, 1H), 7.27 (d, J=1.6 Hz, 1H), 7.26-7.24 (m, 1H), 7.13 (dd, J=8.2, 1.7 Hz, 1H), 3.47 (s, 2H).

Example 134: 6-(3,5-Dichloro-4-pyridyl)-3H-1,3-benzothiazol-2-one

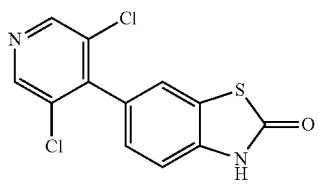 [SMILES: O=c1[nH]c2ccc(-c3c(Cl)cncc3Cl)cc2s1]

The title compound was prepared in a manner analogous to Example 2 (Step B), substituting 3,5-dichloro-4-iodopyridine for 2,6-dimethyliodobenzene, and 6-(4,4,5,5-tetramethyl-1,3,2-dioxaborolan-2-yl)benzo[d]thiazol-2(3H)-one (Intermediate 2) for 5-(4,4,5,5-tetramethyl-1,3,2-dioxaborolan-2-yl)-1H-benzo[d]imidazol-2(3H)-one (Intermediate 28) in Step B. MS (ESI): mass calcd. for $C_{12}H_6Cl_2N_2OS$, 297.1; m/z found, 298.1 [M+H]$^+$. $^1$H NMR (500 MHz, DMSO-d$_6$) δ 8.75 (s, 2H), 7.61 (dd, J=1.4, 0.8 Hz, 1H), 7.30-7.21 (m, 2H), 3.17 (s, 1H).

Example 135: 2-[3-(4-Fluorophenyl)-2-(2-oxo-1,3-dihydrobenzimidazol-5-yl)phenyl]acetonitrile

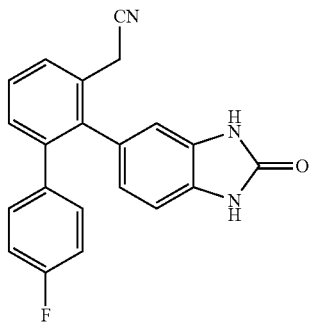 [SMILES: N#CCc1cccc(-c2ccc(F)cc2)c1-c1ccc2[nH]c(=O)[nH]c2c1]

To a suspension of (4-fluorophenyl)boronic acid (48 mg, 0.34 mmol) and 2-[3-bromo-2-(2-oxo-1,3-dihydrobenzimidazol-5-yl)phenyl]acetonitrile (Example 132, 75 mg, 0.23 mmol) in 4:1 dioxane:water (2.0 mL) were added potassium phosphate (97 mg, 0.46 mmol) and $PdCl_2(dppf)\text{-}CH_2Cl_2$ (17 mg, 0.02 mmol). The mixture was degassed with nitrogen for 10 minutes and then heated at 100° C. for 16 h. After cooling to rt, the reaction mixture was diluted with water and extracted with DCM (×2). The combined organic extracts were dried ($Na_2SO_4$), filtered and concentrated. Purification by reverse-phase HPLC (XBridge C18 column (5 µm, 100×4.6 mm), mobile phase of 10-100% ACN in 20 mM $NH_4OH$) afforded the title product (49 mg, 63% yield). MS (ESI): mass calcd. for $C_{21}H_{14}FN_3O$, 343.1; m/z found, 344.1 [M+H]$^+$. $^1$H NMR (400 MHz, DMSO-d$_6$) δ 10.62 (s, 1H), 10.56 (s, 1H), 7.59-7.53 (m, 1H), 7.49 (t, J=7.6 Hz, 1H), 7.37 (dd, J=7.6, 1.4 Hz, 1H), 7.14-7.05 (m, 2H), 7.05-6.96 (m, 2H), 6.85 (d, J=7.9 Hz, 1H), 6.65 (dd, J=7.9, 1.6 Hz, 1H), 6.57 (d, J=1.5 Hz, 1H), 3.71 (s, 2H).

Example 136: 2-[3-(2-Fluorophenyl)-2-(2-oxo-1,3-dihydrobenzimidazol-5-yl)phenyl]acetonitrile

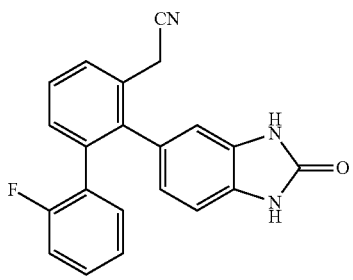 [SMILES: N#CCc1cccc(-c2ccccc2F)c1-c1ccc2[nH]c(=O)[nH]c2c1]

The title compound was prepared in a manner analogous to Example 135, substituting (2-fluorophenyl)boronic acid for (4-fluorophenyl)boronic acid. MS (ESI): mass calcd. for $C_{21}H_{14}FN_3O$, 343.1; m/z found, 344.1 [M+H]$^+$. $^1$H NMR (500 MHz, CD$_3$OD) δ 7.59 (dd, J=7.8, 1.3 Hz, 1H), 7.48 (t, J=7.7 Hz, 1H), 7.39-7.31 (m, 1H), 7.15 (m, 1H), 7.05 (dt, J=7.6, 1.8 Hz, 1H), 6.98-6.94 (m, 1H), 6.94-6.85 (m, 2H), 6.80-6.73 (m, 2H), 3.65 (s, 2H).

Example 137: 2-[3-(4-Methoxyphenyl)-2-(2-oxo-1,3-dihydrobenzimidazol-5-yl)phenyl]acetonitrile

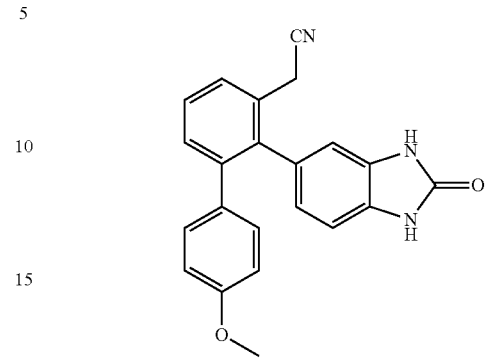

The title compound was prepared in a manner analogous to Example 135, substituting (4-methoxyphenyl)boronic acid for (4-fluorophenyl)boronic acid. MS (ESI): mass calcd. for $C_{22}H_{17}N_3O_2$, 355.1; m/z found, 356.1 [M+H]$^+$. $^1$H NMR (500 MHz, CD$_3$OD) δ 7.53-7.49 (m, 1H), 7.44 (t, J=7.7 Hz, 1H), 7.38-7.34 (m, 1H), 7.02-6.94 (m, 3H), 6.77 (dd, J=8.0, 1.5 Hz, 1H), 6.74-6.66 (m, 3H), 3.68 (s, 3H), 3.63 (s, 2H).

Example 138: 2-[3-Cyclopropyl-2-(2-oxo-1,3-dihydrobenzimidazol-5-yl)phenyl]acetonitrile

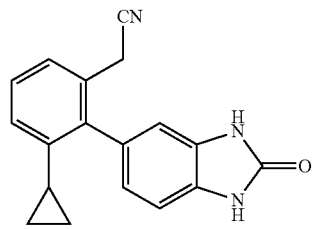 [SMILES: N#CCc1cccc(C2CC2)c1-c1ccc2[nH]c(=O)[nH]c2c1]

The title compound was prepared in a manner analogous to Example 135, substituting cyclopropylboronic acid for (4-fluorophenyl)boronic acid. MS (ESI): mass calcd. for $C_{18}H_{15}N_3O$, 289.1; m/z found, 290.1 [M+H]$^+$. $^1$H NMR (400 MHz, CD$_3$OD) δ 7.34-7.26 (m, 2H), 7.16 (dd, J=7.9, 0.6 Hz, 1H), 6.98-6.85 (m, 3H), 3.51 (s, 2H), 1.54 (tt, J=8.4, 5.3 Hz, 1H), 0.72 (ddt, J=8.2, 6.8, 3.0 Hz, 2H), 0.66-0.56 (m, 2H).

Example 139: 5-[2,6-Dichloro-3-(morpholinomethyl)phenyl]-1,3-dihydrobenzimidazol-2-one

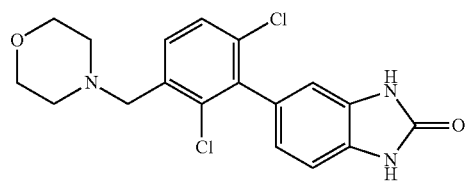 [SMILES: O=c1[nH]c2ccc(-c3c(Cl)ccc(CN4CCOCC4)c3Cl)cc2[nH]1]

The title compound was prepared in a manner analogous to Example 2 (Step B), substituting 4-(3-bromo-2,4-dichlorobenzyl)morpholine (Intermediate 13) for 2,6-dimethyl-iodobenzene and PdCl₂(dppf)-CH₂Cl₂ for PdCl₂(dtbpf). MS (ESI): mass calcd. for C₁₈H₁₇Cl₂N₃O₂, 377.1; m/z found, 378.1 [M+H]⁺. ¹H NMR (400 MHz, DMSO-d₆) δ 10.74 (s, 1H), 10.67 (s, 1H), 7.60-7.47 (m, 2H), 7.05-6.94 (m, 1H), 6.80-6.64 (m, 2H), 3.70-3.51 (m, 6H), 2.49-2.39 (m, 4H).

Example 140: 5-[2,6-Dichloro-3-(1-piperidylmethyl)phenyl]-1,3-dihydrobenzimidazol-2-one

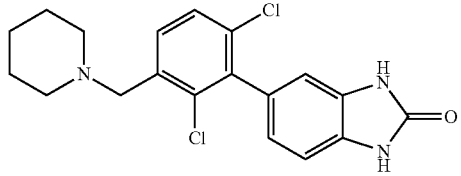 [SMILES: O=c1[nH]c2ccc(-c3c(Cl)ccc(CN4CCCCC4)c3Cl)cc2[nH]1]

The title compound was prepared in a manner analogous to Example 139, substituting 1-(2,4-dichloro-3-iodobenzyl)piperidine (Intermediate 20) for 4-(3-bromo-2,4-dichlorobenzyl)morpholine (Intermediate 13). MS (ESI): mass calcd. for C₁₉H₁₉Cl₂N₃O, 375.1; m/z found, 376.1 [M+H]⁺. ¹H NMR (400 MHz, DMSO-d₆) δ 10.72 (s, 1H), 10.67 (s, 1H), 7.52 (d, J=3.5 Hz, 2H), 7.00 (d, J=7.9 Hz, 1H), 6.79-6.70 (m, 2H), 3.52 (s, 2H), 2.44-2.36 (m, 4H), 1.59-1.48 (m, 4H), 1.47-1.37 (m, 2H).

Example 141: 5-[2-Chloro-3-(morpholinomethyl)phenyl]-1,3-dihydrobenzimidazol-2-one

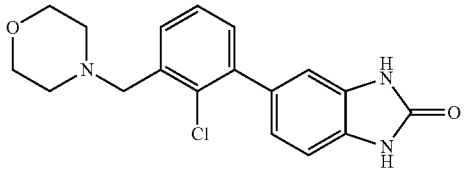 [SMILES: O=c1[nH]c2ccc(-c3cccc(CN4CCOCC4)c3Cl)cc2[nH]1]

The title compound was prepared in a manner analogous to Example 139, substituting 4-(2-chloro-3-iodobenzyl)morpholine (Intermediate 21) for 4-(3-bromo-2,4-dichlorobenzyl)morpholine (Intermediate 13). MS (ESI): mass calcd. for C₁₈H₁₈ClN₃O₂, 343.1; m/z found, 344.1 [M+H]⁺. ¹H NMR (400 MHz, DMSO-d₆) δ 10.70 (s, 1H), 10.64 (s, 1H), 7.49 (dd, J=7.6, 1.8 Hz, 1H), 7.35 (t, J=7.6 Hz, 1H), 7.26 (dd, J=7.6, 1.8 Hz, 1H), 7.02-6.88 (m, 3H), 3.64-3.58 (m, 6H), 2.48-2.43 (m, 4H).

Example 142: 5-[2-Chloro-3-(1-piperidylmethyl)phenyl]-1,3-dihydrobenzimidazol-2-one

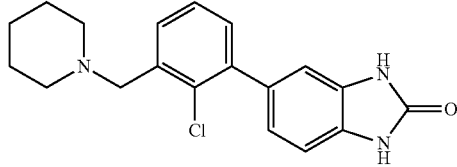 [SMILES: O=c1[nH]c2ccc(-c3cccc(CN4CCCCC4)c3Cl)cc2[nH]1]

The title compound was prepared in a manner analogous to Example 139, substituting 1-(2-chloro-3-iodobenzyl)piperidine (Intermediate 22) for 4-(3-bromo-2,4-dichlorobenzyl)morpholine (Intermediate 13). MS (ESI): mass calcd. for C₁₉H₂₀ClN₃O, 341.1; m/z found, 342.1 [M+H]⁺. ¹H NMR (400 MHz, DMSO-d₆) δ 10.68 (s, 1H), 10.64 (s, 1H), 7.47 (dd, J=7.6, 1.8 Hz, 1H), 7.35 (t, J=7.6 Hz, 1H), 7.24 (dd, J=7.5, 1.8 Hz, 1H), 7.01-6.88 (m, 3H), 3.56 (s, 2H), 2.46-2.38 (m, 4H), 1.60-1.47 (m, 4H), 1.46-1.37 (m, 2H).

Example 143: 5-[2-Chloro-3-[(2,2-dimethylmorpholin-4-yl)methyl]phenyl]-1,3-dihydrobenzimidazol-2-one

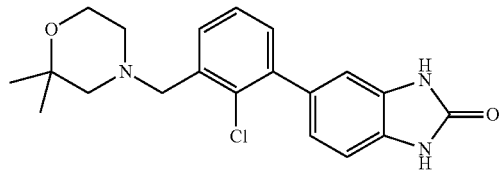 [SMILES: CC1(C)CN(Cc2cccc(-c3ccc4[nH]c(=O)[nH]c4c3)c2Cl)CCO1]

The title compound was prepared in a manner analogous to Example 139, substituting 4-(2-chloro-3-iodobenzyl)-2,2-dimethylmorpholine (Intermediate 23) for 4-(3-bromo-2,4-dichlorobenzyl)morpholine (Intermediate 13). MS (ESI): mass calcd. for C₂₀H₂₂ClN₃O₂, 371.1; m/z found, 372.1 [M+H]⁺. ¹H NMR (400 MHz, DMSO-d₆) δ 10.76-10.59 (m, 2H), 7.51 (dd, J=7.6, 1.8 Hz, 1H), 7.38 (t, J=7.6 Hz, 1H), 7.25 (dd, J=7.6, 1.8 Hz, 1H), 7.02-6.86 (m, 3H), 3.68-3.61 (m, 2H), 3.56 (s, 2H), 2.44-2.34 (m, 2H), 2.24 (s, 2H), 1.18 (s, 6H).

Example 144: (±)-5-[2-Chloro-3-[[2-(trifluoromethyl)morpholin-4-yl]methyl]phenyl]-1,3-dihydrobenzimidazol-2-one

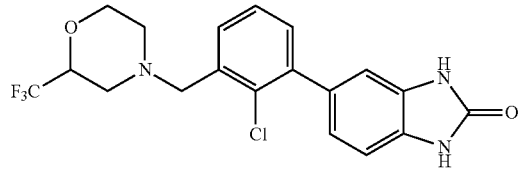 [SMILES: O=c1[nH]c2ccc(-c3cccc(CN4CCOC(C(F)(F)F)C4)c3Cl)cc2[nH]1]

The title compound was prepared in a manner analogous to Example 139, substituting 4-(2-chloro-3-iodobenzyl)-2-(trifluoromethyl)morpholine (Intermediate 24) for 4-(3-bromo-2,4-dichlorobenzyl)morpholine (Intermediate 13). MS (ESI): mass calcd. for C₁₉H₁₇ClF₃N₃O₂, 411.1; m/z found, 412.1 [M+H]⁺. ¹H NMR (400 MHz, DMSO-d₆) δ 10.71 (s, 1H), 10.67 (s, 1H), 7.51 (dd, J=7.6, 1.8 Hz, 1H), 7.38 (t, J=7.6 Hz, 1H), 7.29 (dd, J=7.6, 1.8 Hz, 1H), 7.02-6.96 (m, 1H), 6.96-6.90 (m, 2H), 4.27-4.17 (m, 1H), 3.95 (dd, J=10.3, 2.8 Hz, 1H), 3.74 (s, 2H), 3.70-3.62 (m, 1H), 2.95 (d, J=10.9 Hz, 1H), 2.78-2.71 (m, 1H), 2.34-2.21 (m, 2H).

Example 145: 5-[2-Chloro-6-(morpholinomethyl)phenyl]-1,3-dihydrobenzimidazol-2-one

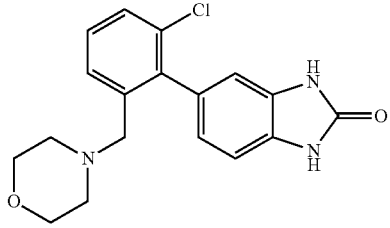 [SMILES: O=c1[nH]c2ccc(-c3c(Cl)cccc3CN3CCOCC3)cc2[nH]1]

The title compound was prepared in a manner analogous to Example 139, substituting 4-(3-Chloro-2-iodobenzyl)morpholine (Intermediate 25) for 4-(3-bromo-2,4-dichlorobenzyl)morpholine (Intermediate 13). MS (ESI): mass calcd. for $C_{18}H_{18}ClN_3O_2$, 343.1; m/z found, 344.1 [M+H]$^+$. $^1$H NMR (400 MHz, CD$_3$OD) δ 7.48 (dd, J=7.6, 1.2 Hz, 1H), 7.41-7.37 (m, 1H), 7.32-7.26 (m, 1H), 7.14-7.06 (m, 1H), 6.90-6.80 (m, 2H), 3.22 (d, J=3.8 Hz, 2H), 2.99 (s, 2H), 2.85 (d, J=0.6 Hz, 2H), 2.31-2.19 (m, 4H).

Example 146: 5-[2-Chloro-6-[(4-methylpiperazin-1-yl)methyl]phenyl]-1,3-dihydrobenzimidazol-2-one

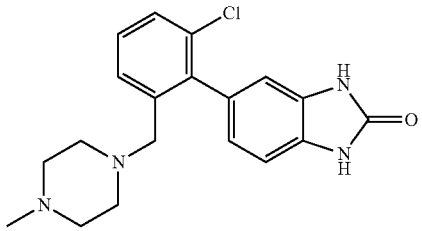 [SMILES: CN1CCN(Cc2cccc(Cl)c2-c2ccc3[nH]c(=O)[nH]c3c2)CC1]

The title compound was prepared in a manner analogous to Example 139, substituting 1-(3-chloro-2-iodobenzyl)-4-methylpiperazine (Intermediate 26) for 4-(3-bromo-2,4-dichlorobenzyl)morpholine (Intermediate 13). MS (ESI): mass calcd. for $C_{19}H_{21}ClN_4O$, 356.1; m/z found, 357.0 [M+H]$^+$. $^1$H NMR (400 MHz, CD$_3$OD) δ 7.46 (dd, J=7.6, 1.2 Hz, 1H), 7.41-7.35 (m, 1H), 7.35-7.26 (m, 1H), 7.10 (d, J=8.0 Hz, 1H), 6.90-6.77 (m, 2H), 3.35-3.28 (m, 4H), 2.48-2.16 (m, 9H).

Example 147: 5-[2-Methyl-3-(1-piperidylmethyl)phenyl]-1,3-dihydrobenzimidazol-2-one

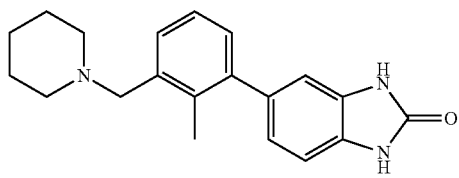 [SMILES: Cc1c(CN2CCCCC2)cccc1-c1ccc2[nH]c(=O)[nH]c2c1]

Step A: 1-(3-Bromo-2-methylbenzyl)piperidine

To a solution of 3-bromo-2-methylbenzaldehyde (253 mg, 1.3 mmol) and piperidine (0.15 mL, 1.5 mmol) in DCM (4.2 mL) was added sodium triacteoxyborohydride (323 mg, 1.5 mmol). After stirring at rt for 1 h, water was added. The layers were separated, and the aqueous layer was extracted three times with EtOAc. The combined organic extracts were dried (Na$_2$SO$_4$), filtered and concentrated in vacuo to provide an oil, which was used without further purification. MS (ESI): mass calcd. for $C_{13}H_{18}BrN$, 267.1; m/z found, 268.1 [M+H]$^+$. $^1$H NMR (400 MHz, DMSO-d$_6$) δ 7.49 (dd, J=8.0, 1.1 Hz, 1H), 7.22 (d, J=6.9 Hz, 1H), 7.07 (t, J=7.7 Hz, 1H), 3.40 (s, 2H), 2.38 (s, 3H), 2.37-2.25 (m, 4H), 1.53-1.34 (m, 6H).

Step B: 5-[2-Methyl-3-(1-piperidylmethyl)phenyl]-1,3-dihydrobenzimidazol-2-one The title compound was prepared in a manner analogous to Example 2, substituting 1-(3-bromo-2-methylbenzyl)piperidine for 2,6-dimethyliodobenzene. The crude product was purified by reverse-phase HPLC (Agilent 1100 Series XBridge Prep C18 OBD 5 um, 0.05M Ammonium Hydroxide in water/MeCN), to afford the title compound (17 mg, 10% yield). MS (ESI): mass calcd. for $C_{20}H_{23}N_3O$, 321.2; m/z found, 322.2 [M+H]$^+$. $^1$H NMR (400 MHz, DMSO-d$_6$) δ 10.63 (s, 1H), 10.59 (s, 1H), 7.23-7.11 (m, 2H), 7.07 (dd, J=7.5, 1.6 Hz, 1H), 6.96 (d, J=7.9 Hz, 1H), 6.85-6.76 (m, 2H), 3.41 (s, 2H), 2.40-2.30 (m, 4H), 2.19 (s, 3H), 1.53-1.44 (m, 4H), 1.43-1.35 (m, 2H).

Example 148: 5-[2-Methyl-3-(morpholinomethyl)phenyl]-1,3-dihydrobenzimidazol-2-one

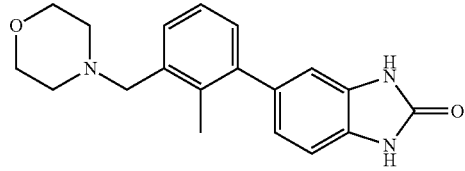

Step A: 2-Methyl-3-(2-oxo-2,3-dihydro-1H-benzo[d]imidazol-5-yl)benzaldehyde The title compound was prepared in a manner analogous to Example 2, substituting 3-bromo-2-methylbenzaldehye for 2,6-dimethyliodobenzene. The crude product was triturated with DCM to provide the title compound. MS (ESI): mass calcd. for $C_{15}H_{12}N_2O_2$, 252.1; m/z found, 253.1 [M+H]$^+$. $^1$H NMR (400 MHz, DMSO-d$_6$) δ 10.81-10.57 (m, 2H), 10.34 (s, 1H), 7.84 (dd, J=7.4, 1.8 Hz, 1H), 7.63-7.34 (m, 2H), 7.03 (d, J=7.9 Hz, 1H), 6.92-6.73 (m, 2H), 2.45 (s, 3H).

Step B: 5-[2-Methyl-3-(morpholinomethyl)phenyl]-1,3-dihydrobenzimidazol-2-one To a solution of 2-methyl-3-(2-oxo-2,3-dihydro-1H-benzo[d]imidazol-5-yl)benzaldehyde (100 mg, 0.4 mmol) and morpholine (0.07 mL, 0.8 mmol) in DCM (1.2 mL) and MeOH (0.8 mL) was added acetic acid (0.002 mL, 0.04 mmol). After 15 minutes, sodium triacteoxyborohydride (168 mg, 0.8 mmol) was added at once. Stirring was maintained at rt for an additional 20 minutes. Solvent was removed in vacuo, water was added, and the aqueous layer was extracted twice with DCM. The combined organic extracts were dried (Na$_2$SO$_4$), filtered and concentrated under reduced pressure. Purification by chromatography (SiO$_2$; hexanes—20% IPA/EtOAc) afforded the desired product (80 mg, 62% yield). MS (ESI): mass calcd. for C$_{19}$H$_{21}$N$_3$O$_2$, 323.2; m/z found, 324.2 [M+H]$^+$. $^1$H NMR (400 MHz, DMSO-d$_6$) δ 10.64 (s, 1H), 10.60 (s, 1H), 7.22 (dd, J=7.5, 1.3 Hz, 1H), 7.16 (t, J=7.5 Hz, 1H), 7.09 (dd, J=7.5, 1.4 Hz, 1H), 6.97 (d, J=7.9 Hz, 1H), 6.86-6.81 (m, 1H), 6.79 (s, 1H), 3.68-3.53 (m, 4H), 3.47 (s, 2H), 2.42-2.36 (m, 4H), 2.21 (s, 3H).

Example 149: 5-[3-[(2,2-Dimethylmorpholin-4-yl)methyl]-2-methyl-phenyl]-1,3-dihydrobenzimidazol-2-one

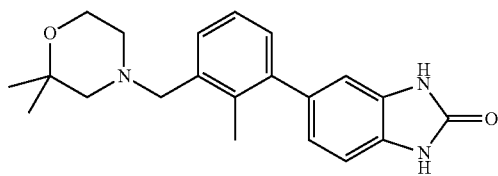 [SMILES: Cc1c(CN2CCOC(C)(C)C2)cccc1-c1ccc2[nH]c(=O)[nH]c2c1]

The title compound was prepared in a manner analogous to Example 148, substituting 2,2-dimethylmorpholine for morpholine in Step B. MS (ESI): mass calcd. for C$_{21}$H$_{25}$N$_3$O$_2$, 351.2; m/z found, 352.2 [M+H]$^+$. $^1$H NMR (500 MHz, DMSO-d$_6$) δ 10.69-10.54 (m, 2H), 7.24-7.19 (m, 1H), 7.16 (t, J=7.5 Hz, 1H), 7.08 (dd, J=7.4, 1.5 Hz, 1H), 6.96 (dd, J=7.9, 1.4 Hz, 1H), 6.84-6.80 (m, 1H), 6.78 (d, J=1.6 Hz, 1H), 3.59 (t, J=4.7 Hz, 2H), 3.42 (s, 2H), 2.32 (s, 2H), 2.25-2.13 (m, 5H), 1.20-1.06 (m, 6H).

Example 150: (±)-5-[2-Methyl-3-[(2-methylmorpholin-4-yl)methyl]phenyl]-1,3-dihydrobenzimidazol-2-one

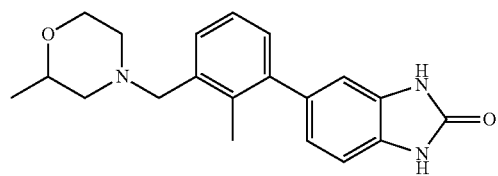 [SMILES: Cc1c(CN2CCOC(C)C2)cccc1-c1ccc2[nH]c(=O)[nH]c2c1]

The title compound was prepared in a manner analogous to Example 148, substituting 2-methylmorpholine for morpholine in Step B. MS (ESI): mass calcd. for C$_{20}$H$_{23}$N$_3$O$_2$, 337.2; m/z found, 338.2 [M+H]$^+$. $^1$H NMR (400 MHz, DMSO-d$_6$) δ 10.64 (s, 1H), 10.60 (s, 1H), 7.24-7.12 (m, 2H), 7.10-7.06 (m, 1H), 6.96 (d, J=7.9 Hz, 1H), 6.84-6.76 (m, 2H), 3.77-3.69 (m, 1H), 3.49-3.42 (m, 4H), 2.73-2.65 (m, 1H), 2.61 (dd, J=11.2, 2.2 Hz, 1H), 2.21 (s, 3H), 2.12-2.02 (m, 1H), 1.78 (dd, J=11.2, 9.8 Hz, 1H), 1.07-1.00 (m, 3H).

Example 151: (±)-5-[2-Methyl-3-[[2-(trifluoromethyl)morpholin-4-yl]methyl]phenyl]-1,3-dihydrobenzimidazol-2-one

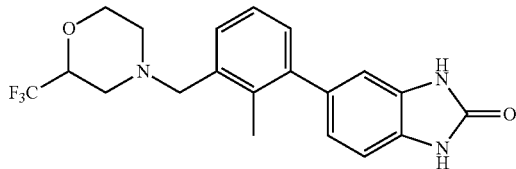 [SMILES: Cc1c(CN2CCOC(C(F)(F)F)C2)cccc1-c1ccc2[nH]c(=O)[nH]c2c1]

The title compound was prepared in a manner analogous to Example 148, substituting 2-trifluoromethylmorpholine for morpholine in Step B. MS (ESI): mass calcd. for C$_{20}$H$_{20}$F$_3$N$_3$O$_2$, 391.2; m/z found, 392.2 [M+H]$^+$. $^1$H NMR (500 MHz, DMSO-d$_6$) δ 10.73-10.51 (s, 2H), 7.28-7.21 (d, J=7.5 Hz, 1H), 7.22-7.14 (t, J=7.5 Hz, 1H), 7.14-7.07 (dd, J=7.5, 1.6 Hz, 1H), 7.01-6.93 (dd, J=7.9, 1.5 Hz, 1H), 6.88-6.76 (m, 2H), 4.14 (d, J=7.1 Hz, 1H), 3.92 (d, J=11.1, 1H), 3.57 (s, 2H), 2.88 (d, J=10.8, 1H), 2.73-2.64 (d, J=11.7 Hz, 1H), 2.25-2.15 (m, 2H), 2.22 (s, 3H).

Example 152: (3R)-5-[2-Methyl-3-[[3-methylmorpholin-4-yl]methyl]phenyl]-1,3-dihydrobenzimidazol-2-one

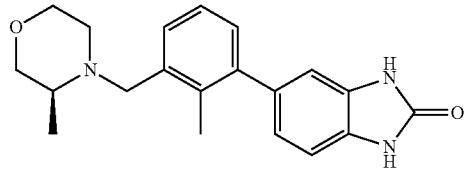 [SMILES: Cc1c(CN2CCOC[C@@H]2C)cccc1-c1ccc2[nH]c(=O)[nH]c2c1]

The title compound was prepared in a manner analogous to Example 148, substituting (R)-3-methylmorpholine for morpholine in Step B. MS (ESI): mass calcd. for C$_{20}$H$_{23}$N$_3$O$_2$, 337.2; m/z found, 338.2 [M+H]$^+$. $^1$H NMR (500 MHz, DMSO-d$_6$) δ 10.74-10.55 (m, 2H), 7.31-7.22 (m, 1H), 7.20-7.12 (m, 1H), 7.11-7.04 (m, 1H), 6.96 (dd, J=7.9, 2.2 Hz, 1H), 6.86-6.76 (m, 2H), 4.10 (d, J=13.0 Hz, 1H), 3.69-3.56 (m, 2H), 3.48-3.35 (m, 2H), 3.21-3.12 (m, 1H), 3.06 (dd, J=13.2, 2.3 Hz, 1H), 2.48-2.34 (m, 1H), 2.24 (d, J=2.2 Hz, 3H), 2.18-2.05 (m, 1H), 1.09-0.98 (m, 3H).

Example 153: (3S)-5-[2-Methyl-3-[[3-methylmorpholin-4-yl]methyl]phenyl]-1,3-dihydrobenzimidazol-2-one

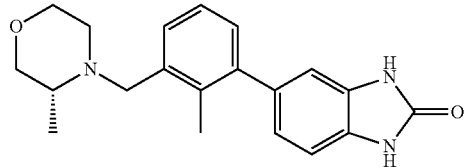 [SMILES: Cc1c(CN2CCOC[C@H]2C)cccc1-c1ccc2[nH]c(=O)[nH]c2c1]

The title compound was prepared in a manner analogous to Example 148, substituting (S)-3-methylmorpholine for morpholine in Step B. MS (ESI): mass calcd. for C₂₀H₂₃N₃O₂, 337.2; m/z found, 338.2 [M+H]⁺. ¹H NMR (500 MHz, DMSO-d₆) δ 10.74-10.55 (m, 2H), 7.31-7.22 (m, 1H), 7.20-7.12 (m, 1H), 7.11-7.04 (m, 1H), 6.96 (dd, J=7.9, 2.2 Hz, 1H), 6.86-6.76 (m, 2H), 4.10 (d, J=13.0 Hz, 1H), 3.69-3.56 (m, 2H), 3.48-3.35 (m, 2H), 3.21-3.12 (m, 1H), 3.06 (dd, J=13.2, 2.3 Hz, 1H), 2.48-2.34 (m, 1H), 2.24 (d, J=2.2 Hz, 3H), 2.18-2.05 (m, 1H), 1.09-0.98 (m, 3H).

Example 154: 5-[2-Methyl-3-(thiomorpholinomethyl)phenyl]-1,3-dihydrobenzimidazol-2-one

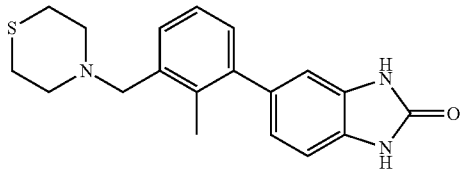 [SMILES: Cc1c(CN2CCSCC2)cccc1-c1ccc2[nH]c(=O)[nH]c2c1]

The title compound was prepared in a manner analogous to Example 148, substituting thiomorpholine for morpholine in Step B. MS (ESI): mass calcd. for C₁₉H₂₁N₃OS, 339.1; m/z found, 340.1 [M+H]⁺. ¹H NMR (500 MHz, DMSO-d₆) δ 10.64 (s, 1H), 10.60 (s, 1H), 7.24-7.20 (m, 1H), 7.16 (t, J=7.5 Hz, 1H), 7.10-7.06 (m, 1H), 6.96 (d, J=7.9 Hz, 1H), 6.83 (dd, J=7.9, 1.6 Hz, 1H), 6.79 (d, J=1.5 Hz, 1H), 3.48 (s, 2H), 2.67 (dd, J=6.3, 3.0 Hz, 4H), 2.60 (dd, J=5.5, 3.4 Hz, 4H), 2.19 (s, 3H).

Example 155: tert-Butyl 4-[[2-methyl-3-(2-oxo-1,3-dihydrobenzimidazol-5-yl)phenyl]methyl]piperazine-1-carboxylate

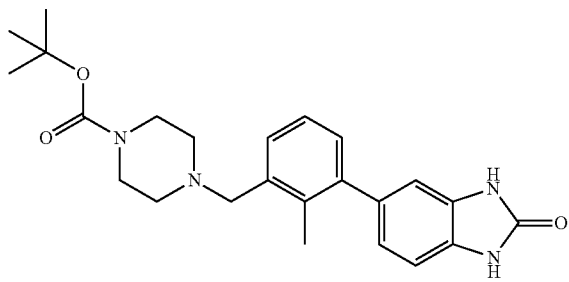 [SMILES: Cc1c(CN2CCN(C(=O)OC(C)(C)C)CC2)cccc1-c1ccc2[nH]c(=O)[nH]c2c1]

The title compound was prepared in a manner analogous to Example 148, substituting tert-butyl piperazine-1-carboxylate for morpholine in Step B. MS (ESI): mass calcd. for C₂₄H₃₀N₄O₃, 422.2; m/z found, 423.2 [M+H]⁺. ¹H NMR (500 MHz, DMSO-d₆) δ 10.64 (s, 1H), 10.60 (s, 1H), 7.22 (dd, J=8.0, 1.3 Hz, 1H), 7.17 (t, J=7.5 Hz, 1H), 7.11-7.07 (m, 1H), 6.96 (d, J=7.9 Hz, 1H), 6.84-6.77 (m, 2H), 3.48 (s, 2H), 3.30 (s, 4H), 2.35 (t, J=5.0 Hz, 4H), 2.20 (s, 3H), 1.39 (s, 9H).

Example 156: 5-[2-Methyl-3-(pyrrolidin-1-ylmethyl)phenyl]-1,3-dihydrobenzimidazol-2-one

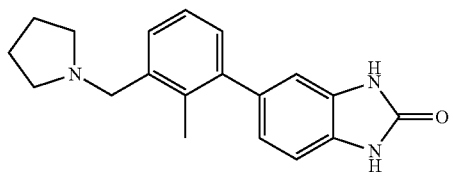 [SMILES: Cc1c(CN2CCCC2)cccc1-c1ccc2[nH]c(=O)[nH]c2c1]

The title compound was prepared in a manner analogous to Example 148, substituting pyrrolidine for morpholine in Step B. MS (ESI): mass calcd. for C₁₉H₂₁N₃O, 307.2; m/z found, 308.2 [M+H]⁺. ¹H NMR (400 MHz, DMSO-d₆) δ 10.68-10.57 (m, 2H), 7.25 (dd, J=7.5, 1.5 Hz, 1H), 7.17 (t, J=7.5 Hz, 1H), 7.07 (dd, J=7.6, 1.4 Hz, 1H), 6.96 (d, J=7.9 Hz, 1H), 6.86-6.74 (m, 2H), 3.59 (s, 2H), 2.50-2.42 (m, 4H), 2.18 (s, 3H), 1.76-1.65 (m, 4H).

Example 157: 5-[3-[(3-Fluoroazetidin-1-yl)methyl]-2-methyl-phenyl]-1,3-dihydrobenzimidazol-2-one

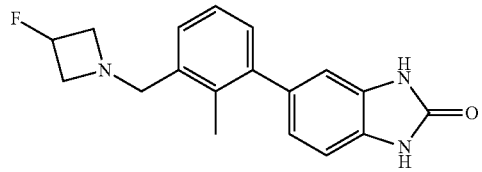 [SMILES: Cc1c(CN2CC(F)C2)cccc1-c1ccc2[nH]c(=O)[nH]c2c1]

The title compound was prepared in a manner analogous to Example 148, substituting 3-fluoroazetidine for morpholine in Step B. MS (ESI): mass calcd. for C₁₈H₁₈FN₃O, 311.1; m/z found, 312.2 [M+H]⁺. ¹H NMR (400 MHz, DMSO) δ ¹H NMR (400 MHz, DMSO-d₆) δ 10.72-10.52 (m, 2H), 7.26-7.21 (m, 1H), 7.17 (t, J=7.5 Hz, 1H), 7.09-7.05 (m, 1H), 6.98-6.94 (m, 1H), 6.81 (dd, J=7.9, 1.6 Hz, 1H), 6.79-6.76 (m, 1H), 5.31-5.08 (m, 1H), 3.68-3.53 (m, 4H), 3.24-3.10 (m, 2H), 2.14 (s, 3H).

Example 158: 5-[2-Methyl-3-(6-oxa-3-azabicyclo[3.1.1]heptan-3-ylmethyl)phenyl]-1,3-dihydrobenzimidazol-2-one

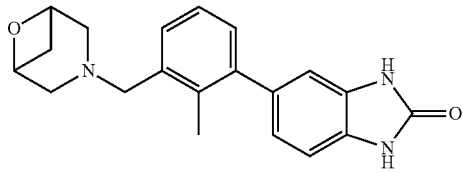 [SMILES: Cc1c(CN2CC3CC(C2)O3)cccc1-c1ccc2[nH]c(=O)[nH]c2c1]

The title compound was prepared in a manner analogous to Example 148, substituting 6-oxa-3-azabicyclo[3.1.1]heptane for morpholine in Step B. MS (ESI): mass calcd. for C₂₀H₂₁N₃O₂, 335.2; m/z found, 336.2 [M+H]⁺. ¹H NMR (400 MHz, DMSO-d₆) δ 10.69-10.55 (m, 2H), 7.28 (dd, J=7.5, 1.5 Hz, 1H), 7.19 (t, J=7.5 Hz, 1H), 7.12-7.05 (m, 1H), 6.97 (d, J=7.9 Hz, 1H), 6.87-6.77 (m, 2H), 4.41 (d, J=5.7 Hz, 2H), 3.75 (s, 2H), 2.99-2.89 (m, 2H), 2.89-2.78 (m, 1H), 2.75-2.64 (m, 2H), 2.25-2.16 (m, 4H).

Example 159: (3R,4S)-5-[3-[[3-Fluoro-4-hydroxy-1-piperidyl]methyl]-2-methyl-phenyl]-1,3-dihydrobenzimidazol-2-one

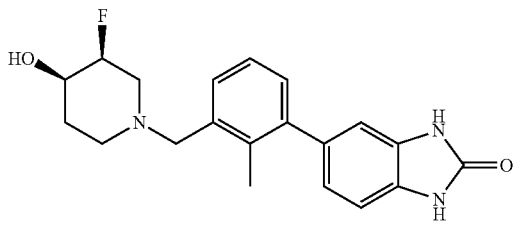 [SMILES: Cc1c(CN2CC[C@@H](O)[C@@H](F)C2)cccc1-c1ccc2[nH]c(=O)[nH]c2c1]

The title compound was prepared in a manner analogous to Example 148, substituting (3R,4S)-3-fluoropiperidin-4-ol for morpholine in Step B. MS (ESI): mass calcd. for $C_{20}H_{22}FN_3O_2$, 355.2; m/z found, 356.2 [M+H]$^+$. $^1$H NMR (400 MHz, DMSO-d$_6$) δ 10.67-10.52 (m, 2H), 7.27-7.11 (m, 2H), 7.08 (dd, J=7.5, 1.6 Hz, 1H), 7.01-6.91 (m, 1H), 6.87-6.72 (m, 2H), 4.91 (d, J=4.8 Hz, 1H), 4.64-4.43 (m, 1H), 3.66 (d, J=20.8 Hz, 1H), 3.50 (s, 2H), 3.16 (d, J=5.0 Hz, 1H), 2.87-2.56 (m, 2H), 2.19 (bs, 4H), 1.77-1.51 (m, 2H).

Example 160: 5-(2-Chloro-6-cyclopropyl-phenyl)-1,3-dihydrobenzimidazol-2-one

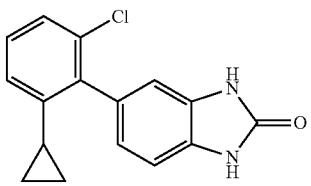 [SMILES: O=c1[nH]c2ccc(-c3c(Cl)cccc3C3CC3)cc2[nH]1]

Step A: 5-(2-Bromo-6-chloro-phenyl)-1,3-dihydrobenzimidazol-2-one

To a solution of 5-(4,4,5,5-tetramethyl-1,3,2-dioxaborolan-2-yl)-1H-benzo[d]imidazol-2(3H)-one (Intermediate 28, 1.0 g, 3.8 mmol), potassium phosphate (1.6 g, 7.7 mmol), and 2-bromo-6-chloroiodobenzene (1.5 g, 4.6 mmol) in 4:1 dioxane:water (10 mL) was added PdCl$_2$(dppf)-CH$_2$Cl$_2$ (281 mg, 0.38 mmol) at once. The mixture was degassed with nitrogen for 10 minutes and then heated at 100° C. for 16 h. After cooling to rt, the reaction mixture was diluted with water and extracted with DCM (×3). The combined organic extracts were dried (Na$_2$SO$_4$), filtered and concentrated under reduced pressure. The crude product was purified by trituration with DCM to afford the title compound as a white solid (835 mg, 67% yield). MS (ESI): mass calcd. for $C_{13}H_8BrClN_2O$, 322.0; m/z found, 322.8 [M+H]$^+$. $^1$H NMR (500 MHz, DMSO-d$_6$) δ 10.71 (s, 2H), 7.72 (dd, J=8.1, 1.1 Hz, 1H), 7.59 (dd, J=8.1, 1.1 Hz, 1H), 7.32 (t, J=8.1 Hz, 1H), 7.01 (dd, J=7.8, 0.6 Hz, 1H), 6.77-6.72 (m, 2H).

Step B: 5-(2-Chloro-6-cyclopropyl-phenyl)-1,3-dihydrobenzimidazol-2-one

To a solution of cyclopropylboronic acid (64 mg, 0.74 mmol), potassium phosphate (210 mg, 0.99 mmol), and 5-(2-bromo-6-chloro-phenyl)-1,3-dihydrobenzimidazol-2-one (160 mg, 0.49 mmol) in 4:1 dioxane:water (2.6 mL) was added PdCl$_2$(dppf)-CH$_2$Cl$_2$ (36 mg, 0.05 mmol) at once. The mixture was degassed with nitrogen for 10 minutes and then heated at 100° C. for 19 h. After cooling to rt, the reaction mixture was diluted with water and extracted with DCM (×3). The crude product was purified by reverse-phase HPLC (Agilent 1100 Series XBridge Prep $^{18}$C OBD 5 um, 0.05M Ammonium Hydroxide in water/MeCN), to afford the title compound (18 mg, 13% yield). MS (ESI): mass calcd. for $C_{16}H_{13}ClN_2O$, 284.1; m/z found, 285.1 [M+H]$^+$. $^1$H NMR (400 MHz, DMSO-d$_6$) δ 10.64 (s, 2H), 7.38-7.21 (m, 2H), 7.01 (d, J=7.9 Hz, 1H), 6.88 (dd, J=7.7, 1.3 Hz, 1H), 6.83-6.72 (m, 2H), 1.51 (tt, J=8.5, 5.3 Hz, 1H), 0.74 (m, J=6.1, 3.9, 2.5 Hz, 2H), 0.64 (m, J=7.7, 4.7, 2.0 Hz, 2H Example 161: 5-(2-Chloro-6-vinyl-phenyl)-1,3-dihydrobenzimidazol-2-one

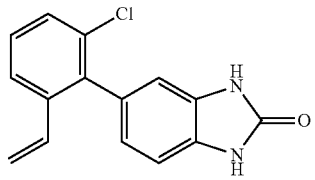 [SMILES: C=Cc1cccc(Cl)c1-c1ccc2[nH]c(=O)[nH]c2c1]

The title compound was prepared in a manner analogous to Example 160, substituting potassium trifluoro(vinyl)borate for cyclopropylboronic acid in Step B. MS (ESI): mass calcd. for $C_{15}H_{11}ClN_2O$, 270.1; m/z found, 271.1 [M+H]$^+$. $^1$H NMR (500 MHz, CD$_3$OD) δ 7.61 (dd, J=7.8, 1.2 Hz, 1H), 7.40 (dd, J=8.0, 1.2 Hz, 1H), 7.34-7.26 (m, 1H), 7.11 (dd, J=8.0, 0.7 Hz, 1H), 6.88-6.77 (m, 2H), 6.38 (dd, J=17.6, 11.1 Hz, 1H), 5.66 (dd, J=17.6, 1.2 Hz, 1H), 5.12 (s, 1H).

Example 162: 5-(2-Chloro-6-phenyl-phenyl)-1,3-dihydrobenzimidazol-2-one

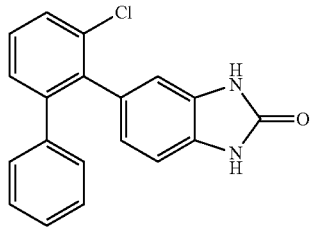 [SMILES: O=c1[nH]c2ccc(-c3c(Cl)cccc3-c3ccccc3)cc2[nH]1]

The title compound was prepared in a manner analogous to Example 160, substituting phenylboronic acid for cyclopropylboronic acid in Step B. MS (ESI): mass calcd. for $C_{19}H_{13}ClN_2O$, 320.1; m/z found, 321.1 [M+H]$^+$. $^1$H NMR (400 MHz, DMSO-d$_6$) δ 10.57 (s, 1H), 10.49 (s, 1H), 7.57 (dd, J=8.0, 1.3 Hz, 1H), 7.44 (t, J=7.8 Hz, 1H), 7.35 (dd, J=7.7, 1.3 Hz, 1H), 7.16 (ddt, J=6.9, 5.2, 3.6 Hz, 3H), 7.09-7.01 (m, 2H), 6.78 (d, J=8.4 Hz, 1H), 6.66-6.56 (m, 2H).

Example 163: 5-[2-Chloro-6-(4-fluorophenyl)phenyl]-1,3-dihydrobenzimidazol-2-one

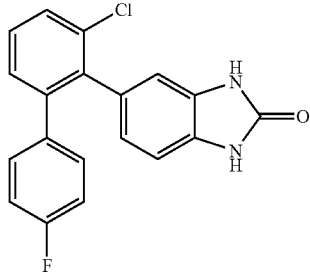 [SMILES: O=c1[nH]c2ccc(-c3c(Cl)cccc3-c3ccc(F)cc3)cc2[nH]1]

The title compound was prepared in a manner analogous to Example 160, substituting (4-fluorophenyl)boronic acid for cyclopropylboronic acid in Step B. MS (ESI): mass calcd. for C₁₉H₁₂ClFN₂O, 338.1; m/z found, 339.0 [M+H]⁺. ¹H NMR (400 MHz, DMSO-d₆) δ 10.55 (s, 2H), 7.57 (dd, J=8.0, 1.1 Hz, 1H), 7.44 (t, J=7.8 Hz, 1H), 7.35 (dd, J=7.7, 1.2 Hz, 1H), 7.13-7.04 (m, 2H), 7.03-6.95 (m, 2H), 6.79 (d, J=7.9 Hz, 1H), 6.65-6.53 (m, 2H).

Example 164: 4-[3-Chloro-2-(2-oxo-1,3-dihydrobenzimidazol-5-yl)phenyl]benzonitrile

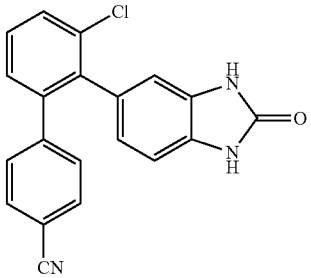 [SMILES: N#Cc1ccc(-c2cccc(Cl)c2-c2ccc3[nH]c(=O)[nH]c3c2)cc1]

The title compound was prepared in a manner analogous to Example 160, substituting (4-cyanophenyl)boronic acid for cyclopropylboronic acid in Step B. MS (ESI): mass calcd. for C₂₀H₁₂ClN₃O, 345.1; m/z found, 346.1 [M+H]⁺. ¹H NMR (400 MHz, DMSO-d₆) δ 10.61 (s, 1H), 10.55 (s, 1H), 7.70-7.61 (m, 3H), 7.49 (t, J=7.8 Hz, 1H), 7.39 (dd, J=7.7, 1.3 Hz, 1H), 7.31-7.22 (m, 2H), 6.82-6.77 (m, 1H), 6.69-6.64 (m, 1H), 6.59 (dd, J=8.0, 1.6 Hz, 1H).

Example 165: 5-[2-Chloro-6-(3-pyridyl)phenyl]-1,3-dihydrobenzimidazol-2-one

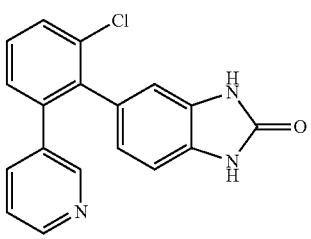 [SMILES: O=c1[nH]c2ccc(-c3c(Cl)cccc3-c3cccnc3)cc2[nH]1]

The title compound was prepared in a manner analogous to Example 160, substituting pyridin-3-ylboronic acid for cyclopropylboronic acid in Step B. MS (ESI): mass calcd. for C₁₈H₁₂ClN₃O, 321.1; m/z found, 321.7 [M+H]⁺. ¹H NMR (400 MHz, DMSO-d₆) δ 10.62 (s, 1H), 10.55 (s, 1H), 8.34 (dd, J=4.8, 1.6 Hz, 1H), 8.27 (dd, J=2.3, 0.9 Hz, 1H), 7.63 (dd, J=8.0, 1.3 Hz, 1H), 7.53-7.45 (m, 2H), 7.44-7.38 (m, 1H), 7.22 (ddd, J=7.9, 4.8, 0.9 Hz, 1H), 6.80 (d, J=7.9 Hz, 1H), 6.69-6.58 (m, 2H).

Example 166: 5-[2-Chloro-6-(5-fluoro-3-pyridyl)phenyl]-1,3-dihydrobenzimidazol-2-one

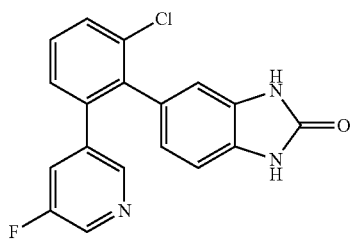 [SMILES: O=c1[nH]c2ccc(-c3c(Cl)cccc3-c3cncc(F)c3)cc2[nH]1]

The title compound was prepared in a manner analogous to Example 160, substituting (5-fluoropyridin-3-yl)boronic acid for cyclopropylboronic acid in Step B. MS (ESI): mass calcd. for C₁₈H₁₁ClFN₃O, 339.1; m/z found, 340.1 [M+H]⁺. ¹H NMR (400 MHz, DMSO-d₆) δ 10.64 (s, 1H), 10.57 (s, 1H), 8.36 (d, J=2.7 Hz, 1H), 8.11 (t, J=1.8 Hz, 1H), 7.66 (dd, J=7.8, 1.5 Hz, 1H), 7.55-7.43 (m, 3H), 6.82 (d, J=7.9 Hz, 1H), 6.72-6.58 (m, 2H).

Example 167: 5-[2-Chloro-6-(6-fluoro-3-pyridyl)phenyl]-1,3-dihydrobenzimidazol-2-one

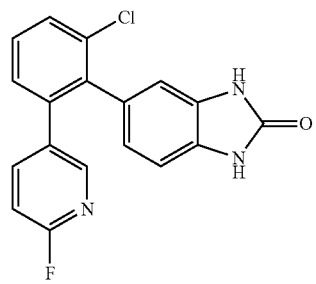 [SMILES: O=c1[nH]c2ccc(-c3c(Cl)cccc3-c3ccc(F)nc3)cc2[nH]1]

The title compound was prepared in a manner analogous to Example 160, substituting 2-fluoro-5-(4,4,5,5-tetramethyl-1,3,2-dioxaborolan-2-yl)pyridine for cyclopropylboronic acid in Step B. MS (ESI): mass calcd. for C₁₈H₁₁ClFN₃O, 339.1; m/z found, 340.1 [M+H]⁺. ¹H NMR (400 MHz, CD₃OD) δ 7.92 (dt, J=2.6, 0.8 Hz, 1H), 7.65-7.56 (m, 2H), 7.48-7.35 (m, 2H), 6.95 (dd, J=8.0, 0.6 Hz, 1H), 6.86 (ddd, J=8.5, 2.5, 0.7 Hz, 1H), 6.81-6.70 (m, 2H).

Example 168: 5-[2-Chloro-6-(5-methoxy-3-pyridyl)phenyl]-1,3-dihydrobenzimidazol-2-one

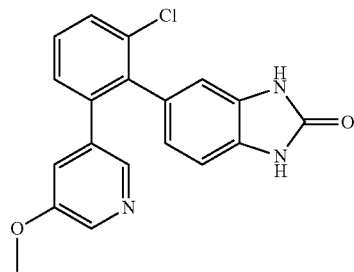 [SMILES: COc1cncc(-c2cccc(Cl)c2-c2ccc3[nH]c(=O)[nH]c3c2)c1]

The title compound was prepared in a manner analogous to Example 160, substituting (5-methoxypyridin-3-yl)boronic acid for cyclopropylboronic acid in Step B. MS (ESI): mass calcd. for C₁₉H₁₄ClN₃O₂, 351.1; m/z found, 352.1 [M+H]⁺. ¹H NMR (400 MHz, CD₃OD) δ 7.98 (d, J=2.8 Hz, 1H), 7.84 (d, J=1.8 Hz, 1H), 7.59 (dd, J=7.7, 1.6 Hz, 1H), 7.50-7.37 (m, 2H), 7.09 (dd, J=2.8, 1.7 Hz, 1H), 6.95 (dd, J=8.0, 0.7 Hz, 1H), 6.81-6.74 (m, 2H), 3.66 (s, 3H).

Example 169: 5-[2-Chloro-6-[5-(trifluoromethyl)-3-pyridyl]phenyl]-1,3-dihydrobenzimidazol-2-one

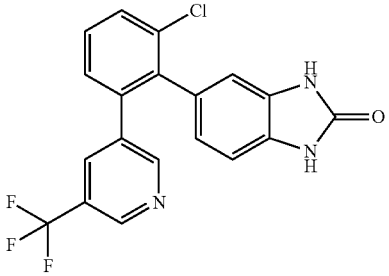 [SMILES: O=c1[nH]c2ccc(-c3c(Cl)cccc3-c3cncc(C(F)(F)F)c3)cc2[nH]1]

The title compound was prepared in a manner analogous to Example 160, substituting (5-(trifluoromethyl)pyridin-3-yl)boronic acid for cyclopropylboronic acid in Step B. MS (ESI): mass calcd. for $C_{19}H_{11}ClF_3N_3O$, 389.1; m/z found, 390.1 [M+H]$^+$. $^1$H NMR (400 MHz, DMSO-d$_6$) δ 10.61 (s, 1H), 10.56 (s, 1H), 8.75 (dd, J=2.2, 1.0 Hz, 1H), 8.59 (d, J=2.0 Hz, 1H), 7.86-7.76 (m, 1H), 7.72-7.65 (m, 1H), 7.57-7.51 (m, 2H), 6.81 (dd, J=8.0, 0.6 Hz, 1H), 6.70 (dd, J=1.7, 0.6 Hz, 1H), 6.63 (dd, J=8.0, 1.6 Hz, 1H).

Example 170: 5-[2-Chloro-6-(4-pyridyl)phenyl]-1,3-dihydrobenzimidazol-2-one

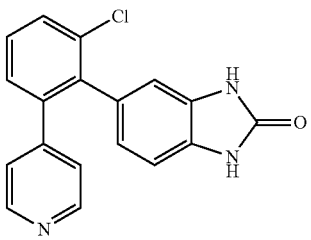 [SMILES: O=c1[nH]c2ccc(-c3c(Cl)cccc3-c3ccncc3)cc2[nH]1]

The title compound was prepared in a manner analogous to Example 160, substituting pyridin-4-ylboronic acid for cyclopropylboronic acid in Step B. MS (ESI): mass calcd. for $C_{18}H_{12}ClN_3O$, 321.1; m/z found, 322.1 [M+H]$^+$. $^1$H NMR (400 MHz, DMSO-d$_6$) δ 10.64 (s, 1H), 10.57 (s, 1H), 8.37 (dd, J=4.5, 1.7 Hz, 2H), 7.65 (dd, J=8.1, 1.3 Hz, 1H), 7.50 (t, J=7.8 Hz, 1H), 7.41 (dd, J=7.7, 1.3 Hz, 1H), 7.07 (dd, J=4.4, 1.7 Hz, 2H), 6.81 (d, J=7.9 Hz, 1H), 6.68-6.59 (m, 2H).

Example 171: 5-[2-Chloro-6-(3-methoxy-4-pyridyl)phenyl]-1,3-dihydrobenzimidazol-2-one

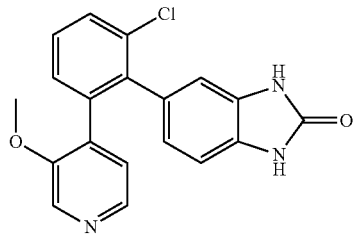 [SMILES: COc1cnccc1-c1cccc(Cl)c1-c1ccc2[nH]c(=O)[nH]c2c1]

The title compound was prepared analogous to Example 160, substituting 3-methoxy-4-(4,4,5,5-tetramethyl-1,3,2-dioxaborolan-2-yl)pyridine for cyclopropylboronic acid in Step B. MS (ESI): mass calcd. for $C_{19}H_{14}ClN_3O_2$, 351.1; m/z found, 352.1 [M+H]$^+$. $^1$H NMR (400 MHz, DMSO-d$_6$) δ 10.56 (s, 1H), 10.51 (s, 1H), 8.17 (s, 1H), 8.04 (d, J=4.7 Hz, 1H), 7.60 (dd, J=8.1, 1.2 Hz, 1H), 7.44 (t, J=7.8 Hz, 1H), 7.26 (dd, J=7.6, 1.2 Hz, 1H), 7.01 (d, J=4.7 Hz, 1H), 6.74 (d, J=7.9 Hz, 1H), 6.66-6.55 (m, 2H), 3.64 (s, 3H).

Example 172: 5-[2-Chloro-6-[1-(2-methoxyethyl)pyrazol-4-yl]phenyl]-1,3-dihydrobenzimidazol-2-one

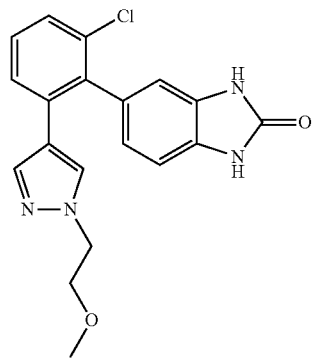 [SMILES: COCCn1cc(-c2cccc(Cl)c2-c2ccc3[nH]c(=O)[nH]c3c2)cn1]

The title compound was prepared in a manner analogous to Example 160, substituting 1-(2-methoxyethyl)-4-(4,4,5,5-tetramethyl-1,3,2-dioxaborolan-2-yl)-1H-pyrazole for cyclopropylboronic acid in Step B. MS (ESI): mass calcd. for $C_{19}H_{17}ClN_4O_2$, 368.1; m/z found, 369.1 [M+H]$^+$. $^1$H NMR (400 MHz, DMSO-d$_6$) δ 10.72 (s, 1H), 10.61 (s, 1H), 7.57 (dd, J=7.5, 1.6 Hz, 1H), 7.46-7.32 (m, 2H), 7.09-6.95 (m, 3H), 6.75-6.60 (m, 2H), 4.05 (t, J=5.1 Hz, 2H), 3.49 (dd, J=5.6, 4.7 Hz, 2H), 3.09 (s, 3H).

Example 173: 5-[2-Chloro-6-(1-methylpyrazol-4-yl)phenyl]-1,3-dihydrobenzimidazol-2-one

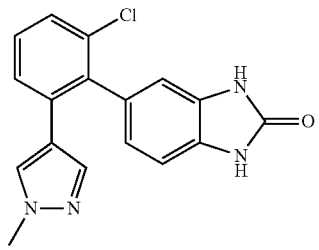 [SMILES: Cn1cc(-c2cccc(Cl)c2-c2ccc3[nH]c(=O)[nH]c3c2)cn1]

The title compound was prepared in a manner analogous to Example 160, substituting 1-methyl-4-(4,4,5,5-tetramethyl-1,3,2-dioxaborolan-2-yl)-1H-pyrazole for cyclopropylboronic acid in Step B. MS (ESI): mass calcd. for $C_{17}H_{13}ClN_4O$, 324.1; m/z found, 325.1 [M+H]$^+$. $^1$H NMR (400 MHz, DMSO-d$_6$) δ 10.73 (s, 1H), 10.62 (s, 1H), 7.53 (dd, J=7.5, 1.5 Hz, 1H), 7.47-7.27 (m, 3H), 6.98 (d, J=7.9 Hz, 1H), 6.79-6.60 (m, 3H), 3.67 (s, 3H).

Example 174: 5-[2-Chloro-6-(3,5-dimethylisoxazol-4-yl)phenyl]-1,3-dihydrobenzimidazol-2-one

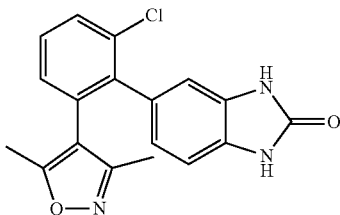 [SMILES: Cc1noc(C)c1-c1cccc(Cl)c1-c1ccc2[nH]c(=O)[nH]c2c1]

The title compound was prepared in a manner analogous to Example 160, substituting (3,5-dimethylisoxazol-4-yl)boronic acid for cyclopropylboronic acid in Step B. MS (ESI): mass calcd. for $C_{18}H_{14}ClN_3O_2$, 339.1; m/z found, 340.1 [M+H]. $^1$H NMR (400 MHz, DMSO-$d_6$) δ 10.64 (s, 1H), 10.54 (s, 1H), 7.64 (dd, J=8.1, 1.3 Hz, 1H), 7.46 (t, J=7.9 Hz, 1H), 7.31 (dd, J=7.6, 1.3 Hz, 1H), 6.92-6.82 (m, 1H), 6.72-6.61 (m, 2H), 2.03 (s, 3H), 1.84 (s, 3H).

Example 175: 5-[2-Chloro-6-(2-isopropylpyrazol-3-yl)phenyl]-1,3-dihydrobenzimidazol-2-one

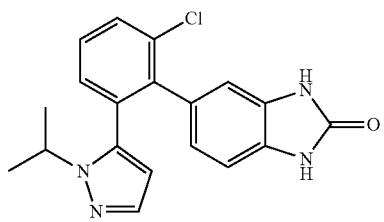 [SMILES: CC(C)n1nccc1-c1cccc(Cl)c1-c1ccc2[nH]c(=O)[nH]c2c1]

The title compound was prepared in a manner analogous to Example 160, substituting (1-isopropyl-5-(4,4,5,5-tetramethyl-1,3,2-dioxaborolan-2-yl)-1H-pyrazole for cyclopropylboronic acid in Step B. MS (ESI): mass calcd. for $C_{19}H_{17}ClN_4O$, 352.1; m/z found, 353.1 [M+H]$^+$. $^1$H NMR (400 MHz, CD$_3$OD) δ 7.64 (dd, J=8.1, 1.3 Hz, 1H), 7.44 (t, J=7.9 Hz, 1H), 7.37-7.29 (m, 2H), 6.94 (d, J=8.1 Hz, 1H), 6.82 (s, 2H), 6.09 (d, J=1.9 Hz, 1H), 4.18-4.07 (m, 1H), 1.19-1.05 (m, 6H).

Example 176 5-[2-Chloro-6-(1H-pyrazol-4-yl)phenyl]-1,3-dihydrobenzimidazol-2-one

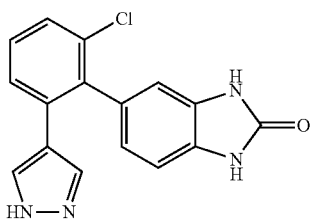 [SMILES: O=c1[nH]c2ccc(-c3c(Cl)cccc3-c3cn[nH]c3)cc2[nH]1]

The title compound was prepared in a manner analogous to Example 160, substituting tert-butyl4-(4,4,5,5-tetramethyl-1,3,2-dioxaborolan-2-yl)-1H-pyrazole-1-carboxylate for cyclopropylboronic acid in Step B. MS (ESI): mass calcd. for $C_{16}H_{11}ClN_4O$, 310.1; m/z found, 311.7 [M+H]$^+$.

$^1$H NMR (400 MHz, DMSO-$d_6$) δ 12.44 (s 1H), 10.73 (s, 1H), 10.62 (s, 1H), 7.60 (dd, J=7.5, 1.6 Hz, 1H), 7.46-7.30 (m, 2H), 7.17-6.94 (m, 3H), 6.74-6.63 (m, 2H).

Example 177: 5-[2-Chloro-6-(1,5-dimethylpyrazol-4-yl)phenyl]-1,3-dihydrobenzimidazol-2-one

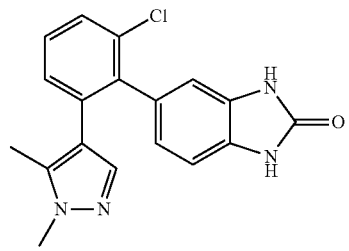 [SMILES: Cc1c(-c2cccc(Cl)c2-c2ccc3[nH]c(=O)[nH]c3c2)cnn1C]

The title compound was prepared in a manner analogous to Example 160, substituting 1,5-dimethyl-4-(4,4,5,5-tetramethyl-1,3,2-dioxaborolan-2-yl)-1H-pyrazole for cyclopropylboronic acid in Step B. MS (ESI): mass calcd. for $C_{18}H_{15}ClN_4O$, 338.1; m/z found, 339.1 [M+H]$^+$. $^1$H NMR (400 MHz, CD$_3$OD) δ 7.46 (dd, J=8.0, 1.3 Hz, 1H), 7.35 (t, J=7.8 Hz, 1H), 7.23 (dd, J=7.6, 1.3 Hz, 1H), 6.99-6.93 (m, 1H), 6.84 (s, 1H), 6.81-6.73 (m, 2H), 3.65 (s, 3H), 2.06 (s, 3H).

Example 178: 5-(2-Chloro-6-pyrimidin-5-yl-phenyl)-1,3-dihydrobenzimidazol-2-one

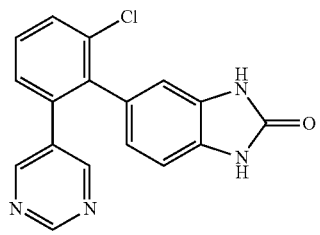 [SMILES: O=c1[nH]c2ccc(-c3c(Cl)cccc3-c3cncnc3)cc2[nH]1]

The title compound was prepared analogous to Example 160, substituting pyrimidin-5-ylboronic acid for (4-fluorophenyl)boronic acid in Step B. MS (ESI): mass calcd. for $C_{17}H_{11}ClN_4O$, 322.1; m/z found, 323.1 [M+H]$^+$. $^1$H NMR (400 MHz, CD$_3$OD) 8.91 (s, 1H), 8.52 (s, 1H), 7.66 (s, 1H), 7.55-7.46 (m, 2H), 6.96 (d, J=10.4 Hz, 1H), 6.81 (s, 3H).

Example 179: 5-(2-Methyl-6-phenyl-phenyl)-1,3-dihydrobenzimidazol-2-one

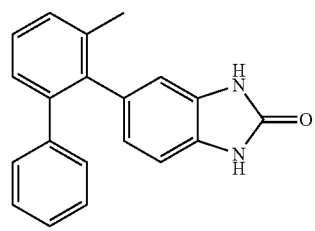 [SMILES: Cc1cccc(-c2ccccc2)c1-c1ccc2[nH]c(=O)[nH]c2c1]

Step A: 5-(2-Bromo-6-methyl-phenyl)-1,3-dihydrobenzimidazol-2-one

To a solution of 5-(4,4,5,5-tetramethyl-1,3,2-dioxaborolan-2-yl)-1H-benzo[d]imidazol-2(3H)-one (Intermediate 28, 250 mg, 0.96 mmol), potassium phosphate (408 mg, 1.9 mmol), and 1-bromo-2-iodo3-methylbenzene (342 mg, 1.1 mmol) in 4:1 dioxane:water (6.6 mL) was added PdCl$_2$(dppf)-CH$_2$Cl$_2$ (35 mg, 0.05 mmol) at once. The mixture was degassed with nitrogen for 10 minutes and then heated at 100° C. for 16 h. After cooling to rt, the reaction mixture was diluted with water and extracted with DCM (×3). The combined organic extracts were dried (Na$_2$SO$_4$), filtered and concentrated under reduced pressure. The crude product was purified by flash column chromatography (SiO$_2$; 0-5% DCM/MeOH) to provide the title compound as a white solid (98 mg, 34% yield). MS (ESI): mass calcd. for C$_{14}$H$_{11}$BrN$_2$O, 302.0; m/z found, 303.1 [M+H]$^+$. $^1$H NMR (400 MHz, DMSO-d$_6$) δ 10.69 (s, 1H), 10.65 (s, 1H), 7.53 (dt, J=8.0, 0.9 Hz, 1H), 7.30 (dt, J=7.5, 1.1 Hz, 1H), 7.23-7.12 (m, 1H), 6.99 (d, J=7.9 Hz, 1H), 6.73-6.61 (m, 2H), 2.04 (s, 3H).

Step B: 5-(2-Methyl-6-phenyl-phenyl)-1,3-dihydrobenzimidazol-2-one

To a solution of phenylboronic acid (18 mg, 0.15 mmol), potassium phosphate (42 mg, 0.2 mmol), and 5-(2-Bromo-6-methyl-phenyl)-1,3-dihydrobenzimidazol-2-one (30 mg, 0.10 mmol) in 4:1 dioxane:water (1.0 mL) was added PdCl$_2$(dtbpf) (6.5 mg, 0.01 mmol) at once. The mixture was degassed with nitrogen for 10 minutes and then heated at 100° C. for 19 h. After cooling to rt, the reaction mixture was diluted with water and extracted with DCM (×3). The combined organic extracts were dried over Na$_2$SO$_4$ and concentrated to remove solvent. The crude product was triturated with DCM to provide the title compound as a white solid (12 mg, 41% yield). MS (ESI): mass calcd. for C$_{20}$H$_{16}$N$_2$O, 300.1; m/z found, 301.1 [M+H]. $^1$H NMR (400 MHz, DMSO-d$_6$) δ 10.52 (d, J=1.9 Hz, 1H), 10.44 (s, 1H), 7.34-7.25 (m, 2H), 7.24-7.09 (m, 4H), 7.09-6.99 (m, 2H), 6.79 (d, J=7.9 Hz, 1H), 6.60 (dd, J=7.9, 1.6 Hz, 1H), 6.52 (d, J=1.4 Hz, 1H), 2.09 (s, 3H).

Example 180: 5-[2-(2-Fluorophenyl)-6-methyl-phenyl]-1,3-dihydrobenzimidazol-2-one

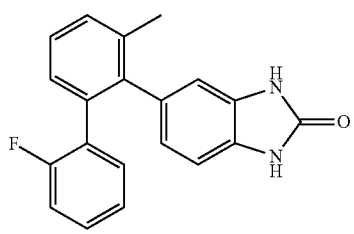 [SMILES: Cc1cccc(-c2ccccc2F)c1-c1ccc2[nH]c(=O)[nH]c2c1]

The title compound was prepared in a manner analogous to Example 179, substituting (2-fluorophenyl)boronic acid for phenylboronic acid in Step B. MS (ESI): mass calcd. for C$_{20}$H$_{15}$FN$_2$O, 318.1; m/z found, 319.1 [M+H]$^+$. $^1$H NMR (400 MHz, DMSO-d$_6$) δ 10.51 (s, 1H), 10.45 (s, 1H), 7.40-7.27 (m, 2H), 7.23-7.12 (m, 2H), 7.11-6.95 (m, 3H), 6.75 (d, J=7.8 Hz, 1H), 6.62-6.51 (m, 2H), 2.09 (s, 3H).

Example 181: 5-[2-(4-Fluorophenyl)-6-methyl-phenyl]-1,3-dihydrobenzimidazol-2-one

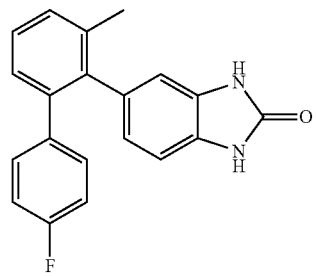 [SMILES: Cc1cccc(-c2ccc(F)cc2)c1-c1ccc2[nH]c(=O)[nH]c2c1]

The title compound was prepared in a manner analogous to Example 179, substituting (4-fluorophenyl)boronic acid for phenylboronic acid in Step B. MS (ESI): mass calcd. for C$_{20}$H$_{15}$FN$_2$O, 318.1; m/z found, 319.1 $^1$H NMR (400 MHz, CD$_3$OD) δ 7.35-7.29 (m, 2H), 7.23-7.18 (m, 1H), 7.11-7.03 (m, 2H), 6.96 (d, J=8.4 Hz, 1H), 6.89-6.81 (m, 2H), 6.76-6.67 (m, 2H), 2.15 (s, 3H).

Example 182: 5-[2-Methoxy-6-(8-quinolyl)phenyl]-1,3-dihydrobenzimidazol-2-one

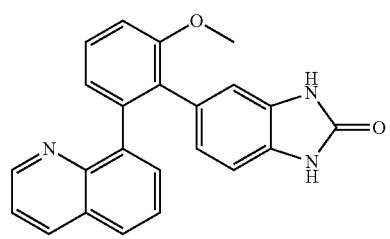 [SMILES: COc1cccc(-c2cccc3cccnc23)c1-c1ccc2[nH]c(=O)[nH]c2c1]

The title compound was prepared in a manner analogous to Example 179, substituting 1-bromo-2-iodo-3-methoxybenzene for 1-bromo-2-iodo-3-methylbenzene in Step A and 8-(4,4,5,5-tetramethyl-1,3,2-dioxaborolan-2-yl) quinolone for phenylboronic acid in Step B. MS (ESI): mass calcd. for C$_{23}$H$_{17}$N$_3$O$_2$, 367.1; m/z found, 368.1 [M+H]$^+$. $^1$H NMR (500 MHz, DMSO-d$_6$) δ 10.28 (s, 2H), 8.83-8.73 (m, 1H), 8.25 (m, J=8.2, 3.5, 1.7 Hz, 1H), 7.95 (d, J=3.3 Hz, 1H), 7.81-7.71 (m, 1H), 7.50-7.26 (m, 4H), 7.15-7.07 (m, 1H), 6.94-6.84 (m, 1H), 6.45 (s, 2H), 3.77-3.67 (m, 3H).

Example 183: 5-[2-Chloro-3-(1-methylpyrazol-3-yl)phenyl]-1,3-dihydrobenzimidazol-2-one

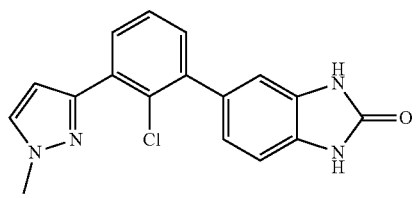 [SMILES: Cn1ccc(-c2cccc(-c3ccc4[nH]c(=O)[nH]c4c3)c2Cl)n1]

Step A: 5-(3-Bromo-2-chloro-phenyl)-1,3-dihydrobenzimidazol-2-one

To a solution of 5-(4,4,5,5-tetramethyl-1,3,2-dioxaborolan-2-yl)-1H-benzo[d]imidazol-2(3H)-one (Intermediate 28, 2.0 g, 7.7 mmol), potassium phosphate (3.3 g, 15 mmol), and 1,3-dibromo-2-chlorobenzene (2.1 g, 7.7 mmol) in 4:1 dioxane:water (20 mL) was added PdCl$_2$(dppf)-CH$_2$Cl$_2$ (563 mg, 0.77 mmol) at once. The mixture was degassed with nitrogen for 10 minutes and then heated at 100° C. for 16 h. After cooling to rt, the reaction mixture was diluted with water and extracted with DCM (×3). The combined organic extracts were dried (Na$_2$SO$_4$), filtered and concentrated under reduced pressure. The crude product was triturated with DCM to provide the title compound as a white solid (1.7 g, 65% yield). MS (ESI): mass calcd. for C$_{13}$H$_8$BrClN$_2$O, 322.0; m/z found, 322.9 [M+H]$^+$. $^1$H NMR (500 MHz, DMSO-d$_6$) δ 10.72 (s, 1H), 10.70 (s, 1H), 7.76 (dd, J=7.9, 1.6 Hz, 1H), 7.46-7.26 (m, 2H), 7.06-6.89 (m, 3H).

Step B: 5-[2-Chloro-3-(1-methylpyrazol-3-yl)phenyl]-1,3-dihydrobenzimidazol-2-one To a solution of 1-methyl-3-(4,4,5,5-tetramethyl-1,3,2-dioxaborolan-2-yl)-1H-pyrazole (48 mg, 0.23 mmol), potassium phosphate (66 mg, 0.31 mmol), and 5-(3-bromo-2-chloro-phenyl)-1,3-dihydrobenzimidazol-2-one (50 mg, 0.15 mmol) in 4:1 dioxane:water (2.0 mL) was added PdCl$_2$(dppf)-CH$_2$Cl$_2$ (11 mg, 0.02 mmol) at once. The mixture was degassed with nitrogen for 10 minutes and then heated in a microwave at 130° C. for 40 minutes. After cooling to rt, the reaction mixture was diluted with water and extracted with DCM (×3). The crude product was purified by flash column chromatography (SiO$_2$; 0-10% DCM/MeOH) to afford the title compound (26 mg, 52% yield). MS (ESI): mass calcd. for C$_{17}$H$_{13}$ClN$_4$O, 324.1; m/z found, 325.1 [M+H]. $^1$H NMR (500 MHz, DMSO-d$_6$): δ 10.73 (s, 1H), 10.70 (s, 1H), 7.56-7.39 (m, 4H), 7.05-6.97 (m, 3H), 6.41-6.28 (m, 1H), 3.68 (s, 3H).

Example 184: 5-[2-Chloro-3-(4-pyridyl)phenyl]-1,3-dihydrobenzimidazol-2-one

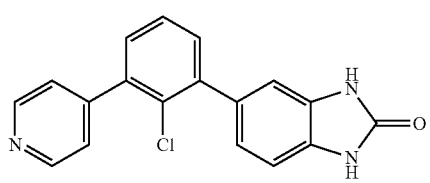 [SMILES: O=c1[nH]c2ccc(-c3cccc(-c4ccncc4)c3Cl)cc2[nH]1]

The title compound was prepared in a manner analogous to Example 183, substituting 4-pyridylboronic acid for 1-methyl-3-(4,4,5,5-tetramethyl-1,3,2-dioxaborolan-2-yl)-1H-pyrazole and sodium carbonate for potassium phosphate in Step B. MS (ESI): mass calcd. for C$_{18}$H$_{12}$ClN$_3$O, 321.1; m/z found, 322.0 [M+H]$^+$. $^1$H NMR (400 MHz, DMSO-d$_6$): δ 10.82-10.65 (m, 2H), 8.78-8.60 (m, 2H), 7.60-7.32 (m, 5H), 7.05-6.95 (m, 3H).

Example 185: 5-[2-Chloro-3-(1-methylpyrazol-4-yl)phenyl]-1,3-dihydrobenzimidazol-2-one

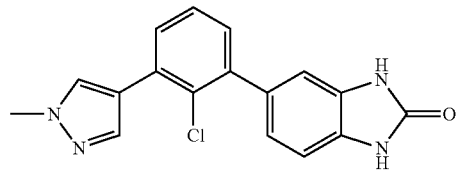 [SMILES: Cn1cc(-c2cccc(-c3ccc4[nH]c(=O)[nH]c4c3)c2Cl)cn1]

The title compound was prepared in a manner analogous to Example 183, substituting 1-methyl-4-(4,4,5,5-tetramethyl-1,3,2-dioxaborolan-2-yl)-1H-pyrazole for 1-methyl-3-(4,4,5,5-tetramethyl-1,3,2-dioxaborolan-2-yl)-1H-pyrazole and sodium carbonate for potassium phosphate in Step B. MS (ESI): mass calcd. for C$_{17}$H$_{13}$ClN$_4$O, 324.1; m/z found, 325.1 [M+H]$^+$. $^1$H NMR (400 MHz, DMSO-d$_6$) δ 10.76-10.72 (m, 2H), 8.14 (s, 1H), 7.80 (s, 1H), 7.51 (d, J=8.0 Hz, 1H), 7.37 (t, J=7.3 Hz, 1H), 7.23 (d, J=5.5 Hz, 1H), 7.02-6.97 (m, 1H), 6.95 (d, J=3.3 Hz, 2H), 3.89 (s, 3H).

Example 186: tert-Butyl 5-[2-chloro-3-(2-oxo-1,3-dihydrobenzimidazol-5-yl)phenyl]-3,6-dihydro-2H-pyridine-1-carboxylate

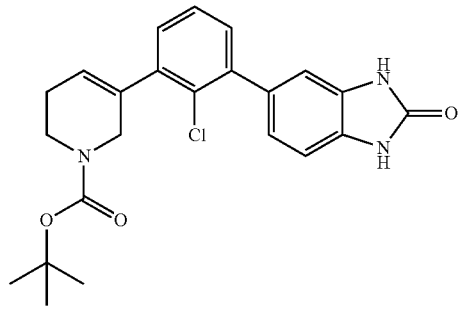 [SMILES: CC(C)(C)OC(=O)N1CCC=C(c2cccc(-c3ccc4[nH]c(=O)[nH]c4c3)c2Cl)C1]

The title compound was prepared in a manner analogous to Example 183, substituting tert-butyl 3-(4,4,5,5-tetramethyl-1,3,2-dioxaborolan-2-yl)-5,6-dihydropyridine-1(2H)-carboxylate for 1-methyl-3-(4,4,5,5-tetramethyl-1,3,2-dioxaborolan-2-yl)-1H-pyrazole and potassium carbonate for potassium phosphate in Step B. MS (ESI): mass calcd. for C$_{23}$H$_{24}$ClN$_3$O$_3$, 425.1; m/z found, 426.0 [M+H]$^+$. $^1$H NMR (500 MHz, DMSO-d$_6$) δ 10.71 (s, 1H), 10.68 (s, 1H), 7.37 (t, J=7.5 Hz, 1H), 7.32 (dd, J=7.7, 1.9 Hz, 1H), 7.25 (dd, J=7.4, 1.9 Hz, 1H), 7.03-6.90 (m, 3H), 5.81 (dd, J=3.8, 1.9 Hz, 1H), 4.09-4.04 (m, 2H), 3.52-3.46 (m, 2H), 2.27-2.21 (m, 2H), 1.41 (s, 9H).

Example 187: 5-(2-Chloro-3-imidazol-1-yl-phenyl)-1,3-dihydrobenzimidazol-2-one

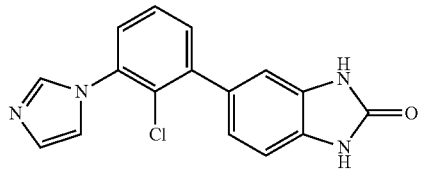 [SMILES: O=c1[nH]c2ccc(-c3cccc(-n4ccnc4)c3Cl)cc2[nH]1]

DMSO (4 mL) was added to a flask containing 5-[3-bromo-2-chlorophenyl]1,3-dihydrobenzimidazol-2-one (200 mg, 0.46 mmol), imidazole (158 mg, 2.3 mmol), cesium carbonate (454 mg, 1.4 mmol) and copper (I) iodide (18 mg, 0.09 mmol). The solution was degassed with nitrogen and heated at 135° C. for 16 h. After cooling to rt, the reaction was diluted with water (5 mL) and extracted with EtOAc (3×5 mL). The combined organic extracts were dried (Na$_2$SO$_4$), filtered and concentrated under reduced pressure. The residue was purified by reverse-phase HPLC (0.05% NH$_3$/ACN; Phenomenex Gemini 150×25 mm×5 µm; 55% ACN) to provide the product the title compound (19 mg, 13% yield). MS (ESI): mass calcd. for C$_{16}$H$_{11}$ClN$_4$O, 310.1; m/z found, 311.1 [M+H]$^+$. $^1$H NMR (400 MHz, DMSO-d$_6$): δ 10.74-10.70 (m, 2H), 7.90 (s, 1H), 7.56-7.46 (m, 3H), 7.45 (s, 1H), 7.07 (s, 1H), 7.04-6.92 (m, 3H).

Example 188: 5-[2-Chloro-3-(1-piperidyl)phenyl]-1,3-dihydrobenzimidazol-2-one

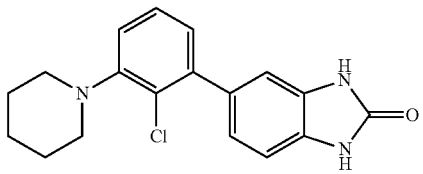 [SMILES: O=c1[nH]c2ccc(-c3cccc(N4CCCCC4)c3Cl)cc2[nH]1]

Step A: 1-(3-Bromo-2-chlorophenyl)piperidine

A mixture of 3-bromo-2-chloroaniline (300 mg, 1.1 mmol), 1,5-dibromopentane (483 mg, 2.1 mmol), potassium carbonate (159 mg, 1.2 mmol), and sodium iodide (16 mg, 0.11 mmol) in DMF (5 mL) was heated at 140° C. in a microwave oven for 60 minutes. After cooling to rt, the reaction mixture was diluted with water (5 mL) and extracted with EtOAc (3×5 mL). The combined organic extracts were dried (Na$_2$SO$_4$), filtered and concentrated to give crude product, which was purified by FCC (SiO$_2$; 0-40% EtOAc/petroleum ether) to provide the desired product (250 mg, 76% yield). MS (ESI): mass calcd. for C$_{11}$H$_{13}$BrClN, 273.0; m/z found, 273.7 [M+H]$^+$.

Step B: 5-[2-Chloro-3-(1-piperidyl)phenyl]-1,3-dihydrobenzimidazol-2-one

The title compound was prepared in a manner analogous to Example 2, substituting 1-(3-bromo-2-chlorophenyl)piperidine for 2,6-dimethyliodobenzene and heating to 80° C. instead of 100° C. The crude product was purified by reverse-phase HPLC (Phenomenex Gemini 150×25 mm×10 um; 41%-71% ACN (w/0.05% NH$_3$)) to provide the title compound (30 mg, 18% yield). MS (ESI): mass calcd. for C$_{18}$H$_{18}$ClN$_3$O, 327.1; m/z found, 327.9 [M+H]$^+$. $^1$H NMR (400 MHz, DMSO-d$_6$): δ 10.67 (br s, 2H), 7.37-7.27 (m, 1H), 7.12 (br s, 1H), 7.03-6.82 (m, 4H), 2.93 (br s, 4H), 1.75-1.44 (m, 6H).

Example 189: 5-[2-Chloro-3-(dimethylamino)phenyl]-1,3-dihydrobenzimidazol-2-one

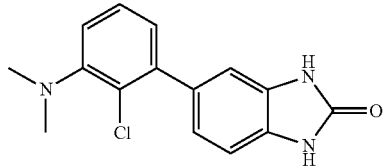 [SMILES: CN(C)c1cccc(-c2ccc3[nH]c(=O)[nH]c3c2)c1Cl]

The title compound was prepared in a manner analogous to Example 2, substituting 3-bromo-2-chloro-N,N-dimethylaniline (Intermediate 27) for 2,6-dimethyliodobenzene and heating to 80° C. instead of 100° C. MS (ESI): mass calcd. for C$_{18}$H$_{18}$ClN$_3$O, 287.1; m/z found, 288.1 [M+H]$^+$. $^1$H NMR (400 MHz, DMSO-d$_6$) δ 10.67 (m, 2H), 7.33-7.26 (m, 1H), 7.16 (dd, J=8.0, 1.5 Hz, 1H), 7.02-6.95 (m, 2H), 6.94-6.89 (m, 2H), 2.74 (s, 6H).

Example 190: 5-[2-Chloro-3-(1,3,4-oxadiazol-2-yl)phenyl]-1,3-dihydrobenzimidazol-2-one

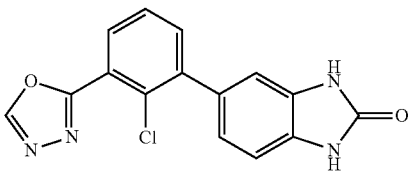 [SMILES: O=c1[nH]c2ccc(-c3cccc(-c4nnco4)c3Cl)cc2[nH]1]

Step A: 3-Bromo-2-chlorobenzohydrazide

To a suspension of methyl 3-bromo-2-chlorobenzoate (1.4 g, 5.5 mmol) in EtOH (5.5 mL) was added hydrazine monohydrate (2.2 mL, 45 mmol) at once. The resulting slurry was heated to 80° C. and stirred for 2 h. After cooling to 23° C., water was added. The resulting white precipitate was filtered and washed with EtOH to provide (1.4 g, 78% yield) of the desired product. MS (ESI): mass calcd. for C$_7$H$_6$BrClN$_2$O, 247.9; m/z found, 249.0 [M+H]$^+$. $^1$H NMR (400 MHz, DMSO-d$_6$) δ 9.63 (t, J=4.0 Hz, 1H), 7.83 (dd, J=7.9, 1.7 Hz, 1H), 7.42-7.25 (m, 2H), 4.51 (d, J=4.2 Hz, 2H).

Step B: 2-(3-Bromo-2-chlorophenyl)-1,3,4-oxadiazole

A solution of 3-bromo-2-chlorobenzohydrazide (250 mg, 0.97 mmol) in triethylorthoformate (3 mL) was heated at 145° C. for 4 h. The reaction was cooled to room temperature and the solvent was removed in vacuo. The residue was diluted with saturated aq. NaHCO$_3$ and extracted with DCM (×3). The combined organic extracts were dried (Na$_2$SO$_4$), filtered and concentrated to afford the desired product as a white solid (148 mg, 57% yield). MS (ESI): mass calcd. for C$_8$H$_4$BrClN$_2$O, 257.9; m/z found, 259.0 [M+H]$^+$. $^1$H NMR (400 MHz, DMSO-d$_6$) δ 9.50 (s, 1H), 8.07 (dd, J=8.1, 1.5 Hz, 1H), 7.99 (dd, J=7.8, 1.5 Hz, 1H), 7.52 (t, J=7.9 Hz, 1H).

Step C: 5-[2-Chloro-3-(1,3,4-oxadiazol-2-yl)phenyl]-1,3-dihydrobenzimidazol-2-one The title compound was prepared in a manner analogous to Example 2, substituting 2-(3-bromo-2-chlorophenyl)-1,3, 4-oxadiazole for 2,6-dimethyliodobenzene and PdCl$_2$(dppf)-CH$_2$Cl$_2$ for PdCl$_2$(dtbpf) in Step B. The crude product was purified by trituration with DCM to provide the title compound (16 mg, 13% yield). MS (ESI): mass calcd. for C$_{15}$H$_9$ClN$_4$O$_2$, 312.0; m/z found, 313.0 [M+H]$^+$. $^1$H NMR (500 MHz, DMSO-d$_6$) δ 10.76 (s, 1H), 10.73 (s, 1H), 9.48 (s, 1H), 7.80 (dd, J=7.6, 1.8 Hz, 1H), 7.69-7.64 (m, 1H), 7.64-7.58 (m, 1H), 7.07-6.94 (m, 3H).

Example 191: 5-[2-Chloro-3-(5-methyl-1,3,4-oxadiazol-2-yl)phenyl]-1,3-dihydrobenzimidazol-2-one

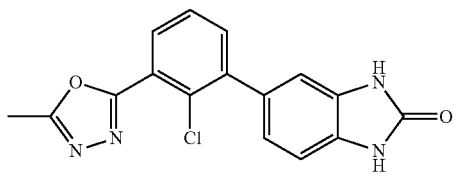 [SMILES: Cc1nnc(-c2cccc(-c3ccc4[nH]c(=O)[nH]c4c3)c2Cl)o1]

The title compound was prepared in a manner analogous to Example 190, substituting triethylorthoacetate for triethylorthoformate in Step B. MS (ESI): mass calcd. for C$_{16}$H$_{11}$ClN$_4$O$_2$, 326.1; m/z found, 327.1 [M+H]$^+$. $^1$H NMR (400 MHz, DMSO-d$_6$) δ 10.84-10.61 (m, 2H), 7.84 (dd, J=7.4, 2.0 Hz, 1H), 7.68-7.52 (m, 2H), 7.09-6.93 (m, 3H), 2.61 (s, 3H).

Example 192: 5-[2,6-Dichloro-3-(1,3,4-oxadiazol-2-yl)phenyl]-1,3-dihydrobenzimidazol-2-one

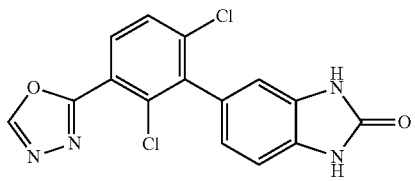 [SMILES: O=c1[nH]c2ccc(-c3c(Cl)ccc(-c4nnco4)c3Cl)cc2[nH]1]

The title compound was prepared in a manner analogous to Example 190, substituting methyl 3-bromo-2,4-dichlorobenzoate for methyl 3-bromo-2-chlorobenzoate in Step A and PdCl$_2$(dtbpf) for PdCl$_2$(dppf)-CH$_2$Cl$_2$ in Step C. MS (ESI): mass calcd. for C$_{15}$H$_8$Cl$_2$N$_4$O$_2$, 346.0; m/z found, 346.9 [M+H]$^+$. $^1$H NMR (500 MHz, CD$_3$OD) δ 9.14 (s, 1H), 8.04-7.87 (m, 1H), 7.72 (d, J=8.5 Hz, 1H), 7.27-7.11 (m, 1H), 7.04-6.84 (m, 2H).

Example 193: 5-[2-Bromo-3-(1,3,4-oxadiazol-2-yl)phenyl]-1,3-dihydrobenzimidazol-2-one

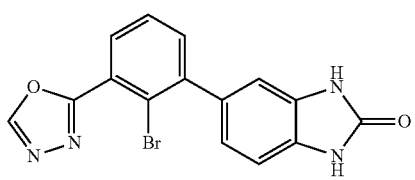 [SMILES: O=c1[nH]c2ccc(-c3cccc(-c4nnco4)c3Br)cc2[nH]1]

The title compound was prepared in a manner analogous to Example 190, substituting methyl 2-bromo-3-iodobenzoate for methyl 3-bromo-2-chlorobenzoate in Step A. MS (ESI): mass calcd. for C$_{15}$H$_9$BrN$_4$O$_2$, 356.0; m/z found, 356.9 [M+H]$^+$. $^1$H NMR (500 MHz, DMSO-d$_6$) δ 10.80-10.69 (m, 2H), 9.45 (s, 1H), 7.78 (dd, J=6.2, 3.1 Hz, 1H), 7.69-7.57 (m, 2H), 7.07-6.97 (m, 1H), 6.97-6.90 (m, 2H).

Example 194: 5-[2-Methyl-3-(1,3,4-oxadiazol-2-yl)phenyl]-1,3-dihydrobenzimidazol-2-one

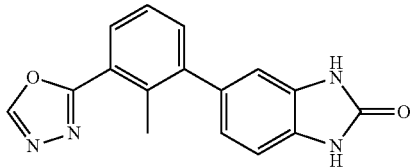 [SMILES: Cc1c(-c2ccc3[nH]c(=O)[nH]c3c2)cccc1-c1nnco1]

The title compound was prepared in a manner analogous to Example 190, substituting methyl 3-bromo-2-methylbenzoate for methyl 3-bromo-2-chlorobenzoate in Step A. MS (ESI): mass calcd. for C$_{16}$H$_{12}$N$_4$O$_2$, 292.1; m/z found, 293.0 [M+H]$^+$. $^1$H NMR (500 MHz, DMSO-d$_6$) δ 10.72 (s, 1H), 10.70 (s, 2H), 9.39 (s, 1H), 7.85 (dd, J=5.2, 4.0 Hz, 1H), 7.51-7.40 (m, 2H), 7.02 (d, J=7.9 Hz, 1H), 6.97-6.82 (m, 2H), 2.45 (s, 3H).

Example 195: 5-[2-Methyl-3-(5-methyl-1,3,4-oxadiazol-2-yl)phenyl]-1,3-dihydrobenzimidazol-2-one

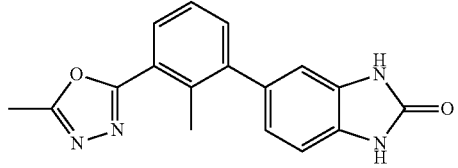 [SMILES: Cc1nnc(-c2cccc(-c3ccc4[nH]c(=O)[nH]c4c3)c2C)o1]

The title compound was prepared in a manner analogous to Example 190, substituting methyl 3-bromo-2-methylbenzoate for methyl 3-bromo-2-chlorobenzoate in Step A and triethylorthoacetate for triethylorthoformate in Step B. MS (ESI): mass calcd. for C$_{17}$H$_{14}$N$_4$O$_2$, 306.1; m/z found, 307.1 [M+H]$^+$. $^1$H NMR (500 MHz, DMSO-d$_6$): δ 10.70 (s, 1H), 10.67 (s, 1H), 7.92-7.67 (m, 1H), 7.51-7.33 (m, 2H), 7.07-6.94 (m, 1H), 6.95-6.82 (m, 2H), 2.60 (s, 3H), 2.43 (s, 3H).

Example 196: 5-[2-Chloro-3-(5-cyclopropyl-1,3,4-oxadiazol-2-yl)phenyl]-1,3-dihydrobenzimidazol-2-one

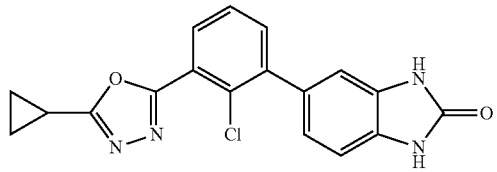 [SMILES: O=c1[nH]c2ccc(-c3cccc(-c4nnc(C5CC5)o4)c3Cl)cc2[nH]1]

Step A: 3-Bromo-2-chloro-N'-(cyclopropanecarbonyl)benzohydrazide

To a cooled (0° C.) solution of 3-bromo-2-chlorobenzohydrazide (Example 190, product from Step A, 350 mg, 1.4 mmol) and triethylamine (0.21 mL, 1.5 mmol) in DCM (5.3 mL) was added cyclopropanecarbonyl chloride (0.14 mL, 1.5 mmol) dropwise. Following the addition, the reaction was warmed to rt and stirred for 1 h. The white precipitate was filtered and washed with ether to provide the desired product (286 mg, 64% yield). MS (ESI): mass calcd. for $C_{11}H_{10}BrClN_2O_2$, 316.0; m/z found, 317.0 [M+H]$^+$.

Step B: 2-(3-Bromo-2-chlorophenyl)-5-cyclopropyl-1,3,4-oxadiazole

A mixture of 3-bromo-2-chloro-N'-(cyclopropanecarbonyl)benzohydrazide (180 mg, 0.57 mmol) and phosphorus oxychloride (2.0 mL, 22 mmol) was heated at 100° C. in a microwave oven for 16 h. After cooling to rt, saturated aq. NaHCO$_3$ was added slowly and the resulting mixture was extracted twice with EtOAc. The combined organic extracts were dried (Na$_2$SO$_4$), filtered and concentrated under reduced pressure. Purification (FCC, SiO$_2$; 0-15% EtOAc/hexanes) provided the desired product as a colorless oil (170 mg, 50% yield). MS (ESI): mass calcd. for $C_{11}H_8BrClN_2O$, 298.0; m/z found, 299.0 [M+H]$^+$. $^1$H NMR (500 MHz, DMSO-d$_6$) δ 8.09-8.00 (m, 1H), 7.98-7.91 (m, 1H), 7.53-7.46 (m, 1H), 2.40-2.29 (m, 1H), 1.27-1.17 (m, 2H), 1.15-1.07 (m, 2H).

Step C: 5-[2-Chloro-3-(5-cyclopropyl-1,3,4-oxadiazol-2-yl)phenyl]-1,3-dihydrobenzimidazol-2-one The title compound was prepared in a manner analogous to Example 2, substituting 2-(3-bromo-2-chlorophenyl)-5-cyclopropyl-1,3,4-oxadiazole for 2,6-dimethyliodobenzene and PdCl$_2$(dppf)-CH$_2$Cl$_2$ for PdCl$_2$(dtbpf) in Step B. The crude product was purified by reverse-phase HPLC (Agilent 1100 Series XBridge Prep C18 OBD 5 um, (0.05M Ammonium Hydroxide in water/MeCN)) to provide the title compound (31 mg, 34% yield). MS (ESI): mass calcd. for $C_{18}H_{13}ClN_4O_2$, 352.1; m/z found, 353.1 [M+H]$^+$. $^1$H NMR (500 MHz, DMSO-d$_6$) δ 10.88-10.59 (m, 2H), 7.93-7.70 (m, 1H), 7.68-7.46 (m, 2H), 7.08-6.86 (m, 3H), 2.42-2.24 (m, 1H), 1.26-0.94 (m, 4H).

Example 197: 5-[3-(5-Cyclopropyl-1,3,4-oxadiazol-2-yl)-2-methyl-phenyl]-1,3-dihydrobenzimidazol-2-one

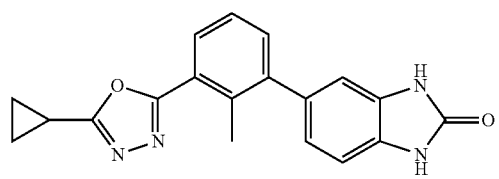 [SMILES: Cc1c(-c2ccc3[nH]c(=O)[nH]c3c2)cccc1-c1nnc(C2CC2)o1]

The title compound was prepared in a manner analogous to Example 196, substituting 3-bromo-2-methylbenzohydrazide for 3-bromo-2-chlorobenzohydrazide in Step A. MS (ESI): mass calcd. for $C_{19}H_{16}N_4O_2$, 332.1; m/z found, 333.1 [M+H]$^+$. $^1$H NMR (500 MHz, DMSO-d$_6$) δ 10.69 (s, 1H), 10.67 (s, 1H), 7.88-7.69 (m, 1H), 7.52-7.33 (m, 2H), 7.01 (d, J=7.9 Hz, 1H), 6.92-6.77 (m, 2H), 2.41 (s, 3H), 2.36-2.29 (m, 1H), 1.22-1.16 (m, 2H), 1.14-1.10 (m, 2H).

Example 198: 5-[2-Methyl-3-[5-(trifluoromethyl)-1,3,4-oxadiazol-2-yl]phenyl]-1,3-dihydrobenzimidazol-2-one

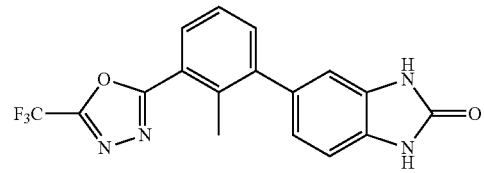 [SMILES: Cc1c(-c2ccc3[nH]c(=O)[nH]c3c2)cccc1-c1nnc(C(F)(F)F)o1]

The title compound was prepared in a manner analogous to Example 196, substituting 3-bromo-2-methylbenzohydrazide for 3-bromo-2-chlorobenzohydrazide in Step A and trifluoroacetic anhydride for cyclopropanecarbonyl chloride in Step B. MS (ESI): mass calcd. for $C_{17}H_{11}F_3N_4O_2$, 360.1; m/z found, 361.0 [M+H]$^+$. $^1$H NMR (500 MHz, CD$_3$OD) δ 7.96 (dd, J=7.8, 1.5 Hz, 1H), 7.55-7.49 (m, 1H), 7.49-7.42 (m, 1H), 7.18-7.11 (m, 1H), 7.03-6.97 (m, 2H), 2.53 (s, 3H).

Example 199: 5-[2-Methyl-3-(1,2,4-oxadiazol-5-yl)phenyl]-1,3-dihydrobenzimidazol-2-one

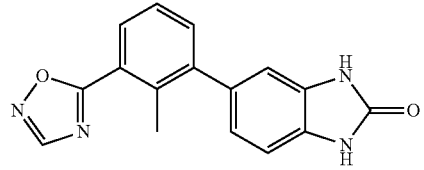 [SMILES: Cc1c(-c2ccc3[nH]c(=O)[nH]c3c2)cccc1-c1ncno1]

Step A: 3-Bromo-N-((dimethylamino)methylene)-2-methylbenzamide

A solution of 3-bromo-2-methyl-benzamide (500 mg, 2.3 mmol) in N,N-dimethylformamide dimethyl acetal (23 mL) was heated at 120° C. for 4 h. Upon cooling, the solvent was removed in vacuo.

The title compound was used crude in the next step without further purification.

Step B: 5-(3-Bromo-2-methylphenyl)-1,2,4-oxadiazole

A solution of 3-bromo-N-((dimethylamino)methylene)-2-methylbenzamide in dioxane (11.5 mL), was treated with 50% aqueous hydroxylamine (0.17 mL) and acetic acid (5.8 mL). The mixture was heated at 90° C. for 4 h. After cooling to 23° C., the reaction was quenched with saturated aq. NaHCO$_3$ and extracted with EtOAc. The organic layer was separated, dried (MgSO$_4$), filtered and concentrated in vacuo. The residue was purified by FCC (SiO$_2$; 0-30% EtOAc/heptanes) to afford the desired product (162 mg, 29% yield). MS (ESI): mass calcd. for $C_8H_8BrNO$, 238.0 m/z found, 238.9 [M+H]$^+$.

Step C: 5-[2-Methyl-3-(1,2,4-oxadiazol-5-yl)phenyl]-1,3-dihydrobenzimidazol-2-one The title compound was prepared in a manner analogous to Example 2, substituting 5-(3-bromo-2-methylphenyl)-1, 2,4-oxadiazole for 2,6-dimethyliodobenzene and sodium bicarbonate for potassium phosphate. MS (ESI): mass calcd. for C$_{16}$H$_{12}$N$_4$O$_2$, 292.1; m/z found, 293.0 [M+H]$^+$. $^1$H NMR (300 MHz, DMSO-d$_6$) δ 10.69 (bs, 1H), 10.67 (bs, 1H), 9.15 (s, 1H), 7.97 (dd, J=6.9, 1.9 Hz, 1H), 7.55-7.42 (m, 2H), 7.01 (d, J=7.8 Hz, 1H), 6.90 (dd, J=8.0, 2.0 Hz, 1H), 6.87 (s, 1H), 2.46 (s, 3H).

Example 200: 6-[2-Methyl-3-(1,2,4-oxadiazol-5-yl)phenyl]-3H-1,3-benzothiazol-2-one

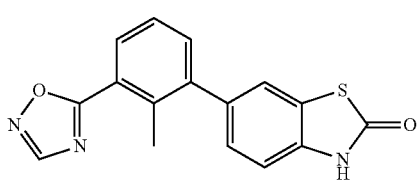 [SMILES: Cc1c(-c2ccc3[nH]c(=O)sc3c2)cccc1-c1ncno1]

The title compound was prepared in a manner analogous to example 199, substituting Intermediate 2, 6-(4,4,5,5-tetramethyl-1,3,2-dioxaborolan-2-yl)benzo[d]thiazol-2(3H)-one), for 5-(4,4,5,5-tetramethyl-1,3,2-dioxaborolan-2-yl)-1H-benzo[d]imidazol-2(3H)-one in Step C. MS (ESI): mass calcd. for C$_{16}$H$_{11}$N$_2$O$_2$S, 309.1; m/z found, 310.0 [M+H]$^+$. $^1$H NMR (300 MHz, DMSO-d$_6$) δ 11.99 (bs, 1H), 9.16 (s, 1H), 8.00 (dd, J=6.6, 2.3 Hz, 1H), 7.62 (s, 1H), 7.56-7.45 (m, 2H), 7.27 (dd, J=8.2, 1.4 Hz, 1H), 7.20 (d, J=8.1 Hz, 1H), 2.46 (s, 3H).

Example 201: 5-(3-(3-Cyclopropyl-1,2,4-oxadiazol-5-yl)-2-methylphenyl)-1H-benzo[d]imidazol-2(3H)-one

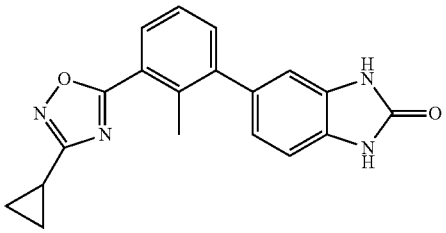 [SMILES: Cc1c(-c2ccc3[nH]c(=O)[nH]c3c2)cccc1-c1nc(C2CC2)no1]

Step A: 5-(3-Bromo-2-methylphenyl)-3-cyclopropyl-1,2,4-oxadiazole

To a solution of 3-bromo-2-methyl-benzoic acid (400 mg, 1.9 mmol) in EtOAc (6 mL) were added N'-hydroxycyclopropanecarboximidamide (180 mg, 1.9 mmol), triethylamine (569 mg, 5.6 mmol), and propylphosphonic anhydride (50 wt % in EtOAc, 2.8 mL, 4.7 mmol). The mixture was heated at 80° C. for 3 h. After cooling to rt, the reaction was diluted with water and extracted with EtOAc. The combined organic extracts were washed with brine, dried (Na$_2$SO$_4$), filtered, and concentrated in vacuo. The residue was purified by FCC (SiO$_2$; 0-30% EtOAc/hexanes) to afford the desired product as a colorless oil (147 mg, 28% yield). MS (ESI): mass calcd. for C$_{12}$H$_{11}$BrN$_2$O, 278.0 m/z found, 279.0 [M+H]$^+$.

Step B: 5-(3-(3-cyclopropyl-1,2,4-oxadiazol-5-yl)-2-methylphenyl)-1H-benzo[d]imidazol-2(3H)-one The title compound was prepared in a manner analogous to Example 2, substituting 5-(3-bromo-2-methylphenyl)-3-cyclopropyl-1,2,4-oxadiazole for 2,6-dimethyliodobenzene, sodium bicarbonate for potassium phosphate, and heating to 70° C. instead of 100° C. MS (ESI): mass calcd. for C$_{19}$H$_{16}$N$_4$O$_2$, 332.1; m/z found, 333.1 [M+H]$^+$. $^1$H NMR (300 MHz, DMSO-d$_6$) δ 10.69 (bs, 2H), 7.89 (dd, J=7.1, 1.7 Hz, 1H), 7.51-7.39 (m, 2H), 7.00 (d, J=7.7 Hz, 1H), 6.89 (dd, J=8.1, 1.4 Hz, 1H), 6.85 (s, 1H), 2.40 (s, 3H), 2.29-2.14 (m, 1H), 1.17-1.08 (m, 2H), 1.03-0.95 (m, 2H).

Example 202: 6-[3-(3-Cyclopropyl-1,2,4-oxadiazol-5-yl)-2-methyl-phenyl]-3H-1,3-benzothiazol-2-one

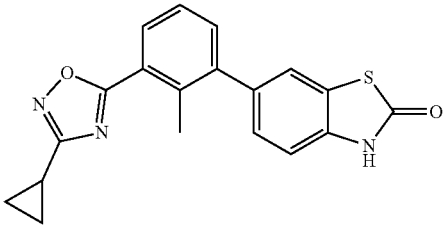 [SMILES: Cc1c(-c2ccc3[nH]c(=O)sc3c2)cccc1-c1nc(C2CC2)no1]

The title compound was prepared in a manner analogous to Example 201, substituting 6-(4,4,5,5-tetramethyl-1,3,2-dioxaborolan-2-yl)benzo[d]thiazol-2(3H)-one) (Intermediate 2) for 5-(4,4,5,5-tetramethyl-1,3,2-dioxaborolan-2-yl)-1H-benzo[d]imidazol-2(3H)-one (Intermediate 28) in Step B. MS (ESI): mass calcd. for C$_{19}$H$_{15}$N$_3$O$_2$S, 349.1; m/z found, 349.9 [M+H]$^+$. $^1$H NMR (300 MHz, DMSO) δ 12.00 (brs, 1H), 7.91 (dd, J=7.1, 2.2 Hz, 1H), 7.61 (d, J=1.6 Hz, 1H), 7.53-7.42 (m, 2H), 7.26 (dd, J=8.2, 1.6 Hz, 1H), 7.19 (d, J=8.2 Hz, 1H), 2.41 (s, 3H), 2.28-2.14 (m, 1H), 1.18-1.07 (m, 2H), 1.03-0.94 (m, 2H).

Example 203: 5-[2-Methyl-3-(3-methyl-1,2,4-oxadiazol-5-yl)phenyl]-1,3-dihydrobenzimidazol-2-one

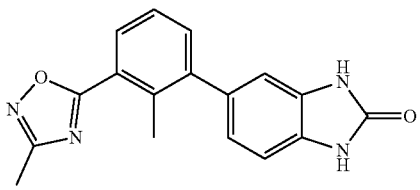 [SMILES: Cc1noc(-c2cccc(-c3ccc4[nH]c(=O)[nH]c4c3)c2C)n1]

The title compound was prepared in a manner analogous to Example 201, substituting N'-hydroxyacetimidamide for N'-hydroxycyclopropanecarboximidamide in Step A. MS (ESI): mass calcd. for C$_{17}$H$_{14}$N$_4$O$_2$, 306.1; m/z found, 307.0 [M+H]$^+$. $^1$H NMR (300 MHz, DMSO-d$_6$) δ 10.68 (bs, 1H), 10.67 (br. s., 1H), 7.93 (dd, J=6.9, 1.9 Hz, 1H), 7.53-7.40 (m, 2H), 7.01 (d, J=8.2 Hz, 1H), 6.95-6.83 (m, 2H), 2.44 (s, 6H).

Example 204: 6-[2-Methyl-3-(3-methyl-1,2,4-oxadiazol-5-yl)phenyl]-3H-1,3-benzothiazol-2-one

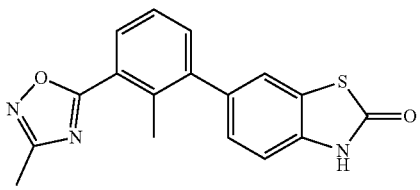 [SMILES: Cc1noc(-c2cccc(-c3ccc4[nH]c(=O)sc4c3)c2C)n1]

The title compound was prepared in a manner analogous to Example 201, substituting N'-hydroxyacetimidamide for N'-hydroxycyclopropanecarboximidamide in Step A, and 6-(4,4,5,5-tetramethyl-1,3,2-dioxaborolan-2-yl)benzo[d]thiazol-2(3H)-one) (Intermediate 2) for 5-(4,4,5,5-tetramethyl-1,3,2-dioxaborolan-2-yl)-1H-benzo[d]imidazol-2(3H)-one (Intermediate 28) in Step B. MS (ESI): mass calcd. for $C_{17}H_{13}N_3O_2S$, 323.1; m/z found, 324.0 [M+H]$^+$. $^1$H NMR (300 MHz, DMSO-d$_6$) δ 11.95 (bs, 1H), 7.95 (dd, J=6.5, 2.5 Hz, 1H), 7.60 (d, J=0.8 Hz, 1H), 7.53-7.43 (m, 2H), 7.26 (dd, J=8.2, 1.4 Hz, 1H), 7.20 (d, J=8.2 Hz, 1H), 2.45 (s, 6H).

Example 205: 5-[2-Methyl-3-[3-(trifluoromethyl)-1,2,4-oxadiazol-5-yl]phenyl]-1,3-dihydrobenzimidazol-2-one

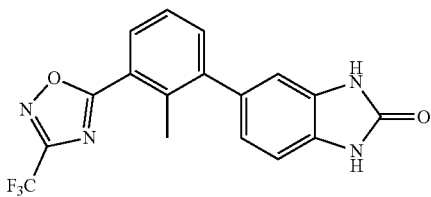 [SMILES: Cc1c(-c2ccc3[nH]c(=O)[nH]c3c2)cccc1-c1nc(C(F)(F)F)no1]

The title compound was prepared in a manner analogous to Example 201, substituting N'-hydroxytrifluoroacetimidamide for N'-hydroxycyclopropanecarboximidamide in Step A. MS (ESI): mass calcd. for $C_{17}H_{11}F_3N_4O_2$, 360.1; m/z found, 361.0 [M+H]$^+$. $^1$H NMR (300 MHz, DMSO-d$_6$) δ 10.71 (bs, 2H), 8.06 (d, J=7.3 Hz, 1H), 7.67-7.42 (m, 2H), 7.03 (d, J=7.7 Hz, 1H), 6.96-6.79 (m, 2H), 2.50 (s, 3H).

Example 206: 5-[2-Methyl-3-(1,2,4-oxadiazol-3-yl)phenyl]-1,3-dihydrobenzimidazol-2-one

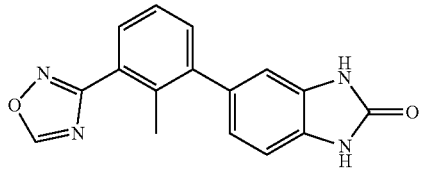 [SMILES: Cc1c(-c2ccc3[nH]c(=O)[nH]c3c2)cccc1-c1ncon1]

Step A:
3-Bromo-N'-hydroxy-2-methylbenzimidamide

To a stirred solution of 3-bromo-2-methyl-benzonitrile (1.5 g, 7.7 mmol) and triethylamine (1.9 mL, 14 mmol) in EtOH (50 mL) was added hydroxylamine hydrochloride (0.8 g, 11 mmol). The mixture was heated at 80° C. overnight. After cooling to rt, the solvent was removed in vacuo. The residue was diluted with water and extracted three times with EtOAc. The combined organic extracts were dried (MgSO$_4$), filtered and concentrated under reduced pressure. The residue was purified by FCC (SiO$_2$; 10%-50% EtOAc/heptanes) to afford the desired product (924 g, 53% yield). MS (ESI): mass calcd. for $C_8H_9BrN_2O$, 228.0 m/z found, 229.0 [M+H]$^+$.

Step B:
3-(3-Bromo-2-methylphenyl)-1,2,4-oxadiazole

To a stirring solution of 3-bromo-N'-hydroxy-2-methyl-benzimidamide (0.5 g, 2.2 mmol) in DMSO (25 mL) were sequentially added trimethylorthoformate (0.99 mL, 9.1 mmol) and boron trifluoride diethyl etherate (0.32 mL, 2.6 mmol). The reaction was stirred was at 23° C. for 1.5 h and then heated at 80° C. for 1 h. After cooling to 23° C., the mixture was diluted with EtOAc (150 mL) and washed successively with water, saturated aq NaHCO$_3$, and water. The organic layer was dried over MgSO$_4$ and concentrated in vacuo. The residue was purified by FCC (SiO$_2$; 0-7% EtOAc/heptanes) to afford the desired product as a colorless oil (308 mg, 58% yield). MS (ESI): mass calcd. for $C_9H_7BrN_2O$, 238.0 m/z found, 238.9 [M+H]$^+$.

Step C: 5-[2-Methyl-3-(1,2,4-oxadiazol-3-yl)phenyl]-1,3-dihydrobenzimidazol-2-one The title compound was prepared in a manner analogous to Example 2, substituting 3-(3-bromo-2-methylphenyl)-1,2,4-oxadiazole for 2,6-dimethyliodobenzene, sodium bicarbonate for potassium phosphate, and heating to 70° C. instead of 100° C. The crude product was purified by reverse-phase HPLC (47% MeOH/25 mM NH$_4$NHCO$_3$—53% MeOH/25 mM NH$_4$NHCO$_3$) to afford the title compound (17 mg, 9% yield). MS (ESI): mass calcd. for $C_{16}H_{12}N_4O_2$, 292.1; m/z found, 293.0 [M+H]$^+$. $^1$H NMR (300 MHz, DMSO-d$_6$) δ 10.69 (bs, 2H), 9.74 (s, 1H), 7.82 (dd, J=5.6, 3.4 Hz, 1H), 7.47-7.38 (m, 2H), 7.00 (d, J=7.8 Hz, 1H), 6.90 (dd, J=8.0, 1.4 Hz, 1H), 6.86 (s, 1H), 2.36 (s, 3H).

Example 207: 6-[2-Methyl-3-(1,2,4-oxadiazol-3-yl)phenyl]-3H-1,3-benzothiazol-2-one

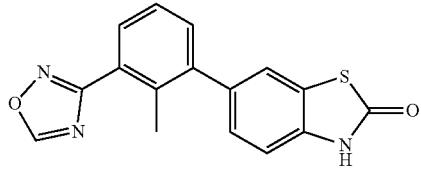 [SMILES: Cc1c(-c2ccc3[nH]c(=O)sc3c2)cccc1-c1ncon1]

The title compound was prepared in a manner analogous to Example 206, substituting 6-(4,4,5,5-tetramethyl-1,3,2-dioxaborolan-2-yl)benzo[d]thiazol-2(3H)-one)(Intermediate 2) for 5-(4,4,5,5-tetramethyl-1,3,2-dioxaborolan-2-yl)-1H-benzo[d]imidazol-2(3H)-one in Step C. MS (ESI): mass calcd. for $C_{16}H_{11}N_3O_2S$, 309.1; m/z found, 310.0 [M+H]$^+$. $^1$H NMR (300 MHz, DMSO-d$_6$) δ 11.97 (bs, 1H), 9.75 (s, 1H), 7.84 (dd, J=6.5, 2.5 Hz, 1H), 7.61 (d, J=1.1 Hz, 1H), 7.50-7.39 (m, 2H), 7.26 (dd, J=8.1, 1.6 Hz, 1H), 7.19 (d, J=8.0 Hz, 1H), 2.36 (s, 3H).

Example 208: 2-Chloro-3-(2-oxo-1,3-dihydrobenzimidazol-5-yl)-4-(trifluoromethoxy) benzonitrile

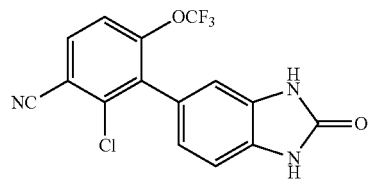 [SMILES: N#Cc1ccc(OC(F)(F)F)c(-c2ccc3[nH]c(=O)[nH]c3c2)c1Cl]

Step A: 2-Chloro-4-(trifluoromethoxy) phenyltrifluoromethanesulfonate

To a cold (0° C.) solution of 2-chloro-4-(trifluoromethoxy)phenol (1.0 g, 4.7 mmol) in toluene (12.5 mL) was added 30 wt % aqueous potassium phosphate (12.5 mL). After 10 minutes at 0° C., trifluoromethanesulfonic anhydride (0.95 mL, 5.7 mmol) was added dropwise and the resulting mixture was stirred at rt for 2 h. The aqueous phase was separated and the organic phase was washed with water, dried over $Na_2SO_4$, and concentrated to obtain the title compound which was used crude in the next step without further purification.

Step B: 2-Chloro-4-(trifluoromethoxy)benzonitrile

To a solution of 2-chloro-4-(trifluoromethoxy) phenyltrifluoromethanesulfonate (1.0 g, 2.9 mmol) in DMF (4.0 mL) were added zinc cyanide (681 mg, 5.8 mmol) and $Pd(PPh_3)_4$ (335 mg, 0.3 mmol). The reaction mixture was degassed with nitrogen for 10 minutes and then heated at 120° C. for 2 h. After cooling to rt, the crude reaction mixture was diluted with saturated aqueous $NaHCO_3$ solution, and extracted with EtOAc (×3). The combined organic extracts were dried ($Na_2SO_4$), filtered and concentrated. Purification (FCC,$SiO_2$; 0-5% EtOAc/hexanes) provided the title compound as an oil (220 mg, 34% yield). $^1H$ NMR (500 MHz, DMSO-$d_6$) δ 8.16 (d, J=8.7 Hz, 1H), 7.93 (dd, J=2.2, 1.0 Hz, 1H), 7.66-6.56 (m, 1H).

Step C: 2-Chloro-3-iodo-4-(trifluoromethoxy)benzonitrile

To a solution of 2-chloro-4-(trifluoromethoxy)benzonitrile (90 mg, 0.41 mmol) in THF (0.5 mL) was added (2,2,6,6-tetramethylpiperidin-1-yl)zinc(II) lithium chloride (TMPZnCl.LiCl) 1.0 M, 0.5 mL, 0.5 mmol) and the mixture was stirred at 60° C. for 16 h. A solution of iodine (101 mg, 0.40 mmol) in THF (2.0 mL) was added to the warm reaction mixture and stirring was maintained at 60° C. for 15 minutes. After cooling to rt, the reaction was quenched with saturated aqueous sodium thiosulfate and extracted with EtOAc (×3). The combined organic extracts were dried over $Na_2SO_4$, concentrated in vacuo, and purified by FCC (0-5% EtOAc/hexanes) to obtain the title compound as a white solid (105 mg, 74% yield). $^1H$ NMR (400 MHz, DMSO-$d_6$) δ 8.15 (d, J=8.7 Hz, 1H), 7.60 (dq, J=8.6, 1.5 Hz, 1H).

Step D: 2-Chloro-3-(2-oxo-1,3-dihydrobenzimidazol-5-yl)-4-(trifluoromethoxy) benzonitrile The title compound was prepared in a manner analogous to Example 2, substituting 2-chloro-3-iodo-4-(trifluoromethoxy)benzonitrile for 2,6-dimethyliodobenzene.

The crude product was purified by reverse-phase HPLC (XBridge C18 column (5 μm, 100×4.6 mm), mobile phase of 10-100% ACN in 20 mM $NH_4OH$) to afford the title compound (20 mg, 45% yield). MS (ESI): mass calcd. for $C_{15}H_7ClF_3N_3O_2$, 353.16; m/z found, 354.1 [M+H]$^+$. $^1H$ NMR (400 MHz, CD$_3$OD) δ 7.95 (d, J=8.7 Hz, 1H), 7.58 (dq, J=9.0, 1.7 Hz, 1H), 7.16 (d, J=8.0 Hz, 1H), 7.02-6.88 (m, 2H).

Example 209: 4-Chloro-3-(2-oxo-1,3-dihydrobenzimidazol-5-yl)-2-(trifluoromethoxy) benzonitrile

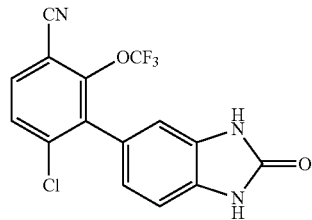 [SMILES: N#Cc1ccc(Cl)c(-c2ccc3[nH]c(=O)[nH]c3c2)c1OC(F)(F)F]

The title compound was prepared in a manner analogous to Example 208, substituting 4-chloro-2-(trifluoromethoxy) benzonitrile for 2-chloro-4-(trifluoromethoxy) benzonitrile in Step C. MS (ESI): mass calcd. for $C_{15}H_7ClF_3N_3O_2$, 353.16; m/z found, 354.1 [M+H]$^+$. $^1H$ NMR (500 MHz, CD$_3$OD) δ 7.89-7.85 (m, 1H), 7.78 (d, J=8.5 Hz, 1H), 7.19-7.14 (m, 1H), 7.03-6.94 (m, 2H).

Example 210: 6-[2-Chloro-6-(trifluoromethoxy) phenyl]-5-fluoro-3H-1,3-benzothiazol-2-one

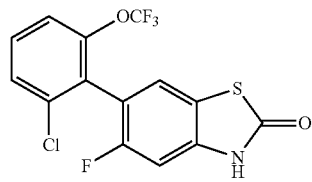 [SMILES: O=c1[nH]c2cc(F)c(-c3c(Cl)cccc3OC(F)(F)F)cc2s1]

The title compound was prepared in a manner analogous to Example 1, substituting tert-butyl 6-bromo-5-fluoro-2-oxobenzo[d]thiazole-3(2H)-carboxylate (Intermediate 5) for 5-bromo-1H-benzo[d]imidazol-2(3H)-one, (2-chloro-6-(trifluoromethoxy)phenyl)boronic acid for (2,3-dimethylphenyl)boronic acid, and $PdCl_2$(dtbpf) for $PdCl_2$(dppf)-$CH_2Cl_2$. MS (ESI): mass calcd. for $C_{14}H_6ClF_4NO_2S$, 363.7; m/z found, 364.7 [M+H]$^+$. $^1H$ NMR (400 MHz, CD$_3$OD) δ 7.59-7.48 (m, 2H), 7.44-7.35 (m, 2H), 7.03 (d, J=9.7 Hz, 1H).

Example 211: 6-(2-Chloro-6-(trifluoromethoxy) phenyl)-4-methyl-1H-benzo[d]imidazol-2(3H)-one

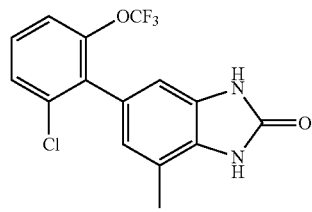 [SMILES: Cc1cc(-c2c(Cl)cccc2OC(F)(F)F)cc2[nH]c(=O)[nH]c12]

Step A: 2'-Chloro-5-methyl-6'-(trifluoromethoxy)-[1,1'-biphenyl]-3,4-diamine To a flask containing 5-bromo-3-methylbenzene-1,2-diamine (1.0 g, 5.0 mmol) and (2-chloro-6-(trifluoromethoxy)

phenyl)boronic acid (2.4 g, 10.0 mmol) in dioxane (8 mL) and water (2 mL) was added potassium phosphate (2.1 g, 10.0 mmol). After purging with nitrogen for 10 minutes, PdCl$_2$(dtbpf) (324 mg, 0.5 mmol) was added at once. The reaction mixture was heated at 100° C. for 2 h. After cooling to rt, the mixture was diluted with water and extracted with DCM (×2). The combined organic extracts were dried (Na$_2$SO$_4$), filtered, and concentrated in vacuo. The crude residue was purified by FCC (SiO$_2$; 0-50% EtOAc/hexanes) to afford the desired product as a brown solid (1.6 g, 63% yield). MS (ESI): mass calcd. for C$_{14}$H$_{12}$ClF$_3$N$_2$O, 316.1; m/z found, 317.0 [M+H]$^+$. 1H NMR (500 MHz, DMSO): δ 7.55 (dd, J=7.9, 1.4 Hz, 1H), 7.49-7.35 (m, 2H), 6.31 (d, J=2.0 Hz, 1H), 6.20 (dd, J=1.9, 0.9 Hz, 1H), 4.65-5=4.25 (m, 4H), 2.06 (s, 3H).

Step B: 6-(2-Chloro-6-(trifluoromethoxy)phenyl)-4-methyl-1H-benzo[d]imidazol-2(3H)-one To a cooled (0° C.) solution of 2'-chloro-5-methyl-6'-(trifluoromethoxy)-[1,1'-biphenyl]-3,4-diamine (1.0 g, 3.2 mmol) in THF (48 mL) was added 1,1'-carbonyldiimidazole (768 mg, 4.7 mmol) at once. The reaction mixture was allowed to warm to rt and stirred for a total of 16 h. The solvent was removed in vacuo and the crude residue was diluted with EtOAc and 1N HCl. The layers were separated, and the aqueous layer was extracted with EtOAc (×2). The combined organic extracts were dried over Na$_2$SO$_4$, filtered, and concentrated in vacuo to afford a yellow solid. Trituration with DCM provided the desired product as a white solid (885 mg, 82% yield). MS (ESI): mass calcd. for C$_{15}$H$_{10}$ClF$_3$N$_2$O$_2$, 342.0; m/z found, 343.0 [M+H]$^+$. 1H NMR (400 MHz, DMSO): δ 10.85 (s, 1H), 10.64 (s, 1H), 7.66-7.58 (m, 1H), 7.54-7.41 (m, 2H), 6.64-6.62 (m, 2H), 2.30 (s, 3H). 15 Example 212: 6-(2-Chloro-3-(1-methyl-1H-pyrazol-4-yl)phenyl)benzo[d]thiazol-2(3H)-one.

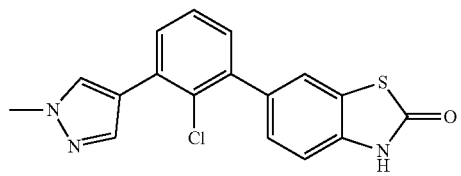 [SMILES: Cn1cc(-c2cccc(-c3ccc4[nH]c(=O)sc4c3)c2Cl)cn1]

Step A:
4-(3-Bromo-2-chlorophenyl)-1-methyl-1H-pyrazole

To a flask containing 1,3-dibromo-2-chlorobenzene (2.0 g, 7.4 mmol), 1-methyl-4-(4,4,5,5-tetramethyl-1,3,2-dioxaborolan-2-yl)-1H-pyrazole (1.5 g, 7.4 mmol), and potassium phosphate (3.1 g, 15 mmol) were added dioxane (32 mL) and water (8 mL). After purging with nitrogen for 10 minutes, PdCl$_2$(dppf)-CH$_2$Cl$_2$ (541 mg, 0.74 mmol) was added at once. The reaction mixture was heated at 95° C. for 1 h. After cooling to rt, the mixture was diluted with water and extracted with DCM (×2). The combined organic extracts were dried over Na$_2$SO$_4$, filtered, and concentrated in vacuo. The crude residue was purified by FCC (SiO$_2$; 0-20% EtOAc/hexanes) to afford the desired product (870 mg, 43% yield). MS (ESI): mass calcd. for C$_{10}$H$_8$BrClN$_2$, 270.0; m/z found, 270.9 [M+H]$^+$. 1H NMR (400 MHz, DMSO): δ 8.23-8.14 (m, 1H), 7.83 (d, J=0.9 Hz, 1H), 7.66 (dd, J=8.0, 1.5 Hz, 1H), 7.57 (dd, J=7.8, 1.5 Hz, 1H), 7.28 (t, J=7.9 Hz, 1H), 3.90 (s, 3H).

Step B: 6-(2-Chloro-3-(1-methyl-1H-pyrazol-4-yl)phenyl)-3-((2-(trimethylsilyl)ethoxy)methyl)benzo[d]thiazol-2(3H)-one To a flask containing 6-(4,4,5,5-tetramethyl-1,3,2-dioxaborolan-2-yl)-3-((2-(trimethylsilyl)ethoxy)methyl)benzo[d]thiazol-2(3H)-one (Intermediate 4, 125 mg, 0.31 mmol), 4-(3-bromo-2-chlorophenyl)-1-methyl-1H-pyrazole (100 mg, 0.37 mmol) and potassium carbonate (85 mg, 0.61 mmol) were added dioxane (6 mL) and water (1.5 mL). After purging with nitrogen for 10 minutes, PdCl$_2$(dppf)-CH$_2$Cl$_2$ (22 mg, 0.03 mmol) was added at once. The reaction mixture was heated at 100° C. for 4 h. After cooling to rt, the mixture was diluted with water and extracted with DCM (×2). The combined organic extracts were dried over Na$_2$SO$_4$, filtered, and concentrated in vacuo. The crude residue was purified by FCC (SiO$_2$; 0-30% EtOAc/hexanes) to afford the desired product (80 mg, 55% yield). MS (ESI): mass calcd. for C$_{23}$H$_{26}$ClN$_3$O$_2$SSi, 471.1; m/z found, 472.0 [M+H]$^+$.

Step C: 6-(2-Chloro-3-(1-methyl-1H-pyrazol-4-yl)phenyl)benzo[d]thiazol-2(3H)-one To a cooled (0° C.) solution of 6-(2-chloro-3-(1-methyl-1H-pyrazol-4-yl)phenyl)-3-((2-(trimethylsilyl)ethoxy)methyl)benzo[d]thiazol-2(3H)-one (80 mg, 0.17 mmol) in DCM (1 mL) was added TFA (1 mL, 13 mmol) dropwise. Following the addition, the reaction mixture was stirred at rt for 20 minutes. The solvent was removed in vacuo and placed under high vacuum for 1 h. To the crude residue was added 2 M NH$_3$ in MeOH (2 mL, 4 mmol) and stirring was maintained for 40 minutes. After removing the solvent in vacuo, the crude residue was diluted with water and extracted with DCM (×2). The combined organic extracts were dried (Na$_2$SO$_4$), filtered, and concentrated to afford the desired product (47 mg, 80% yield). MS (ESI): mass calcd. for C$_{17}$H$_{12}$ClN$_3$OS, 341.0; m/z found, 342.0 [M+H]$^+$. 1H NMR (400 MHz, DMSO): δ 11.99 (s, 1H), 8.13 (d, J=0.8 Hz, 1H), 7.81 (d, J=0.9 Hz, 1H), 7.63 (d, J=1.7 Hz, 1H), 7.55 (dd, J=7.8, 1.7 Hz, 1H), 7.40 (t, J=7.7 Hz, 1H), 7.34-7.29 (m, 1H), 7.26 (dd, J=7.5, 1.7 Hz, 1H), 7.19 (dd, J=8.3, 0.5 Hz, 1H), 3.90 (s, 3H).

Example 213: 6-(2-Chloro-3-(4-methoxypiperidin-1-yl)phenyl)benzo[d]thiazol-2(3H)-one

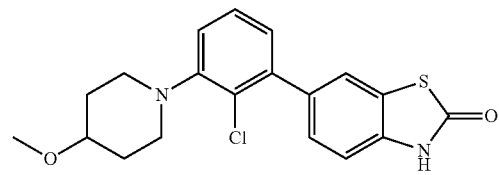 [SMILES: COC1CCN(c2cccc(-c3ccc4[nH]c(=O)sc4c3)c2Cl)CC1]

Step A:
1-(3-Bromo-2-chlorophenyl)-4-methoxypiperidine

To a suspension of 1,3-dibromo-2-chlorobenzene (300 mg, 1.11 mmol), 4-methoxypiperidine (168 mg, 1.11 mmol), sodium tert-butoxide (160 mg, 1.67 mmol) in toluene (3.0 ml), was added BINAP (35 mg, 0.05 mmol) and Pd$_2$(dba)$_3$ (20 mg, 0.02 mmol) at once. The mixture was degassed with nitrogen for 10 minutes and then heated at 140° C. for 1 h in microwave. After cooling to rt, the reaction mixture was diluted with water and extracted with EtOAc (×3). The combined organic extracts were dried ($Na_2SO_4$), filtered and concentrated. Purification (FCC, $SiO_2$; 0-100% EtOAc/hexanes) afforded the title compound as a oil (168 mg, 50% yield). MS (ESI): mass calcd. for $C_{12}H_{15}BrClNO$, 304.6; m/z found, 305.6 [M+H]$^+$. 1 H NMR (400 MHz, DMSO): δ 7.42 (dd, J=7.7, 1.7 Hz, 1H), 7.28-7.14 (m, 2H), 3.39-3.33 (m, 1H), 3.28 (s, 3H), 3.14 (dt, J=10.5, 4.5 Hz, 2H), 2.77 (ddd, J=12.0, 9.2, 3.0 Hz, 2H), 2.04-1.91 (m, 2H), 1.61 (dtd, J=12.2, 8.8, 3.4 Hz, 2H).

Step B: 6-(2-Chloro-3-(4-methoxypiperidin-1-yl) phenyl)benzo[d]thiazol-2(3H)-one To a flask containing 1-(3-bromo-2-chlorophenyl)-4-methoxypiperidine (65 mg, 0.21 mmol), 3-acetyl-6-(4,4,5,5-tetramethyl-1,3,2-dioxaborolan-2-yl)benzo[d]thiazol-2 (3H)-one (57 mg, 0.18 mmol), and potassium carbonate (49 mg, 0.36 mmol) were added dioxane (0.7 mL) and water (0.2 mL). After purging with nitrogen for 10 minutes, $PdCl_2$ (dppf)-$CH_2Cl_2$ (13 mg, 0.02 mmol) was added at once. The reaction mixture was heated at 100° C. for 16 h. After cooling to rt, the mixture was diluted with water and extracted with DCM (×2). The combined organic extracts were dried over $Na_2SO_4$, filtered, and concentrated in vacuo. The crude residue was purified by FCC ($SiO_2$; 0-30% EtOAc/hexanes) to afford the desired product (10 mg, 15% yield). MS (ESI): mass calcd. for $C_{19}H_{19}ClN_2O_2S$, 374.1; m/z found, 375.0 [M+H]$^+$. 1H NMR (500 MHz, $CD_3OD$): δ 7.47 (d, J=1.7 Hz, 1H), 7.34-7.25 (m, 2H), 7.23-7.13 (m, 2H), 7.03 (dd, J=7.6, 1.6 Hz, 1H), 4.64-4.54 (bm, 1H), 3.40 (s, 3H), 3.28 (ddd, J=10.1, 5.8, 2.8 Hz, 2H), 2.85 (ddd, J=12.0, 9.5, 2.9 Hz, 2H), 2.11-2.03 (m, 2H), 1.80-1.69 (m, 2H).

Example 214: 6-(2-chloro-6-(trifluoromethoxy)phenyl)-4-fluoro-1,3-dihydro-2H-benzo[d]imidazol-2-one

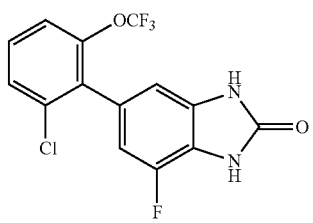 [SMILES: O=c1[nH]c2cc(-c3c(Cl)cccc3OC(F)(F)F)cc(F)c2[nH]1]

The title compound was prepared in a manner analogous to Example 1, substituting 5-bromo-3-fluorobenzene-1,2-diamine for 5-bromo-3-methylbenzene-1,2-diamine in Step A. MS (ESI): mass calcd. for $C_{14}H_7ClF_4N_2O_2$, 346.01; m/z found, 346.9 [M+H]$^+$. $^1$H NMR (500 MHz, DMSO-$d_6$) δ 11.34 (s, 1H), 10.99 (s, 1H), 7.65 (dd, J=8.1, 1.2 Hz, 1H), 7.56 (t, J=8.2 Hz, 1H), 7.53-7.46 (m, 1H), 6.80 (dd, J=11.0, 1.4 Hz, 1H), 6.70-6.64 (m, 1H).

Example 215-Example 220 are prophetic compounds, and may be made in a manner analogous to Example 211.

Example 215: 4-Chloro-6-(2-chloro-6-(trifluoromethoxy)phenyl)-1,3-dihydro-2H-benzo[d]imidazol-2-one

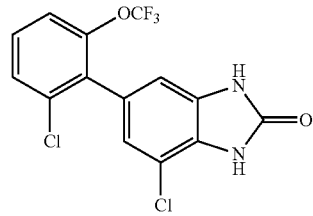 [SMILES: O=c1[nH]c2cc(-c3c(Cl)cccc3OC(F)(F)F)cc(Cl)c2[nH]1]

mass calcd. for $C_{14}H_7Cl_2F_3N_2O_2$, 363.12

Example 216: 6-(2-Chloro-6-(trifluoromethoxy) phenyl)-2-oxo-2,3-dihydro-1H-benzo[d]imidazole-4-carbonitrile

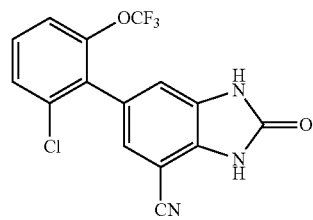 [SMILES: N#Cc1cc(-c2c(Cl)cccc2OC(F)(F)F)cc2[nH]c(=O)[nH]c12]

mass calcd. for $C_{15}H_7ClF_3N_3O_2$, 353.68.

Example 217: 6-(2-Chloro-6-(trifluoromethoxy) phenyl)-4-ethyl-1,3-dihydro-2H-benzo[d]imidazol-2-one

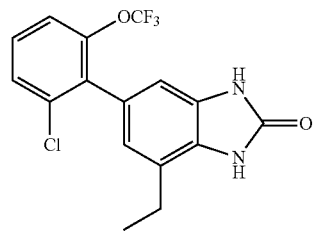 [SMILES: CCc1cc(-c2c(Cl)cccc2OC(F)(F)F)cc2[nH]c(=O)[nH]c12]

mass calcd. for $C_{16}H_{12}ClF_3N_2O_2$, 356.05.

Example 215: 6-(2-Chloro-6-(trifluoromethoxy) phenyl)-4-(trifluoromethyl)-1,3-dihydro-2H-benzo [d]imidazol-2-one

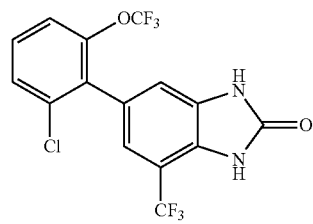 [SMILES: O=c1[nH]c2cc(-c3c(Cl)cccc3OC(F)(F)F)cc(C(F)(F)F)c2[nH]1]

mass calcd. for $C_{15}H_7ClF_6N_2O_2$, 396.01.

Example 219: 6-(2-Chloro-6-(trifluoromethoxy)phenyl)-4-(trifluoromethoxy)-1,3-dihydro-2H-benzo[d]imidazol-2-one

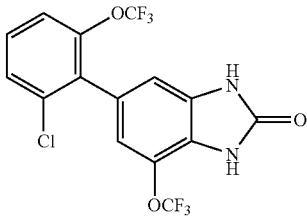

mass calcd. for $C_{15}H_7ClF_6N_2O_3$, 412.00.

Example 220: 6-(2-Chloro-6-(trifluoromethoxy)phenyl)-4-methoxy-1,3-dihydro-2H-benzo[d]imidazol-2-one

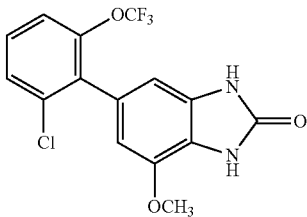 [SMILES: COc1cc(-c2c(Cl)cccc2OC(F)(F)F)cc2[nH]c(=O)[nH]c12]

mass calcd. for $C_{15}H_{10}ClF_3N_2O_3$, 358.03

Biological Assays

Calcium Flux Assay

This assay was used to test compounds for their ability to inhibit TARP γ8 dependent AMPA receptor activity. The AMPA receptor is a non-selective cation channel activated by glutamate. Ionotropic glutamate receptors normally desensitize too rapidly to allow detectable calcium influx in a FLIPR assay (Strange et al. (2006). "Functional characterisation of homomeric ionotropic glutamate receptors GluR1-GluR6 in a fluorescence-based high throughput screening assay." Comb Chem High Throughput Screen 9(2): 147-158). But, this desensitization is incomplete, and a substantial steady-state current remains in the sustained presence of glutamate (Cho et al. (2007). "Two families of TARP isoforms that have distinct effects on the kinetic properties of AMPA receptors and synaptic currents." Neuron 55(6): 890-904).

An in vitro assay was used to determine the potency of test compounds as inhibitors of the glutamate response of the channel formed by GluA1o-g8. To ensure a 1:1 stoichiometry of GluA1o and g8 subunits in the expressed channel, a fusion of the cDNAs for GRIA1o and CACNG8 was used. Channels expressed with this construct appear to have similar properties to channels formed by co-expression of GRIA1o with an excess of CACNG8 (Shi et al. 2009). A clonal cell line in HEK293 cells stably expressing this construct, with a geneticin selection marker, was generated for use in this assay. Cell expressing the GRIA1o-CACNG8 fusion construct were grown in a monolayer in 96- or 384-well microtiter plates. They were washed with assay buffer (135 mM NaCl, 4 mM KCl, 3 mM $CaCl_2$), 1 mM $MgCl2$, 5 mM glucose, 10 mM HEPES, pH 7.4, 300 mOs) using a Biotek EL405 plate washer. The cells were then loaded with a calcium-sensitive dye (Calcium-5 or Calcium-6, Molecular Devices) and the test compounds at a range of concentrations. Calcium flux following the addition of 15 μM glutamate was monitored using a Molecular Devices FLIPR Tetra.

The fluorescence in each well was normalized to the fluorescence of negative and positive control wells. The negative control wells had no added compounds, and the positive control wells had been incubated with 10 μM CP465022 (a non-subtype-selective AMPA receptor antagonist) (Lazzaro et al. (2002). "Functional characterization of CP-465,022, a selective, noncompetitive AMPA receptor antagonist." Neuropharmacology 42(2): 143-153). The responses to glutamate as functions of the test compound concentrations were fitted to a four-parameter logistic function. The fitted parameter corresponding to the midpoint was taken to be the potency of inhibition of the compound. The data in Table 4 below illustrates the observed potentcy for the compounds described herein. $pIC_{50}$ refers to the negative log of the $IC_{50}$ in molar.

Using a similar protocol, compounds were also tested for their ability to inhibit TARP γ2 dependent AMPA receptor activity. The compounds that were tested for TARP γ2 AMPA receptor activity had $pIC_{50}$ values less than 6.

TABLE 4

| Example # | Compound Name | GluR1-γ8 $pIC_{50}$ |
|---|---|---|
| 1 | 5-(2,3-Dimethylphenyl)-1,3-dihydrobenzimidazol-2-one; | 6.6 |
| 2 | 5-(2,6-Dimethylphenyl)-1,3-dihydrobenzimidazol-2-one; | 6.8 |
| 3 | 5-(o-Tolyl)-1,3-dihydrobenzimidazol-2-one; | 5.9 |
| 4 | 5-[2-(Trifluoromethyl)phenyl]-1,3-dihydrobenzimidazol-2-one; | 6.3 |
| 5 | 5-(2-Phenylphenyl)-1,3-dihydrobenzimidazol-2-one; | 7.0 |
| 6 | 5-(2-Isopropylphenyl)-1,3-dihydrobenzimidazol-2-one; | 6.5 |
| 7 | 5-(2,6-Dimethoxyphenyl)-1,3-dihydrobenzimidazol-2-one; | 5.9 |
| 8 | 5-(2-Isopropoxyphenyl)-1,3-dihydrobenzimidazol-2-one; | 5.7 |
| 9 | tert-Butyl 4-[2-(2-oxo-1,3-dihydrobenzimidazol-5-yl)phenyl]piperazine-1-carboxylate; | 6.1 |
| 10 | 5-(5-Chloro-2-methyl-phenyl)-1,3-dihydrobenzimidazol-2-one; | 6.6 |
| 11 | 5-(2-Fluoro-6-isopropoxy-phenyl)-1,3-dihydrobenzimidazol-2-one; | 6.3 |
| 12 | 5-[2-Chloro-6-(trifluoromethyl)phenyl]-1,3-dihydrobenzimidazol-2-one; | 6.2 |
| 13 | 5-[2-(Cyclopropylmethoxy)phenyl]-1,3-dihydrobenzimidazol-2-one; | 6.4 |

TABLE 4-continued

| Example # | Compound Name | GluR1-γ8 pIC$_{50}$ |
|---|---|---|
| 14 | 5-(2-Isobutoxy-6-methoxy-phenyl)-1,3-dihydrobenzimidazol-2-one; | 7.5 |
| 15 | 5-(2-Isobutoxy-5-methyl-phenyl)-1,3-dihydrobenzimidazol-2-one; | 7.5 |
| 16 | 5-(5-Chloro-2-isopropoxy-phenyl)-1,3-dihydrobenzimidazol-2-one; | 6.5 |
| 17 | 5-(2-Chlorophenyl)-1,3-dihydrobenzimidazol-2-one; | 6.2 |
| 18 | 5-(2,5-Dichlorophenyl)-1,3-dihydrobenzimidazol-2-one; | 6.6 |
| 19 | 5-(2-Chloro-5-methyl-phenyl)-1,3-dihydrobenzimidazol-2-one; | 6.7 |
| 20 | 5-(2-Chloro-6-methoxy-phenyl)-1,3-dihydrobenzimidazol-2-one; | 6.6 |
| 21 | 5-(2,5-Dimethylphenyl)-1,3-dihydrobenzimidazol-2-one; | 6.4 |
| 22 | 5-[2-Isopropoxy-5-(trifluoromethyl)phenyl]-1,3-dihydrobenzimidazol-2-one; | 6.5 |
| 23 | 5-(2,6-Dichloro-3-methyl-phenyl)-1,3-dihydrobenzimidazol-2-one; | 7.8 |
| 24 | 5-(2-Phenoxyphenyl)-1,3-dihydrobenzimidazol-2-one; | 6.3 |
| 25 | 5-[2-Chloro-5-(trifluoromethyl)phenyl]-1,3-dihydrobenzimidazol-2-one; | 6.6 |
| 26 | 5-(2-Benzyloxy-6-fluoro-phenyl)-1,3-dihydrobenzimidazol-2-one; | 7.0 |
| 27 | 3-Fluoro-2-(2-oxo-1,3-dihydrobenzimidazol-5-yl)benzaldehyde; | 5.8 |
| 28 | 5-(2-Isopropoxy-6-methoxy-phenyl)-1,3-dihydrobenzimidazol-2-one; | 7.1 |
| 29 | 5-[3-Chloro-2-(trifluoromethoxy)phenyl]-1,3-dihydrobenzimidazol-2-one; | 7.5 |
| 30 | 5-[2-Chloro-4-(trifluoromethoxy)phenyl]-1,3-dihydrobenzimidazol-2-one; | 5.8 |
| 31 | 5-[2-Chloro-6-(trifluoromethoxy)phenyl]-1,3-dihydrobenzimidazol-2-one; | 8.2 |
| 32 | 5-[2-Chloro-6-(trifluoromethoxy)phenyl]-6-tritio-1,3-dihydrobenzimidazol-2-one; | NT |
| 33 | 5-[2-Methoxy-4-(trifluoromethoxy)phenyl]-1,3-dihydrobenzimidazol-2-one; | 6.5 |
| 34 | 5-[3-Chloro-2-(trifluoromethyl)phenyl]-1,3-dihydrobenzimidazol-2-one; | 6.6 |
| 35 | 5-(2-Bromophenyl)-1,3-dihydrobenzimidazol-2-one; | 6.6 |
| 36 | 5-(2-Chloro-6-methyl-phenyl)-1,3-dihydrobenzimidazol-2-one; | 7.2 |
| 37 | 5-(4-Chloro-2,6-dimethyl-phenyl)-1,3-dihydrobenzimidazol-2-one; | 6.1 |
| 38 | 3-Methyl-2-(2-oxo-1,3-dihydrobenzimidazol-5-yl)benzonitrile; | 6.3 |
| 39 | 4-Methyl-3-(2-oxo-1,3-dihydrobenzimidazol-5-yl)benzonitrile; | 5.8 |
| 40 | 4-Chloro-3-(2-oxo-1,3-dihydrobenzimidazol-5-yl)benzonitrile; | 5.8 |
| 41 | 2-[2-(2-Oxo-1,3-dihydrobenzimidazol-5-yl)phenyl]acetonitrile; | 6.3 |
| 42 | Methyl 3-chloro-2-(2-oxo-1,3-dihydrobenzimidazol-5-yl)benzoate; | 6.3 |
| 43 | Methyl 2-chloro-3-(2-oxo-1,3-dihydrobenzimidazol-5-yl)benzoate; | 7.5 |
| 44 | Methyl 4-chloro-3-(2-oxo-1,3-dihydrobenzimidazol-5-yl)benzoate; | 6.5 |
| 45 | Methyl 3-methyl-2-(2-oxo-1,3-dihydrobenzimidazol-5-yl)benzoate; | 6.6 |
| 46 | Methyl 2-methyl-3-(2-oxo-1,3-dihydrobenzimidazol-5-yl)benzoate; | 7.3 |
| 47 | Methyl 4-methyl-3-(2-oxo-1,3-dihydrobenzimidazol-5-yl)benzoate; | 6.3 |
| 48 | Methyl 2-methoxy-3-(2-oxo-1,3-dihydrobenzimidazol-5-yl)benzoate; | 5.2 |
| 49 | 5-(2,6-Dichlorophenyl)-1,3-dihydrobenzimidazol-2-one; | 7.2 |
| 50 | 5-(2,6-Dichloro-4-fluoro-phenyl)-1,3-dihydrobenzimidazol-2-one; | 6.8 |
| 51 | 5-(2,4,6-Trichlorophenyl)-1,3-dihydrobenzimidazol-2-one; | 6.3 |
| 52 | 5-(2,6-Difluorophenyl)-1,3-dihydrobenzimidazol-2-one; | 6.0 |
| 53 | 5-(2-Chloro-6-fluoro-phenyl)-1,3-dihydrobenzimidazol-2-one; | 6.6 |
| 54 | 5-(2-Fluoro-6-methyl-phenyl)-1,3-dihydrobenzimidazol-2-one; | 6.6 |
| 55 | 5-(2-Fluoro-6-methoxy-phenyl)-1,3-dihydrobenzimidazol-2-one; | 6.1 |
| 56 | 3-Chloro-2-(2-oxo-1,3-dihydrobenzimidazol-5-yl)benzonitrile; | 6.2 |
| 57 | 5-[2-Methyl-6-(trifluoromethyl)phenyl]-1,3-dihydrobenzimidazol-2-one; | 6.2 |
| 58 | 5-(8-Quinolyl)-1,3-dihydrobenzimidazol-2-one; | 5.5 |
| 59 | 5-(2-Benzylphenyl)-1,3-dihydrobenzimidazol-2-one; | 6.5 |
| 60 | 5-[2-Methyl-3-(trifluoromethyl)phenyl]-1,3-dihydrobenzimidazol-2-one; | 7.1 |
| 61 | 5-[2-Chloro-3-(trifluoromethyl)phenyl]-1,3-dihydrobenzimidazol-2-one; | 7.4 |

TABLE 4-continued

| Example # | Compound Name | GluR1-γ8 pIC$_{50}$ |
|---|---|---|
| 62 | 2-Isopropoxy-6-(2-oxo-1,3-dihydrobenzimidazol-5-yl)benzonitrile; | 6.7 |
| 63 | 2-Bromo-6-(2-oxo-1,3-dihydrobenzimidazol-5-yl)benzonitrile; | 6.2 |
| 64 | 5-(2-Chloro-3-methyl-phenyl)-1,3-dihydrobenzimidazol-2-one; | 7.0 |
| 65 | 2-(2-Oxo-1,3-dihydrobenzimidazol-5-yl)-6-(trifluoromethyl)benzonitrile; | 5.9 |
| 66 | 5-(2,3,6-Trichlorophenyl)-1,3-dihydrobenzimidazol-2-one; | 8.0 |
| 67 | 2-Methyl-3-(2-oxo-1,3-dihydrobenzimidazol-5-yl)benzonitrile; | 6.6 |
| 68 | 2-Chloro-3-(2-oxo-1,3-dihydrobenzimidazol-5-yl)benzonitrile; | 6.5 |
| 69 | 5-(3,5-Dichloro-4-pyridyl)-1,3-dihydrobenzimidazol-2-one; | 6.3 |
| 70 | 5-(2-Chloro-4-methyl-3-pyridyl)-1,3-dihydrobenzimidazol-2-one; | 6.1 |
| 71 | 5-[2-Methyl-3-(5-methyl-1,2,4-oxadiazol-3-yl)phenyl]-1,3-dihydrobenzimidazol-2-one; | 7.3 |
| 72 | 6-[2-Methyl-3-(5-methyl-1,2,4-oxadiazol-3-yl)phenyl]-3H-1,3-benzothiazol-2-one; | 6.1 |
| 73 | 5-[3-(5-Cyclopropyl-1,2,4-oxadiazol-3-yl)-2-methyl-phenyl]-1,3-dihydrobenzimidazol-2-one; | 7.5 |
| 74 | 6-[3-(5-Cyclopropyl-1,2,4-oxadiazol-3-yl)-2-methyl-phenyl]-3H-1,3-benzothiazol-2-one; | 5.4 |
| 75 | 5-[2-Methyl-3-[5-(4-pyridyl)-1,2,4-oxadiazol-3-yl]phenyl]-1,3-dihydrobenzimidazol-2-one; | 7.7 |
| 76 | 6-[2-Chloro-6-(trifluoromethoxy)phenyl]-3H-1,3-benzothiazol-2-one; | 8.6 |
| 77 | 6-(2-Isopropoxy-6-methoxy-phenyl)-3H-1,3-benzothiazol-2-one; | 7.9 |
| 78 | N-Methyl-2-[2-(2-oxo-1,3-dihydrobenzimidazol-5-yl)-6-(trifluoromethyl)phenyl]acetamide; | 6.7 |
| 79 | 2-Methyl-3-(2-oxo-1,3-dihydrobenzimidazol-5-yl)-N-phenyl-benzamide; | 6.1 |
| 80 | N-Cyclopropyl-2-methyl-3-(2-oxo-1,3-dihydrobenzimidazol-5-yl)benzamide; | 5.4 |
| 81 | N,N,2-Trimethyl-3-(2-oxo-1,3-dihydrobenzimidazol-5-yl)benzamide; | 5.5 |
| 82 | 5-[2-Methyl-3-(morpholine-4-carbonyl)phenyl]-1,3-dihydrobenzimidazol-2-one; | 5.3 |
| 83 | 4-Chloro-3-(2-oxo-1,3-dihydrobenzimidazol-5-yl)-N-phenyl-benzamide; | 5.6 |
| 84 | 5-[2-Chloro-5-(pyrrolidine-1-carbonyl)phenyl]-1,3-dihydrobenzimidazol-2-one; | 5.1 |
| 85 | 5-[2-Chloro-5-(piperidine-1-carbonyl)phenyl]-1,3-dihydrobenzimidazol-2-one; | 5.3 |
| 86 | 5-[2-Chloro-6-(2-furylmethylamino)phenyl]-1,3-dihydrobenzimidazol-2-one; | 6.8 |
| 87 | 5-[2-Chloro-6-(3-furylmethylamino)phenyl]-1,3-dihydrobenzimidazol-2-one; | 6.9 |
| 88 | 5-[2-Isopropoxy-6-(trifluoromethoxy)phenyl]-1,3-dihydrobenzimidazol-2-one; | 8.1 |
| 89 | 5-[2-(Cyclopropylmethoxy)-6-(trifluoromethoxy)phenyl]-1,3-dihydrobenzimidazol-2-one; | 8.4 |
| 90 | 5-[2-Chloro-6-(cyclopropoxy)phenyl]-1,3-dihydrobenzimidazol-2-one; | 6.6 |
| 91 | 5-(2-Chloro-6-isopropoxy-phenyl)-1,3-dihydrobenzimidazol-2-one; | 7.1 |
| 92 | 5-[2-Chloro-6-(cyclopropylmethoxy)phenyl]-1,3-dihydrobenzimidazol-2-one; | 8.0 |
| 93 | (±)-5-[2-Chloro-6-[(2,2-difluorocyclopropyl)methoxy]phenyl]-1,3-dihydrobenzimidazol-2-one; | 7.7 |
| 94 | 5-[2-Chloro-6-(difluoromethoxy)phenyl]-1,3-dihydrobenzimidazol-2-one; | 7.5 |
| 95 | 5-[2-Chloro-6-(2,2,2-trifluoroethoxy)phenyl]-1,3-dihydrobenzimidazol-2-one; | 7.3 |
| 96 | 5-[2-Chloro-6-(2,2-difluoroethoxy)phenyl]-1,3-dihydrobenzimidazol-2-one; | 7.2 |
| 97 | 2-[3-Chloro-2-(2-oxo-1,3-dihydrobenzimidazol-5-yl)phenoxy]acetonitrile; | 6.5 |
| 98 | 5-[2-Chloro-6-(2,2-dimethylpropoxy)phenyl]-1,3-dihydrobenzimidazol-2-one; | 7.3 |
| 99 | 5-(2-Benzyloxy-6-chloro-phenyl)-1,3-dihydrobenzimidazol-2-one; | 7.2 |
| 100 | tert-Butyl 3-[3-chloro-2-(2-oxo-1,3-dihydrobenzimidazol-5-yl)phenoxy]azetidine-1-carboxylate; | 6.5 |
| 101 | 5-(2-Chloro-6-thiazol-5-yloxy-phenyl)-1,3-dihydrobenzimidazol-2-one; | 6.5 |
| 102 | 5-[2-(2,2-Difluoroethoxy)-6-methoxy-phenyl]-1,3-dihydrobenzimidazol-2-one; | 6.4 |

TABLE 4-continued

| Example # | Compound Name | GluR1-γ8 pIC$_{50}$ |
|---|---|---|
| 103 | 5-[2-Methoxy-6-(2,2,2-trifluoroethoxy)phenyl]-1,3-dihydrobenzimidazol-2-one; | 6.4 |
| 104 | 5-[2-(2,2-Dimethylpropoxy)-6-methoxy-phenyl]-1,3-dihydrobenzimidazol-2-one; | 7.0 |
| 105 | 5-(2-Benzyloxy-6-methoxy-phenyl)-1,3-dihydrobenzimidazol-2-one; | 7.4 |
| 106 | 5-[2-[(4-Fluorophenyl)ethoxy]-6-methoxy-phenyl]-1,3-dihydrobenzimidazol-2-one; | 7.4 |
| 107 | 5-(2,6-Diisopropoxyphenyl)-1,3-dihydrobenzimidazol-2-one; | 7.2 |
| 108 | 5-[2-Isopropoxy-6-(trifluoromethyl)phenyl]-1,3-dihydrobenzimidazol-2-one; | 7.1 |
| 109 | 5-[2-Chloro-3-(cyclopropoxy)phenyl]-1,3-dihydrobenzimidazol-2-one; | 7.4 |
| 110 | 5-(2-Chloro-3-isopropoxy-phenyl)-1,3-dihydrobenzimidazol-2-one; | 7.5 |
| 111 | (±)-5-[2-Chloro-3-[(2,2-difluorocyclopropyl)methoxy]phenyl]-1,3-dihydrobenzimidazol-2-one; | 7.3 |
| 112 | 5-[2-Chloro-3-(2,2-difluoroethoxy)phenyl]-1,3-dihydrobenzimidazol-2-one; | 6.9 |
| 113 | 5-[2-Chloro-3-(difluoromethoxy)phenyl]-1,3-dihydrobenzimidazol-2-one; | 7.1 |
| 114 | tert-Butyl 3-[2-chloro-3-(2-oxo-1,3-dihydrobenzimidazol-5-yl)phenoxy]azetidine-1-carboxylate; | 6.7 |
| 115 | 5-(3-Chloro-2-isopropoxy-phenyl)-1,3-dihydrobenzimidazol-2-one; | 5.7 |
| 116 | 5-(2-tert-Butoxy-6-chloro-phenyl)-1,3-dihydrobenzimidazol-2-one; | 6.8 |
| 117 | 5-(2-tert-Butoxy-6-methoxy-phenyl)-1,3-dihydrobenzimidazol-2-one; | 6.0 |
| 118 | (±)-5-[2-Chloro-6-(2,2,2-trifluoro-1-methyl-ethoxy)phenyl]-1,3-dihydrobenzimidazol-2-one; | 7.5 |
| 119 | (R*)-5-[2-Chloro-6-(2,2,2-trifluoro-1-methyl-ethoxy)phenyl]-1,3-dihydrobenzimidazol-2-one; | 7.3 |
| 120 | (S*)-5-[2-Chloro-6-(2,2,2-trifluoro-1-methyl-ethoxy)phenyl]-1,3-dihydrobenzimidazol-2-one; | 7.1 |
| 121 | (±)-5-[2-Methoxy-6-(2,2,2-trifluoro-1-methyl-ethoxy)phenyl]-1,3-dihydrobenzimidazol-2-one; | 6.8 |
| 122 | 2-[3,4-Dichloro-2-(2-oxo-1,3-dihydrobenzimidazol-5-yl)phenyl]acetonitrile; | 8.1 |
| 123 | 2-[2-(2-Oxo-1,3-dihydrobenzimidazol-5-yl)-3-trifluoromethoxy)phenyl]acetonitrile; | 7.8 |
| 124 | 2-[3-Chloro-2-(2-oxo-1,3-dihydrobenzimidazol-5-yl)phenyl]acetonitrile; | 7.9 |
| 125 | 2-[3-Chloro-2-(2-oxo-6-tritio-1,3-dihydrobenzimidazol-5-yl)phenyl]acetonitrile; | NT |
| 126 | (±)-2-[3-Chloro-2-(2-oxo-1,3-dihydrobenzimidazol-5-yl)phenyl]propanenitrile; | 7.9 |
| 127 | 2-[3-Chloro-2-(2-oxo-1,3-dihydrobenzimidazol-5-yl)phenyl]-2-methyl-propanenitrile; | 7.6 |
| 128 | 1-[3-Chloro-2-(2-oxo-1,3-dihydrobenzimidazol-5-yl)phenyl]cyclopropanecarbonitrile; | 6.4 |
| 129 | 1-[3-Chloro-2-(2-oxo-1,3-dihydrobenzimidazol-5-yl)phenyl]cyclobutanecarbonitrile; | 6.1 |
| 130 | 2-[2-Chloro-3-(2-oxo-1,3-dihydrobenzimidazol-5-yl)phenyl]acetonitrile; | 5.7 |
| 131 | 2-[2,4-Dichloro-3-(2-oxo-1,3-dihydrobenzimidazol-5-yl)phenyl]acetonitrile; | 5.7 |
| 132 | 2-[3-Bromo-2-(2-oxo-1,3-dihydrobenzimidazol-5-yl)phenyl]acetonitrile; | 7.5 |
| 133 | 2-[3-Chloro-2-(2-oxo-3H-1,3-benzothiazol-6-yl)phenyl]acetonitrile; | 8.5 |
| 134 | 6-(3,5-Dichloro-4-pyridyl)-3H-1,3-benzothiazol-2-one; | 7.2 |
| 135 | 2-[3-(4-Fluorophenyl)-2-(2-oxo-1,3-dihydrobenzimidazol-5-yl)phenyl]acetonitrile; | 7.7 |
| 136 | 2-[3-(2-Fluorophenyl)-2-(2-oxo-1,3-dihydrobenzimidazol-5-yl)phenyl]acetonitrile; | 6.8 |
| 137 | 2-[3-(4-Methoxyphenyl)-2-(2-oxo-1,3-dihydrobenzimidazol-5-yl)phenyl]acetonitrile; | 6.5 |
| 138 | 2-[3-Cyclopropyl-2-(2-oxo-1,3-dihydrobenzimidazol-5-yl)phenyl]acetonitrile; | 7.0 |
| 139 | 5-[2,6-Dichloro-3-(morpholinomethyl)phenyl]-1,3-dihydrobenzimidazol-2-one; | 6.6 |
| 140 | 5-[2,6-Dichloro-3-(1-piperidylmethyl)phenyl]-1,3-dihydrobenzimidazol-2-one; | 6.4 |
| 141 | 5-[2-Chloro-3-(morpholinomethyl)phenyl]-1,3-dihydrobenzimidazol-2-one; | 6.0 |

TABLE 4-continued

| Example # | Compound Name | GluR1-γ8 pIC$_{50}$ |
|---|---|---|
| 142 | 5-[2-Chloro-3-(1-piperidylmethyl)phenyl]-1,3-dihydrobenzimidazol-2-one; | 6.2 |
| 143 | 5-[2-Chloro-3-[(2,2-dimethylmorpholin-4-yl)methyl]phenyl]-1,3-dihydrobenzimidazol-2-one; | 7.0 |
| 144 | (±)-5-[2-Chloro-3-[[2-(trifluoromethyl)morpholin-4-yl]methyl]phenyl]-1,3-dihydrobenzimidazol-2-one; | 6.9 |
| 145 | 5-[2-Chloro-6-(morpholinomethyl)phenyl]-1,3-dihydrobenzimidazol-2-one; | 6.0 |
| 146 | 5-[2-Chloro-6-[(4-methylpiperazin-1-yl)methyl]phenyl]-1,3-dihydrobenzimidazol-2-one; | 5.1 |
| 147 | 5-[2-Methyl-3-(1-piperidylmethyl)phenyl]-1,3-dihydrobenzimidazol-2-one; | 5.8 |
| 148 | 5-[2-Methyl-3-(morpholinomethyl)phenyl]-1,3-dihydrobenzimidazol-2-one; | 5.7 |
| 149 | 5-[3-[(2,2-Dimethylmorpholin-4-yl)methyl]-2-methyl-phenyl]-1,3-dihydrobenzimidazol-2-one; | 7.7 |
| 150 | (±)-5-[2-Methyl-3-[(2-methylmorpholin-4-yl)methyl]phenyl]-1,3-dihydrobenzimidazol-2-one; | 6.7 |
| 151 | (±)-5-[2-Methyl-3-[[2-(trifluoromethyl)morpholin-4-yl]methyl]phenyl]-1,3-dihydrobenzimidazol-2-one; | 7.5 |
| 152 | (3R)-5-[2-Methyl-3-[[3-methylmorpholin-4-yl]methyl]phenyl]-1,3-dihydrobenzimidazol-2-one; | 6.0 |
| 153 | (3S)-5-[2-Methyl-3-[[3-methylmorpholin-4-yl]methyl]phenyl]-1,3-dihydrobenzimidazol-2-one; | 6.5 |
| 154 | 5-[2-Methyl-3-(thiomorpholinomethyl)phenyl]-1,3-dihydrobenzimidazol-2-one; | 6.7 |
| 155 | tert-Butyl 4-[[2-methyl-3-(2-oxo-1,3-dihydrobenzimidazol-5-yl)phenyl]methyl]piperazine-1-carboxylate; | 6.5 |
| 156 | 5-[2-Methyl-3-(pyrrolidin-1-ylmethyl)phenyl]-1,3-dihydrobenzimidazol-2-one; | 5.2 |
| 157 | 5-[3-[(3-Fluoroazetidin-1-yl)methyl]-2-methyl-phenyl]-1,3-dihydrobenzimidazol-2-one; | 5.2 |
| 158 | 5-[2-Methyl-3-(6-oxa-3-azabicyclo[3;1;1]heptan-3-ylmethyl)phenyl]-1,3-dihydrobenzimidazol-2-one; | 5.2 |
| 159 | (3R,4S)-5-[3-[[3-Fluoro-4-hydroxy-1-piperidyl]methyl]-2-methyl-phenyl]-1,3-dihydrobenzimidazol-2-one; | 5.2 |
| 160 | 5-(2-Chloro-6-cyclopropyl-phenyl)-1,3-dihydrobenzimidazol-2-one; | 8.2 |
| 161 | 5-(2-Chloro-6-vinyl-phenyl)-1,3-dihydrobenzimidazol-2-one; | 7.5 |
| 162 | 5-(2-Chloro-6-phenyl-phenyl)-1,3-dihydrobenzimidazol-2-one; | 7.7 |
| 163 | 5-[2-Chloro-6-(4-fluorophenyl)phenyl]-1,3-dihydrobenzimidazol-2-one; | 7.7 |
| 164 | 4-[3-Chloro-2-(2-oxo-1,3-dihydrobenzimidazol-5-yl)phenyl]benzonitrile; | 7.4 |
| 165 | 5-[2-Chloro-6-(3-pyridyl)phenyl]-1,3-dihydrobenzimidazol-2-one; | 6.9 |
| 166 | 5-[2-Chloro-6-(5-fluoro-3-pyridyl)phenyl]-1,3-dihydrobenzimidazol-2-one; | 7.2 |
| 167 | 5-[2-Chloro-6-(6-fluoro-3-pyridyl)phenyl]-1,3-dihydrobenzimidazol-2-one; | 6.5 |
| 168 | 5-[2-Chloro-6-(5-methoxy-3-pyridyl)phenyl]-1,3-dihydrobenzimidazol-2-one; | 6.4 |
| 169 | 5-[2-Chloro-6-[5-(trifluoromethyl)-3-pyridyl]phenyl]-1,3-dihydrobenzimidazol-2-one; | 6.6 |
| 170 | 5-[2-Chloro-6-(4-pyridyl)phenyl]-1,3-dihydrobenzimidazol-2-one; | 6.5 |
| 171 | 5-[2-Chloro-6-(3-methoxy-4-pyridyl)phenyl]-1,3-dihydrobenzimidazol-2-one; | 6.0 |
| 172 | 5-[2-Chloro-6-[1-(2-methoxyethyl)pyrazol-4-yl]phenyl]-1,3-dihydrobenzimidazol-2-one; | 5.7 |
| 173 | 5-[2-Chloro-6-(1-methylpyrazol-4-yl)phenyl]-1,3-dihydrobenzimidazol-2-one; | 6.4 |
| 174 | 5-[2-Chloro-6-(3,5-dimethylisoxazol-4-yl)phenyl]-1,3-dihydrobenzimidazol-2-one; | 6.1 |
| 175 | 5-[2-Chloro-6-(2-isopropylpyrazol-3-yl)phenyl]-1,3-dihydrobenzimidazol-2-one; | 5.9 |
| 176 | 5-[2-Chloro-6-(1H-pyrazol-4-yl)phenyl]-1,3-dihydrobenzimidazol-2-one; | 5.7 |
| 177 | 5-[2-Chloro-6-(1,5-dimethylpyrazol-4-yl)phenyl]-1,3-dihydrobenzimidazol-2-one; | 6.1 |
| 178 | 5-(2-Chloro-6-pyrimidin-5-yl-phenyl)-1,3-dihydrobenzimidazol-2-one; | 5.4 |
| 179 | 5-(2-Methyl-6-phenyl-phenyl)-1,3-dihydrobenzimidazol-2-one; | 7.2 |
| 180 | 5-[2-(2-Fluorophenyl)-6-methyl-phenyl]-1,3-dihydrobenzimidazol-2-one; | 6.5 |
| 181 | 5-[2-(4-Fluorophenyl)-6-methyl-phenyl]-1,3-dihydrobenzimidazol-2-one; | 7.0 |

TABLE 4-continued

| Example # | Compound Name | GluR1-γ8 pIC$_{50}$ |
|---|---|---|
| 182 | 5-[2-Methoxy-6-(8-quinolyl)phenyl]-1,3-dihydrobenzimidazol-2-one; | 5.8 |
| 183 | 5-[2-Chloro-3-(1-methylpyrazol-3-yl)phenyl]-1,3-dihydrobenzimidazol-2-one; | 5.8 |
| 184 | 5-[2-Chloro-3-(4-pyridyl)phenyl]-1,3-dihydrobenzimidazol-2-one; | 6.9 |
| 185 | 5-[2-Chloro-3-(1-methylpyrazol-4-yl)phenyl]-1,3-dihydrobenzimidazol-2-one; | 7.3 |
| 186 | tert-Butyl 5-[2-chloro-3-(2-oxo-1,3-dihydrobenzimidazol-5-yl)phenyl]-3,6-dihydro-2H-pyridine-1-carboxylate; | 8.2 |
| 187 | 5-(2-Chloro-3-imidazol-1-yl-phenyl)-1,3-dihydrobenzimidazol-2-one; | 5.5 |
| 188 | 5-[2-Chloro-3-(1-piperidyl)phenyl]-1,3-dihydrobenzimidazol-2-one; | 7.9 |
| 189 | 5-[2-Chloro-3-(dimethylamino)phenyl]-1,3-dihydrobenzimidazol-2-one; | 5.4 |
| 190 | 5-[2-Chloro-3-(1,3,4-oxadiazol-2-yl)phenyl]-1,3-dihydrobenzimidazol-2-one; | 5.7 |
| 191 | 5-[2-Chloro-3-(5-methyl-1,3,4-oxadiazol-2-yl)phenyl]-1,3-dihydrobenzimidazol-2-one; | 5.7 |
| 192 | 5-[2,6-Dichloro-3-(1,3,4-oxadiazol-2-yl)phenyl]-1,3-dihydrobenzimidazol-2-one; | 6.2 |
| 193 | 5-[2-Bromo-3-(1,3,4-oxadiazol-2-yl)phenyl]-1,3-dihydrobenzimidazol-2-one; | 6.6 |
| 194 | 5-[2-Methyl-3-(1,3,4-oxadiazol-2-yl)phenyl]-1,3-dihydrobenzimidazol-2-one; | 6.3 |
| 195 | 5-[2-Methyl-3-(5-methyl-1,3,4-oxadiazol-2-yl)phenyl]-1,3-dihydrobenzimidazol-2-one; | 5.6 |
| 196 | 5-[2-Chloro-3-(5-cyclopropyl-1,3,4-oxadiazol-2-yl)phenyl]-1,3-dihydrobenzimidazol-2-one; | 6.5 |
| 197 | 5-[3-(5-Cyclopropyl-1,3,4-oxadiazol-2-yl)-2-methyl-phenyl]-1,3-dihydrobenzimidazol-2-one; | 6.4 |
| 198 | 5-[2-Methyl-3-[5-(trifluoromethyl)-1,3,4-oxadiazol-2-yl]phenyl]-1,3-dihydrobenzimidazol-2-one; | 7.7 |
| 199 | 5-[2-Methyl-3-(1,2,4-oxadiazol-5-yl)phenyl]-1,3-dihydrobenzimidazol-2-one; | 7.2 |
| 200 | 6-[2-Methyl-3-(1,2,4-oxadiazol-5-yl)phenyl]-3H-1,3-benzothiazol-2-one; | 5.6 |
| 201 | 5-(3-(3-cyclopropyl-1,2,4-oxadiazol-5-yl)-2-methylphenyl)-1H-benzo[d]imidazol-2(3H)-one; | 8.0 |
| 202 | 6-[3-(3-Cyclopropyl-1,2,4-oxadiazol-5-yl)-2-methyl-phenyl]-3H-1,3-benzothiazol-2-one; | 5.4 |
| 203 | 5-[2-Methyl-3-(3-methyl-1,2,4-oxadiazol-5-yl)phenyl]-1,3-dihydrobenzimidazol-2-one; | 7.4 |
| 204 | 6-[2-Methyl-3-(3-methyl-1,2,4-oxadiazol-5-yl)phenyl]-3H-1,3-benzothiazol-2-one; | 5.6 |
| 205 | 5-[2-Methyl-3-[3-(trifluoromethyl)-1,2,4-oxadiazol-5-yl]phenyl]-1,3-dihydrobenzimidazol-2-one; | 7.4 |
| 206 | 5-[2-Methyl-3-(1,2,4-oxadiazol-3-yl)phenyl]-1,3-dihydrobenzimidazol-2-one; | 7.5 |
| 207 | 6-[2-Methyl-3-(1,2,4-oxadiazol-3-yl)phenyl]-3H-1,3-benzothiazol-2-one; | 6.9 |
| 208 | 2-Chloro-3-(2-oxo-1,3-dihydrobenzimidazol-5-yl)-4-(trifluoromethoxy)benzonitrile; | 7.8 |
| 209 | 4-Chloro-3-(2-oxo-1,3-dihydrobenzimidazol-5-yl)-2-(trifluoromethoxy)benzonitrile; | 7.8 |
| 210 | 6-[2-Chloro-6-(trifluoromethoxy)phenyl]-5-fluoro-3H-1,3-benzothiazol-2-one; | 7.2 |
| 211 | 6-(2-Chloro-6-(trifluoromethoxy)phenyl)-4-methyl-1H-benzo[d]imidazol-2(3H)-one; | 10.0 |
| 212 | 6-(2-Chloro-3-(1-methyl-1H-pyrazol-4-yl)phenyl)benzo[d]thiazol-2(3H)-one; | 6.7 |
| 213 | 6-(2-Chloro-3-(4-methoxypiperidin-1-yl)phenyl)benzo[d]thiazol-2(3H)-one; and | 5.6 |
| 214 | 6-(2-chloro-6-(trifluoromethoxy)phenyl)-4-fluoro-1,3-dihydro-2H-benzo[d]imidazol-2-one. | 8.6 |

NT means not tested

Electrophysiology Assay

The effects of selected compounds upon endogenous γ8-containing AMPA receptor currents was evaluated using whole-cell electrophysiology on acutely-dissociated mouse hippocampal neurons. Hippocampus was chosen for this assay, since CACNG8 (the protein encoded by this gene is a type I transmembrane AMPA receptor regulatory protein i.e., TARP) is preferentially enriched in this brain region (Tomita et al. (2003). "Functional studies and distribution define a family of transmembrane AMPA receptor regulatory proteins." *J Cell Biol* 161(4): 805-816.2003).

Hippocampi were dissected from C57black6 mice at 4-12 weeks postnatal, following the protocol described by Brewer (Brewer, G. J. (1997). "Isolation and culture of adult rat hippocampal neurons." *Journal of Neuroscience Methods* 71(2): 143-155). The following is a brief summary of the procedure. Mice were asphyxiated with $CO_2$ then decapitated. The brain was rapidly removed, then placed into ice-cold HABG medium. The recipe for HABG medium was: HibernateA supplemented with 2% B27 and 0.5 mM Glutamax (all reagents from Life Technologies). Hippocampi were micro-dissected from the brains, then washed with HABG without calcium (Hibernate A minus Calcium, BrainBits; 2% B27, Life Technologies; 0.5 mM glutamax, Life Technologies).

The hippocampi were then transferred to HABG without calcium, supplemented with 2 mg/mL papain (Worthington Biochemical). They were incubated at 30° C. on a roller for 40 min, then gently triturated with a fire-polished glass pipette. The supernatant containing dissociated neurons was collected, then centrifuged for 2 min at 200 g. The cell pellet was collected, and then resuspended in 8 mL of HABG. Live cells were counted, then plated onto 12 mm glass coverslips in HABG (2 mL) in 24-well plates at a density of 50-100 cells per coverslip. These cells were maintained at room temperature until use.

Whole-cell electrophysiology was performed using 1.5 mm diameter glass capillary tubes (World Precision Instruments TW150-4), pulled to a fine tip with a Sutter P-97 micropipette puller. The intracellular buffer was 90 mM KF, 30 mM KCl, 10 mM HEPES, and 5 mM EGTA, pH 7.4, 290 mOs. The extracellular buffer was 135 mM NaCl, 4 mM KCl, 2 mM $CaCl_2$), 1 mM $MgCl_2$, 5 mM glucose, 10 mM HEPES, pH 7.4, 300 mOs. The open-tip resistances of the micropipettes using these solutions were 2-4MΩ. Whole-cell recordings of neuron cell bodies were performed in voltage-clamp mode using an Axon Axopatch 200B amplifier. Whole-cell current was measured holding the interior of the cell at −60 mV, using a 5 kHz lowpass filter. The cells were continuously perfused through 7 mm square glass barrels using a solenoid-controlled solution switching device (Warner Instruments, PF-77B). The peak current in response to a 500 ms exposure to 10 mM glutamate every 5 seconds was measured, before and after exposure to test compound.

For analysis, the mean peak current of 5 traces in the presence of test compound was divided by the mean peak current of 5 traces prior to the addition of test compound. Compounds were tested at concentrations at least ten times higher than their estimated potency in the calcium flux assay, in order to ensure near-saturating occupancy of the receptor.

The table below summarizes the results of this electrophysiological assay. Peak current (% control) is mean of the peak response to glutamate in the presence of the indicated compound, normalized to the peak response to glutamate in the absence of test compound. N is the number of neurons tested. The compounds were tested at concentrations noted below in Table 5. At the said tested concentrations, the peak response to glutamate was reduced compared to controls for all tested compounds.

TABLE 5

| Example No. | concentration (μM) | peak current (% control) | N |
|---|---|---|---|
| 36 | 1 | 72% | 9 |
| 31 | 1 | 61% | 6 |
| 66 | 1 | 86% | 5 |
| 124 | 1 | 63% | 9 |
| 123 | 1 | 59% | 6 |
| 160 | 1 | 70% | 4 |

TABLE 5-continued

| Example No. | concentration (μM) | peak current (% control) | N |
|---|---|---|---|
| 14 | 1 | 69% | 11 |
| 2 | 10 | 70% | 3 |

All patents, patent applications, publications and presentations referred to herein are incorporated by reference in their entirety.

Any combination of the groups described above for the various variables is contemplated herein. Throughout the specification, groups and substituents thereof are chosen by one skilled in the field to provide stable moieties and compounds.

While the foregoing specification teaches the principles of the present invention, and specific embodiments of the invention have been described for the purposes of illustration, and examples have been provided for the purposes of illustration, it will be understood that various modifications may be made without deviating from the spirit and scope of the invention as come within the scope of the following claims and their equivalents.

What is claimed:

1. A compound having the structure of Formula (IA), and pharmaceutically acceptable salts, N-oxides, or solvates thereof,

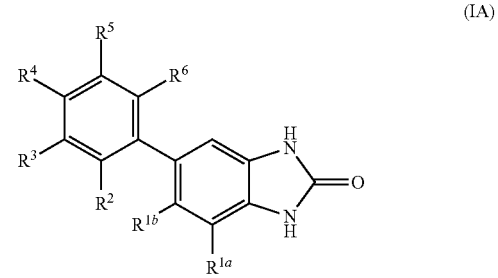

(IA)

$R^{1a}$ is H or F;
$R^{1b}$ is H;
$R^2$ is halo or $C_{1-5}$haloalkoxy;
$R^3$ is CN, or oxadiazolyl optionally substituted with $C_{1-5}$haloalkyl;
$R^4$ is H;
$R^5$ is H or halo; and
$R^6$ is halo, $C_{1-5}$ haloalkoxy, cyclopropyl, $C(CH_3)_2CN$, or —O—$CH_2$-cyclopropyl.

2. A compound having the structure of Formula (IB), and pharmaceutically acceptable salts, N-oxides, or solvates thereof,

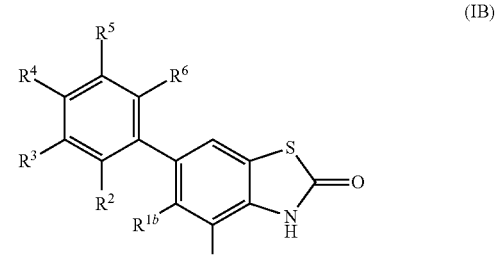

(IB)

wherein $R^{1a}$ is H or F;
$R^{1b}$ is H;
$R^2$ is halo or $C_{1-5}$haloalkoxy;
$R^3$ is CN, or oxadiazolyl optionally substituted with $C_{1-5}$haloalkyl;
$R^4$ is H;
$R^5$ is H or halo; and
$R^6$ is halo, $C_{1-5}$haloalkoxy, cyclopropyl, —C(CH$_3$)$_2$CN, or —O—CH$_2$-cyclopropyl.

3. A compound selected from the group consisting of:
5-(2,3-Dimethylphenyl)-1,3-dihydrobenzimidazol-2-one;
5-(2,6-Dimethylphenyl)-1,3-dihydrobenzimidazol-2-one;
5-(o-Tolyl)-1,3-dihydrobenzimidazol-2-one;
5-[2-(Trifluoromethyl)phenyl]-1,3-dihydrobenzimidazol-2-one;
5-(2-Phenylphenyl)-1,3-dihydrobenzimidazol-2-one;
5-(2-Isopropylphenyl)-1,3-dihydrobenzimidazol-2-one;
5-(2,6-Dimethoxyphenyl)-1,3-dihydrobenzimidazol-2-one;
5-(2-Isopropoxyphenyl)-1,3-dihydrobenzimidazol-2-one;
tert-Butyl 4-[2-(2-oxo-1,3-dihydrobenzimidazol-5-yl)phenyl]piperazine-1-carboxylate;
5-(5-Chloro-2-methyl-phenyl)-1,3-dihydrobenzimidazol-2-one;
5-(2-Fluoro-6-isopropoxy-phenyl)-1,3-dihydrobenzimidazol-2-one;
5-[2-Chloro-6-(trifluoromethyl)phenyl]-1,3-dihydrobenzimidazol-2-one;
5-[2-(Cyclopropylmethoxy)phenyl]-1,3-dihydrobenzimidazol-2-one;
5-(2-Isobutoxy-6-methoxy-phenyl)-1,3-dihydrobenzimidazol-2-one;
5-(2-Isobutoxy-5-methyl-phenyl)-1,3-dihydrobenzimidazol-2-one;
5-(5-Chloro-2-isopropoxy-phenyl)-1,3-dihydrobenzimidazol-2-one;
5-(2-Chlorophenyl)-1,3-dihydrobenzimidazol-2-one;
5-(2,5-Dichlorophenyl)-1,3-dihydrobenzimidazol-2-one;
5-(2-Chloro-5-methyl-phenyl)-1,3-dihydrobenzimidazol-2-one;
5-(2-Chloro-6-methoxy-phenyl)-1,3-dihydrobenzimidazol-2-one;
5-(2,5-Dimethylphenyl)-1,3-dihydrobenzimidazol-2-one;
5-[2-Isopropoxy-5-(trifluoromethyl)phenyl]-1,3-dihydrobenzimidazol-2-one;
5-(2,6-Dichloro-3-methyl-phenyl)-1,3-dihydrobenzimidazol-2-one;
5-(2-Phenoxyphenyl)-1,3-dihydrobenzimidazol-2-one;
5-[2-Chloro-5-(trifluoromethyl)phenyl]-1,3-dihydrobenzimidazol-2-one;
5-(2-Benzyloxy-6-fluoro-phenyl)-1,3-dihydrobenzimidazol-2-one;
3-Fluoro-2-(2-oxo-1,3-dihydrobenzimidazol-5-yl)benzaldehyde;
5-(2-Isopropoxy-6-methoxy-phenyl)-1,3-dihydrobenzimidazol-2-one;
5-[3-Chloro-2-(trifluoromethoxy)phenyl]-1,3-dihydrobenzimidazol-2-one;
5-[2-Chloro-4-(trifluoromethoxy)phenyl]-1,3-dihydrobenzimidazol-2-one;
5-[2-Chloro-6-(trifluoromethoxy)phenyl]-1,3-dihydrobenzimidazol-2-one;
5-[2-Chloro-6-(trifluoromethoxy)phenyl]-6-tritio-1,3-dihydrobenzimidazol-2-one;
5-[2-Methoxy-4-(trifluoromethoxy)phenyl]-1,3-dihydrobenzimidazol-2-one;
5-[3-Chloro-2-(trifluoromethyl)phenyl]-1,3-dihydrobenzimidazol-2-one;
5-(2-Bromophenyl)-1,3-dihydrobenzimidazol-2-one;
5-(2-Chloro-6-methyl-phenyl)-1,3-dihydrobenzimidazol-2-one;
5-(4-Chloro-2,6-dimethyl-phenyl)-1,3-dihydrobenzimidazol-2-one;
3-Methyl-2-(2-oxo-1,3-dihydrobenzimidazol-5-yl)benzonitrile;
4-Methyl-3-(2-oxo-1,3-dihydrobenzimidazol-5-yl)benzonitrile;
4-Chloro-3-(2-oxo-1,3-dihydrobenzimidazol-5-yl)benzonitrile;
2-[2-(2-Oxo-1,3-dihydrobenzimidazol-5-yl)phenyl]acetonitrile;
Methyl 3-chloro-2-(2-oxo-1,3-dihydrobenzimidazol-5-yl)benzoate;
Methyl 2-chloro-3-(2-oxo-1,3-dihydrobenzimidazol-5-yl)benzoate;
Methyl 4-chloro-3-(2-oxo-1,3-dihydrobenzimidazol-5-yl)benzoate;
Methyl 3-methyl-2-(2-oxo-1,3-dihydrobenzimidazol-5-yl)benzoate;
Methyl 2-methyl-3-(2-oxo-1,3-dihydrobenzimidazol-5-yl)benzoate;
Methyl 4-methyl-3-(2-oxo-1,3-dihydrobenzimidazol-5-yl)benzoate;
Methyl 2-methoxy-3-(2-oxo-1,3-dihydrobenzimidazol-5-yl)benzoate;
5-(2,6-Dichlorophenyl)-1,3-dihydrobenzimidazol-2-one;
5-(2,6-Dichloro-4-fluoro-phenyl)-1,3-dihydrobenzimidazol-2-one;
5-(2,4,6-Trichlorophenyl)-1,3-dihydrobenzimidazol-2-one;
5-(2,6-Difluorophenyl)-1,3-dihydrobenzimidazol-2-one;
5-(2-Chloro-6-fluoro-phenyl)-1,3-dihydrobenzimidazol-2-one;
5-(2-Fluoro-6-methyl-phenyl)-1,3-dihydrobenzimidazol-2-one;
5-(2-Fluoro-6-methoxy-phenyl)-1,3-dihydrobenzimidazol-2-one;
3-Chloro-2-(2-oxo-1,3-dihydrobenzimidazol-5-yl)benzonitrile;
5-[2-Methyl-6-(trifluoromethyl)phenyl]-1,3-dihydrobenzimidazol-2-one;
5-(2-Benzylphenyl)-1,3-dihydrobenzimidazol-2-one;
5-[2-Methyl-3-(trifluoromethyl)phenyl]-1,3-dihydrobenzimidazol-2-one;
5-[2-Chloro-3-(trifluoromethyl)phenyl]-1,3-dihydrobenzimidazol-2-one;
2-Isopropoxy-6-(2-oxo-1,3-dihydrobenzimidazol-5-yl)benzonitrile;
2-Bromo-6-(2-oxo-1,3-dihydrobenzimidazol-5-yl)benzonitrile;
5-(2-Chloro-3-methyl-phenyl)-1,3-dihydrobenzimidazol-2-one;
2-(2-Oxo-1,3-dihydrobenzimidazol-5-yl)-6-(trifluoromethyl)benzonitrile;
5-(2,3,6-Trichlorophenyl)-1,3-dihydrobenzimidazol-2-one;
2-Methyl-3-(2-oxo-1,3-dihydrobenzimidazol-5-yl)benzonitrile;
2-Chloro-3-(2-oxo-1,3-dihydrobenzimidazol-5-yl)benzonitrile;
5-[2-Methyl-3-(5-methyl-1,2,4-oxadiazol-3-yl)phenyl]-1,3-dihydrobenzimidazol-2-one;

6-[2-Methyl-3-(5-methyl-1,2,4-oxadiazol-3-yl)phenyl]-3H-1,3-benzothiazol-2-one;
5-[3-(5-Cyclopropyl-1,2,4-oxadiazol-3-yl)-2-methyl-phenyl]-1,3-dihydrobenzimidazol-2-one;
6-[3-(5-Cyclopropyl-1,2,4-oxadiazol-3-yl)-2-methyl-phenyl]-3H-1,3-benzothiazol-2-one;
5-[2-Methyl-3-[5-(4-pyridyl)-1,2,4-oxadiazol-3-yl]phenyl]-1,3-dihydrobenzimidazol-2-one;
6-[2-Chloro-6-(trifluoromethoxy)phenyl]-3H-1,3-benzothiazol-2-one;
6-(2-Isopropoxy-6-methoxy-phenyl)-3H-1,3-benzothiazol-2-one;
N-Methyl-2-[2-(2-oxo-1,3-dihydrobenzimidazol-5-yl)-6-(trifluoromethyl)phenyl]acetamide;
2-Methyl-3-(2-oxo-1,3-dihydrobenzimidazol-5-yl)-N-phenyl-benzamide;
N-Cyclopropyl-2-methyl-3-(2-oxo-1,3-dihydrobenzimidazol-5-yl)benzamide;
N,N,2-Trimethyl-3-(2-oxo-1,3-dihydrobenzimidazol-5-yl)benzamide;
5-[2-Methyl-3-(morpholine-4-carbonyl)phenyl]-1,3-dihydrobenzimidazol-2-one;
4-Chloro-3-(2-oxo-1,3-dihydrobenzimidazol-5-yl)-N-phenyl-benzamide;
5-[2-Chloro-5-(pyrrolidine-1-carbonyl)phenyl]-1,3-dihydrobenzimidazol-2-one;
5-[2-Chloro-5-(piperidine-1-carbonyl)phenyl]-1,3-dihydrobenzimidazol-2-one;
5-[2-Chloro-6-(2-furylmethylamino)phenyl]-1,3-dihydrobenzimidazol-2-one;
5-[2-Chloro-6-(3-furylmethylamino)phenyl]-1,3-dihydrobenzimidazol-2-one;
5-[2-Isopropoxy-6-(trifluoromethoxy)phenyl]-1,3-dihydrobenzimidazol-2-one;
5-[2-(Cyclopropylmethoxy)-6-(trifluoromethoxy)phenyl]-1,3-dihydrobenzimidazol-2-one;
5-[2-Chloro-6-(cyclopropoxy)phenyl]-1,3-dihydrobenzimidazol-2-one;
5-(2-Chloro-6-isopropoxy-phenyl)-1,3-dihydrobenzimidazol-2-one;
5-[2-Chloro-6-(cyclopropylmethoxy)phenyl]-1,3-dihydrobenzimidazol-2-one;
(±)-5-[2-Chloro-6-[(2,2-difluorocyclopropyl)methoxy]phenyl]-1,3-dihydrobenzimidazol-2-one;
5-[2-Chloro-6-(difluoromethoxy)phenyl]-1,3-dihydrobenzimidazol-2-one;
5-[2-Chloro-6-(2,2,2-trifluoroethoxy)phenyl]-1,3-dihydrobenzimidazol-2-one;
5-[2-Chloro-6-(2,2-difluoroethoxy)phenyl]-1,3-dihydrobenzimidazol-2-one;
2-[3-Chloro-2-(2-oxo-1,3-dihydrobenzimidazol-5-yl)phenoxy]acetonitrile;
5-[2-Chloro-6-(2,2-dimethylpropoxy)phenyl]-1,3-dihydrobenzimidazol-2-one;
5-(2-Benzyloxy-6-chloro-phenyl)-1,3-dihydrobenzimidazol-2-one;
tert-Butyl 3-[3-chloro-2-(2-oxo-1,3-dihydrobenzimidazol-5-yl)phenoxy]azetidine-1-carboxylate;
5-(2-Chloro-6-thiazol-5-yloxy-phenyl)-1,3-dihydrobenzimidazol-2-one;
5-[2-(2,2-Difluoroethoxy)-6-methoxy-phenyl]-1,3-dihydrobenzimidazol-2-one;
5-[2-Methoxy-6-(2,2,2-trifluoroethoxy)phenyl]-1,3-dihydrobenzimidazol-2-one;
5-[2-(2,2-Dimethylpropoxy)-6-methoxy-phenyl]-1,3-dihydrobenzimidazol-2-one;
5-(2-Benzyloxy-6-methoxy-phenyl)-1,3-dihydrobenzimidazol-2-one;
5-[2-[(4-Fluorophenyl)ethoxy]-6-methoxy-phenyl]-1,3-dihydrobenzimidazol-2-one;
5-(2,6-Diisopropoxyphenyl)-1,3-dihydrobenzimidazol-2-one;
5-[2-Isopropoxy-6-(trifluoromethyl)phenyl]-1,3-dihydrobenzimidazol-2-one;
5-[2-Chloro-3-(cyclopropoxy)phenyl]-1,3-dihydrobenzimidazol-2-one;
5-(2-Chloro-3-isopropoxy-phenyl)-1,3-dihydrobenzimidazol-2-one;
(±)-5-[2-Chloro-3-[(2,2-difluorocyclopropyl)methoxy]phenyl]-1,3-dihydrobenzimidazol-2-one;
5-[2-Chloro-3-(2,2-difluoroethoxy)phenyl]-1,3-dihydrobenzimidazol-2-one;
5-[2-Chloro-3-(difluoromethoxy)phenyl]-1,3-dihydrobenzimidazol-2-one;
tert-Butyl 3-[2-chloro-3-(2-oxo-1,3-dihydrobenzimidazol-5-yl)phenoxy]azetidine-1-carboxylate;
5-(3-Chloro-2-isopropoxy-phenyl)-1,3-dihydrobenzimidazol-2-one;
5-(2-tert-Butoxy-6-chloro-phenyl)-1,3-dihydrobenzimidazol-2-one;
5-(2-tert-Butoxy-6-methoxy-phenyl)-1,3-dihydrobenzimidazol-2-one;
(±)-5-[2-Chloro-6-(2,2,2-trifluoro-1-methyl-ethoxy)phenyl]-1,3-dihydrobenzimidazol-2-one;
(R*)-5-[2-Chloro-6-(2,2,2-trifluoro-1-methyl-ethoxy)phenyl]-1,3-dihydrobenzimidazol-2-one;
(S*)-5-[2-Chloro-6-(2,2,2-trifluoro-1-methyl-ethoxy)phenyl]-1,3-dihydrobenzimidazol-2-one;
(±)-5-[2-Methoxy-6-(2,2,2-trifluoro-1-methyl-ethoxy)phenyl]-1,3-dihydrobenzimidazol-2-one;
2-[3,4-Dichloro-2-(2-oxo-1,3-dihydrobenzimidazol-5-yl)phenyl]acetonitrile;
2-[2-(2-Oxo-1,3-dihydrobenzimidazol-5-yl)-3-trifluoromethoxy)phenyl]acetonitrile;
2-[3-Chloro-2-(2-oxo-1,3-dihydrobenzimidazol-5-yl)phenyl]acetonitrile;
2-[3-Chloro-2-(2-oxo-6-tritio-1,3-dihydrobenzimidazol-5-yl)phenyl]acetonitrile;
(±)-2-[3-Chloro-2-(2-oxo-1,3-dihydrobenzimidazol-5-yl)phenyl]propanenitrile;
2-[3-Chloro-2-(2-oxo-1,3-dihydrobenzimidazol-5-yl)phenyl]-2-methyl-propanenitrile;
1-[3-Chloro-2-(2-oxo-1,3-dihydrobenzimidazol-5-yl)phenyl]cyclopropanecarbonitrile;
1-[3-Chloro-2-(2-oxo-1,3-dihydrobenzimidazol-5-yl)phenyl]cyclobutanecarbonitrile;
2-[2-Chloro-3-(2-oxo-1,3-dihydrobenzimidazol-5-yl)phenyl]acetonitrile;
2-[2,4-Dichloro-3-(2-oxo-1,3-dihydrobenzimidazol-5-yl)phenyl]acetonitrile;
2-[3-Bromo-2-(2-oxo-1,3-dihydrobenzimidazol-5-yl)phenyl]acetonitrile;
2-[3-Chloro-2-(2-oxo-3H-1,3-benzothiazol-6-yl)phenyl]acetonitrile;
2-[3-(4-Fluorophenyl)-2-(2-oxo-1,3-dihydrobenzimidazol-5-yl)phenyl]acetonitrile;
2-[3-(2-Fluorophenyl)-2-(2-oxo-1,3-dihydrobenzimidazol-5-yl)phenyl]acetonitrile;
2-[3-(4-Methoxyphenyl)-2-(2-oxo-1,3-dihydrobenzimidazol-5-yl)phenyl]acetonitrile;
2-[3-Cyclopropyl-2-(2-oxo-1,3-dihydrobenzimidazol-5-yl)phenyl]acetonitrile;

5-[2,6-Dichloro-3-(morpholinomethyl)phenyl]-1,3-dihydrobenzimidazol-2-one;
5-[2,6-Dichloro-3-(1-piperidylmethyl)phenyl]-1,3-dihydrobenzimidazol-2-one;
5-[2-Chloro-3-(morpholinomethyl)phenyl]-1,3-dihydrobenzimidazol-2-one;
5-[2-Chloro-3-(1-piperidylmethyl)phenyl]-1,3-dihydrobenzimidazol-2-one;
5-[2-Chloro-3-[(2,2-dimethylmorpholin-4-yl)methyl]phenyl]-1,3-dihydrobenzimidazol-2-one;
(±)-5-[2-Chloro-3-[[2-(trifluoromethyl)morpholin-4-yl]methyl]phenyl]-1,3-dihydrobenzimidazol-2-one;
5-[2-Chloro-6-(morpholinomethyl)phenyl]-1,3-dihydrobenzimidazol-2-one;
5-[2-Chloro-6-[(4-methylpiperazin-1-yl)methyl]phenyl]-1,3-dihydrobenzimidazol-2-one;
5-[2-Methyl-3-(1-piperidylmethyl)phenyl]-1,3-dihydrobenzimidazol-2-one;
5-[2-Methyl-3-(morpholinomethyl)phenyl]-1,3-dihydrobenzimidazol-2-one;
5-[3-[(2,2-Dimethylmorpholin-4-yl)methyl]-2-methylphenyl]-1,3-dihydrobenzimidazol-2-one;
(±)-5-[2-Methyl-3-[(2-methylmorpholin-4-yl)methyl]phenyl]-1,3-dihydrobenzimidazol-2-one;
(±)-5-[2-Methyl-3-[[2-(trifluoromethyl)morpholin-4-yl]methyl]phenyl]-1,3-dihydrobenzimidazol-2-one;
(3R)-5-[2-Methyl-3-[[3-methylmorpholin-4-yl]methyl]phenyl]-1,3-dihydrobenzimidazol-2-one;
(3S)-5-[2-Methyl-3-[[3-methylmorpholin-4-yl]methyl]phenyl]-1,3-dihydrobenzimidazol-2-one;
5-[2-Methyl-3-(thiomorpholinomethyl)phenyl]-1,3-dihydrobenzimidazol-2-one;
tert-Butyl 4-[[2-methyl-3-(2-oxo-1,3-dihydrobenzimidazol-5-yl)phenyl]methyl]piperazine-1-carboxylate;
5-[2-Methyl-3-(pyrrolidin-1-ylmethyl)phenyl]-1,3-dihydrobenzimidazol-2-one;
5-[3-[(3-Fluoroazetidin-1-yl)methyl]-2-methyl-phenyl]-1,3-dihydrobenzimidazol-2-one;
5-[2-Methyl-3-(6-oxa-3-azabicyclo[3;1;1]heptan-3-ylmethyl)phenyl]-1,3-dihydrobenzimidazol-2-one;
(3R,4S)-5-[3-[[3-Fluoro-4-hydroxy-1-piperidyl]methyl]-2-methyl-phenyl]-1,3-dihydrobenzimidazol-2-one;
5-(2-Chloro-6-cyclopropyl-phenyl)-1,3-dihydrobenzimidazol-2-one;
5-(2-Chloro-6-vinyl-phenyl)-1,3-dihydrobenzimidazol-2-one;
5-(2-Chloro-6-phenyl-phenyl)-1,3-dihydrobenzimidazol-2-one;
5-[2-Chloro-6-(4-fluorophenyl)phenyl]-1,3-dihydrobenzimidazol-2-one;
4-[3-Chloro-2-(2-oxo-1,3-dihydrobenzimidazol-5-yl)phenyl]benzonitrile;
5-[2-Chloro-6-(3-pyridyl)phenyl]-1,3-dihydrobenzimidazol-2-one;
5-[2-Chloro-6-(5-fluoro-3-pyridyl)phenyl]-1,3-dihydrobenzimidazol-2-one;
5-[2-Chloro-6-(6-fluoro-3-pyridyl)phenyl]-1,3-dihydrobenzimidazol-2-one;
5-[2-Chloro-6-(5-methoxy-3-pyridyl)phenyl]-1,3-dihydrobenzimidazol-2-one;
5-[2-Chloro-6-[5-(trifluoromethyl)-3-pyridyl]phenyl]-1,3-dihydrobenzimidazol-2-one;
5-[2-Chloro-6-(4-pyridyl)phenyl]-1,3-dihydrobenzimidazol-2-one;
5-[2-Chloro-6-(3-methoxy-4-pyridyl)phenyl]-1,3-dihydrobenzimidazol-2-one;
5-[2-Chloro-6-[1-(2-methoxyethyl)pyrazol-4-yl]phenyl]-1,3-dihydrobenzimidazol-2-one;
5-[2-Chloro-6-(1-methylpyrazol-4-yl)phenyl]-1,3-dihydrobenzimidazol-2-one;
5-[2-Chloro-6-(3,5-dim ethyl isoxazol-4-yl)phenyl]-1,3-dihydrobenzimidazol-2-one;
5-[2-Chloro-6-(2-isopropylpyrazol-3-yl)phenyl]-1,3-dihydrobenzimidazol-2-one;
5-[2-Chloro-6-(1H-pyrazol-4-yl)phenyl]-1,3-dihydrobenzimidazol-2-one;
5-[2-Chloro-6-(1,5-dimethylpyrazol-4-yl)phenyl]-1,3-dihydrobenzimidazol-2-one;
5-(2-Chloro-6-pyrimidin-5-yl-phenyl)-1,3-dihydrobenzimidazol-2-one;
5-(2-Methyl-6-phenyl-phenyl)-1,3-dihydrobenzimidazol-2-one;
5-[2-(2-Fluorophenyl)-6-methyl-phenyl]-1,3-dihydrobenzimidazol-2-one;
5-[2-(4-Fluorophenyl)-6-methyl-phenyl]-1,3-dihydrobenzimidazol-2-one;
5-[2-Methoxy-6-(8-quinolyl)phenyl]-1,3-dihydrobenzimidazol-2-one;
5-[2-Chloro-3-(1-methylpyrazol-3-yl)phenyl]-1,3-dihydrobenzimidazol-2-one;
5-[2-Chloro-3-(4-pyridyl)phenyl]-1,3-dihydrobenzimidazol-2-one;
5-[2-Chloro-3-(1-methylpyrazol-4-yl)phenyl]-1,3-dihydrobenzimidazol-2-one;
tert-Butyl 5-[2-chloro-3-(2-oxo-1,3-dihydrobenzimidazol-5-yl)phenyl]-3,6-dihydro-2H-pyridine-1-carboxylate;
5-(2-Chloro-3-imidazol-1-yl-phenyl)-1,3-dihydrobenzimidazol-2-one;
5-[2-Chloro-3-(1-piperidyl)phenyl]-1,3-dihydrobenzimidazol-2-one;
5-[2-Chloro-3-(dimethylamino)phenyl]-1,3-dihydrobenzimidazol-2-one;
5-[2-Chloro-3-(1,3,4-oxadiazol-2-yl)phenyl]-1,3-dihydrobenzimidazol-2-one;
5-[2-Chloro-3-(5-methyl-1,3,4-oxadiazol-2-yl)phenyl]-1,3-dihydrobenzimidazol-2-one;
5-[2,6-Dichloro-3-(1,3,4-oxadiazol-2-yl)phenyl]-1,3-dihydrobenzimidazol-2-one;
5-[2-Bromo-3-(1,3,4-oxadiazol-2-yl)phenyl]-1,3-dihydrobenzimidazol-2-one;
5-[2-Methyl-3-(1,3,4-oxadiazol-2-yl)phenyl]-1,3-dihydrobenzimidazol-2-one;
5-[2-Methyl-3-(5-methyl-1,3,4-oxadiazol-2-yl)phenyl]-1,3-dihydrobenzimidazol-2-one;
5-[2-Chloro-3-(5-cyclopropyl-1,3,4-oxadiazol-2-yl)phenyl]-1,3-dihydrobenzimidazol-2-one;
5-[3-(5-Cyclopropyl-1,3,4-oxadiazol-2-yl)-2-methylphenyl]-1,3-dihydrobenzimidazol-2-one;
5-[2-Methyl-3-[5-(trifluoromethyl)-1,3,4-oxadiazol-2-yl]phenyl]-1,3-dihydrobenzimidazol-2-one;
5-[2-Methyl-3-(1,2,4-oxadiazol-5-yl)phenyl]-1,3-dihydrobenzimidazol-2-one;
6-[2-Methyl-3-(1,2,4-oxadiazol-5-yl)phenyl]-3H-1,3-benzothiazol-2-one;
5-(3-(3-Cyclopropyl-1,2,4-oxadiazol-5-yl)-2-methylphenyl)-1H-benzo[d]imidazol-2(3H)-one;
6-[3-(3-Cyclopropyl-1,2,4-oxadiazol-5-yl)-2-methyl-phenyl]-3H-1,3-benzothiazol-2-one;
5-[2-Methyl-3-(3-methyl-1,2,4-oxadiazol-5-yl)phenyl]-1,3-dihydrobenzimidazol-2-one;
6-[2-Methyl-3-(3-methyl-1,2,4-oxadiazol-5-yl)phenyl]-3H-1,3-benzothiazol-2-one;

5-[2-Methyl-3-[3-(trifluoromethyl)-1,2,4-oxadiazol-5-yl] phenyl]-1,3-dihydrobenzimidazol-2-one;
5-[2-Methyl-3-(1,2,4-oxadiazol-3-yl)phenyl]-1,3-dihydrobenzimidazol-2-one;
6-[2-Methyl-3-(1,2,4-oxadiazol-3-yl)phenyl]-3H-1,3-benzothiazol-2-one;
2-Chloro-3-(2-oxo-1,3-dihydrobenzimidazol-5-yl)-4-(trifluoromethoxy)benzonitrile;
4-Chloro-3-(2-oxo-1,3-dihydrobenzimidazol-5-yl)-2-(trifluoromethoxy)benzonitrile;
6-[2-Chloro-6-(trifluoromethoxy)phenyl]-5-fluoro-3H-1,3-benzothiazol-2-one;
6-(2-Chloro-6-(trifluoromethoxy)phenyl)-4-methyl-1H-benzo[d]imidazol-2(3H)-one;
6-(2-Chloro-3-(1-methyl-1H-pyrazol-4-yl)phenyl)benzo[d]thiazol-2(3H)-one; and
6-(2-Chloro-3-(4-methoxypiperidin-1-yl)phenyl)benzo[d]thiazol-2(3H)-one;
and pharmaceutically acceptable salts, N-oxides or solvates thereof.

4. A compound selected from the group consisting of:
4-Chloro-6-(2-chloro-6-(trifluoromethoxy)phenyl)-1,3-dihydro-2H-benzo[d]imidazol-2-one;
6-(2-Chloro-6-(trifluoromethoxy)phenyl)-2-oxo-2,3-dihydro-1H-benzo[d]imidazole-4-carbonitrile;
6-(2-Chloro-6-cyclopropylphenyl)-4-methyl-1,3-dihydro-2H-benzo[d]imidazol-2-one;
4-Chloro-6-(2-chloro-6-cyclopropylphenyl)-1,3-dihydro-2H-benzo[d]imidazol-2-one; and
6-(2-Chloro-6-cyclopropylphenyl)-2-oxo-2,3-dihydro-1H-benzo[d]imidazole-4-carbonitrile;
and pharmaceutically acceptable salts, N-oxides or solvates thereof.

5. A compound of claim 3 wherein the compound is: 6-[2-Chloro-6-(trifluoromethoxy)phenyl]-3H-1,3-benzothiazol-2-one; and pharmaceutically acceptable salts, N-oxides or solvates thereof.

6. A compound of claim 3 wherein the compound is: 6-[2-Chloro-6-(trifluoromethoxy)phenyl]-4-methyl-1,3-dihydrobenzimidazol-2-one; and pharmaceutically acceptable salts, N-oxides or solvates thereof.

7. A compound of claim 3 wherein the compound is: 5-[2-Chloro-6-(trifluoromethoxy)phenyl]-1,3-dihydrobenzimidazol-2-one; and pharmaceutically acceptable salts, N-oxides or solvates thereof.

8. A compound of claim 3 wherein the compound is: 5-(2-Chloro-6-cyclopropyl-phenyl)-1,3-dihydrobenzimidazol-2-one; and pharmaceutically acceptable salts, N-oxides or solvates thereof.

9. A compound of claim 3 wherein the compound is: 2-[3-Chloro-2-(2-oxo-1,3-dihydrobenzimidazol-5-yl)phenyl]acetonitrile; and pharmaceutically acceptable salts, N-oxides or solvates thereof.

10. A compound of claim 3 wherein the compound is: 5-[2-Chloro-3-(1-piperidyl)phenyl]-1,3-dihydrobenzimidazol-2-one; and pharmaceutically acceptable salts, N-oxides or solvates thereof.

11. A compound of claim 3 wherein the compound is: 5-[2-Chloro-6-(cyclopropylmethoxy)phenyl]-1,3-dihydrobenzimidazol-2-one; and pharmaceutically acceptable salts, N-oxides or solvates thereof.

12. A compound of claim 3 wherein the compound is: 5-[2-Isopropoxy-6-(trifluoromethoxy)phenyl]-1,3-dihydrobenzimidazol-2-one; and pharmaceutically acceptable salts, N-oxides or solvates thereof.

13. A compound of claim 3 wherein the compound is: 5-(2,3,6-Trichlorophenyl)-1,3-dihydrobenzimidazol-2-one; and pharmaceutically acceptable salts, N-oxides or solvates thereof.

14. A compound selected from the group consisting of:
5-(8-quinolyl)-1,3-dihydrobenzimidazol-2-one;
5-(3,5-dichloro-4-pyridyl)-1,3-dihydrobenzimidazol-2-one;
5-(2-chloro-4-methyl-3-pyridyl)-1,3-dihydrobenzimidazol-2-one; and
6-(3,5-dichloro-4-pyridyl)-3H-1,3-benzothiazol-2-one;
and pharmaceutically acceptable salts, N-oxides or solvates thereof.

15. A pharmaceutical composition comprising an effective amount of at least one compound of claim 3 and at least one pharmaceutically acceptable excipient.

16. A pharmaceutical composition comprising an effective amount of at least one compound of claim 4 and at least one pharmaceutically acceptable excipient.

17. A method of treating a subject suffering from or diagnosed with a disease, disorder, or medical condition mediated by AMPA receptor activity, comprising administering to a subject in need of such treatment an effective amount of at least one compound of Formula (I):

(I)

wherein
X is NH or S;
$R^{1a}$ and $R^{1b}$ are independently selected from the group consisting of H, $^3$H, halo, —CH$_3$, —CH$_2$CH$_3$, —CF$_3$, —OCH$_3$, —OCF$_3$, and —CN;
$R^2$ is selected from the group consisting of: halo; C$_{1-5}$ alkyl; C$_{2-5}$ alkenyl; C$_{1-5}$haloalkyl; C$_{1-5}$alkoxy; C$_{1-5}$haloalkoxy; —(C=O)H; —CH$_2$C(=O)NH(CH$_3$); —CO$_2$C$_{1-5}$ alkyl; —CN; —CH$_2$CN; —CH(CH$_3$)CN; —C(CH$_3$)$_2$CN; —OCH$_2$CN; phenyl; phenyl substituted with halo, C$_{1-5}$ alkoxy, or —CN; —O-phenyl; benzyl; benzyl substituted with halo; —O-benzyl; C$_{3-6}$ cycloalkyl; —OC$_{3-6}$ cycloalkyl; —O-thiazolyl; pyrimidinyl; pyridyl; pyridyl substituted with halo, C$_{1-5}$ alkoxy, or C$_{1-5}$haloalkyl; —NH—CH$_2$-furyl; —C$_{3-6}$ cycloalkyl substituted with CN; -CH$_2$morpholine; CH$_2$—N-methylpiperazine; pyrazolyl; pyrazole substituted with —CH$_2$CH$_2$OCH$_3$, or C$_{1-5}$ alkyl; isoxazole substituted with two C$_{1-5}$ alkyl; —O—CH$_2$—C$_{3-6}$ cycloalkyl optionally substituted with halo; piperazine substituted with —CO$_2$tBu; —O-azetidine substituted with —CO$_2$tBu; and 8-quinolyl;
$R^3$ is selected from the group consisting of: H; halo; C$_{1-5}$ alkyl; C$_{1-5}$haloalkyl; C$_{1-5}$alkoxy; C$_{1-5}$haloalkoxy; —CN; —CH$_2$CN; CO$_2$C$_{1-5}$ alkyl; —N(CH$_3$)$_2$; —(C=O)N(C$_{1-5}$alkyl)$_2$; —(C=O)NH-cyclopropyl; —(C=O)NH-phenyl; —(C=O)morpholine; —O-cyclopropyl; —O—CH$_2$-cyclopropyl substituted with halo; —O-azetidinyl substituted with —CO$_2$tBu; CH$_2$- pyrrolidine; piperidine; piperidine substituted with —OCH$_3$; —CH$_2$-piperidine; —CH$_2$-piperidine substituted with OH and halo; —CH$_2$-morpholine; CH$_2$-morpholine substituted with one or two C$_{1-5}$ alkyl or C$_{1-5}$haloalkyl; CH$_2$-thiomorpholine; CH$_2$-piperazine substituted with —CO$_2$tBu; CH$_2$-azetidine substituted with halo; —CH$_{2-6}$-oxa-3-azabicyclo[3.1.1]heptan-3-yl; pyrazole substituted with C$_{1-5}$ alkyl; pyridyl; 3,6-dihydro-2H-pyridine substituted with —CO$_2$tBu; imidazole; oxadiazolyl; and oxadiazole substituted with C$_{1-5}$ alkyl, cyclopropyl, pyridyl, or C$_{1-5}$haloalkyl;

R$^4$ is selected from the group consisting of: H, halo, and C$_{1-5}$haloalkoxy;

R$^5$ is selected from the group consisting of: H, halo, C$_{1-5}$ alkyl, C$_{1-5}$haloalkyl, —CN, —CO$_2$C$_{1-5}$ alkyl, —(C=O)NH-phenyl, —(C=O)pyrrolidine, and —(C=O)piperidine; and R$^6$ is selected from the group consisting of: H, halo, C$_{1-5}$ alkyl, —CH$_2$CN, C$_{1-5}$alkoxy, C$_{1-5}$haloalkyl, and C$_{1-5}$haloalkoxy; and wherein when R$^6$ is H and R$^2$ is C$_{1-5}$ alkoxy, R$^3$ is not C$_{1-5}$ alkoxy;

and pharmaceutically acceptable salts, N-oxides or solvates of compounds of Formula (I).

18. The method of claim 17, wherein the AMPA receptor mediated disease, disorder, or medical condition is selected from cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain, diabetic neuropathy, encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder (for example, CNS lupus erythematodes, polyarteritis nodosa, Sjogren syndrome, sarcoidosis, isolated cerebral vasculitis, etc.), schizophrenia, prodromal schizophrenia, cognitive disorder, depression, anxiety disorders, anxious depression, and bipolar disorder.

19. The method of claim 17, wherein the AMPA receptor mediated disease, disorder or condition is depression, post traumatic stress disorder, epilepsy, schizophrenia, prodromal schizophrenia, or a cognitive disorder.

* * * * *